(12) United States Patent
Dreyfuss et al.

(10) Patent No.: US 6,646,113 B1
(45) Date of Patent: Nov. 11, 2003

(54) NUCLEIC ACID MOLECULE ENCODING HUMAN SURVIVAL OF MOTOR NEURON-INTERACTING PROTEIN 1 (SIP1) DELETION MUTANTS

(75) Inventors: Gideon Dreyfuss, Wynnewood, PA (US); Utz Fischer, Gauting (DE); Qing Liu, Encinitas, CA (US); Bernard Charroux, Philadelphia, PA (US); Livio Pellizzoni, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 09/399,081

(22) Filed: Sep. 17, 1999

Related U.S. Application Data
(60) Provisional application No. 60/100,866, filed on Sep. 17, 1998.

(51) Int. Cl.[7] .................... C12N 1/20; C12N 15/00; C12N 5/00; C07K 14/00; C07H 21/04
(52) U.S. Cl. ............... 536/23.1; 435/252.3; 435/320.1; 435/325; 530/350; 536/23.1; 536/23.5
(58) Field of Search .................... 435/69.1, 70.1, 435/252.3, 320.1, 325; 530/300, 350; 536/23.1, 23.5, 24.1

(56) References Cited

U.S. PATENT DOCUMENTS

| 4,160,452 A | 7/1979 | Theeuwes .................... 128/260 |
|---|---|---|
| 4,256,108 A | 3/1981 | Theeuwes .................... 128/260 |
| 4,265,874 A | 5/1981 | Bonsen et al. ................. 424/15 |
| 5,023,243 A | 6/1991 | Tullis .......................... 514/44 |
| 5,168,053 A | 12/1992 | Altman et al. ................. 435/91 |
| 5,190,931 A | 3/1993 | Inouye ........................ 435/91 |

FOREIGN PATENT DOCUMENTS

| FR | EP 0711833 | * 5/1996 |
|---|---|---|

OTHER PUBLICATIONS

Dietz, H. Polishing the cutting edge of gems. Nature Genetics 20: 321–322, 1998.*
Pellizzoni et al. A novel function for SMN, the spinal muscular atrophy disease gene product, in pre–mRNA splicing. Cell 95: 615–624, 1998.*
Liu and Dreyfuss. Accession AF027150, GenEmbl, Oct. 30, 1997.*
Liu et al. Accession No. AF027151, direct submission, GENEMBL, Oct. 30, 1997.*
Fischer et al. The SMN–SIP1 complex has an essential role in spliceosomal snRNP biogenesis. Cell 90: 1023–1029, 1997.*
Altschul et al., 1990, J. Mol. Biol. 215:403–410.
Andrade et al., 1991, J. Exp. Med. 173:1407–1419.
Andrade et al., 1993, Proc. Natl. Acad. Sci. USA 90:1947–1951.
Arenas and Abelson, 1997, Proc. Natl. Acad. Sci. USA 94:11798–11802.
Barbas, 1995, Nature Medicine 1:837–839.
Bohmann et al., 1995, J. Cell Biol. 131:817–831.
Bohmann et al., 1995, J. Cell Sci. 19:107–113.
Branlant et al., 1982, EMBO J. 1:1259–1265.
Brzustowicz et al., 1990, Nature 344:540–541.
Burghes, 1997, Am. J. Hum. Genet. 61:9–15.
Burton et al., 1994, Adv. Immunol. 57:191–280.
Bussaglia et al., 1995, Nat. Genet. 11:335–337.
Carmo–Fonseca et al., 1991, EMBO J. 10:195–206.
Cech et al., 1992, J. Biol. Chem. 267:17479–17482.
Cech, 1988, J. Amer. Med. Assn. 260:3030.
Chang et al., 1995, Am. J. Hum. Genet. 57:1503–1505.
Choi and Dreyfuss, 1984, J. Cell. Biol. 99:1997–2004.
Cobben et al., 1995, Am. J. Hum. Genet. 57:805–808.
Company et al., 1991, Nature 349:487–493.
Coovert et al., 1997, Hum. Mol. Gen. 6:1205–1214.
Cranage et al., 1986, EMBO J. 5:3057–3063.
Cross et al., 1994, Nature Genet. 6:236–244.
Czeizel and Hamular, 1989, J. Med. Genet. 26761–763.
de Kruff et al. 1995, J. Mol. Biol. 248:97–105.
DeRobertis, 1983, Cell 32:1021–1025.
Dignam et al., 1983, Nucl. Acids Res. 11:1475–1489.
Dreyfuss et al., 1993, Ann. Rev. Biochem. 62:289–321.
Feeney et al., 1989, J. Biol. Chem. 264:5776–5783.
Fischer and Luhrmann, 1990, Science 249:786–790.
Fischer et al., 1993, EMBO J. 12:573–583.
Fisher et al., 1985, Cell 42:751–758.
Fischer et al., 1995, Cell 82:475–483.
Gall et al., 1995, Dev. Genet. 16:25–35.
Gennarelli et al., 1995, Biochem. Biophys. Res. Commun. 213:342–348.
Gu et al., 1997, Thrombosis and Haemostates 77:755–759.
Hahnen et al., 1995, Hum. Mol. Genet. 4:1927–1933.
Hahnen et al., 1996, Am. J. Hum. Genet. 59:1057–1065.

(List continued on next page.)

Primary Examiner—Elizabeth Kemmerer
Assistant Examiner—Bridget Bunner
(74) Attorney, Agent, or Firm—Morgan, Lewis & Bockius, LLP

(57) ABSTRACT

The invention relates to an isolated nucleic acid encoding a eukaryotic Survival of Motor Neuron-Interacting Protein 1 (SIP1), compositions comprising SIP1 and SIP1 and the spinal muscular atrophy (SMA) disease gene product Survival of Motor Neuron protein (SMN), and diagnostic and therapeutic assays directed to SMA. The invention also relates to another protein that specifically interacts with SMN and is a component of gems, designated Gemin3, and the nucleic acid encoding the protein. Additionally, the invention relates to a novel cell line wherein the endogenous SMN genes have been deleted and where an exogenous nucleic acid encoding SMN has been inserted into the cell such that expression of SMN in the cell is under the control of an inducible promoter. This novel cell line provides a stable genetic system for the study of SMA and for the development of SMA therapeutics.

8 Claims, 56 Drawing Sheets

OTHER PUBLICATIONS

Hamm and Lamond, 1998, Curr. Biol. 8:R532–R534.
Hamm et al., 1990, Cell 62:569–577.
Hampel et al., 1989, Biochemistry 28:4929–4933.
Hasselhoff, 1988, Nature 334:585.
Herrmann et al., 1995, EMBO J. 14:2076–2088.
Huang and Spector, 1992, Proc. Natl. Acad. Sci. USA 89:305–308.
Jarmolowski and Mattaj, 1993, EMBO J. 12:223–232.
Jarmolowski et al., 1994, J. Cell Biol. 124:627–635.
Ma et al., 1997, Proc. Natl. Acad. Sci. U.S.A. 94:12744–12746.
Konarska et al., 1984, Cell 38:731–736.
Konarska, 1989, Methods Enzymol. 180:442–453.
Krainer, 1988, Nucleic Acids Res. 16:9415–9429.
Lamond and Carmo–Fonesca, 1993, Trends Cell Biol. 3:198–204.
Lamond and Earnshaw, 1998, Science 280:547–553.
Lefebvre et al., 1995, Cell 89:155–165.
Lefebvre et al., 1997, Nature Genet. 16:265–269.
Lehmeier et al., 1994, Proc. Natl. Acad. Sci. USA 91:12317–12321.
Liu and Dreyfuss, 1996, EMBO J. 15:3555–3565.
Liu et al., 1996, Cold Spring Harbor Symp. Quant. Biol. 61:689–697.
Liu et al., 1997, Cell 90:1013–1021.
Lorson et al., 1998, Nature Genet. 19:63–66.
Luhrmann et al., 1990, Biochim. Biophys. Acta Gene Struct. Express. 1087:265–292.
Mann and Wilm, 1994, Analytical Chemistry 66:4390–4399.
Marcus–Sakura, 1988, Anal. Biochem. 172:289.
Marks et al., 1991, J. Mol. Biol. 222:581–597.
Matera and Frey, 1998, Am. J. Hum. Genet. 63:317–321.
Matera and Ward, 1993, J. Cell Biol. 121:715–727.
Mattaj and DeRobertis, 1985, Cell 40:111–118.
Moore et al., 1993, In: The RNA World, pp. 303–358.
Mylin et al., 1994, Genetics 137:689–700.
Nakielny and Dreyfuss, 1996, J. Cell. Biol. 134:1365–1373.
Neumann de Vegvar and Dahlberg, 1990, Mol. Cell. Biol. 10:3365–3375.
Noble and Guthrie, 1996, Genetics 143:67–80.
Noble and Guthrie, 1996, EMBO J. 15:4368–4379.
Ohno and Shimura, 1996, Genes & Dev. 10:997–1007.
O'Keefe et al., 1994, J. Cell Biol. 124:249–260.
Padgett et al., 1983, Cell 35:101–107.
Pearn, 1973, J. Med. Genet. 10:260–265.
Pinol–Roma et al., 1988, Genes Dev. 2:215–227.
Raghunathan and Guthrie, 1998, Science 279:857–860.
Raker et al., 1996, EMBO J. 15:2256–2269.
Raska et al., 1990, J. Struct. Biol. 104:120–127.
Roberts et al., 1970, Arch. Dis. Child. 45:33–38.
Rodrigues et al., 1995, Hum. Mol. Genet. 4:631–634.
Roth, 1995, Curr. Opin. Cell Biol. 7:325–328.
Salazar Grueso et al., Neuroreport. 2:505–508, 1991.
Schrank et al., 1997, Proc. Natl. Acad. Sci. 94:9920–9925.
Shevchenko et al., 1996, Anal. Chemistry 68: 850–858.
Singh and Reddy, 1989, Proc. Natl. Acad. Sci. USA 86:8280–8283.
Siomi and Dreyfuss, 1995, J. Cell Biol. 129:551–560.
Staley and Guthrie, 1998, Cell 92:315–326.
Talbot et al., 1997, Hum. Mol. Genet. 6:497–500.
Terns et al., 1993, Genes Dev. 7:1898–1906.
Trupp et al., Nature 381:785–788, 1996.
Tuszynski et al., 1988, Blood, 72:109–115.
Velasco et al., 1996, Hum. Mol. Genet. 5:257–263.
Verschueren et al., 1999, J. Biol. Chem. 274:20489–20498.
Wassarman and Steitz, 1991, Mol. Cell. Biol. 11:3432–3445.
Weintraub, 1990, Scientific American 262:40.
Wilm and Mann, 1996, Anal. chem. 68:1–8.
Wright et al., 1992, Critical Rev. Immunol. 12:125–168.
Zeller et al., 1983, Cell 32:425–434.
Zeng et al., 1997, EMBO J. 16:1401–1412.
Zhang et al., 1998, Mol. Cell. Biol. 18:676–684.
Zieve and Sauterer, 1990, Crit. Rev. Biochem. Mol. Biol. 25:1–46.

* cited by examiner

```
huSIP1    1   MRRAE------LAGLKTMAWVPAESAVEELMPRLLP    30
XeSIP1    1   ------------------------------MPRLLP     6
Brr1      1   MKRGESQAPDAIFGQSRAFALSDSSVNPDVIEYLKS    36 huSIP1   31   VEPCDLTEGFDPSVPPRTPQEYLRRVQIEAAQCP-D    65
XeSIP1    7   VEACDLPEDYDPSVPPRTPQEYLRRVQIEAARCP-D    41
Brr1     37   VRQEALRTNAISIKNHMNLQKRTRKSSMYDDEDEGA    72 huSIP1   66   VVVAQIDPKKLKRKQSVNISLSGCQPAPEGYSP---    98
XeSIP1   42   VVIAQIDPKKLRKKQTVSISLSGCQPAPDGYSP---    74
Brr1     73   LKRHAISPSLIRLQRNVEIWVRWFNSVKATVLTNAY   108 huSIP1   99   -TLQWQQQQVAQFSTVRQNVNKHRSHWKSQQ-----   128
XeSIP1   75   -SLRWQQQQVAQFSAVRQSLHKHRGHWRSQP-----   104
Brr1    109   EFTGYEDETLDLLLFLKNYLEDMPSKCTTVEKIISV   144 huSIP1  129   LDSNVTMPKSED-------EEGWKKFCLG----EKL   153
XeSIP1  105   LDSNVTMPSTED-------EESWKKFCLG----ERL   129
Brr1    145   LNQHSFPEKAEEKEENLQIDEEWAKNILVRLEKTKI   180 huSIP1  154   CADGAVGPATN--------ESPGIDYVQIGFPPLLS   181
XeSIP1  130   YSDLAALNSES-------QHPGIDYIKVGFPPLLS    158
Brr1    181   DSEDVKKVITEGDKHELVGYNQWFQYLINNEPQHTT   216 huSIP1  182   IVSRMNQATVTSVLEYLSN-WFGERD----FTPELG   212
XeSIP1  159   IVSRMSQATVTSVLEYLVN-WFEERN----FTPELG   189
Brr1    217   FHEKITSKQLWVLIKYMSNTWIKEIHKKGRHYRRLQ   252 huSIP1  213   RWLYALLACLEKPLLPEAHSLIRQLARRCSEVR--L   246
XeSIP1  190   RWLYALLACLEKPLLPEAHSLIRQLARRCSQIR--A   223
Brr1    253   DWLFYILVHTPERVTAEYTSILRDLGKKCLELIQKK   288 huSIP1  247   LVDSKDD-------------------ERVPALNLLI   263
XeSIP1  224   GVEHKED-------------------DRVSPLNLFI   240
Brr1    289   PVEAHENKITLPKEMAELNVEIPAAVENMTITELTV   324 huSIP1  264   CLVSRYFDQRDLADE--PS                   280
XeSIP1  241   CLVGRYFEQRDLADCGDPS                   259
Brr1    325   SVIAVNYGQKDLIE-----                   338
```

FIG. 1

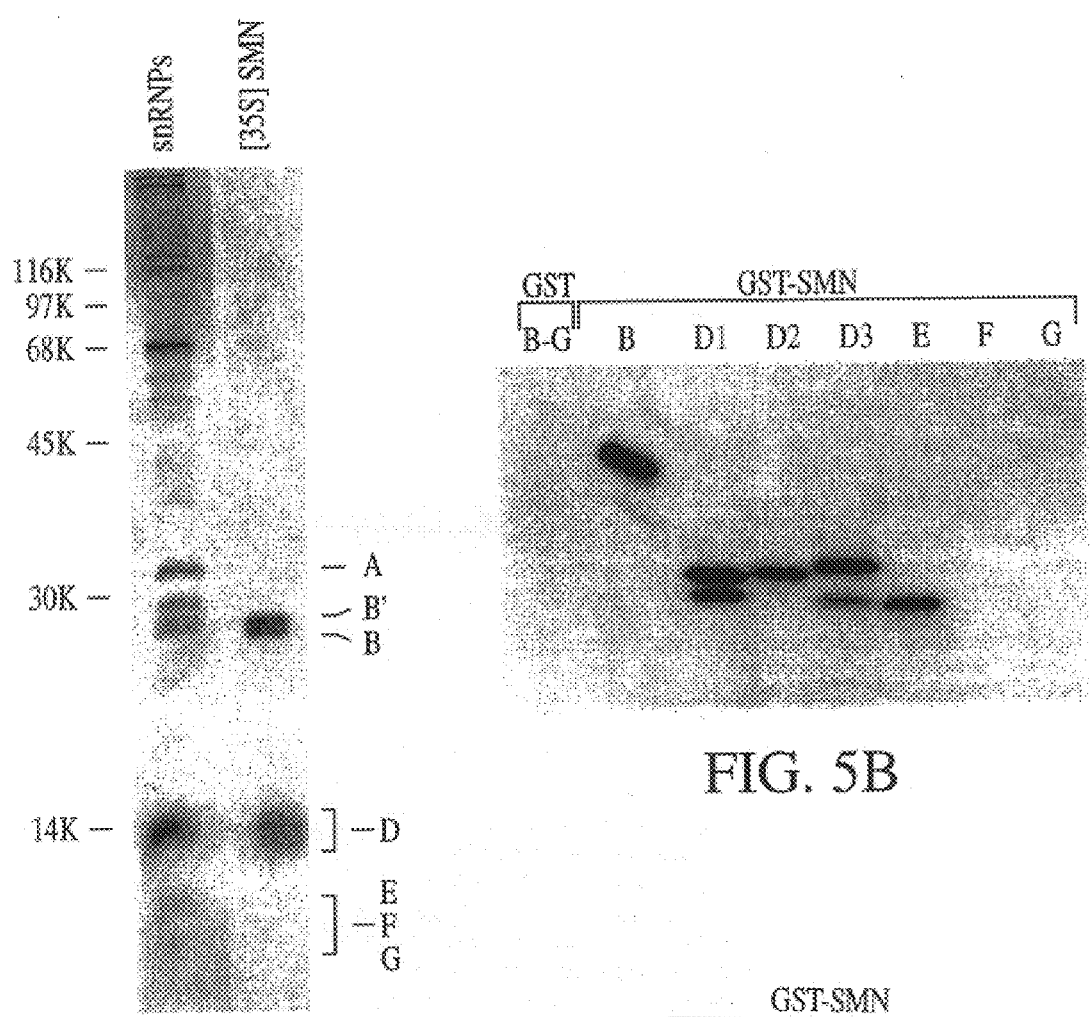
FIG. 5A
FIG. 5B
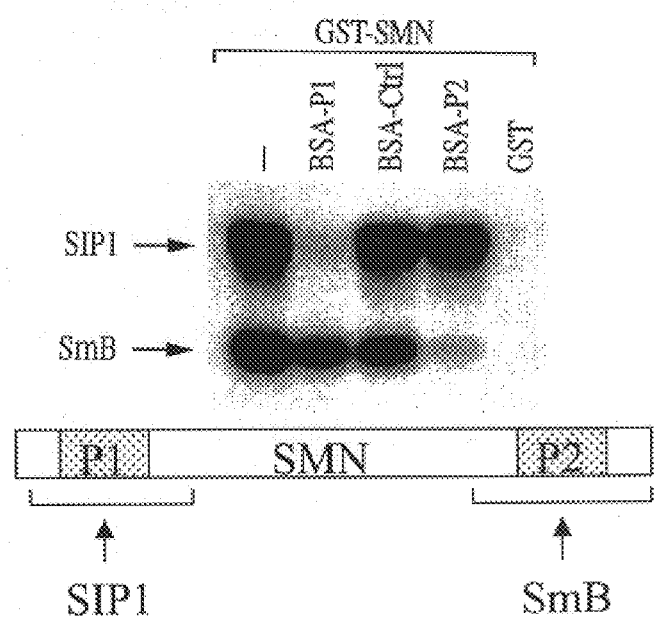
FIG. 5C

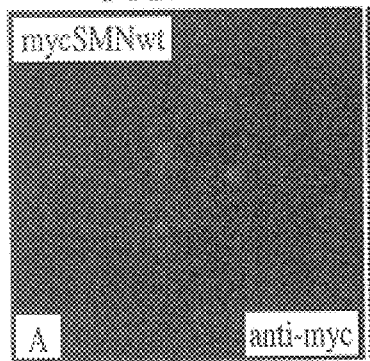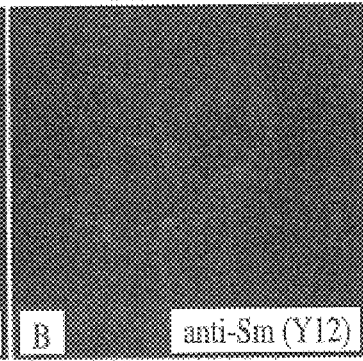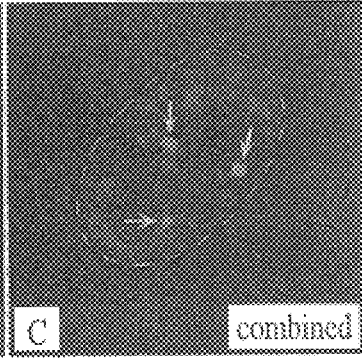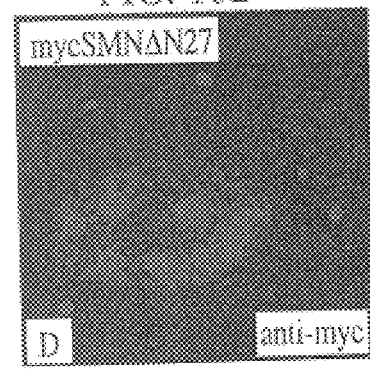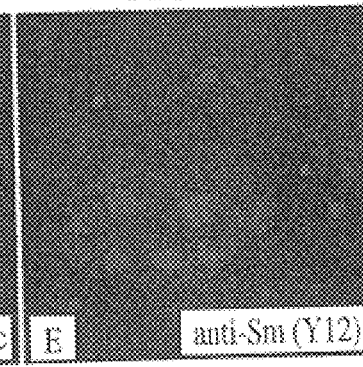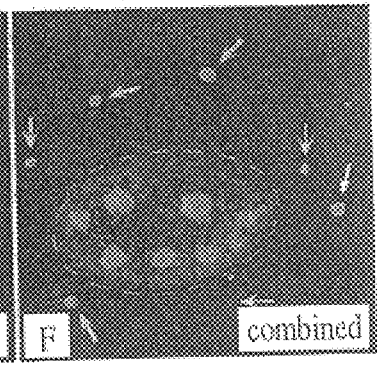

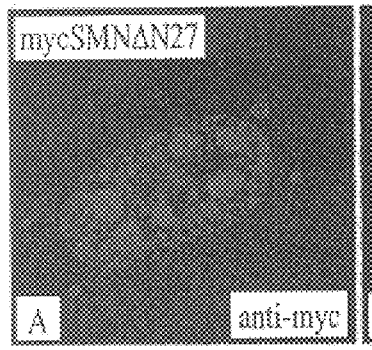
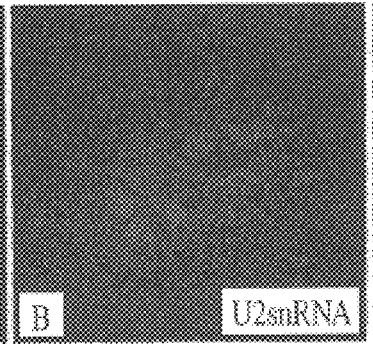
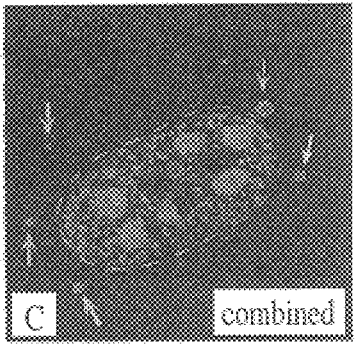
FIG. 17A  FIG. 17B  FIG. 17C
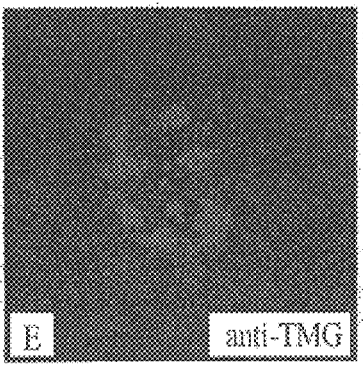
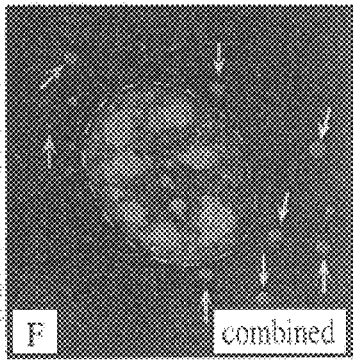
FIG. 17D  FIG. 17E  FIG. 17F

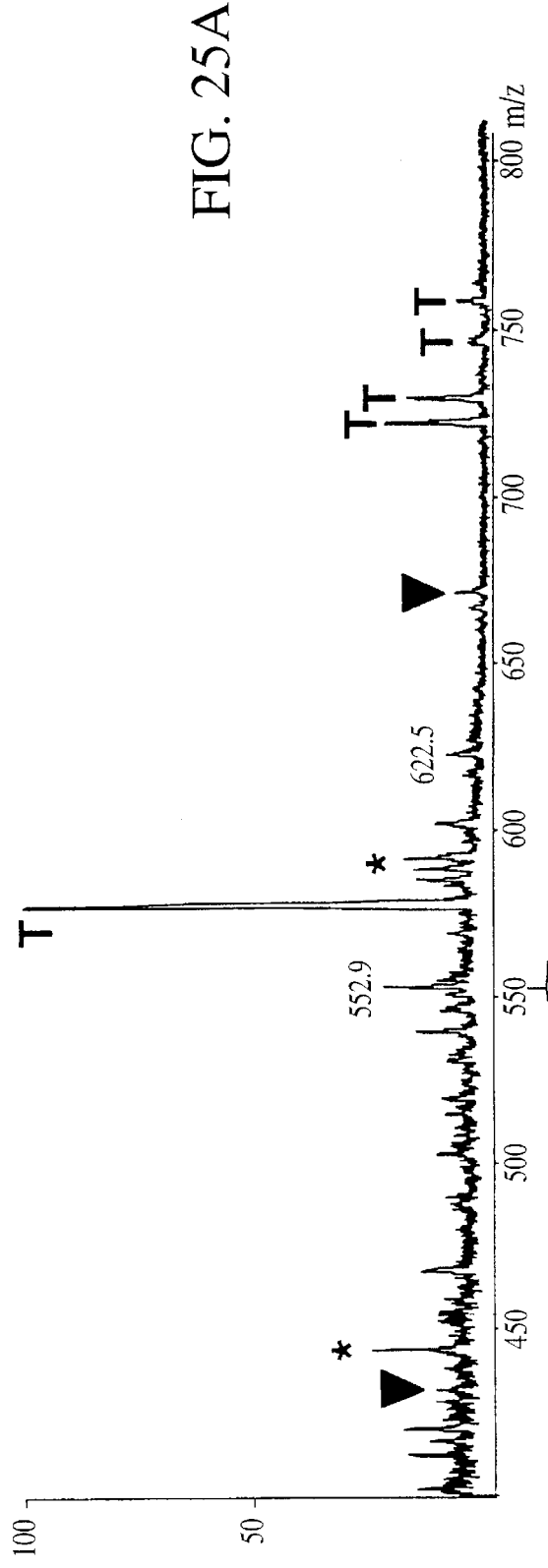
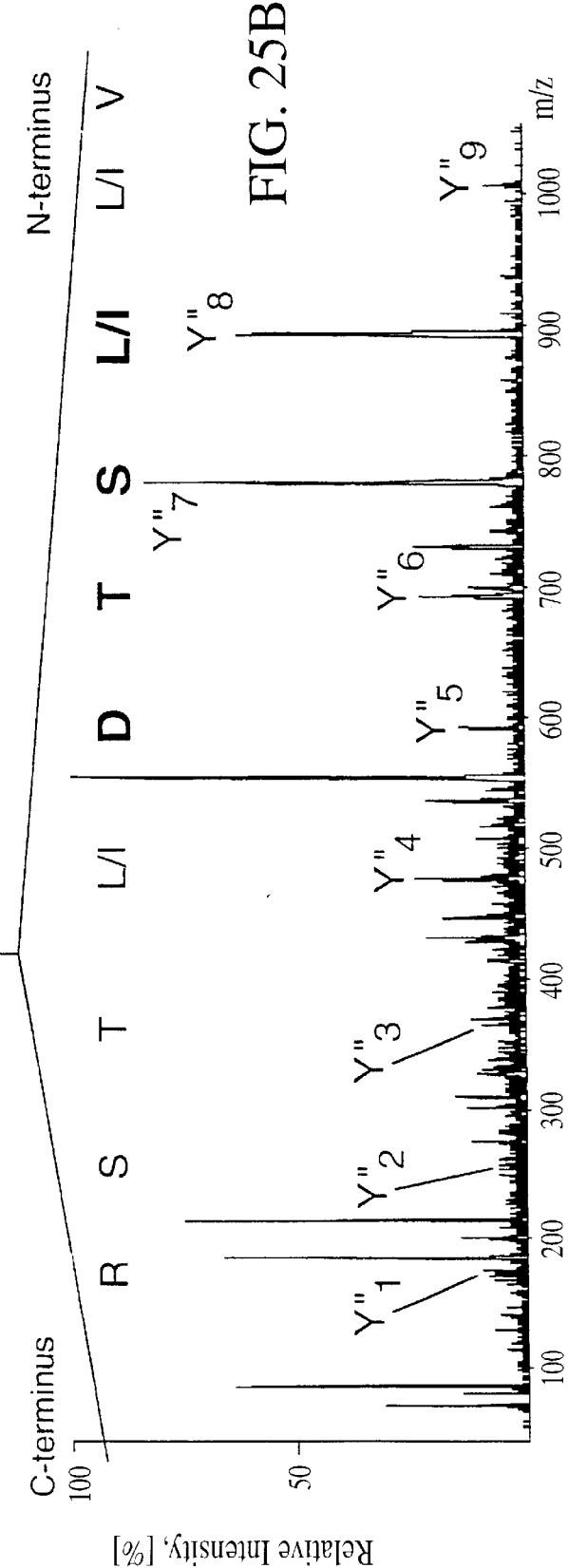
FIG. 25A
FIG. 25B

| | | | |
|---|---|---|---|
| Gemin3 | 1 | MAAAFEASGALAAVATAMPAEHVAVQVPAPEPTPGPVRLRTAQDLSSPRTRTGDVLLAE | 60 |
| eIF4A-II | 1 | MSGGSADYNREHG---GPEGMDPDG--VHESNWNEIVD------ | 33 |
| Gemin3 | 61 | PADEESLLSRPVLEGLRAAGFERPSPVQLKAIPLGRCGLDLTIVQAKSGTGKTCMFSTIA | 120 |
| eIF4A-II | 34 | --NFDDMNLKESLLRGIYAYGFEKPSAIQQRAIIPCIKGYDVIAQAQSGTGKTATFAISI | 91 |
| Gemin3 | 121 | LDSVLENLSTQILILAPTREIAVQIHSVITAIGIKMEGLECHVFIGGTPLSQD--KTRL | 178 |
| eIF4A-II | 92 | LQQLELEFKETQGALVAPTRELAQQIQKVILALG-DYMGATCHACIGGTNVRNEMQKLQA | 150 |
| Gemin3 | 179 | KKCHIAVGSPGRIKQLIELDYLNPGSTRLFILDEADKLLEEGSFQEQINWIYSSLPASKQ | 238 |
| eIF4A-II | 151 | EAPHIVVGTPGRVFDMLNRRYLSPKWIKMFVLDEADEMLSRG-FKDQIYEIFQKLNTSIQ | 209 |
| Gemin3 | 239 | MIAVSATYPEFLANALTKYMRDPTFVRLNSSDPSLIGLKQYYKVVNSYPLAHKVFEEKTQ | 298 |
| eIF4A-II | 210 | VVFASATMPTDVLEVTKKFMRDPIRILVKKEELTLEGIKQFYINVERE----EWKLD | 262 |
| Gemin3 | 299 | HLQELFSRIPFNQAVIFSNLHSRAQHLADILSKGFPAECISGNMNQRLDAMAKLKHF | 358 |
| eIF4A-II | 263 | TLCDLYETLTITQAVIFLNTRRKVDWLTEKMHARDFTVSALHGDMDQKERDVIMREFRSG | 322 |
| Gemin3 | 359 | HCRVLISTDLTSRGIDAEKVNLVVNLDVPLDWETYMHRIGRAGRFGTLGLTVTYCCRGEE | 418 |
| eIF4A-II | 323 | SSRVLITTDLLARGIDVQQVSLVINYDLPTNRENYIHRIGRGGRFGRKGVAINFVTE-ED | 381 |
| Gemin3 | 419 | ENMMRLAQKCNINLLPLPDPIPSGLMEECVDWDVEVKAAVHTYGIASVPNQPLKKQIQK | 478 |
| eIF4A-II | 382 | KRLLRDIETFYNTTVEEMPMNVADLI | |
| Gemin3 | 479 | IERTLQIQKAHGDHMASSRNNSVSGLSVKSKNNTKQKLPVKSHSECGIIEKATSPKELGC | 538 |
| Gemin3 | 539 | DRQSEEQMKNSVQTPVENSTNSQHQVKEALPVSLPQIPCLSSFKIHQPYTLTFAELVEDY | 598 |
| Gemin3 | 599 | EHYIKEGLEKPVEIIRHYTGPGDQTVNPQNGFVRNKVIEQKVPVLASSQSGDSESDSDS | 658 |
| Gemin3 | 659 | YSSRTSSQSKGNKSYLESSSDNQLKDSESTPVDDRISLEQPPNGTDTPNPEKYQESPGIQ | 718 |
| Gemin3 | 719 | MKTRLKEGASQRAKQSRRNLPRRSSFRLQTEAQEDDWYDCHREIRLSFSDTYQDYEEYWR | 778 |
| Gemin3 | 779 | AYYRAWQEYYAAAASHSYYWNAQRHPSWMAAYHMNTIYLQEMMHSNQ | 824 |

FIG. 27

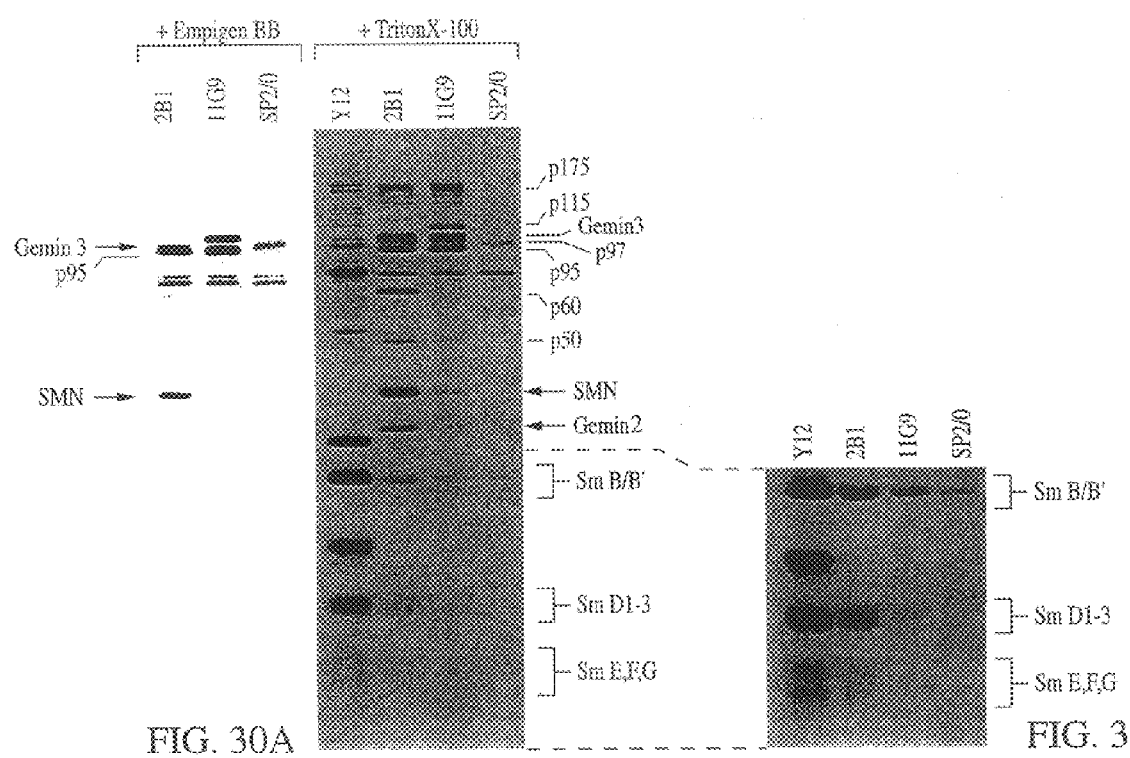

Chicken SMN Protein Sequence

MAGRVLFRRGAGQSDDSDMWDDTALIKAYDKAVASFKNALKNGCDSEPSDKQ
EQRAGVKRKNSKKNRNRNKSNAVPLKQWKVGDSCNAVWSEDGNVYPATIASI
NLKRGTCVVTYTGYGNKEEQNLADLLPPASDETNENETPYSTDESEKSSQSHHN
ENNCTKARFSPKNLRFPIPPTPPGLGRHGSKFRTLPPFLSCWPPPFPAGPPLIPPPPP
MGPDSPEDDEALGSMLIAWYMSGYHTGYYLGLKQSRMEAALEREAYLK

FIG. 35A

Chicken SMN DATA Sequence

ATGGCGGGCAGGGTGCTGTTCCGGCGCGGCGCCGGGCAGAGCGACGACTCG
GACATGTGGGACGACACGGCCCTCATCAAGGCGTACGACAAGGCGGTGGCCT
CCTTCAAGAATGCTTTAAAGAACGGGGACTGCTCAGAGCCTTCGGACAAACA
GGAGCAGCGGGCGGGGGTGAAAAGGAAAAACAGCAAGAAGAACAGGAACA
GAAACAAGAGCAACGCCGTGCCGTTGAAGCAGTGGAAAGTTGGCGACAGCT
GTAACGCTGTTTGGTCTGAGGATGGTAATGTCTACCCTGCAACTATTGCCTCC
ATAAATCTGAAGAGGGGTACATGCGTTGTTACTTACACCGGATATGGAAACA
AGGAGGAACAGAACCTGGCTGATCTACTTCCTCCAGCTAGCGATGAAACAA
TGAAAATGAGACTCCGTATTCAACAGATGAAAGTGAAAAATCTTCCAGTCA
CATCACAATGAAAACAACTGCACAAAAGCAAGATTCTCTCCTAAAAACTTAC
GGTTTCCCATCCCACCAACACCTCCAGGATTGGGAAGGCATGGTTCAAAATT
CAGAACACTTCCACCATTCTTGTCTTGCTGGCCCCCACCCTTTCCAGCAGGAC
CACCGTTGATTCCTCCTCCACCACCTATGGGGCCAGATTCTCCTGAGGATGAT
GAAGCGTTGGGGAGCATGTTGATAGCTTGGTATATGAGTGGTTATCACACTCG
GATATTACCTGGGGTTAAAACAAAGTCGAATGGAAGCAGCCCTAGAGAGAG
AAGCCTATCTAAAATAG

FIG. 35B

```
                                                                50
                                                                 *
MAA AFE ASG ALA AVA TAM PAE HVA VQV PAP EPT PGP VIR LRT AQD LSS PRT
                                                               100
                                                                 *
RTG DVL LAE PAD FES LLL SRP VLE GLR AAG FER PSP VQL KAI PLG RCG LDL
                                                               150
                                                                 *
IVQ AKS GTG KTC VFS TIA LDS LVL ENL STQ ILI LAP TRE IAV QIH SVI TAI
                                                               200
                                                                 *
GIK MEG LEC HVF IGG TPL SQD KTR LKK CHI AVG SPG RIK QLI ELD YLN PGS
                                                               250
                                                                 *
IRL FIL DEA DKL LEE GSF QEQ INW IYS SLP ASK QML AVS ATY PEF LAN ALT
                                                               300
                                                                 *
KYM RDP TFV RLN SSD PSL IGL KQY YKV VNS YPL AHK VFE EKT QHL QEL FSR
                                                               350
                                                                 *
IPF NQA LVF SNL HSR AQH LAD ILS SKG FPA ECI SGN MNQ NQR LDA MAK LKH
                                                               400
                                                                 *
FHC RVL IST DLT SRG IDA EKV NLV VNL DVP LDW ETY MHR IGR AGR FGT LGL
                                                               450
                                                                 *
TVT YCC RGE EEN MMM RIA QKC NIN LLP LPD PIP SGL MEE CVD WDV EVK AAV
                                                               500
                                                                 *
HTY GIA SVP NQP LKK QIQ KIE RTL QIQ KAH GDH MAS SRN NSV SGL SVK SKN
                                                               550
                                                                 *
NTK QKL PVK SHS ECG IIE KAT SPK ELG CDR QSE EQM KNS VQT PVE NST NSQ
                                                               600
                                                                 *
HQV KEA LPV SLP QIP CLS SFK IHQ PYT LTF AEL VED YEH YIK EGL EKP VEI
                                                               650
                                                                 *
IRH YTG PGD QTV NPQ NGF VRN KVI EQK VPV LAS SSQ SGD SES DSD SYS SRT
                                                               700
                                                                 *
SSQ SKG NKS YLE SSS DNQ LKD SES TPV DDR ISL EQP PNG TDT PNT EKY QES
                                  750
```

FIG. 36A

```
                                                               *
PGI QMK TRL KEG ASQ RAK QSR RNL PRR SSF RLQ TEA QED DWY DCH REI RLS
                                              800
                                                *
FSD TYQ DYE EYW RAT YRA WQE YYA AAS HSY YWN AQR HPS WMA AYH MNT IYL

QEM MHS NQ
```

FIG. 36B

```
                                                    50
                                                     *
ATG GCG GCG GCA TTT GAA GCC TCG GGA GCC TTA GCA GCA GTG GCG ACT GCT
                                                    100
                                                     *
ATG CCG GCT GAG CAT GTG GCC GTG CAG GTC CCG GCC CCA GAG CCA ACA CCC
                                                    150
                                                     *
GGG CCT GTG AGG ATC CTG CGG ACC GCT CAG GAT CTC AGC AGC CCG CGG ACC
                                                    200
                                                     *
CGC ACG GGG GAT GTG CTG TTG GCG GAG CCG GCC GAC TTC GAG TCA CTG CTG
                                                    250
                                                     *
CTT TCG CGG CCG GTG CTG GAG GGG CTG CGG GCG GCC GGC TTC GAG AGG CCC
                                                    300
                                                     *
TCG CCG GTG CAG CTC AAG GCC ATC CCG TTG GGG CGC TGC GGG CTC GAT TTA
                                                    350
                                                     *
ATT GTT CAA GCT AAA TCT GGC ACC GGG AAA ACC TGT GTG TTC TCC ACC ATA
                                                    400
                                                     *
GCT TTG GAC TCT CTT GTT CTT GAA AAC TTA AGT ACC CAG ATT TTG ATC TTG
                                                    450
                                                     *
GCT CCT ACA AGA GAA ATT GCT ATA CAG ATA CAT TCT GTT ATT ACA GCC ATT
                                                    500
                                                     *
GGA ATA AAA ATG GAA GGC TTA GAG TGT CAT GTC TTT ATT GGA GGG ACC CCA
                                                    550
                                                     *
TTA TCA CAA GAC AAA ACC AGA CTT AAA AAG TGT CAT ATT GCT GTT GGA TCT
                                                    600
                                                     *
CCT GGC AGA ATT AAG CAA CTC ATA GAA CTT GAC TAC TTG AAC CCA GGC AGT
                                                    650
                                                     *
ATA CGC CTC TTT ATT CTT GAT GAA GCA GAT AAG CTT TTA GAA GAA GGC AGC
                                                    700
                                                     *
TTC CAG GAG CAA ATA AAT TGG ATT TAT TCT TCC TTG CCT GCC AGT AAA CAG
                                                    750
```

FIG. 36C

```
ATG CTG GCA GTA TCA GCT ACT TAT CCC GAA TTT TTG GCT AAT GCT TTG ACA
                                              800
AAG TAC ATG AGA GAT CCC ACT TTT GTA AGA CTG AAT TCC AGT GAT CCA AGT
                                              850
CTC ATA GGT TTG AAG CAG TAT TAC AAA GTT GTC AAT TCA TAC CCT TTG GCA
                                              900
CAT AAG GTT TTT GAG GAA AAG ACT CAG CAT TTA CAG GAA CTG TTC AGC AGA
                                              950
ATT CCA TTT AAT CAA GCT TTA GTC TTT TCT AAT TTG CAC AGC AGA GCA CAA
                                              1000
CAT TTG GCT GAT ATC CTT TCT TCT AAA GGC TTT CCT GCT GAG TGC ATT TCA
                                              1050
GGC AAT ATG AAT CAG AAT CAG CGT CTT GAT GCT ATG GCT AAA CTG AAG CAC
                                              1100
TTT CAT TGC AGA GTC CTC ATT TCC ACA GAT TTG ACT TCT CGT GGG ATT GAT
                                              1150
GCT GAG AAG GTG AAT CTG GTT GTA AAT CTG GAT GTA CCA TTG GAT TGG GAG
                                              1200
ACA TAC ATG CAT CGC ATT GGG AGA GCT GGC CGT TTT GGT ACA TTG GGG CTG
                                              1250
ACA GTG ACC TAC TGT TGC CGG GGA GAG GAA GAA AAT ATG ATG ATG AGA ATT
                                              1300
GCC CAG AAA TGT AAT ATC AAC CTT CTC CCT TTA CCA GAT CCC ATT CCT TCT
                                              1350
GGT CTG ATG GAA GAA TGT GTG GAT TGG GAT GTG GAA GTT AAA GCT GCT GTG
                                              1400
CAT ACA TAT GGT ATA GCA AGT GTA CCT AAC CAA CCC TTA AAA AAG CAA ATT
                                              1450
```

FIG. 36D

```
CAG AAA ATA GAG AGA ACC CTT CAA ATT CAG AAA GCT CAT GGT GAC CAC ATG
                              1500
GCT TCC TCT AGA AAT AAT TCT GTA TCT GGA CTA TCA GTC AAA TCA AAA AAT
                              1550
AAT ACC AAA CAA AAG CTT CCT GTG AAA AGC CAC TCA GAA TGT GGA ATC ATA
                              1600
GAA AAA GCA ACG TCA CCA AAA GAA CTG GCT GTG ACA GGC AAT CCG AAG AGG
                              1650
CAA ATG AAG AAT TCT GTT CAG ACT CCC GTT GAA AAC TCC ACC AAC AGT CAG
                              1700
CAC CAG GTC AAA GAA GCT TTA CCT GTG TCA CTC CCC AGA TTC CTT GTC TG
                              1750
TCT TCC TTT AAA ATC CAT CAG CCA TAC ACG TTG ACT TTT GCT GAA TTG GTA
                              1800
GAG GAT TAT GAA CAT TAT ATTT AAA GAG GGG TTA GAG AAA CCT TG GAA ATC
                              1850
ATC AGG CAC TAC ACA GGC CCT GGG GAT CAG ACT GTG AAT CCT CAA AAT GGT
                              1900
TTT GTG AGA AAT AAA GTT ATT GAA CAG AAA GTC CCT GTG TTG GCA AGT AGT
                              1950
AGC CAA TCT GGA GAC TCT GAG AGT GAC AGT GAT TCT TAC AGC TCA AGA ACC
                              2000
TCT TCC CAG AGC AAA GGA AAT AAG TCA TAC TTG GAA AGC TCT TCT GAT AAT
                              2050
CAG CTG AAA GAC TCT GAA TCT ACG CCT GTG GAT GAT CGT ATT TCT TTG GAA
                              2100
CAA CCA CCA AAT GGA ACT GAC ACC CCC AAT CCA GAG AAA TAT CAA GAA TCA
                              2150
CCT GGA ATC AGA TGA AGA CAA GAC TTA AAG AGG GGC TAG CAG AGA GCT
```

FIG. 36E

```
                      2200
                        *
AAG CAG AGC CGG AGA AAC CTA CCC AGG CGG TCT TCC TTC AGA TTG CAG ACT

2250
              *
GAA GCC CAG GAA GAT GAT TGG TAT GAC TGT CAT AGG GAA ATA CGT CTG AGT

2300
        *
TTT TCT GAT ACC TAT CAG GAT TAT GAG GAG TAC TGG AGA GCT TAC TAC AGG

2350
     *
GCA TGG CAA GAA TAT TAT GCT GCC GCT TCT CAT TCA TAT TAT TGG AAT GCT

2400
  *
CAG AGA CAT CCA AGT TGG ATG GCA GCT TAT CAC ATG AAT ACC ATT TAT CTA

2450
  *
CAA GAA ATG ATG CAT AGT AAC CAG TGA TTA TAG GAT ATA CCT GAG ACC ATC 2500                                                              2550
  *                                                                 *
AGG AAC TGT CAA CAA ATG ATA CCT TTG GAT ATC CAT CCT CCT CGA CTT ATA

2600
                                                                *
GTA CAG TGG TGT ATA GTG GCA TTT CTG ATA AAC TTG AAA AGA CTT GGA TCT

2650
                                                           *
TTC CAC TGG GAC ACA TCC ATT TTT CAG ATT GTT TTG ATT TAG GCC AGG TAT

2700
                                                      *
ATT ATC TTC ATT TTT AAG AGT TTC TTT AAG AAA CCT CAT CAG AGT GTT GAA

2750
                                                 *
AGC ATC AGT TTC TGG GAC CAT AGA TGC TGA CAG TTT CAG GGT GCC ATT GTC

2800
                                            *
CAT AAG ATC TTC CCA AAC GAT ACA GTT GAA GCG AGG ACA TAT ACC TCC ACT

2850
                                        *
TAC CTA GCT ACG ATA AAA GCA GTA GAC TTG GTT AGT AAA AAA AAA AAA AAA

AAA
```

FIG. 36F

```
   1 taacgctccc taaactgcca cttgntcagc tccgcgccta aggtgtctat tagtgcgcct
  61 gcgctgtgac ctagaatggg cgcatgcgcc gagcgcgcc gagcggaact ggctggtttg aaaaccatgg
 121 cgtgggtacc agcggagtcc gcagtggaag agttgatgcc tcggctattg ccggtagagc
 181 cttgcgactt gacggaaggt ttcgatccct cggtacccc gaggacgcct caggaatacc
 241 tgaggcgggt ccagatcgaa gcagctcaat gtccagatgt tgtgtagct caaattgacc
 301 caaagaagtt gaaaaggaag caaagtgtga atattctct ttcaggatgc caacccgccc
 361 ctgaaggtta ttcccaaaca cttcaatggc aacagcaaca agtggcacag ttttcaactg
 421 ttcgacagaa tgtgaacaaa catagaagtc acaacagttg gatagtaatg
 481 tgacaatgcc aaaatctgaa gatgaagaag gctggaagag atttttgtctg ggtgaaaagt
 541 tatgtgctga cgggctgtt ggaccagcca caaatgaaag tcctggaata gattatgtac
 601 aaatttgttt tcctccctttg cttagtattg ttagcagaat gaatcaggca acagtaacta
 661 gtgtcttgga atatctgagt aattgttttg gagaaagaga cttttctcca gaattggaa
 721 gatggcttta tgcttttattg gcttgtctg aaaagccttt gttacctgag gctcattcac
 781 tgattcggca gcttgcaaga aggtgctctg aagtgaggct cttagtggat agcaggatg
 841 atgagaggt tcctgcttg aatttattaa tctgcttggt tagcaggtat tttgaccaac
 901 gtgattagc tgatgagcca tctttgatgta gctgatctct caggagataga agatattct
 961 catgaaggca gcctaactct aagtaccaattc aagtacagat ccactcagtt tttgatgaac
1021 cttcaacact atgtgaaggg ttcacacatct aacctgtgca atcagattg atactcagaa
1081 tatgggttga tttgaatatc tgaaatatca atgccaattca aagtacagat agatatttct
1141 agtttgaaca gttttctgta atcaagcagc ttgcatagaa attgtatgat gaatttac
1201 ataggttctt ggtgctgttt tgttcttttt ccactcagtt tttgatgaac
1261 atacatataa aatttattg aaaat
```

FIG. 37

```
   1 gaattcggca cgagcggggc cgaagagct gatgcccagg ctgttaccgg ttgaggcctg
  61 tgatcttccc gaggactatg atccctccgt gccgcctcgg agtatctgcg
 121 gagagtccag attgaagcag cacgttgtcc tgatgtagtc attgcacaga ttgatcccaa
 181 aaagttgcga aagaaacaga ccgttagcat atctctgtcg ggatgccagc ctgctgcctga
 241 tgggtactct ccaagcctcc gctgcagca gcaacaagta gcacagtttt ctgctgtccg
 301 ccagagtctg cacaagcaca ggggtcactg gagtctcag cctttggaca gcaatgttac
 361 aatgccaagc acagaggatg aagagagctg gaaaaagttc tgtctggggg aacggctata
 421 ttctgaccta gcagctgccc taaacagcga gagccagcat ccaggaattg attacattaa
 481 ggttggtttc ccaccgttgc tgagcattgt tagtcggatg agccaggcga cagtaacaag
 541 tgtgctagaa tacttggtga actggtttga agagaggaac tttactccag agctgggtcg
 601 ttgcttgctt gctttgtga cctgcctgga gaaaccactg ctgcctgagg ctcactctct
 661 tattaggcag gatgcacgaa gatgctcaca aatcagagct ggggtggaac ataaggaaga
 721 tgatcggtg tctccactga acttatttcat tgtctgtgtt ggcaggtact ttgaacagcg
 781 agatttggct gactgtggtg cccatcttg atgatcca cccccctc tctcagtgcc
 841 cccactctcc cagagcatct cggcaatatc catgctatcc actccccttc agatcttcactt
 901 gtgcaccaac tatatcgttt ttggattcag gaaactgtgt ggttttaaccc gccattggca
 961 aaaaagggcc ttgaaggagc aanaagttgc agtgataatc tctanccttc actttcacttt
1021 ctacaactac caagaagccg accgaccgtcna cctcttgcct tatttattgt
1081 gccaatccct gaattttgc ttctttggga acaacngtct nttttccat atattggccn
1141 ntatantata aaaatattaa nttgcctcnn tttcnantc ngaaaaccat tttccnttcc
1201 tccgttctnt ccctgctgt ttaccccctcc tgggtttgtt ggaaaaccat tttccnttcc
1261 aantttggaa aaaatattaa nttgcctcnn ttaccccctcc ttgttcnaca anctggaaa
1321 ttaaaaccc ccctgctgt tnttncntn gggaaaacn nttaaactnt tncnnttnaa
1381 aaaattcttt aaatccntc aantttgnan tgttcccc ccnnttt gcctntttn
1441 aantattttt tttgcctttt aanttgnan tgtcccc ccnnnccc nnggaancc
1501 cnccttttn tnaaacnncc ccngttnntn tnggtcnncc ccnnnccc nnggaancc
1561 nncntntttt tnaaaanncc ccntnttn ngtccnaat ttnnnnnnn
1621 naaaccnntt t
```

FIG. 38

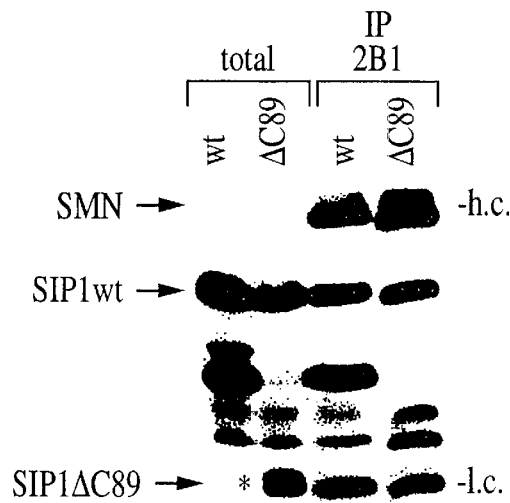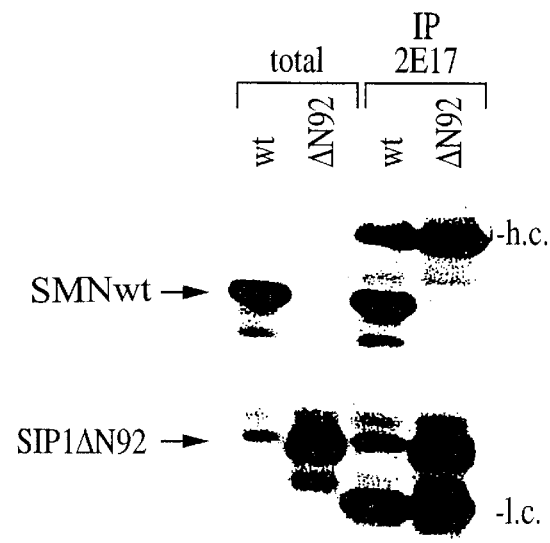
FIG. 46A    FIG. 46B
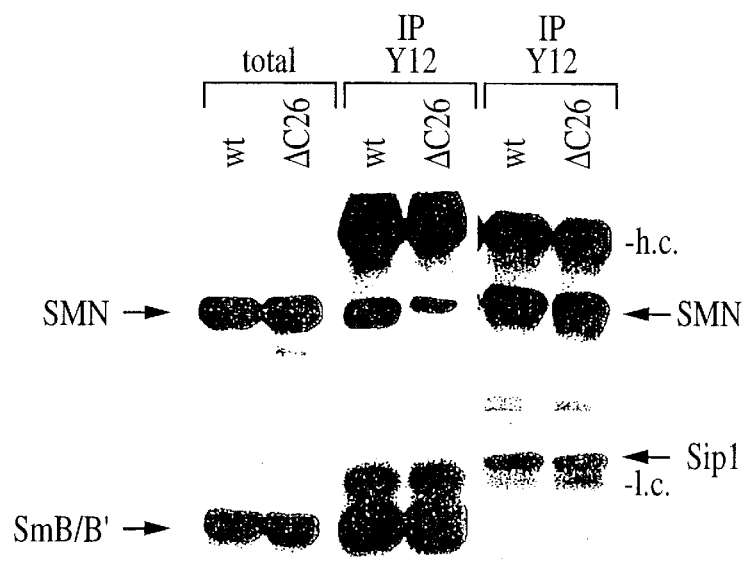
FIG. 47

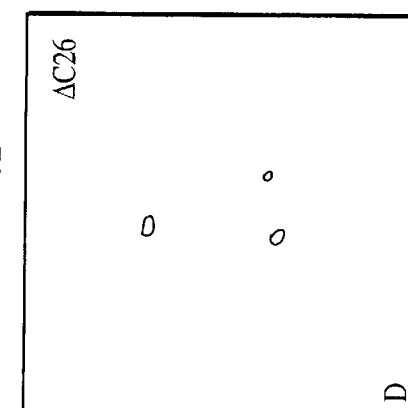
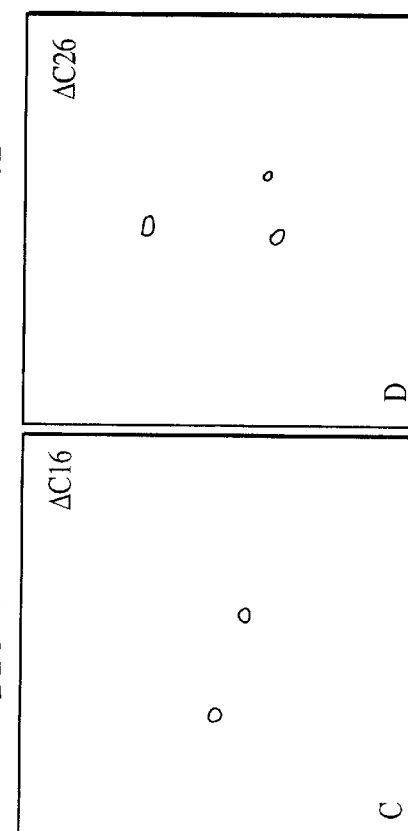
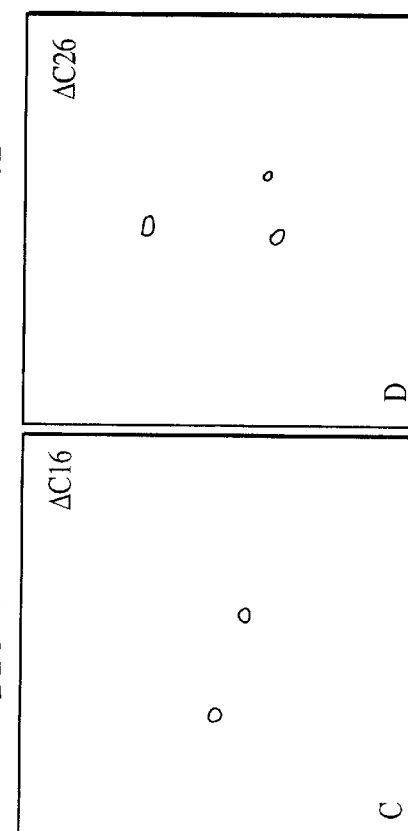
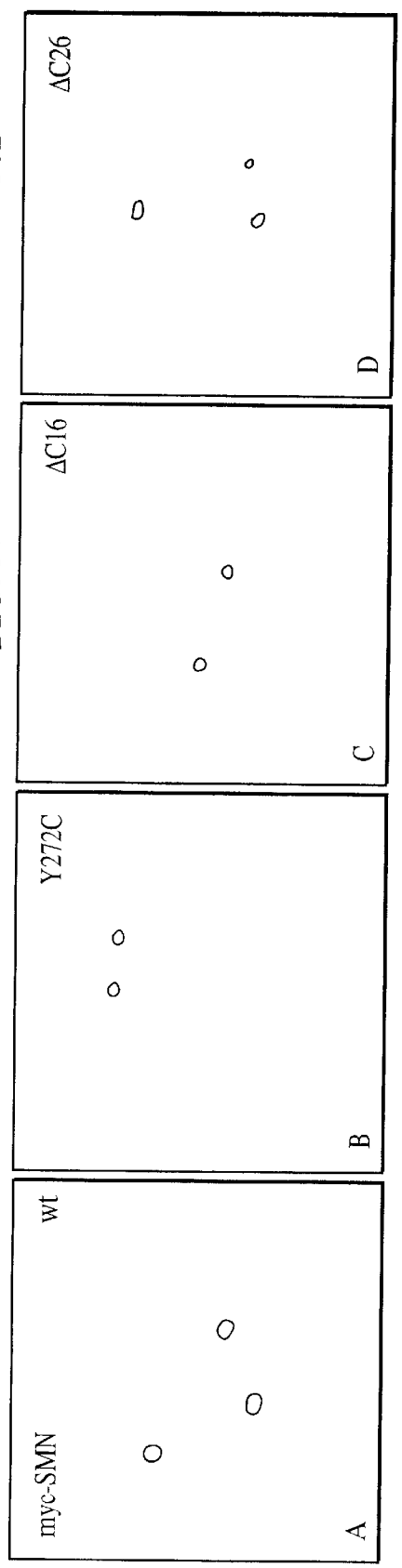
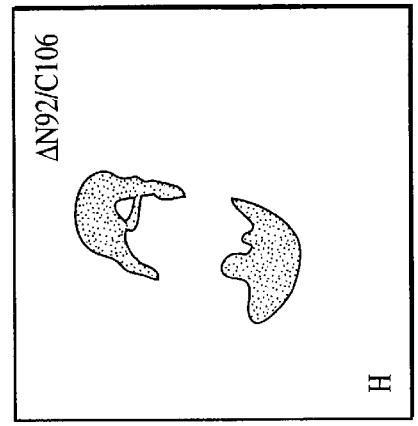
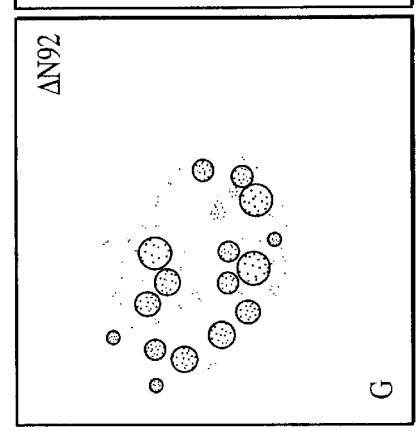
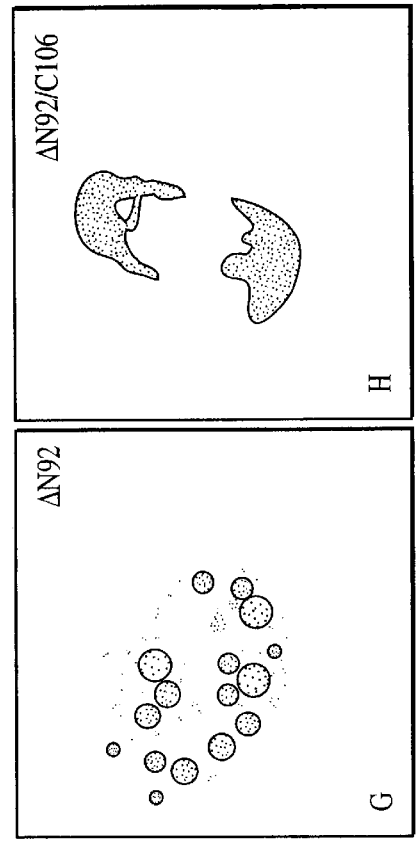
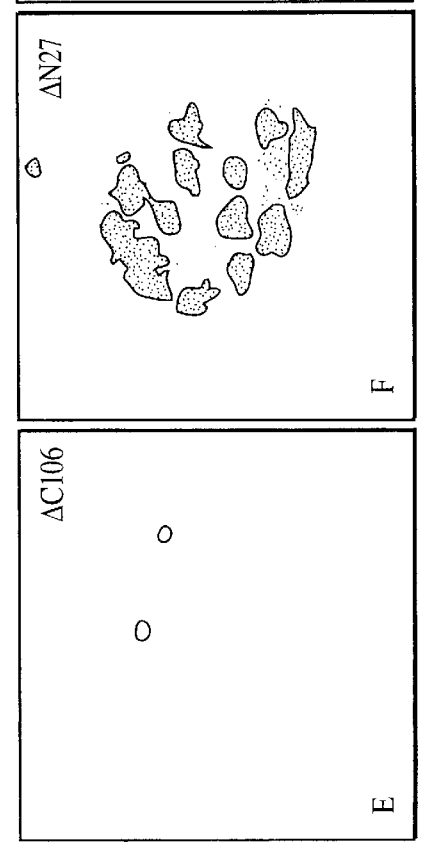
FIG. 50A  FIG. 50B  FIG. 50C  FIG. 50D
FIG. 50E  FIG. 50F  FIG. 50G  FIG. 50H

SEQUENCE LISTING

<160> NUMBER OF SEQ ID NOS: 11

<210> SEQ ID NO 1
<211> LENGTH: 1285
<212> TYPE: DNA
<213> ORGANISM: Homo sapiens
<220> FEATURE:
<221> NAME/KEY: misc_feature
<222> LOCATION: (25)..(25)
<223> OTHER INFORMATION: n is a, t, g, or c

<400> SEQUENCE: 1

```
taacgctccc taaactgcca cttgntcagc tccgcgccta aggtgtctat tagtgcgcct      60
gcgctgtgac ctagaatggg cgcatgcgcc gagcggaact ggctggtttg aaaaccatgg     120
cgtgggtacc agcggagtcc gcagtggaag agttgatgcc tcggctattg ccggtagagc     180
cttgcgactt gacggaaggt ttcgatccct cggtaccccc gaggacgcct caggaatacc     240
tgaggcgggt ccagatcgaa gcagctcaat gtccagatgt tgtggtagct caaattgacc     300
caaagaagtt gaaaaggaag caaagtgtga atatttctct ttcaggatgc caacccgccc     360
ctgaaggtta ttccccaaca cttcaatggc aacagcaaca agtggcacag ttttcaactg     420
ttcgacagaa tgtgaacaaa catagaagtc actggaaatc acaacagttg gatagtaatg     480
tgacaatgcc aaaatctgaa gatgaagaag gctggaagaa attttgtctg ggtgaaaagt     540
tatgtgctga cggggctgtt ggaccagcca caaatgaaag tcctggaata gattatgtac     600
aaattggttt tcctcccttg cttagtattg ttagcagaat gaatcaggca acagtaacta     660
gtgtcttgga atatctgagt aattggtttg gagaaagaga ctttactcca gaattgggaa     720
```

```
gatggcttta tgctttattg gcttgtcttg aaaagccttt gttacctgag gctcattcac    780
tgattcggca gcttgcaaga aggtgctctg aagtgaggct cttagtggat agcaaagatg    840
atgagagggt tcctgctttg aatttattaa tctgcttggt tagcaggtat tttgaccaac    900
gtgatttagc tgatgagcca tcttgatgta gctgatctct cagggataga agatatttct    960
catgaaggca gcctaactct gaggaaaaca atgccaattc aagtacagat ttcaacacat   1020
cttcaacact atgtgaaggg ttcacatctt aacctgtgca attcagattg atactcagaa   1080
tatgggttga tttgaatatc tgaaatatca atggaaaatc ccactcagtt tttgatgaac   1140
agtttgaaca gttttctgta atcaagcagc ttgcatagaa attgtatgat gaaattttac   1200
ataggttctt ggtgctgttt tgttcttttt ttgttttttg ttgttttgtt atttacttat   1260
atacatataa aattttattg aaaat                                         1285
```

<210> SEQ ID NO 2
<211> LENGTH: 280
<212> TYPE: PRT
<213> ORGANISM: Homo sapiens

<400> SEQUENCE: 2

```
Met Arg Arg Ala Glu Leu Ala Gly Leu Lys Thr Met Ala Trp Val Pro
 1               5                   10                  15

Ala Glu Ser Ala Val Glu Glu Leu Met Pro Arg Leu Leu Pro Val Glu
                20                  25                  30

Pro Cys Asp Leu Thr Glu Gly Phe Asp Pro Ser Val Pro Pro Arg Thr
            35                  40                  45

Pro Gln Glu Tyr Leu Arg Arg Val Gln Ile Glu Ala Ala Gln Cys Pro
        50                  55                  60

Asp Val Val Ala Gln Ile Asp Pro Lys Lys Leu Lys Arg Lys Gln
65                  70                  75                  80

Ser Val Asn Ile Ser Leu Ser Gly Cys Gln Pro Ala Pro Glu Gly Tyr
                85                  90                  95

Ser Pro Thr Leu Gln Trp Gln Gln Gln Val Ala Gln Phe Ser Thr
            100                 105                 110

Val Arg Gln Asn Val Asn Lys His Arg Ser His Trp Lys Ser Gln Gln
        115                 120                 125

Leu Asp Ser Asn Val Thr Met Pro Lys Ser Glu Asp Glu Gly Trp
    130                 135                 140

Lys Lys Phe Cys Leu Gly Glu Lys Leu Cys Ala Asp Gly Ala Val Gly
145                 150                 155                 160

Pro Ala Thr Asn Glu Ser Pro Gly Ile Asp Tyr Val Gln Ile Gly Phe
                165                 170                 175

Pro Pro Leu Leu Ser Ile Val Ser Arg Met Asn Gln Ala Thr Val Thr
            180                 185                 190

Ser Val Leu Glu Tyr Leu Ser Asn Trp Phe Gly Glu Arg Asp Phe Thr
        195                 200                 205

Pro Glu Leu Gly Arg Trp Leu Tyr Ala Leu Leu Ala Cys Leu Glu Lys
    210                 215                 220

Pro Leu Leu Pro Glu Ala His Ser Leu Ile Arg Gln Leu Ala Arg Arg
225                 230                 235                 240

Cys Ser Glu Val Arg Leu Leu Val Asp Ser Lys Asp Glu Arg Val
                245                 250                 255

Pro Ala Leu Asn Leu Leu Ile Cys Leu Val Ser Arg Tyr Phe Asp Gln
            260                 265                 270
```

Arg Asp Leu Ala Asp Glu Pro Ser
    275                 280

<210> SEQ ID NO 3
<211> LENGTH: 1631
<212> TYPE: DNA
<213> ORGANISM: Xenopus laevis
<220> FEATURE:
<221> NAME/KEY: misc_feature
<222> LOCATION: (1005)..(1005)
<223> OTHER INFORMATION: n is a, c, t, or g
<220> FEATURE:
<221> NAME/KEY: misc_feature
<222> LOCATION: (1043)..(1043)
<223> OTHER INFORMATION: n is a, c, t, or g
<220> FEATURE:
<221> NAME/KEY: misc_feature
<222> LOCATION: (1119)..(1119)
<223> OTHER INFORMATION: n is a, c, t, or g
<220> FEATURE:
<221> NAME/KEY: misc_feature
<222> LOCATION: (1141)..(1141)
<223> OTHER INFORMATION: n is a, c, t, or g
<220> FEATURE:
<221> NAME/KEY: misc_feature
<222> LOCATION: (1146)..(1146)
<223> OTHER INFORMATION: n is a, c, t, or g
<220> FEATURE:
<221> NAME/KEY: misc_feature
<222> LOCATION: (1178)..(1178)
<223> OTHER INFORMATION: n is a, c, t, or g
<220> FEATURE:
<221> NAME/KEY: misc_feature
<222> LOCATION: (1186)..(1186)
<223> OTHER INFORMATION: n is a, c, t, or g
<220> FEATURE:
<221> NAME/KEY: misc_feature
<222> LOCATION: (1209)..(1209)
<223> OTHER INFORMATION: n is a, c, t, or g
<220> FEATURE:
<221> NAME/KEY: misc_feature
<222> LOCATION: (1367)..(1367)
<223> OTHER INFORMATION: n is a, c, t, or g
<220> FEATURE:
<221> NAME/KEY: misc_feature
<222> LOCATION: (1372)..(1372)
<223> OTHER INFORMATION: n is a, c, t, or g
<220> FEATURE:
<221> NAME/KEY: misc_feature
<222> LOCATION: (1397)..(1397)
<223> OTHER INFORMATION: n is a, c, t, or g
<220> FEATURE:
<221> NAME/KEY: misc_feature
<222> LOCATION: (1402)..(1402)
<223> OTHER INFORMATION: n is a, c, t, or g
<220> FEATURE:
<221> NAME/KEY: misc_feature
<222> LOCATION: (1405)..(1405)
<223> OTHER INFORMATION: n is a, c, t, or g
<220> FEATURE:
<221> NAME/KEY: misc_feature
<222> LOCATION: (1408)..(1408)
<223> OTHER INFORMATION: n is a, c, t, or g
<220> FEATURE:
<221> NAME/KEY: misc_feature
<222> LOCATION: (1420)..(1421)
<223> OTHER INFORMATION: n is a, c, t, or g
<220> FEATURE:
<221> NAME/KEY: misc_feature
<222> LOCATION: (1429)..(1429)
<223> OTHER INFORMATION: n is a, c, t, or g
<220> FEATURE:
<221> NAME/KEY: misc_feature
<222> LOCATION: (1432)..(1432)
<223> OTHER INFORMATION: n is a, c, t, or g
<220> FEATURE:
<221> NAME/KEY: misc_feature -continued

```
<222> LOCATION: (1434)..(1435)
<223> OTHER INFORMATION: n is a, c, t, or g
<220> FEATURE:
<221> NAME/KEY: misc_feature
<222> LOCATION: (1438)..(1438)
<223> OTHER INFORMATION: n is a, c, t, or g
<220> FEATURE:
<221> NAME/KEY: misc_feature
<222> LOCATION: (1443)..(1443)
<223> OTHER INFORMATION: n is a, c, t, or g
<220> FEATURE:
<221> NAME/KEY: misc_feature
<222> LOCATION: (1486)..(1487)
<223> OTHER INFORMATION: n is a, c, t, or g
<220> FEATURE:
<221> NAME/KEY: misc_feature
<222> LOCATION: (1495)..(1495)
<223> OTHER INFORMATION: n is a, c, t, or g
<220> FEATURE:
<221> NAME/KEY: misc_feature
<222> LOCATION: (1500)..(1500)
<223> OTHER INFORMATION: n is a, c, t, or g
<220> FEATURE:
<221> NAME/KEY: misc_feature
<222> LOCATION: (1502)..(1502)
<223> OTHER INFORMATION: n is a, c, t, or g
<220> FEATURE:
<221> NAME/KEY: misc_feature
<222> LOCATION: (1510)..(1510)
<223> OTHER INFORMATION: n is a, c, t, or g
<220> FEATURE:
<221> NAME/KEY: misc_feature
<222> LOCATION: (1512)..(1512)
<223> OTHER INFORMATION: n is a, c, t, or g
<220> FEATURE:
<221> NAME/KEY: misc_feature
<222> LOCATION: (1517)..(1518)
<223> OTHER INFORMATION: n is a, c, t, or g
<220> FEATURE:
<221> NAME/KEY: misc_feature
<222> LOCATION: (1523)..(1523)
<223> OTHER INFORMATION: n is a, c, t, or g
<220> FEATURE:
<221> NAME/KEY: misc_feature
<222> LOCATION: (1527)..(1528)
<223> OTHER INFORMATION: n is a, c, t, or g
<220> FEATURE:
<221> NAME/KEY: misc_feature
<222> LOCATION: (1530)..(1530)
<223> OTHER INFORMATION: n is a, c, t, or g
<220> FEATURE:
<221> NAME/KEY: misc_feature
<222> LOCATION: (1532)..(1532)
<223> OTHER INFORMATION: n is a, c, t, or g
<220> FEATURE:
<221> NAME/KEY: misc_feature
<222> LOCATION: (1537)..(1538)
<223> OTHER INFORMATION: n is a, c, t, or g
<220> FEATURE:
<221> NAME/KEY: misc_feature
<222> LOCATION: (1544)..(1547)
<223> OTHER INFORMATION: n is a, c, t, or g
<220> FEATURE:
<221> NAME/KEY: misc_feature
<222> LOCATION: (1551)..(1552)
<223> OTHER INFORMATION: n is a, c, t, or g
<220> FEATURE:
<221> NAME/KEY: misc_feature
<222> LOCATION: (1558)..(1558)
<223> OTHER INFORMATION: n is a, c, t, or g
<220> FEATURE:
<221> NAME/KEY: misc_feature
<222> LOCATION: (1561)..(1562)
<223> OTHER INFORMATION: n is a, c, t, or g
<220> FEATURE:
<221> NAME/KEY: misc_feature
<222> LOCATION: (1564)..(1564)
<223> OTHER INFORMATION: n is a, c, t, or g
<220> FEATURE:
```

-continued

```
<221> NAME/KEY: misc_feature
<222> LOCATION: (1566)..(1566)
<223> OTHER INFORMATION: n is a, c, t, or g
<220> FEATURE:
<221> NAME/KEY: misc_feature
<222> LOCATION: (1572)..(1572)
<223> OTHER INFORMATION: n is a, c, t, or g
<220> FEATURE:
<221> NAME/KEY: misc_feature
<222> LOCATION: (1577)..(1578)
<223> OTHER INFORMATION: n is a, c, t, or g
<220> FEATURE:
<221> NAME/KEY: misc_feature
<222> LOCATION: (1583)..(1583)
<223> OTHER INFORMATION: n is a, c, t, or g
<220> FEATURE:
<221> NAME/KEY: misc_feature
<222> LOCATION: (1589)..(1589)
<223> OTHER INFORMATION: n is a, c, t, or g
<220> FEATURE:
<221> NAME/KEY: misc_feature
<222> LOCATION: (1594)..(1594)
<223> OTHER INFORMATION: n is a, c, t, or g
<220> FEATURE:
<221> NAME/KEY: misc_feature
<222> LOCATION: (1596)..(1597)
<223> OTHER INFORMATION: n is a, c, t, or g
<220> FEATURE:
<221> NAME/KEY: misc_feature
<222> LOCATION: (1600)..(1601)
<223> OTHER INFORMATION: n is a, c, t, or g
<220> FEATURE:
<221> NAME/KEY: misc_feature
<222> LOCATION: (1606)..(1607)
<223> OTHER INFORMATION: n is a, c, t, or g
<220> FEATURE:
<221> NAME/KEY: misc_feature
<222> LOCATION: (1613)..(1621)
<223> OTHER INFORMATION: n is a, c, t, or g
<220> FEATURE:
<221> NAME/KEY: misc_feature
<222> LOCATION: (1627)..(1628)
<223> OTHER INFORMATION: n is a, c, t, or g
<220> FEATURE:
<221> NAME/KEY: misc_feature
<222> LOCATION: (1211)..(1215)
<223> OTHER INFORMATION: n is a, c, t, or g
<220> FEATURE:
<221> NAME/KEY: misc_feature
<222> LOCATION: (1219)..(1220)
<223> OTHER INFORMATION: n is a, c, t, or g
<220> FEATURE:
<221> NAME/KEY: misc_feature
<222> LOCATION: (1224)..(1224)
<223> OTHER INFORMATION: n is a, c, t, or g
<220> FEATURE:
<221> NAME/KEY: misc_feature
<222> LOCATION: (1226)..(1230)
<223> OTHER INFORMATION: n is a, c, t, or g
<220> FEATURE:
<221> NAME/KEY: misc_feature
<222> LOCATION: (1236)..(1236)
<223> OTHER INFORMATION: n is a, c, t, or g
<220> FEATURE:
<221> NAME/KEY: misc_feature
<222> LOCATION: (1238)..(1238)
<223> OTHER INFORMATION: n is a, c, t, or g
<220> FEATURE:
<221> NAME/KEY: misc_feature
<222> LOCATION: (1241)..(1241)
<223> OTHER INFORMATION: n is a, c, t, or g
<220> FEATURE:
<221> NAME/KEY: misc_feature
<222> LOCATION: (1260)..(1260)
<223> OTHER INFORMATION: n is a, c, t, or g
<220> FEATURE:
<221> NAME/KEY: misc_feature
<222> LOCATION: (1263)..(1263)
<223> OTHER INFORMATION: n is a, c, t, or g
```

```
<220> FEATURE:
<221> NAME/KEY: misc_feature
<222> LOCATION: (1281)..(1281)
<223> OTHER INFORMATION: n is a, c, t, or g
<220> FEATURE:
<221> NAME/KEY: misc_feature
<222> LOCATION: (1289)..(1290)
<223> OTHER INFORMATION: n is a, c, t, or g
<220> FEATURE:
<221> NAME/KEY: misc_feature
<222> LOCATION: (1316)..(1316)
<223> OTHER INFORMATION: n is a, c, t, or g
<220> FEATURE:
<221> NAME/KEY: misc_feature
<222> LOCATION: (1359)..(1359)
<223> OTHER INFORMATION: n is a, c, t, or g
<220> FEATURE:
<221> NAME/KEY: misc_feature
<222> LOCATION: (1410)..(1410)
<223> OTHER INFORMATION: n is a, c, t, or g
<220> FEATURE:
<221> NAME/KEY: misc_feature
<222> LOCATION: (1463)..(1463)
<223> OTHER INFORMATION: n is a, c, t, or g
<220> FEATURE:
<221> NAME/KEY: misc_feature
<222> LOCATION: (1468)..(1468)
<223> OTHER INFORMATION: n is a, c, t, or g
<220> FEATURE:
<221> NAME/KEY: misc_feature
<222> LOCATION: (1470)..(1470)
<223> OTHER INFORMATION: n is a, c, t, or g

<400> SEQUENCE: 3
gaattcggca cgagcggggc ccgaagagct gatgcccagg ctgttaccgg ttgaggcctg      60
tgatcttccc gaggactatg atccctccgt gccgcctcgg acccctcagg agtatctgcg     120
gagagtccag attgaagcag cacgttgtcc tgatgtagtc attgcacaga ttgatcccaa     180
aaagttgcga agaaaacaga ccgttagcat atctctgtcg ggatgccagc ctgctcctga     240
tgggtactct ccaagcctcc gctggcagca gcaacaagta gcacagtttt ctgctgtccg     300
ccagagtctg cacaagcaca ggggtcactg gaggtctcag cctttggaca gcaatgttac     360
aatgccaagc acagaggatg aagagagctg gaaaaagttc tgtctggggg aacggctata     420
ttctgaccta gcagctgccc taaacagcga gagccagcat ccaggaattg attacattaa     480
ggttggtttc ccaccgttgc tgagcattgt tagtcggatg agccaggcga cagtaacaag     540
tgtgctagaa tacttggtga actggtttga agagaggaac tttactccag agctgggtcg     600
ttggctttat gctttgctgg cctgcctgga gaaaccactg ctgcctgagg ctcactctct     660
tattaggcag ttggcacgaa gatgctcaca aatcagagct ggggtggaac ataaggaaga     720
tgatcgggtg tctccactga acttattcat ctgtctggtt ggcaggtact ttgaacagcg     780
agatttggct gactgtggtg acccatcttg atgatgatca ggcagcttta cccccctcc      840 cccactctcc cagagcatct cggcaatatc catgctatcc actcccttc tcatccagtg      900 gtgcaccaac tatatcgttt ttggattcag gaaactgtgt ggtttaaccc tctcagtgcc     960 aaaagggcc ttgaaggagc taggacaggc atggataatc tctanccttc agatgtttaa    1020
ctacaactac caagaagccg aanaagttgc agttgaaccg catctacagc acttcacttt    1080
gccaatccct gaattttggc accgaccaat gcacgtcna cctcttgcct gccattggca    1140
ntatantata atgttttccc tttcttggga atctgaanga acaacngtct tatttattgt    1200
tccgttctnt nnnnngttnn ggtntnnnnn ttttcnantc nttttccat atattggccn     1260 aanttgggaa aaaatattaa nttgcctcnn tgggtttgtt ggaaaaccat tttccnttcc    1320
```

-continued

```
ttaaaacccc ccctgctgt ttaccctcc ttttgccnt tgttcnaca anctgggaaa      1380 aaaattcttt aaatccnttc tnttnccntn gggaaaaccn nttaaactnt tncnnttnaa      1440
aantattttt tttgccctt aantttgnan tgttcccccc cccnnttt gcctntttt      1500 cnccttttn tnaaacnncc ccngttnntn tnggtcnncc cccnnnnccc nngggaancc      1560
nncntntttt tnaaaannc ttncccccnt cccntnttn ngtccnaat ttnnnnnnnn      1620 naaaccntt t                                                             1631
```

<210> SEQ ID NO 4
<211> LENGTH: 259
<212> TYPE: PRT
<213> ORGANISM: Xenopus laevis

<400> SEQUENCE: 4

```
Met Pro Arg Leu Leu Pro Val Glu Ala Cys Asp Leu Pro Glu Asp Tyr
1               5                   10                  15

Asp Pro Ser Val Pro Pro Arg Thr Pro Gln Glu Tyr Leu Arg Arg Val
            20                  25                  30

Gln Ile Glu Ala Ala Arg Cys Pro Asp Val Val Ile Ala Gln Ile Asp
        35                  40                  45

Pro Lys Lys Leu Arg Lys Lys Gln Thr Val Ser Ile Ser Leu Ser Gly
    50                  55                  60

Cys Gln Pro Ala Pro Asp Gly Tyr Ser Pro Ser Leu Arg Trp Gln Gln
65                  70                  75                  80

Gln Gln Val Ala Gln Phe Ser Ala Val Arg Gln Ser Leu His Lys His
                85                  90                  95

Arg Gly His Trp Arg Ser Gln Pro Leu Asp Ser Asn Val Thr Met Pro
            100                 105                 110

Ser Thr Glu Asp Glu Glu Ser Trp Lys Lys Phe Cys Leu Gly Glu Arg
        115                 120                 125

Leu Tyr Ser Asp Leu Ala Ala Ala Leu Asn Ser Glu Ser Gln His Pro
    130                 135                 140

Gly Ile Asp Tyr Ile Lys Val Gly Phe Pro Pro Leu Leu Ser Ile Val
145                 150                 155                 160

Ser Arg Met Ser Gln Ala Thr Val Thr Ser Val Leu Glu Tyr Leu Val
                165                 170                 175

Asn Trp Phe Glu Glu Arg Asn Phe Thr Pro Glu Leu Gly Arg Trp Leu
            180                 185                 190

Tyr Ala Leu Leu Ala Cys Leu Glu Lys Pro Leu Leu Pro Glu Ala His
        195                 200                 205

Ser Leu Ile Arg Gln Leu Ala Arg Arg Cys Ser Gln Ile Arg Ala Gly
    210                 215                 220

Val Glu His Lys Glu Asp Asp Arg Val Ser Pro Leu Asn Leu Phe Ile
225                 230                 235                 240

Cys Leu Val Gly Arg Tyr Phe Glu Gln Arg Asp Leu Ala Asp Cys Gly
                245                 250                 255

Asp Pro Ser
```

<210> SEQ ID NO 5

<400> SEQUENCE: 5

000

<210> SEQ ID NO 6

<211> LENGTH: 341
<212> TYPE: PRT
<213> ORGANISM: Saccharomyces cerevisiae

<400> SEQUENCE: 6

```
Met Lys Arg Gly Glu Ser Gln Ala Pro Asp Ala Ile Phe Gly Gln Ser
1               5                   10                  15

Arg Ala Phe Ala Leu Ser Asp Ser Ser Val Asn Pro Asp Val Ile Glu
            20                  25                  30

Tyr Leu Lys Ser Val Arg Gln Glu Ala Leu Arg Thr Asn Ala Ile Ser
        35                  40                  45

Ile Lys Asn His Met Asn Leu Gln Lys Arg Thr Arg His Lys Ser Ser
    50                  55                  60

Met Tyr Asp Asp Glu Asp Glu Gly Ala Leu Lys Arg His Ala Ile Ser
65                  70                  75                  80

Pro Ser Leu Ile Arg Leu Gln Arg Asn Val Glu Ile Trp Val Arg Trp
                85                  90                  95

Phe Asn Ser Val Lys Ala Thr Val Leu Thr Asn Ala Tyr Glu Phe Thr
            100                 105                 110

Gly Tyr Glu Asp Glu Thr Leu Asp Leu Leu Leu Phe Leu Lys Asn
        115                 120                 125

Tyr Leu Glu Asp Met Pro Ser Lys Cys Thr Thr Val Glu Lys Ile Ile
130                 135                 140

Ser Val Leu Asn Gln His Ser Phe Pro Glu Lys Ala Glu Glu Lys Glu
145                 150                 155                 160

Glu Asn Leu Gln Ile Asp Glu Glu Trp Ala Lys Asn Ile Leu Val Arg
                165                 170                 175

Leu Glu Lys Thr Lys Ile Asp Ser Val Glu Asp Val Lys Lys Val Ile
            180                 185                 190

Thr Glu Gly Asp Lys His Glu Leu Val Gly Tyr Asn Gln Trp Phe Gln
        195                 200                 205

Tyr Leu Ile Asn Asn Glu Pro Gln His Thr Thr Phe His Glu Lys Ile
    210                 215                 220

Thr Ser Lys Gln Leu Trp Val Leu Ile Lys Tyr Met Ser Asn Thr Trp
225                 230                 235                 240

Ile Lys Glu Ile His Lys Lys Gly Arg His Tyr Arg Arg Leu Gln Asp
                245                 250                 255

Trp Leu Phe Tyr Ile Leu Val His Thr Pro Glu Arg Val Thr Ala Glu
            260                 265                 270

Tyr Thr Ser Ile Leu Arg Asp Leu Gly Lys Lys Cys Leu Glu Leu Ile
        275                 280                 285

Gln Lys Lys Pro Val Glu Ala His Glu Asn Lys Ile Thr Leu Pro Lys
    290                 295                 300

Glu Met Ala Glu Leu Asn Val Gly Ile Pro Ala Ala Val Glu Asn Met
305                 310                 315                 320

Thr Ile Thr Glu Leu Thr Val Ser Val Ile Ala Val Asn Tyr Gly Gln
                325                 330                 335

Lys Asp Leu Ile Glu
            340
```

<210> SEQ ID NO 7
<211> LENGTH: 3152
<212> TYPE: DNA
<213> ORGANISM: Homo sapiens

<400> SEQUENCE: 7

```
ccgagaggcg gggcggtgcc cccaccgcag gcccgcggcg ccctctgcag gccacaggca      60
gcgactcacc agttgcctca tctttcctct cctccctctt ggggctttcc tcaggccaca     120
ttttttgtgt gtctgggcag tctctcagcc tccgactccc gtccctttct tccacttcca     180 ggccggcgt gttagtgtct tcgcgggaaa actgccaata aagttttttct tcttctcgct    240 cccaagatcc ccgcctcccc ttaagcaccg cgagatctga cggcgcggct accatggcgg     300
cggcatttga agcctcggga gccttagcag cagtggcgac tgctatgccg gctgagcatg     360
tggccgtgca ggtcccggcc ccagagccaa cacccgggcc tgtgaggatc ctgcggaccg     420
ctcaggatct cagcagcccg cggacccgca cgggggatgt gctgttggcg agccggccg     480 acttcgagtc actgctgctt tcgcggccgg tgctggaggg gctgcgggcg gccggcttcg     540
agaggccctc gccggtgcag ctcaaggcca tcccgttggg gcgctgcggg ctcgatttaa     600
ttgttcaagc taaatctggc accgggaaaa cctgtgtgtt ctccaccata gctttggact     660
ctcttgttct tgaaaactta agtacccaga ttttgatctt ggctcctaca agagaaattg     720
ctgtacagat acattctgtt attacagcca ttggaataaa aatggaaggc ttagagtgtc     780
atgtctttat tggagggacc ccattatcac aagacaaaac cagacttaaa aagtgtcata     840
ttgctgttgg atcctctggc agaattaagc aactcataga acttgactac ttgaacccag     900
gcagtatacg cctctttatt cttgatgaag cagataagct tttagaagaa ggcagcttcc     960
aggagcaaat aaattggatt tattcttcct tgcctgccag taaacagatg ctggcagtat    1020
cagctactta tcccgaattt ttggctaatg ctttgacaaa gtacatgaga gatcccactt    1080
ttgtaagact gaattccagt gatccaagtc tcataggttt gaagcagtat acaaagttg    1140 tcaattcata cccttttggca cataaggttt ttgaggaaaa gactcagcat ttacaggaac    1200
tgttcagcag aattccattt aatcaagctt tagtcttttc taatttgcac agcagagcac    1260
aacatttggc tgatatcctt tcttctaaag ctttcctgc tgagtgcatt tcaggcaata    1320
tgaatcagaa tcagcgtctt gatgctatgg ctaaactgaa gcactttcat tgcagagtcc    1380
tcatttccac agatttgact ctcgtgggat tgatgctga aaggtgaat ctggttgtaa    1440 atctggatgt accattggat tgggagacat acatgcatcg gattgggaga gctggccgtt    1500
ttggtacatt ggggctgaca gtgacctact gttgccgggg agaggaagaa aatatgatga    1560
tgagaattgc ccagaaatgt aatatcaacc ttctcccttt accagatccc attccttctg    1620
gtctgatgga agaatgtgtg gattgggatg tggaagttaa agctgctgtg catacatatg    1680
gtatagcaag tgtacctaac caaccttaa aaaagcaaat tcagaaaata gagagaaccc    1740
ttcaaattca gaaagctcat ggtgaccaca tggcttcctc tagaaataat tctgtatctg    1800
gactatcagt caaatcaaaa ataataccca acaaaagct tcctgtgaaa agccactcag    1860
aatgtggaat catagaaaaa gcaacgtcac caaaagaact gggctgtgac aggcaatccg    1920
aagagcaaat gaagaattct gttcagactc ccgttgaaaa ctccaccaac agtcagcacc    1980
aggtcaaaga agctttacct gtgtcactcc cccagattcc ttgtctgtct tcctttaaaa    2040
tccatcagcc atacacgttg acttttgctg aattggtaga ggattatgaa cattatatta    2100 aagagggtt agagaaacct gtggaaatca tcaggcacta cacaggccct ggggatcaga    2160
ctgtgaatcc tcaaaatggt tttgtgagaa ataaagttat tgaacagaaa gtccctgtgt    2220
tggcaagtag tagccaatct ggagactctg agagtgacag tgattcttac agctcaagaa    2280
cctcttccca gagcaaagga aataagtcat acttggaaag ctcttctgat aatcagctga    2340
```

-continued

```
aagactctga atctacgcct gtggatgatc gtatttcttt ggaacaacca ccaaatggaa    2400
ctgacacccc caatccagag aaatatcaag aatcacctgg aatccagatg aagacaagac    2460
ttaaagaggg ggctagccag agagctaagc agagccggag aaacctaccc aggcggtctt    2520
ccttcagatt gcagactgaa gcccaggaag atgattggta tgactgtcat agggaaatac    2580
gtctgagttt ttctgatacc tatcaggatt atgaggagta ctggagagct tactacaggg    2640
catggcaaga atattatgct gccgcttctc attcatatta ttggaatgct cagagacatc    2700
caagttggat ggcagcttat cacatgaata ccatttatct acaagaaatg atgcatagta    2760
accagtgatt ataggatata cctgagacca tcaggaactg tcaacaaatg atacctttgg    2820
atatccatcc tcctcgactt atagtacagt ggtgtatagt ggcatttctg ataaacttga    2880
aaagacttgg atctttccac tgggacacat ccattttca gattgttttg atttaggcca    2940
ggtatattat cttcattttt aagagtttct ttaagaaacc tcatcagagt gttgaaagca    3000
tcagtttctg ggaccataga tgctgacagt ttcagggtgc cattgtccat aagatcttcc    3060
caaacgatac agttgaagcg aggacatata cctccactta cctagctacg ataaaagcag    3120
tagacttggt tagtaaaaaa aaaaaaaaaa aa                                  3152
```

<210> SEQ ID NO 8
<211> LENGTH: 824
<212> TYPE: PRT
<213> ORGANISM: Homo sapiens

<400> SEQUENCE: 8

```
Met Ala Ala Ala Phe Glu Ala Ser Gly Ala Leu Ala Ala Val Ala Thr
1               5                   10                  15

Ala Met Pro Ala Glu His Val Ala Val Gln Val Pro Ala Pro Glu Pro
                20                  25                  30

Thr Pro Gly Pro Val Arg Ile Leu Arg Thr Ala Gln Asp Leu Ser Ser
            35                  40                  45

Pro Arg Thr Arg Thr Gly Asp Val Leu Leu Ala Glu Pro Ala Asp Phe
        50                  55                  60

Glu Ser Leu Leu Leu Ser Arg Pro Val Leu Glu Gly Leu Arg Ala Ala
65                  70                  75                  80

Gly Phe Glu Arg Pro Ser Pro Val Gln Leu Lys Ala Ile Pro Leu Gly
                85                  90                  95

Arg Cys Gly Leu Asp Leu Ile Val Gln Ala Lys Ser Gly Thr Gly Lys
            100                 105                 110

Thr Cys Val Phe Ser Thr Ile Ala Leu Asp Ser Leu Val Leu Glu Asn
        115                 120                 125

Leu Ser Thr Gln Ile Leu Ile Leu Ala Pro Thr Arg Glu Ile Ala Val
    130                 135                 140

Gln Ile His Ser Val Ile Thr Ala Ile Gly Ile Lys Met Glu Gly Leu
145                 150                 155                 160

Glu Cys His Val Phe Ile Gly Gly Thr Pro Leu Ser Gln Asp Lys Thr
                165                 170                 175

Arg Leu Lys Lys Cys His Ile Ala Val Gly Ser Pro Gly Arg Ile Lys
            180                 185                 190

Gln Leu Ile Glu Leu Asp Tyr Leu Asn Pro Gly Ser Ile Arg Leu Phe
        195                 200                 205

Ile Leu Asp Glu Ala Asp Lys Leu Leu Glu Glu Gly Ser Phe Gln Glu
    210                 215                 220

Gln Ile Asn Trp Ile Tyr Ser Ser Leu Pro Ala Ser Lys Gln Met Leu
```

```
                    225                 230                 235                 240
        Ala Val Ser Ala Thr Tyr Pro Glu Phe Leu Ala Asn Ala Leu Thr Lys
                            245                 250                 255
        Tyr Met Arg Asp Pro Thr Phe Val Arg Leu Asn Ser Ser Asp Pro Ser
                            260                 265                 270
        Leu Ile Gly Leu Lys Gln Tyr Tyr Lys Val Val Asn Ser Tyr Pro Leu
                            275                 280                 285
        Ala His Lys Val Phe Glu Lys Thr Gln His Leu Gln Glu Leu Phe
                            290                 295                 300
        Ser Arg Ile Pro Phe Asn Gln Ala Leu Val Phe Ser Asn Leu His Ser
        305                 310                 315                 320
        Arg Ala Gln His Leu Ala Asp Ile Leu Ser Ser Lys Gly Phe Pro Ala
                            325                 330                 335
        Glu Cys Ile Ser Gly Asn Met Asn Gln Asn Gln Arg Leu Asp Ala Met
                            340                 345                 350
        Ala Lys Leu Lys His Phe His Cys Arg Val Leu Ile Ser Thr Asp Leu
                            355                 360                 365
        Thr Ser Arg Gly Ile Asp Ala Glu Lys Val Asn Leu Val Val Asn Leu
                            370                 375                 380
        Asp Val Pro Leu Asp Trp Glu Thr Tyr Met His Arg Ile Gly Arg Ala
        385                 390                 395                 400
        Gly Arg Phe Gly Thr Leu Gly Leu Thr Val Thr Tyr Cys Cys Arg Gly
                            405                 410                 415
        Glu Glu Glu Asn Met Met Met Arg Ile Ala Gln Lys Cys Asn Ile Asn
                            420                 425                 430
        Leu Leu Pro Leu Pro Asp Pro Ile Pro Ser Gly Leu Met Glu Glu Cys
                            435                 440                 445
        Val Asp Trp Asp Val Glu Val Lys Ala Ala Val His Thr Tyr Gly Ile
        450                 455                 460
        Ala Ser Val Pro Asn Gln Pro Leu Lys Lys Gln Ile Gln Lys Ile Glu
        465                 470                 475                 480
        Arg Thr Leu Gln Ile Gln Lys Ala His Gly Asp His Met Ala Ser Ser
                            485                 490                 495
        Arg Asn Asn Ser Val Ser Gly Leu Ser Val Lys Ser Lys Asn Asn Thr
                            500                 505                 510
        Lys Gln Lys Leu Pro Val Lys Ser His Ser Glu Cys Gly Ile Ile Glu
                            515                 520                 525
        Lys Ala Thr Ser Pro Lys Glu Leu Gly Cys Asp Arg Gln Ser Glu Glu
                            530                 535                 540
        Gln Met Lys Asn Ser Val Gln Thr Pro Val Glu Asn Ser Thr Asn Ser
        545                 550                 555                 560
        Gln His Gln Val Lys Glu Ala Leu Pro Val Ser Leu Pro Gln Ile Pro
                            565                 570                 575
        Cys Leu Ser Ser Phe Lys Ile His Gln Pro Tyr Thr Leu Thr Phe Ala
                            580                 585                 590
        Glu Leu Val Glu Asp Tyr Glu His Tyr Ile Lys Glu Gly Leu Glu Lys
                            595                 600                 605
        Pro Val Glu Ile Ile Arg His Tyr Thr Gly Pro Gly Asp Gln Thr Val
                            610                 615                 620
        Asn Pro Gln Asn Gly Phe Val Arg Asn Lys Val Ile Glu Gln Lys Val
        625                 630                 635                 640
        Pro Val Leu Ala Ser Ser Ser Gln Ser Gly Asp Ser Glu Ser Asp Ser
                            645                 650                 655
```

```
Asp Ser Tyr Ser Ser Arg Thr Ser Gln Ser Lys Gly Asn Lys Ser
            660                 665                 670

Tyr Leu Glu Ser Ser Ser Asp Asn Gln Leu Lys Asp Ser Glu Ser Thr
            675                 680                 685

Pro Val Asp Asp Arg Ile Ser Leu Glu Gln Pro Pro Asn Gly Thr Asp
            690                 695                 700

Thr Pro Asn Pro Glu Lys Tyr Gln Glu Ser Pro Gly Ile Gln Met Lys
705                 710                 715                 720

Thr Arg Leu Lys Glu Gly Ala Ser Gln Arg Ala Lys Gln Ser Arg Arg
                725                 730                 735

Asn Leu Pro Arg Arg Ser Ser Phe Arg Leu Gln Thr Glu Ala Gln Glu
            740                 745                 750

Asp Asp Trp Tyr Asp Cys His Arg Glu Ile Arg Leu Ser Phe Ser Asp
            755                 760                 765

Thr Tyr Gln Asp Tyr Glu Glu Tyr Trp Arg Ala Tyr Tyr Arg Ala Trp
            770                 775                 780

Gln Glu Tyr Tyr Ala Ala Ala Ser His Ser Tyr Tyr Trp Asn Ala Gln
785                 790                 795                 800

Arg His Pro Ser Trp Met Ala Ala Tyr His Met Asn Thr Ile Tyr Leu
                805                 810                 815

Gln Glu Met Met His Ser Asn Gln
            820

<210> SEQ ID NO 9
<211> LENGTH: 797
<212> TYPE: DNA
<213> ORGANISM: Gallus gallus

<400> SEQUENCE: 9
ccatggcggg cagggtgctg ttccggcgcg gcgccgggca gagcgacgac tcggacatgt      60
gggacgacac ggccctcatc aaggcgtacg acaaggcggt ggcctccttc aagaatgctt     120
taaagaacgg ggactgctca gagccttcgg acaaacagga gcagcgggcg ggggtgaaaa     180
ggaaaaacag caagaagaac aggaacagaa acaagagcaa cgccgtgccg ttgaagcagt     240
ggaaagttgg cgacagctgt aacgctgttt ggtctgagga tggtaatgtc taccctgcaa     300
ctattgcctc cataaatctg aagagggta catgcgttgt tacttacacc ggatatggaa      360
acaaggagga acagaacctg gctgatctac ttcctccagc tagcgatgaa acaaatgaaa     420
atgagactcc gtattcaaca gatgaaagtg aaaaatcttc ccagtcacat cacaatgaaa     480
acaactgcac aaaagcaaga ttctctccta aaaacttacg gtttcccatc ccaccaacac     540
ctccaggatt gggaaggcat ggttcaaaat tcagaacact tccaccattc ttgtcttgct     600
ggcccccacc ctttccagca ggaccaccgt tgattcctcc tccaccacct atggggccag     660
attctcctga ggatgatgaa gcgttgggga gcatgttgat agcttggtat atgagtggtt     720
atcacactgg atattacctg gggttaaaac aaagtcgaat ggaagcagcc ctagagagag     780
aagcctatct aaaatag                                                   797

<210> SEQ ID NO 10
<211> LENGTH: 264
<212> TYPE: PRT
<213> ORGANISM: Gallus gallus

<400> SEQUENCE: 10

Met Ala Gly Arg Val Leu Phe Arg Arg Gly Ala Gly Gln Ser Asp Asp
```

```
1               5                   10                  15
Ser Asp Met Trp Asp Asp Thr Ala Leu Ile Lys Ala Tyr Asp Lys Ala
                20                  25                  30
Val Ala Ser Phe Lys Asn Ala Leu Lys Asn Gly Asp Cys Ser Glu Pro
            35                  40                  45
Ser Asp Lys Gln Glu Gln Arg Ala Gly Val Lys Arg Lys Asn Ser Lys
        50                  55                  60
Lys Asn Arg Asn Arg Asn Lys Ser Asn Ala Val Pro Leu Lys Gln Trp
65                  70                  75                  80
Lys Val Gly Asp Ser Cys Asn Ala Val Trp Ser Glu Asp Gly Asn Val
                85                  90                  95
Tyr Pro Ala Thr Ile Ala Ser Ile Asn Leu Lys Arg Gly Thr Cys Val
            100                 105                 110
Val Thr Tyr Thr Gly Tyr Gly Asn Lys Glu Glu Gln Asn Leu Ala Asp
        115                 120                 125
Leu Leu Pro Pro Ala Ser Asp Glu Thr Asn Glu Asn Glu Thr Pro Tyr
    130                 135                 140
Ser Thr Asp Glu Ser Glu Lys Ser Ser Gln Ser His His Asn Glu Asn
145                 150                 155                 160
Asn Cys Thr Lys Ala Arg Phe Ser Pro Lys Asn Leu Arg Phe Pro Ile
                165                 170                 175
Pro Pro Thr Pro Pro Gly Leu Gly Arg His Gly Ser Lys Phe Arg Thr
            180                 185                 190
Leu Pro Pro Phe Leu Ser Cys Trp Pro Pro Phe Pro Ala Gly Pro
        195                 200                 205
Pro Leu Ile Pro Pro Pro Pro Met Gly Pro Asp Ser Pro Glu Asp
    210                 215                 220
Asp Glu Ala Leu Gly Ser Met Leu Ile Ala Trp Tyr Met Ser Gly Tyr
225                 230                 235                 240
His Thr Gly Tyr Tyr Leu Gly Leu Lys Gln Ser Arg Met Glu Ala Ala
                245                 250                 255
Leu Glu Arg Glu Ala Tyr Leu Lys
            260

<210> SEQ ID NO 11
<211> LENGTH: 407
<212> TYPE: PRT
<213> ORGANISM: Homo sapiens

<400> SEQUENCE: 11

Met Ser Gly Gly Ser Ala Asp Tyr Asn Arg Glu His Gly Gly Pro Glu
1               5                   10                  15
Gly Met Asp Pro Asp Gly Val Ile Glu Ser Asn Trp Asn Glu Ile Val
                20                  25                  30
Asp Asn Phe Asp Asp Met Asn Leu Lys Glu Ser Leu Leu Arg Gly Ile
            35                  40                  45
Tyr Ala Tyr Gly Phe Glu Lys Pro Ser Ala Ile Gln Gln Arg Ala Ile
        50                  55                  60
Ile Pro Cys Ile Lys Gly Tyr Asp Val Ile Ala Gln Ala Gln Ser Gly
65                  70                  75                  80
Thr Gly Lys Thr Ala Thr Phe Ala Ile Ser Ile Leu Gln Gln Leu Glu
                85                  90                  95
Ile Glu Phe Lys Glu Thr Gln Ala Leu Val Leu Ala Pro Thr Arg Glu
            100                 105                 110
```

-continued

```
Leu Ala Gln Gln Ile Gln Lys Val Ile Leu Ala Leu Gly Asp Tyr Met
        115                 120                 125

Gly Ala Thr Cys His Ala Cys Ile Gly Gly Thr Asn Val Arg Asn Glu
    130                 135                 140

Met Gln Lys Leu Gln Ala Glu Ala Pro His Ile Val Val Gly Thr Pro
145                 150                 155                 160

Gly Arg Val Phe Asp Met Leu Asn Arg Arg Tyr Leu Ser Pro Lys Trp
                165                 170                 175

Ile Lys Met Phe Val Leu Asp Glu Ala Asp Glu Met Leu Ser Arg Gly
            180                 185                 190

Phe Lys Asp Gln Ile Tyr Glu Ile Phe Gln Lys Leu Asn Thr Ser Ile
        195                 200                 205

Gln Val Val Leu Leu Ser Ala Thr Met Pro Thr Asp Val Leu Glu Val
    210                 215                 220

Thr Lys Lys Phe Met Arg Asp Pro Ile Arg Ile Leu Val Lys Lys Glu
225                 230                 235                 240

Glu Leu Thr Leu Glu Gly Ile Lys Gln Phe Tyr Ile Asn Val Glu Arg
                245                 250                 255

Glu Glu Trp Lys Leu Asp Thr Leu Cys Asp Leu Tyr Glu Thr Leu Thr
            260                 265                 270

Ile Thr Gln Ala Val Ile Phe Leu Asn Thr Arg Arg Lys Val Asp Trp
        275                 280                 285

Leu Thr Glu Lys Met His Ala Arg Asp Phe Thr Val Ser Ala Leu His
    290                 295                 300

Gly Asp Met Asp Gln Lys Glu Arg Asp Val Ile Met Arg Glu Phe Arg
305                 310                 315                 320

Ser Gly Ser Ser Arg Val Leu Ile Thr Thr Asp Leu Leu Ala Arg Gly
                325                 330                 335

Ile Asp Val Gln Gln Val Ser Leu Val Ile Asn Tyr Asp Leu Pro Thr
            340                 345                 350

Asn Arg Glu Asn Tyr Ile His Arg Ile Gly Arg Gly Gly Arg Phe Gly
        355                 360                 365

Arg Lys Gly Val Ala Ile Asn Phe Val Thr Glu Glu Asp Lys Arg Ile
    370                 375                 380

Leu Arg Asp Ile Glu Thr Phe Tyr Asn Thr Thr Val Glu Glu Met Pro
385                 390                 395                 400

Met Asn Val Ala Asp Leu Ile
                405
```

NUCLEIC ACID MOLECULE ENCODING HUMAN SURVIVAL OF MOTOR NEURON-INTERACTING PROTEIN 1 (SIP1) DELETION MUTANTS

CROSS-REFERENCE TO RELATED APPLICATIONS

This application claims priority pursuant to 35 U.S.C. §119(e) to U.S. Provisional Application No. 60/100,866, filed on Sep. 17, 1998.

STATEMENT OF FEDERALLY SPONSORED RESEARCH AND DEVELOPMENT

This invention was supported in part by funds from the U.S. Government (National Institutes of Health Grant No. R01-GM37125) and the U.S. Government may therefore have certain rights in the invention.

BACKGROUND OF THE INVENTION

Spinal muscular atrophy (SMA) is characterized by degeneration of the anterior horn cells of the spinal cord, leading to progressive symmetrical limb and trunk paralysis and muscular atrophy. SMA is the second most common fatal autosomal recessive disorder, second only to cystic fibrosis, and the most common genetic cause of childhood mortality affecting 1 in 6,000 newborns (Roberts et al., 1970, Arch. Dis. Child. 45:33–38; Pearn, 1973, J. Med. Genet. 10:260–265; Pearn, 1978, J. Med. Genet. 15:409–413; Czeizel and Hamular, 1989, J. Med. Genet. 21:761–763). Childhood spinal muscular atrophies are divided into severe (type I, Werdnig-Hoffman disease) and mild forms (type II and III) according to the age of onset and the severity of the disease (Munsat, 1991, Neuromusc. Disord. 1:81; Crawford and Pardo, 1996, Neurobiol. Dis. 3:97–110). The Survival of Motor Neurons (SMN) gene (Lefebvre et al., 1995, Cell 89:155–165) has been shown to be the SMA disease gene, and it is deleted or mutated in over 98% of SMA patients (Bussaglia et al., 1995, Nat. Genet. 11:335–337; Chang et al., 1995, Am. J. Hum. Genet. 57:1503–1505; Cobben et al., 1995, Am. J. Hum. Genet. 57:805–808; Hahnen et al., 1995, Hum. Mol. Genet. 4:1927–1933; Hahnen et al., 1996, Am. J. Hum. Genet. 59:1057–1065; Lefebvre et al., 1995, Cell 89:155–165; Rodrigues et al., 1995, Hum. Mol. Genet. 4:631–634; Velasco et al., 1996, Hum. Mol. Genet. 5:257–263; Lefebvre et al., 1997, Nat. Genet. 16:265–269).

Two inverted gene copies of the SMN gene are located in a 500 kb inverted repeat at chromosome 5q13. In over 98% of all SMA patients, the telomeric copy of SMN ($SMN^T$) is deleted or mutated while the centromeric copy of the gene ($SMN^C$) is unaffected (Lefebvre et al., 1995, Cell 89:155–165).

The SMN gene encodes a protein of about 296 amino acids having a molecular mass of approximately 40 kDa. The sequence of the protein does not exhibit any significant homology to any other protein of known function in the currently available protein databases.

Recently, in the course of studies of the functions of heterogeneous nuclear ribonucleoproteins (hnRNPs) (Dreyfuss et al., 1993, Ann. Rev. Biochem. 62:289–321), it was found that the SMN protein interacts with fibrillarin, an RNA-binding protein involved in rRNA processing, and with several other RNA-binding proteins (Liu and Dreyfuss, 1996, EMBO J. 15:3555–3565). Monoclonal antibodies to SMN localized the protein to a unique cellular location. SMN exhibits a general localization in the cytoplasm and is particularly concentrated in several prominent nuclear bodies called gems (for gemini of coiled bodies). Gems are novel nuclear structures which are related in number and size to coiled bodies and are usually found in close proximity to them (Liu and Dreyfuss, 1996, EMBO J. 15:3555–3565). Coiled bodies, which were first described by Ramón y Cajal (1903, Trab. Lab. Invest. Biol. 2:129–221), are prominent nuclear bodies found in widely divergent organisms, including plant and animal cells (Bohmann et al., 1995, J. Cell Sci. 19:107–113; Gall et al., 1995, Dev. Genet. 16:25–35). Coiled bodies contain the spliceosomal U1, U2, U4/U6, and U5 snRNPs, U3 snoRNAs, and several proteins, including the specific marker p80-coilin, fibrillarin, and NOP140 (Bohmann et al., 1995, J. Cell Sci. 19:107–113, and references therein; Gall et al., 1995, Dev. Genet. 16:25–35). Expression of p80-coilin mutants and microscopic observations suggests a close association between coiled bodies and the nucleolus (Raska et al., 1990, J. Struct. Biol. 104:120–127; Andrade et al., 1991, J. Exp. Med. 173:1407–1419; Bohmann et al., 1995, J. Cell Biol. 131:817–831). However, the specific functions of coiled bodies are not clear. Current ideas propose that coiled bodies may be involved in processing, sorting, and assembly of snRNAs and snoRNAs in the nucleus. The close association of gems and coiled bodies raises the possibility that the SMN protein and gems are also involved in the processing and metabolism of small nuclear RNAs (Liu and Dreyfuss, 1996, EMBO J. 15:3555–3565).

The Sm class of small nuclear ribonucleoproteins (snRNPs) U1, U2, U4/6, and U5 are major constituents of the spliceosome, the catalytic center of the pre-mRNA splicing reaction (Moore et al., 1993, In: The RNA World, pp. 303–358, Gesteland and Atkins, eds., Cold Spring Harbor Laboratory Press, Plainview, N.Y.; Madhani and Guthrie, 1994, Annu. Rev. Genet. 28:1–26). Each spliceosomal snRNP consists of one (U1, U2, and U5) or two (U4/6) snRNAs, a common set of at least eight Sm proteins, termed B, B', D1, D2, D3, E, F, and G, and specific polypeptides that are associated with only one individual U snRNP (reviewed by Lührmann et al., 1990, Biochim. Biophys. Acta Gene Struct. Express. 1087:265–292). With the exception of U6, all spliceosomal snRNAs share two structural features: the 5'-terminal trimethylguanosine ($m_3G$) cap and a short, single-stranded, eight-to-ten nucleotide uridine-rich sequence flanked by two hairpin loops, referred to as the Sm site (Branlant et al., 1982, EMBO J. 1: 1259–1265; Reddy and Busch, 1988, In: Structure and Function of Major and Minor Small Nuclear Ribonucleoprotein Particles, pp. 1–37, Birnstiel, ed., Springer-Verlag, Berlin). The Sm site is the primary binding site for the Sm proteins. The remaining snRNA domains provide binding sites for the snRNA-specific snRNP proteins and for RNA-RNA interactions (Lührmann et al., 1990, Biochim. Biophys. Acta Gene Struct. Express. 1087:265–292). U6 differs from the other spliceosomal U snRNAs in that it contains a γ-monomethyl cap instead of the ($m_3G$) cap and does not bind directly to Sm proteins due to its lack of an Sm site (Reddy and Busch, 1988, supra; Singh and Reddy, 1989, Proc. Natl. Acad. Sci. USA 86:8280–8283). The snRNP-specific proteins have snRNP-specific functions in the splicing reaction. In contrast, the only known function for the Sm proteins is in the biogenesis of U snRNPs.

The biogenesis of snRNPs, which is illustrated in FIG. 26 herein, is a complex, multistep process (DeRobertis, 1983, Cell 32:1021–1025; Fisher et al., 1985, Cell 42:751–758; Mattaj, 1988, In: Structure and Function of Major and Minor Small Nuclear Ribonucleoprotein Particles, pp. 100–114, Birnstiel, ed., Springer-Verlag, Berlin; Feeney et al., 1989, J. Biol. Chem. 264:5776–5783; Neuman de Vegvar and Dahlberg, 1990, Mol. Cell. Biol. 10:3365–3375; Zieve and Sauterer, 1990, Crit. Rev. Biochem. Mol. Biol. 25:1–46). Spliceosomal snRNAs that contain the Sm site are first exported to the cytoplasm, where they associate with the Sm proteins (B, B', D1, D2, D3, E, F, and G) (Mattaj and DeRobertis, 1985, Cell 40:111–118). Next, in a reaction that requires the assembled Sm core domain (comprising the Sm proteins bound to the Sm site), the 7-methylguanosine ($m^7G$) cap of the snRNAs is hypermethylated to yield 2,2,7-trimethylguanosine ($m_3G$) (Mattaj, 1986, Cell 46:905–911). In addition, varying numbers of nucleotides are trimmed from the 3' end of several of the snRNAs. Proper Sm core assembly, cap hypermethylation, and 3'-end processing are important for nuclear import of the assembled snRNP particles (Fischer and Lührmann, 1990, Science 249:786–790; Hamm et al., 1990, Cell 62:569–577). Finally, just before or after the nuclear import, many internal nucleotides are modified and more than 30 snRNP-specific proteins associate with the individual snRNP precursors to complete their biogenesis (Mattaj, 1988, In: Structure and Function of Major and Minor Small Nuclear Ribonucleoprotein Particles, pp. 100–114, Birnstiel, ed., Springer-Verlag, Berlin; Lührmann et al., 1990, Biochim. Biophys. Acta Gene Struct. Express. 1087:265–292; Neuman de Vegvar and Dahlberg, 1990, Mol. Cell. Biol. 10:3365–3375; Zieve and Sauterer, 1990, Crit. Rev. Biochem. Mol. Biol. 25:1–46). However, the detailed mechanism of how the Sm core proteins and the snRNP-specific proteins form functional assembled snRNPs is not clear.

There is, to date, no effective treatment for SMA and the mechanism underlying the disease process is poorly understood. Thus, there is an acute and long-felt need to understand the mechanism of the disease process and, more importantly, for the development of methods of treating this common and usually fatal disease. The present invention addresses these needs.

SUMMARY OF THE INVENTION

The invention relates to an isolated nucleic acid encoding a eukaryotic SIP1, and any mutants, derivatives, variants, and fragments thereof.

In one aspect, the isolated nucleic acid shares at least about 20% homology with at least one of huSIP1 (SEQ ID NO:1) and XeSIP1 (SEQ ID NO:3).

In another aspect, the isolated nucleic acid is selected from the group consisting of (SEQ ID NO:1), and (SEQ ID NO:3).

The invention further relates to an isolated nucleic acid encoding a eukaryotic SIP1, wherein the SIP1 shares at least about 20% homology with at least one of huSIP1 (SEQ ID NO:2), and XeSIP1 (SEQ ID NO:4), and any mutants, derivatives, variants, and fragments thereof.

Also included in the invention is an isolated polypeptide comprising a eukaryotic SIP1, and any mutants, derivatives, variants, and fragments thereof.

In one aspect, the SIP1 shares at least about 20% homology with at least one of SEQ ID NO:2 and SEQ ID NO: 4.

In another aspect, the amino acid sequence of the SIP1 is at least one of SEQ ID NO:2 and SEQ ID NO:4.

In another aspect, the nucleic acid further comprises a nucleic acid encoding a tag polypeptide covalently linked thereto.

In one aspect, the tag polypeptide is selected from the group consisting of a myc tag polypeptide, a myc-pyruvate kinase tag polypeptide, a His6 tag polypeptide, an influenza virus hemagglutinin tag polypeptide, a maltose binding protein tag polypeptide, and a glutathione-S-transferase tag polypeptide.

In another aspect, the nucleic acid of the invention further comprises a nucleic acid encoding a promoter/regulatory sequence operably linked thereto.

In yet another aspect, the nucleic acid further comprises a nucleic acid a tag polypeptide.

The invention also includes a cell comprising the nucleic acid of the invention.

In one embodiment, the cell is a DT40 cell.

Also included is a vector comprising the isolated nucleic acid of the invention.

In one aspect, the vector further comprises a nucleic acid encoding a promoter/regulatory sequence operably linked thereto.

Also included is a recombinant cell comprising the isolated nucleic acid of the invention.

In one aspect, the recombinant cell comprises the aforementioned vector.

In addition, the invention relates to an antisense isolated nucleic acid complementary to the nucleic acid of the invention.

Further, the invention relates to a cell comprising the antisense nucleic acid of the invention.

In addition, there is included an antibody that specifically binds to a eukaryotic SIP1 polypeptide, or a fragment thereof.

The antibody may be selected from the group consisting of a polyclonal antibody, a monoclonal antibody, and a synthetic antibody.

In a preferred embodiment, the antibody is a monoclonal antibody selected from the group consisting of 2S7 and 2E17.

The invention also relates to an isolated nucleic acid encoding a mammalian Gemin3, and any mutants, derivatives, variants, and fragments thereof.

In one aspect, the nucleic acid shares at least about 20% homology with human Gemin3 (SEQ ID NO:7).

In another aspect, the isolated nucleic acid is SEQ ID NO:7.

The invention further relates to an isolated nucleic acid encoding a mammalian Gemin3, wherein the Gemin3 shares at least about 20% homology with human Gemin3 (SEQ ID NO:8), and any mutants, derivatives, variants, and fragments thereof.

In addition, there is included an isolated polypeptide comprising a mammalian Gemin3, and any mutants, derivatives, variants, and fragments thereof.

In one aspect, the Gemin3 shares at least about 20% homology with SEQ ID NO:8.

In another aspect, the Gemin3 is SEQ ID NO:8.

In another aspect, the nucleic acid further comprises a nucleic acid encoding a tag polypeptide covalently linked thereto.

In one embodiment, the tag polypeptide is selected from the group consisting of a myc tag polypeptide, a myc-pyruvate kinase tag polypeptide, a His6 tag polypeptide, an influenza virus hemagglutinin tag polypeptide, a maltose binding protein tag polypeptide, and a glutathione-S-transferase tag polypeptide.

In another embodiment, the nucleic acid further comprises a nucleic acid encoding a promoter/regulatory sequence operably linked thereto.

Also included is a vector comprising the just-mentioned nucleic acid.

The vector may further comprise a nucleic acid encoding a promoter/regulatory sequence operably linked thereto.

In addition, the invneiton includes a recombinant cell comprising the just-mentioned nucleic acid.

The invention also includes a recombinant cell comprising the just-mentioned vector.

The invention further includes an antisense isolated nucleic acid complementary to the just-mentioned nucleic acid, and a cell comprising the same.

In addition, the invention relates to an nntibody that specifically binds to a mammalian Gemin3 polypeptide, or a fragment thereof In one aspect, the antibody is selected from the group consisting of a polyclonal antibody, a monoclonal antibody, and a synthetic antibody.

In one embodiment, the antibody is a monoclonal antibody selected from the group consisting of 11G9 and 12H12.

Also included is an antibody that specifically binds to a eukaryotic Survival of Motor Neurons (SMN) polypeptide, or a fragment thereof.

In one aspect, the SMN is human SMN and further wherein the antibody is monoclonal antibody 2B1.

In another embodiment, the SMN is chicken SMN.

In addition, the invention includes an isolated nucleic acid encoding a eukaryotic SIP1, and any mutants, derivatives, variants, and fragments thereof., wherein the nucleic acid comprises a mutation that affects binding of SIP1 with SMN.

Further, the invention includes an isolated nucleic acid encoding human SMN, wherein the nucleic acid comprises a mutation which mutation affects binding of SMN with at least one of another SMN protein, a Gemin3 protein, and an SIP1 protein.

In addition, the invention includes nn isolated nucleic acid encoding the human SMN protein, wherein the nucleic acid comprises a mutation which mutation affects pre-mRNA splicing.

The invention further includes a cell comprising the just-mentioned nucleic acid.

The invention also includes an isolated nucleic acid encoding a eukaryotic SIP1, and any mutants, derivatives, variants, and fragments thereof, wherein the nucleic acid comprises a mutation which mutation affects binding of SIP1 with SMN.

The invention also includes a fusion protein comprising a tag polypeptide and at least a portion of an SMN protein.

In one aspect, the tag polypeptide is selected from the group consisting of a myc tag polypeptide, a myc-pyruvate kinase tag polypeptide, a His 6 tag polypeptide, an influenza virus hemagglutinin tag polypeptide, a maltose binding tag polypeptide, and a glutathione-S-transferase tag polypeptide.

The invention further includes a fusion protein comprising a tag polypeptide and at least a portion of an SIP1 protein.

In addition, the invention includes a fusion protein comprising a tag polypeptide and at least a portion of a Gemin3 protein.

The invention also includes a vector comprising a nucleic acid encoding human SMN wherein the nucleic acid comprises a mutation and further wherein the mutation affects SMN binding to at least one of another SMN protein, a Gemin3 protein, and an SIP1 protein.

The invention also includes a composition comprising an isolated purified SMN protein and a protein that binds specifically with SMN.

In one aspect, the protein that binds specifically with SMN is selected from at least one of another SMN protein, an SIP1 protein, a Gemin3 protein, and an Sm protein.

In one embodiment, the composition further comprising a ribonucleic acid.

The invention further relates to a method of stimulating snRNP assembly. The method comprises contacting an extract comprising snRNP components with SMN, thereby stimulating snRNP assembly.

Also included is a mammalian cell comprising an exogenous SMN modulating sequence selected from the group consisting of a nucleic acid encoding SMN, an antisense nucleic acid complementary to a nucleic acid encoding SMN, and a ribozyme specific for ribonucleic acid encoding SMN, wherein the cell exhibits higher or lower levels of SMN protein compared with an otherwise identical cell which does not comprise the exogenous SMN modulating sequence.

In one embodiment, the exogenous SMN modulating sequence is an antisense nucleic acid and further wherein the cell exhibits a lower level of SMN protein compared with an otherwise identical cell which does not comprise the antisense nucleic acid.

In another embodiment, the cell further exhibits an altered growth characteristic compared with an otherwise identical cell which does not comprise the antisense nucleic acid.

In yet another embodiment, the exogenous SMN modulating sequence is a nucleic acid encoding SMN wherein the nucleic acid encoding SMN is covalently linked to a nucleic acid encoding a HA tag polypeptide, and further wherein expression of the exogenous SMN modulating sequence inhibits expression of endogenous SMN.

Also included is a method of identifying a compound which affects the level of SMN expression in a cell. The method comprises contacting the cell with a test compound and comparing the level of SMN expression in the cell with the level of SMN expression in a otherwise identical cell which is not contacted with the test compound, wherein a higher or lower level of SMN expression in the cell contacted with the compound compared with the level of SMN expression in the otherwise identical cell which is not contacted with the compound is an indication that the compound affects the level of SMN protein in the cell.

In one aspect, the compound increases the level of SMN expression in a cell.

In another aspect, the cell is obtained from a SMA type I patient.

In a further aspect, the cell is selected from the group consisting of a fibroblast and a lymphoblastoid cell.

In addition, the invention includes a method of identifying a test compound which is a candidate SMA therapeutic. The method comprises contacting a cell with a test compound and comparing the level of SMN expression in the cell with the level of SMN expression in an otherwise identical cell which is not contacted with the test compound, wherein a lower level of SMN expression in the cell contacted with the test compound compared with the level of SMN expression in the otherwise identical cell which is not contacted with the test compound is an indication that the test compound is a candidate SMA therapeutic, thereby identifying a compound which is a candidate SMA therapeutic.

In one aspect, the cell is obtained from a SMA type I patient.

In another aspect, the cell is selected from the group consisting of a fibroblast and a lymphoblastoid cell.

The invention further includes a method of identifying a compound which affects the level of SMN expression in a cell comprising an SMN modulating sequence. The method comprises contacting the cell with a test compound and comparing the level of SMN expression in the cell with the level of SMN expression in an otherwise identical cell which is not contacted with the test compound, wherein a higher or lower level of SMN expression in the cell contacted with the compound compared with the level of SMN expression in the cell which is not contacted with the compound is an indication that the compound affects the level of SMN expression in the cell.

In one aspect, the SMN modulating sequence is selected from the group consisting of an isolated nucleic acid encoding SMN, an antisense nucleic acid complementary to a nucleic acid encoding SMN, and a ribozyme specific for ribonucleic acid encoding SMN.

In another aspect, the SMN modulating sequence is an antisense nucleic acid complementary to a nucleic acid encoding SMN.

Also included in the invention is a method of identifying a compound useful for the treatment of SMA. The method comprises contacting a cell comprising an antisense nucleic acid complementary to a nucleic acid encoding SMN with a test compound and comparing the level of SMN expression in the cell with the level of SMN expression in an otherwise dentical cell which is not contacted with the test compound, wherein a higher level of SMN expression in the cell contacted with the compound compared with the level of SMN expression in the cell which is not contacted with the compound is an indication that the compound is useful to treat SMA, thereby identifying a compound useful for the treatment of SMA.

In addition, the invention relates to a method of assessing whether a test compound affects binding of SMN with a protein that specifically binds with SMN. The method comprises (a) making a first preparation comprising a surface having at least a portion of SMN bound thereon, the test compound, and a labeled protein that specifically binds with SMN; (b) assessing the amount of the labeled protein bound with the surface in the first preparation; and (c) comparing the amount of the labeled protein bound with the surface in the first preparation and the amount of labeled protein bound with the surface in an otherwise identical preparation to which the test compound is not added, whereby a difference between the amount of labeled protein bound with the surface in the first preparation and in the otherwise identical preparation is an indication that the test compound affects the binding of SMN with a protein that specifically binds with SMN.

In one aspect, the protein that specifically binds with SMN is selected from the group consisting of another SMN protein, a SIP1 protein, a Gemin3 protein, a SmB protein, a SmB' protein, a SmD1 protein, a SmD2 protein, and a SmD3 protein.

The invention further relates to a method of assessing whether a test compound is useful for treatment of SMA. The method comprises (a) making a first preparation comprising a surface having at least a portion of SMN bound thereon, the test compound, and a labeled protein that specifically binds with SMN; (b) assessing the amount of the labeled protein bound with the surface in the first preparation; and (c) comparing the amount of the labeled protein bound with the surface in the first preparation and the amount of labeled protein bound with the surface in an otherwise identical preparation to which the test compound is not added, whereby a lower amount of the labeled protein bound with the surface in the first preparation and in the otherwise identical preparation is an indication that the test compound is useful for treatment of SMA.

In one aspect, the protein that specifically binds with SMN is selected from the group consisting of another SMN protein, a SIP1 protein, a Gemin3 protein, a SmB protein, a SmB' protein, a SmD1 protein, a SmD2 protein, and a SmD3 protein.

Also included is a method of enhancing splicing of mRNA. The method comprises incubating an in vitro pre-mRNA processing extract in the presence of SMN, or any mutant, derivative, variant, and fragment thereof, thereby enhancing splicing of the mRNA.

In addition, the invention includes a method of identifying a compound that affects pre-mRNA splicing. The method comprises incubating an extract capable of pre-mRNA splicing in the presence or absence of a test compound and comparing the level of pre-mRNA splicing in the extract in the presence of the test compound with the level of splicing of pre-mRNA in the absence of the test compound, wherein a higher or a lower level of pre-mRNA splicing in the extract in the presence of the test compound, compared with the level of pre-mRNA splicing in the extract in the absence of the test compound, is an indication that the test compound affects pre-mRNA splicing.

In addition, the invention relates to a method of identifying a test compound that is useful to treat SMA. The method comprises incubating an extract capable of pre-mRNA splicing in the presence or absence of a test compound and comparing the level of pre-mRNA splicing in the extract in the presence of the test compound with the level of splicing of pre-mRNA in the absence of the test compound, wherein a higher level of pre-mRNA splicing in the extract in the presence of the test compound, compared with the level of pre-mRNA splicing in the extract in the absence of the test compound, is an indication that the test compound is useful to treat SMA.

The invention further relates to a method of identifying a compound that affects snRNP assembly. The method comprises incubating an extract capable of snRNP assembly in the presence or absence of a test compound and comparing the level of snRNP assembly in the extract in the presence of the test compound with the level of snRNP assembly in the absence of the test compound, wherein a higher or a lower level of snRNP assembly in the extract in the presence of the test compound, compared with the level of snRNP assembly in the extract in the absence of the test compound, is an indication that the test compound affects snRNP assembly.

In addition, there is provided a method of identifying a test compound that is useful to treat SMA. The method comprises incubating an extract capable of snRNP assembly in the presence or absence of a test compound and comparing the level of snRNP assembly in the extract in the presence of the test compound with the level of snRNP assembly in the absence of the test compound, wherein a higher level of snRNP assembly in the extract in the presence of the test compound, compared with the level of snRNP assembly in the extract in the absence of the test compound, is an indication that the test compound is useful to treat SMA.

The invention further includes a method of assessing the presence or degree of SMA in a mammal. The method comprises obtaining a biopsy comprising motor neurons from the mammal and assessing the number and morphology of gems in the motor neurons, wherein a lower number of gems in the motor neurons, compared with the number of gems in motor neurons obtained from an otherwise identical mammal which does not have SMA, is an indication that the mammal has SMA, and further wherein the absence of or the presence of a minimal number of gems in the mammal having SMA is directly related to the severity of the SMA in the mammal.

The is further provided in the invention a method of assessing the presence or degree of SMA in a mammal. The method comprises comparing the level of binding of SMN obtained from the mammal to a protein that specifically binds with SMN with the level of binding of SMN wild type to an identical protein that specifically binds with SMN, wherein a lower level of binding of the SMN from the mammal to the protein that specifically binds with SMN compared with the level of binding of SMN wild type with the identical protein that specifically binds with SMN is an indication of the presence or degree of SMA in a mammal.

In one aspect, the protein that specifically binds with SMN is selected from the group consisting of an SMN protein, an SIP1 protein, and a Gemin3 protein.

The invention additionally includes a knock-out targeting vector, the vector comprising a first nucleic acid portion encoding a sequence 5' of the open reading frame encoding SMN and a second nucleic acid portion encoding a nucleic acid sequence 3' of the open reading frame encoding SMN.

In one aspect, the SMN is chicken SMN (SEQ ID NO:9).

In another aspect, the vector further comprises a nucleic acid encoding a selectable marker covalently linked thereto.

In one aspect, the first and second nucleic acid portions flank the nucleic acid encoding the selectable marker.

Also included is a recombinant cell comprising the aforementioned knock-out targeting vector.

The cell amy further comprise a vector comprising an isolated nucleic acid encoding SMN.

In one embodiment, the cell is a chicken pre-B lymphoid DT40 cell.

In addition, the invnetion includes a method of identifying a compound that affects SMN expression in a cell. The method comprises contacting the just-mentioned cell with a test compound and comparing the level of SMN expression in the cell with the level of SMN expression in an otherwise identical cell which is not contacted with the test compound, wherein a higher or lower level of SMN expression in the cell contacted with the test compound compared with the level of SMN expression in the otherwise identical cell which is not contacted with the compound is an indication that the compound affects SMN expression in a cell, thereby identifying a compound that affects SMN expression in a cell.

There is also provided a method of identifying a compound that is useful to treat SMA. The method comprises contacting the aforementioned cell with a test compound and comparing the level of SMN expression in the cell with the level of SMN expression in an otherwise identical cell which is not contacted with the test compound, wherein a higher level of SMN expression in the cell contacted with the test compound compared with the level of SMN expression in the otherwise identical cell which is not contacted with the compound is an indication that the compound increases SMN expression in a cell, thereby identifying a compound that is useful to treat SMA.

In addition, the invention includes a method of identifying a compound useful for the treatment of SMA. The method comprises contacting the aforementioned cell with a test compound and comparing the level of growth of the cell with the level of growth of an otherwise identical cell which is not contacted with the test compound, wherein a higher level of growth of the cell contacted with the compound compared with the level of growth of the cell which is not contacted with the compound is an indication that the compound is useful to treat SMA.

Also included in the invention is an isolated nucleic acid encoding a chicken SMN.

In one aspect, the nucleic acid shares at least about 20% homology with SEQ ID NO:9.

Further included is an isolated nucleic acid encoding chicken SMN, wherein the chicken SMN shares at least about 20% homology with SEQ ID NO:10.

In addition, the invention includes an isolated polypeptide comprising chicken SMN.

In one aspect, the SMN shares at least about 20% homology with SEQ ID NO:10.

In another aspect, the SMN is SEQ ID NO:10.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 1 is a diagram depicting the amino acid sequence alignment of human SIP1 (huSIP1) (also referred to as Gemin2) (SEQ ID NO:2) and of *Xenopus laevis* SIP1 (XeSIP1) (SEQ ID NO:4) sequences. Also shown is the amino acid sequence alignment of SIP1 with the *S. cerevisiae* Brr1 protein (SEQ ID NO:6). The boxes indicate identical amino acids, and the borderless gray boxes indicate similar amino acids.

FIG. 5A is an image of a gel depicting the fact that SMN protein bound directly with Sm B/B', D1–3, and E proteins. Purified snRNP proteins were analyzed on SDS-PAGE (lane designated "snRNPs") and were transferred to a nitrocellulose membrane. The membrane was then probed with 2×10$^6$ cpm of in vitro translated $^{35}$[S]-labeled SMN protein. After washing away the nonspecific binding proteins, the membrane was exposed to an X-ray film (lane "$^{35}$[S]SMN"). The three D Sm proteins could not be resolved using this gel system. The data disclosed herein demonstrate that SMN has two distinct binding domains for the Sm proteins and for SIP1, respectively.

FIG. 5B is an image of a gel depicting binding of Sm proteins with SMN in vitro. $^{35}$[S]-labeled, in vitro-translated Sm proteins B, D1, D2, D3, E, F, and G were incubated for 30 minutes at 4° C. with GST-SMN immobilized on glutathione-Sepharose beads. The beads were then washed six times with binding buffer as described elsewhere herein. Proteins that remained bound to the beads after washing were eluted by boiling the beads in SDS-PAGE sample buffer and the proteins were analyzed by SDS-PAGE followed by fluorography.

FIG. 5C is an image of a gel depicting the competition for SMN binding by two polypeptide fragments of SMN which were conjugated to BSA. In vitro translated $^{35}$[S]-labeled Sm B and SIP1 proteins were mixed, and binding to GST-SMN immobilized on glutathione-Sepharose beads was performed as described in FIG. 5B herein, either in the absence (−) or presence of BSA-coupled SMN peptide fragments corresponding to amino acids 13–44 (P1) or 240–267 (P2) of human SMN protein or to an unrelated control sequence from HIV-1 Rev NES (ctrl). After washing the beads, bound proteins were eluted by boiling the beads in SDS-PAGE sample buffer and the eluted proteins were analyzed by SDS-PAGE followed by fluorography. The data disclosed herein demonstrate that SMN has two distinct, non-overlapping binding domains for SIP1 (domain P1) and for the Sm proteins (domain P2), respectively, as depicted in the illustration at the bottom of this figure.

FIG. 16A is an image depicting the redistribution of Sm proteins in cells expressing the SMNΔN27 deletion mutant. The image depicts immunostaining of HeLa cells transiently transfected with myc-SMN wt using anti-myc tag monoclonal antibody 9E10 (green).

FIG. 16B is an image depicting the immunostaining of HeLa cells transiently transfected with myc-SMN wt using the anti-Sm monoclonal antibody Y12 (red).

FIG. 16C is an image depicting double-label confocal immunofluorescence combining the images depicted in FIGS. 16A (anti-myc [green]) and 16B (anti-Sm [Y12] red) of HeLa cells transiently transfected with myc-SMN wt. Co-localization of the green and red signals results in a yellow signal. The nuclear gems are indicated by arrows and the dashed line demarcates the nucleus.

FIG. 16D is an image depicting the redistribution of Sm proteins in cells expressing the SMNΔN27 deletion mutant. The image depicts immunostaining of HeLa cells transiently transfected with myc-SMNΔN27 using anti-myc tag monoclonal antibody 9E10 (green).

FIG. 16E is an image depicting the immunostaining of HeLa cells transiently transfected with SMNΔN27 using the anti-Sm monoclonal antibody Y12 (red).

FIG. 16F is an image of double-label confocal immunofluorescence combining the images depicted in FIGS. 16C (anti-myc [green]) and 16D (anti-Sm [Y12] red) on HeLa cells transiently transfected with myc-SMNΔN27. Co-localization of the green and red signals results in a yellow signal. The cytoplasmic accumulations are indicated by arrows and the dashed line demarcates the nucleus.

FIG. 17A is an image depicting the distribution of SMNΔN27 in cells expressing the SMNΔN27 deletion mutant protein. This image depicts the immunostaining of HeLa cells transiently transfected with myc-SMNΔN27 using anti-myc tag monoclonal antibody 9E10 (green).

FIG. 17B is an image depicting the redistribution of U snRNAs in cells expressing the SMNΔN27 deletion mutant. This image depicts in situ hybridization demonstrating U2 snRNA localization using a U2-specific antisense oligo probe (red).

FIG. 17C is an image depicting the co-localization of SMNΔN27 and U2 snRNAs in cells expressing the SMNΔN27 deletion mutant protein. This image depicts double-label confocal immunofluorescence using anti-myc tag monoclonal antibody 9E10 (green) and U2-specific antisense oligo probe (red). Co-localization results in a yellow signal. The cytoplasmic accumulations are indicated by arrows and the dashed line demarcates the nucleus.

FIG. 17D is an image depicting the distribution of SMNΔN27 in cells expressing the SMNΔN27 deletion mutant protein. This image depicts the immunostaining of HeLa cells transiently transfected with myc-SMNΔN27 using an anti-myc tag rabbit affinity-purified polyclonal antibody against the 9E10 epitope (green).

FIG. 17E is an image depicting the cap hypermethylation of snRNAs in the cytoplasm of cells transiently transfected with SMNΔN27 deletion mutant. This image depicts the immunostaining of HeLa cells transiently transfected with myc-SMNΔN27 using anti-TMG cap monoclonal antibody K121 (red).

FIG. 17F is an image depicting the co-localization of SMNΔN27 and TMG capped snRNAs in cells expressing the SMNΔN27 deletion mutant protein. This image depicts double-label confocal immunofluorescence using an anti-myc tag rabbit affinity purified polyclonal antibody against the 9E10 epitope (green) and anti-TMG cap monoclonal antibody K121 (red). Co-localization of green and red signals results in a yellow signal. The cytoplasmic accumulations are indicated by arrows and the dashed line demarcates the nucleus.

FIG. 25A is a diagram depicting sequencing of Gemin3 using nanoelectrospray tandem mass spectrometry. A selected portion of the spectrum of the unseparated in-gel tryptic digest of p105 band is depicted. Peptide ions designated by "T" are autolysis products of trypsin and were identified by comparison with the spectrum acquired from the control sample. Other peptide ions observed in the spectrum were, in turn, isolated by the first mass analyzer of a triple quadrupole instrument, fragmented in the collision cell and their tandem mass spectra was acquired. Upon searching a comprehensive protein sequence database using tandem mass spectrometric data, peptide ions designated with filled triangles were identified as tryptic peptides originating from PTB-associated splicing factor (PSF) (P23246). The presence of PSF in the SMN complex turned out to be negative by both co-immunoprecipitation and direct binding to several components of the SMN complex. Peptide ions designated using asterisks (*) were identified as peptides from immunoglobulins used for immunoaffinity purification. Tandem mass spectra acquired from the peptide ions having m/z 552.9 and 622.5 did not identify any protein in the protein sequence database(s) searched. However, when the search was performed against a comprehensive database of expressed sequence tags (i.e., dbEST) the peptide sequence VLISTDLTSR from EST clone W65908 was identified as matching the tandem mass spectrum. After full length sequence had been obtained as described elsewhere herein, the tandem mass spectrum acquired from the peptide ion at m/z 622.5 was matched to the peptide LNSSDPS-LIGLK (SEQ ID NO: 9) present in the sequence of Gemin3.

FIG. 25B is a diagram depicting the tandem mass spectrum acquired from doubly charged peptide precursor ion having m/z552.9. Continuous series of the fragment ions containing the C-terminus of the peptide (Yii-ions) (Roepstorff and Fohlman, 1984, Biomed. Mass Spectrom. 11:601) was produced upon collisional fragmentation of tryptic peptides. A short stretch of the peptide sequence was deduced unambiguously by considering precise mass differences between adjacent Yii-ions (designated in bold capital letters) observed in a part of the spectrum above m/z of the parent ion. Leucine and isoleucine residues have the same nominal mass and are usually not distinguishable by mass spectrometry and are therefore indicated as "L/I." The determined portion of a peptide sequence was combined with the masses of correspondent Yii-ions and with the mass of intact peptide into a peptide sequence tag as described by Mann and Wilm (1994, Analytical Chemistry 66:4390–4399), which was subsequently used to searching protein and EST databases using the program PeptideSearch. Once the database search produced a hit, the correspondent peptide sequence was retrieved from a database and masses of the ions from the N-terminal fragment series (A- and B-ions) were used to verify the match. This protocol enabled highly confident protein identification of a single peptide containing ten amino acid residues was matched to the sequence of a single EST clone.

FIG. 27 is a diagram depicting the amino acid sequence alignment of human Gemin3 (SEQ ID NO:8) and the human DEAD box ATP-dependent RNA helicase eIF4A-II. The N-terminal half of Gemin3 contains a DEAD box RNA helicase domain while the C-terminal half does not exhibit homology to any protein in the database. Amino acids shaded in light grey indicate similar amino acids, and dark grey indicates identical aimno acids. The position of the seven helicase motifs as well as the SMN interacting domain are indicated.

FIG. 30A is an image depicting a gel demonstrating that Gemin3 is in a complex with SMN, Gemin2 (also referred to as SIP1), and the spliceosomal Sm proteins. This image depicts immunoprecipitations of [$^{35}$S)methionine labeled HeLa cell using monoclonal antibodies specific to SMN (2B1), Gemin3 (11G9)), and the snRNP core Sm proteins (Y12). The immunoprecipitated proteins were analyzed using SDS-PAGE followed by autoradiography (24 hours exposure). The immunoprecipitations were performed in the presence of Empigen BB or Triton X-100 as indicated elsewhere herein. The identity of several pertinent proteins immunoprecipitated is indicated on the right side of the figure.

FIG. 30B is an image depicting a longer exposure (36 hours) of the bottom portion of the gel depicting immunoprecipitation in the presence of TritonX-100 (i.e., FIG. 30A). The longer exposure was performed to visualize the Sm proteins more clearly.

FIG. 35A is the amino acid sequence of chicken SMN (SEQ ID NO:10).

FIG. 35B is the nucleic acid sequence of chicken SMN (SEQ ID NO:9).

FIGS. 36A–B is the polypeptide sequence and 36C–F is the nucleic acid sequence of human Gemin3 (SEQ ID NO:7).

FIG. 37 is the nucleic acid sequence of human SIP1 (SEQ ID NO:1; Gen Bank Accession No. AF027150).

FIG. 38 is the nucleic acid sequence of frog SIP1 (SEQ ID NO:3; Gen Bank Accession No. AF0271501).

FIG. 46A is an image of an SDS-PAGE gel depicting the in vivo analysis of the SMN complex by co-immunoprecipitation experiments. 293T cells were transiently transfected with the indicated myc-tagged DNA constructs. 48 hours post-transfection, the cells were collected and the total extracts were prepared as described elsewhere herein. Extracts from cells transfected with myc-SIP1 wild-type (wt) or with deletion mutant (ΔC89) were immunoprecipitated with the anti-SMN antibody (2B1). Total and immunoprecipitated fractions were analyzed by Western blot with 2B1 and anti-myc (9E10) antibodies.

FIG. 46B is an image of a gel depicting the proteins in extracts from cells transfected with myc-SMN wildtype (wt) or with deletion mutant (ΔN92) which were immunoprecipitated with anti-SIP1 (2E17) antibody. Total and immunoprecipitated fractions were analyzed by Western blot with anti-myc 9E10.

FIG. 47 is an image of a gel depicting the proteins in extracts from cells transfected with myc-SMN wildtype (wt) or deletion mutant (ΔC26) which were immunoprecipitated with both anti-Sm (Y12) and anti-SIP1 (2E17) antibodies. Total and Y12 immunoprecipitations were analyzed by Western blot with anti-myc 9E10 and anti-sm Y12. Immunoprecipitations with anti-SMN (2E17) were analyzed by Western blot with 9E10 and 2E17. The heavy and light chains of the immunoglobulins are indicated (h.c. and l.c., respectively).

FIGS. 50A–H is an image (comprising 8 panels) of photomicrographs depicting the subcellular localization of SMN deletion mutants using confocal immunofluorescence microscopy. HeLa cells were transiently transfected with SMN constructs expressing myc-tagged SMN wild-type or with the indicated myc-tagged SMN deletion mutants (see FIG. 40). Indirect immunofluorescence was performed using monoclonal antibody 9E10 against the myc-tag protein. Gems staining was detected by anti-myc antibodies and the staining completely co-localizes with immunostaining of endogenous SIP1. The intensity of the cytoplasmic staining is underestimated by approximately two-fold in the sections shown.

DETAILED DESCRIPTION OF THE INVENTION

Figure 2A:
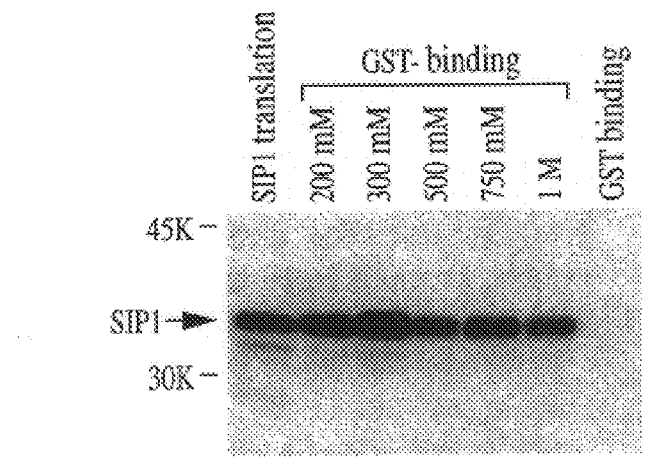
FIG. 2A is an image of an SDS-PAGE gel depicting the interaction of SIP1 with SMN in vitro. SIP1 interacted with immobilized GST-SMN chimeric protein in vitro. The interaction was resistant to a 1 M salt (NaCl) wash. Under the same conditions, SIP1 did not bind with GST alone even at low salt (200 mM NaCl) concentration.

The invention is based on the discovery of a novel gene (SEQ ID NO:1) and a protein encoded thereby (SEQ ID NO:2), designated the Survival of Motor Neuron-Interacting Protein 1 (SIP1), so called because the protein is tightly associated with the SMA disease gene product, SMN. Further, the protein has been provisionally designated Gemin2 since it is the second component of gems to be identified to date, SMN being the first. In addition, the nucleic and amino acid sequences of frog and yeast homologs of human SIP1 are also disclosed herein.

The invention further relates to the discovery that SMN and SIP1 form a large, approximately 300 kDa, more preferably, a 800 kDa, complex in vivo which includes other SMN-associated proteins such as the Sm proteins. The data provided herein establish that these proteins (e.g., SMN and SIP1) play an important role in mRNA biogenesis and that SMA is the first human disease identified involving a defect in mRNA metabolism. Indeed, the data disclosed herein demonstrate that the SMN proteins of SMA patients bind with themselves, with SIP1, or both, with less affinity that does wild type SMN. These results further indicate a causal connection between decreased association between SMN and SIP1 and SMA disease processes. Additionally, the invention relates to the discovery of a novel gene (SEQ ID NO:7) and protein encoded thereby (SEQ ID NO:8) which is the third protein component of gems identified to date and has therefore been designated Gemin3. Further, the invention relates to the discovery that Gemin3 also binds with SMN such that Gemin3 is associated with the aforementioned complex involved in mRNA biogenesis.

The invention also relates to a novel cell line which lacks endogenous SMN but which comprises an exogenous nucleic acid encoding chicken SMN (a novel homolog of human SMN [SEQ ID NO:9] which is disclosed elsewhere herein) under the control of an inducible promoter/regulatory sequence. This cell line is an important tool for the study of SMA disease mechanism(s) and for the identification of novel therapeutics useful for treatment of this deadly hereditary disease for which there is no known cure.

Nucleic Acids and Proteins

The present invention, therefore, provides a novel isolated nucleic acid (SEQ ID NO:1) encoding the human SIP1 protein (huSIP1 [SEQ ID NO:2]). In addition, the invention provides an isolated nucleic acid (SEQ ID NO:3) encoding the *Xenopus laevis* SIP1 protein (XeSIP1 [SEQ ID NO:4.

The invention includes isolated nucleic acids encoding a eukaryotic SIP1 which is, preferably, at least about 20% homologous to at least one of huSIP1 (SEQ ID NO:1), and XeSIP1 (SEQ ID NO:3). More preferably, the isolated nucleic acid encoding a eukaryotic SIP1 is at least about 25%, preferably, at least about 35%, more preferably, at least about 45%, even more preferably, at least about 55%, more preferably, at least about 65%, even more preferably, at least about 75%, yet more preferably, at least about 85% homologous, more preferably, at least about 95% and even more preferably, at least about 99% homologous to at least one of huSIP1 (SEQ ID NO:1) and XeSIP1 (SEQ ID NO:3). More preferably, the isolated nucleic acid encoding a eukaryotic SIP is human huSIP1 and frog XeSIP1. Most preferably, the isolated nucleic acid encoding a eukaryotic SIP1 is SEQ ID NO:1 or SEQ ID NO:3.

Thus, the invention also includes an isolated nucleic acid encoding a eukaryotic SIP1 where the nucleic acid encodes a protein which protein is preferably, at least about 20% homologous to the amino acid sequence of at least one of human SIP1 (SEQ ID NO:2) and frog SIP1 (SEQ ID NO:4). More preferably, the isolated nucleic acid encodes a eukaryotic SIP1 which is at least about 25%, more preferably, at least about 35%, even more preferably, at least about 45%, more preferably, at least about 55%, yet more preferably, at least about 65%, even more preferably, at least about 75%, yet more preferably, at least about 85% homologous, and more preferably, at least about 95%, and even more preferably, at least about 99% homologous to at least one of human SIP1 (SEQ ID NO:2) and frog SIP1 (SEQ ID NO:4). More preferably, the isolated nucleic acid encodes a eukaryotic SIP1 that is human SIP1 or frog SIP1. Most preferably, the isolated nucleic acid encodes a eukaryotic SIP1 having the amino acid sequence SEQ ID NO:2 or SEQ ID NO:4.

Thus, the invention should be construed to include nucleic acids which encode human SIP1 (SEQ ID NO:2) and frog SIP1 (SEQ ID NO:4).

The invention also includes a nucleic acid encoding a mammalian Gemin3 protein. Preferably, the nucleic acid encoding a mammalian Gemin3 is at least about 20% homologous to human Gemin3 (SEQ ID NO:7). More preferably, the isolated nucleic acid encoding a mammalian Gemin3 is at least about 25%, preferably, at least about 35%, more preferably, at least about 45%, even more preferably, at least about 55%, more preferably, at least about 65%, even more preferably, at least about 75%, yet more preferably, at least about 85% homologous, more preferably, at least about 95% and even more preferably, at least about 99% homologous to (SEQ ID NO:7). More preferably, the isolated nucleic acid encoding a mammalian Gemin3 is human Gemin3. Most preferably, the isolated nucleic acid encoding a mammalian Gemin3 is SEQ ID NO:7.

In another aspect, the present invention includes an isolated nucleic acid encoding a mammalian Gemin3, or a fragment thereof, wherein the protein encoded by the nucleic acid shares at least about 20% homology with the amino acid sequence of SEQ ID NO:8. Preferably, the nucleic acid encodes a protein that is about 35% homologous, more preferably 65% homologous, even more preferably 95% homologous, and most preferably about 99% homologous to the human Gemin3 disclosed herein (SEQ ID NO:8). Even more preferably, the Gemin3 protein encoded by the nucleic acid is SEQ ID NO:8.

The present invention includes a nucleic acid encoding chicken SMN, or a fragment thereof, wherein the nucleic acid shares at least about 20% homology with chicken SMN (SEQ ID NO:9). Preferably, the nucleic acid is about 35% homologous, more preferably about 65% homologous, even more preferably 95% homologous, and most preferably about 99% homologous to the chicken SMN disclosed herein (SEQ ID NO:9). Even more preferably, the nucleic acid is SEQ ID NO:9.

In another aspect, the present invention includes an isolated nucleic acid encoding chicken SMN, or a fragment thereof, wherein the protein encoded by the nucleic acid shares at least about 80% homology with the amino acid sequence of SEQ ID NO:10. Preferably, the nucleic acid encodes a protein that is about 85% homologous, more preferably 85% homologous, even more preferably 95% homologous, and most preferably about 99% homologous to the chicken SMN disclosed herein (SEQ ID NO:10). Even more preferably, the chicken SMN protein encoded by the nucleic acid is SEQ ID NO:10.

Thus, the invention should be construed to include nucleic acids which encode chicken SMN (SEQ ID NO:10).

The isolated nucleic acid of the invention should be construed to include an RNA or a DNA sequence encoding an SIP1 protein of the invention, and any modified forms thereof, including chemical modifications of the DNA or RNA which render the nucleotide sequence more stable when it is cell free or when it is associated with a cell. Similarly, the invention includes such modified forms of Gemin3 and chicken SMN. Chemical modifications of nucleotides may also be used to enhance the efficiency with which a nucleotide sequence is taken up by a cell or the efficiency with which it is expressed in a cell. Any and all combinations of modifications of the nucleotide sequences are contemplated in the present invention.

The present invention should not be construed as being limited solely to the nucleic and amino acid sequences disclosed herein. Once armed with the present invention, it is readily apparent to one skilled in the art that other nucleic acids encoding SIP1, SMN, and Gemin3 proteins may be obtained by following the procedures described herein in the experimental details section for the isolation of the human, frog and yeast nucleic acids encoding SIP1 proteins, as well as those procedures used to identify and isolate human Gemin3 and chicken SMN, and the respective polypeptides encoded thereby (i.e., Gemin3 and chicken SMN), as disclosed elsewhere herein.

Further, the invention should be construed to include naturally occurring variants or recombinantly derived mutants of wild type SIP1 DNA sequences, which variants or mutants render the protein encoded thereby either more, less, or just as biologically active as the full-length wild type SIP1 of the invention. Any number of procedures may be used for the generation of mutant, derivative or variant forms of SIP1, Gemin3, and SMN, using recombinant DNA methodology well known in the art such as, for example, that described in Sambrook et al. (1989, Molecular Cloning: A Laboratory Manual, Cold Spring Harbor Laboratory Press, New York), Ausubel et al. (1997, Current Protocols in Molecular Biology, Green & Wiley, New York), and elsewhere herein.

As will be apparent from the experiments described herein, SIP1 comprises a binding domain which mediates SIP1 binding to SMN. The invention includes a mutant of SIP1, wherein a mutation is introduced into the sequence of SIP1 cDNA such that the protein encoded thereby does not bind SMN or binds to a lesser extent. Such mutant is useful in the methods of the invention and for the study of the role of SMN-SIP1 interaction in mRNA biogenesis. Preferably, a mutant SIP1 gene which encodes an SIP1 protein comprising a deletion whereby amino acids from the carboxyl terminal of the SIP1 protein have been removed is useful in studying the association of SIP1 with SMN. Examples of such mutants (SIP1ΔC89 and SIP1ΔC162) have been disclosed herein. However, the invention is not limited solely to these mutants; rather, the invention encompasses other mutants, comprising deletion and point mutations, which demonstrate altered binding to SMN or other SMN-SIP1 complex associated proteins (e.g., Gemin3 and various Sm proteins) and ribonucleic acids. These mutants allow the functional mapping of various portions of the protein to determine which portion(s) of the protein mediate which function(s) of the full-length protein.

Likewise, the present invention includes an isolated nucleic acid encoding SMN and mutants, homologs and variants thereof which exhibit altered binding with another SMN molecule and/or decreased binding with the SMN-associated protein SIP1. These proteins are important tools to determine which portion(s) of the proteins mediate the biological effect(s) associated with the full-length protein. Further, they are useful in elucidating the mechanisms of SMA and in the identification of therapeutics for treatment of this disease.

The invention also includes selected mutant, homologs, and variants of Gemin3. Several of the proteins exhibited unchanged binding with SMN despite deletions of selected portions of the amino acid sequence (e.g., ΔN368C272Gemin3) while other proteins demonstrated lack of binding with SMN (e.g., ΔC328Gemin3 and ΔN548Gemin3). Such proteins are important tools in elucidating the effect of naturally-occurring and/or artificially produced amino acid sequences in cell processes and, more specifically, for assessing the function of various proteins, and fragments thereof, in SMA.

The invention also includes a nucleic acid encoding SMN or SIP1, and mutants, derivatives, variants, and fragments thereof, that may retain biological activity. Such variants, i.e., analogs of SMN or SIP1, include proteins or polypeptides which have been or may be modified using recombinant DNA technology such that the protein or polypeptide possesses additional properties which enhance its suitability for use in the methods described herein, for example, but not limited to, variants conferring enhanced stability on the SMN-SIP1 complex, enhanced specific binding of SIP1 to SMN, and the like.

Procedures for the introduction of amino acid changes in a protein or polypeptide by altering the DNA sequence encoding the polypeptide are well known in the art and are also described in Sambrook et al. (1989, supra); Ausubel et al. (1997, supra).

The invention includes a nucleic acid encoding a mammalian SMN, SIP1, or Gemin3 wherein a nucleic acid encoding a tag polypeptide is covalently linked thereto. That is, the invention encompasses a chimeric nucleic acid wherein a nucleic acid sequence encoding a tag polypeptide is covalently linked to a nucleic acid encoding at least one of human SIP1, frog SIP1, yeast Brr1, human Gemin3, and chicken SMN. Such chimeric (i.e., fusion) tag polypeptides are well known in the art and include, for instance, myc, myc-pyruvate kinase (myc-PK), $His_6$, maltose biding protein (MBP), and glutathione-S-transferase (GST). However, the invention should in no way be construed to be limited to the nucleic acids encoding the above-listed tag polypeptides. Rather, any nucleic acid sequence encoding a polypeptide which may function in a manner substantially similar to these tag polypeptides should be construed to be included in the present invention.

A nucleic acid encoding a protein of interest (e.g., SMN, SIP1, Gemin3, and any mutant, derivative, variant, or fragment thereof) comprising a nucleic acid encoding a tag polypeptide and a fusion protein produced therefrom can be used to localize SMN, SIP1, and Gemin3 within a cell and to study expression, localization, and role(s) of the tagged protein in a cell before, during, and/or after exposing the cell to a test compound potentially useful for treatment of SMA. Further, addition of a tag to a protein of interest (e.g., SMN, SIP1, Gemin3) polypeptide facilitates isolation and purification of the "tagged" protein such that the protein of interest can be easily produced and purified.

Additionally, variants may be chemically linked to another protein. For example, SMN was conjugated with bovine serum albumin (BSA) as described in Fischer et al. (1995, Cell 82:475–483). However, the invention is not limited to chemically linking SMN with BSA, but also includes cross-linking SMN, SIP1, and Gemin3 proteins by chemical means to any suitable composition. Thus, it should be appreciated that the use of BSA is described herein by way of example only. In certain situations, it may be desirable to inhibit expression of SMN, SIP1, or Gemin3 in a cell that would otherwise express the protein. Therefore, the invention includes compositions useful for inhibition of expression of SMN, SIP1, and Gemin3. One such method of the invention features an isolated nucleic acid complementary to a portion or all of a nucleic acid encoding an SMN, SIP1, or Gemin3 which is in an antisense orientation with respect to transcription. Preferably, the antisense nucleic acid useful for inhibition of SIP1 expression shares at least 20%, homology with at least one of SEQ ID NO:1, SEQ ID NO:3, SEQ ID NO:5.

Similarly, an antisense nucleic acid useful for inhibition of Gemin3 expression shares at least about homology 20% with SEQ ID NO:7.

Likewise, an antisense nucleic acid useful for inhibition of Gemin3 expression shares at least about homology 20% with SEQ ID NO:9.

The above-referred to antisense nucleic acids serve to inhibit the expression, function, or both, of human SIP1, frog SIP1, human Gemin3, and chicken SMN.

The invention also includes an isolated polypeptide comprising a eukaryotic SIP1. Preferably, the isolated polypeptide comprising a eukaryotic SIP1 is at least about 20% homologous to at least one of human SIP1 (SEQ ID NO:2) and frog SIP1 (SEQ ID NO:4). More preferably, the isolated polypeptide comprising a eukaryotic SIP1 is at least about 35%, more preferably, at least about 65%, even more preferably, at least about 95%, and more preferably, at least about 99% homologous to at least one of human SIP1 and frog SIP1. More preferably, the isolated polypeptide comprising a eukaryotic SIP1 is at least one human SIP1 and frog SIP1. Most preferably, the isolated polypeptide comprising a mammalian eukaryotic SIP1 is at least one of SEQ ID NO:2 and SEQ ID NO:4.

The invention also includes an isolated polypeptide comprising a mammalian Gemin3. Preferably, the isolated polypeptide comprising a mammalian Gemin3 is at least about 20% homologous to human Gemin3 (SEQ ID NO:8). More preferably, the isolated polypeptide comprising a mammalian Gemin3 is at least about 35%, more preferably, at least about 65%, even more preferably, at least about 95%, and more preferably, at least about 99% homologous to human Gemin3. More preferably, the isolated polypeptide comprising a mammalian Gemin3 is human Gemin3. Most preferably, the isolated polypeptide comprising a mammalian Gemin3 is SEQ ID NO:8.

The invention also includes an isolated polypeptide comprising a chicken SMN. Preferably, the isolated polypeptide comprising a chicken SMN is at least about 20% homologous to SEQ ID NO:8. More preferably, the isolated polypeptide comprising a chicken SMN is at least about 35%, more preferably, at least about 65%, even more preferably, at least about 95%, and more preferably, at least about 99% homologous to chicken SMN. More preferably, the isolated polypeptide comprising is chicken SMN. Most preferably, the isolated polypeptide comprising a chicken SMN is SEQ ID NO:10.

The present invention also provides for analogs of proteins or peptides which comprise a eukaryotic SIP1, a mammalian Gemin3, and chicken SMN protein as disclosed herein. Analogs may differ from naturally occurring proteins or peptides by conservative amino acid sequence differences or by modifications which do not affect sequence, or by both. For example, conservative amino acid changes may be made, which although they alter the primary sequence of the protein or peptide, do not normally alter its function. Conservative amino acid substitutions typically include substitutions within the following groups:

glycine, alanine;

valine, isoleucine, leucine;

aspartic acid, glutamic acid;

asparagine, glutamine;

serine, threonine;

lysine, arginine;

phenylalanine, tyrosine.

Modifications (which do not normally alter primary sequence) include in vivo, or in vitro, chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

The present invention should also be construed to encompass "mutants," "derivatives," and "variants" of the peptides of the invention (or of the DNA encoding the same) which mutants, derivatives and variants are SMN, SIP1, and Gemin3 peptides which are altered in one or more amino acids (or, when referring to the nucleotide sequence encoding the same, are altered in one or more base pairs) such that the resulting peptide (or DNA) is not identical to the sequences recited herein, but has the same biological property as the peptides disclosed herein, in that the peptide has biological/biochemical properties of the SMN, SIP1, or Gemin3 peptide of the present invention. A biological property of a SMN protein should be construed but not be limited to include, the ability of the peptide to bind specifically and avidly with another SMN molecule and also to bind with SIP1, Gemin3, and various Sm proteins.

Likewise, a biological property of the Gemin3 peptide of the invention is to bind specifically with SMN.

A biological activity of the SIP1 of the invention is the ability to bind specifically with SMN.

Similarly, a biological function of Gemin3 is the ability to specifically bind with SMN. In addition, a biological property of Gemin3 is the ability to function as a helicase as indicated by the presence of a DEAD motif conserved in RNA helicases as reviewed by reviewed in Staley and Guthrie (1998, Cell 92:315–326). Further, a biological activity of SMN, SIP1, and Gemin3 is to be able to participate in mRNA biosynthesis.

Further, the invention should be construed to include naturally occurring variants or recombinantly derived mutants of SIP1 and Gemin3 sequences, which variants or mutants render the protein encoded thereby either more, less, or just as biologically active as the full-length proteins of the invention.

The nucleic acids, and peptides encoded thereby, are useful tools for elucidating the function(s) of SMN, SIP1 and Gemin3 in a cell. Further, they are useful for localizing the nucleic acid, protein, or both, in a cell and for assessing the level of expression of the nucleic acid and/or protein under selected conditions including in response to therapeutic treatment. Further, nucleic and amino acids comprising eukaryotic SIP1, and mammalian Gemin3 are useful diagnostics which can be used, for example, to identify a compound that affects expression of the protein and is a candidate SMA therapeutic.

In addition, the nucleic acids, the proteins encoded thereby, or both, can be administered to a mammal to increase or decrease expression of SIP1 or Gemin3 in the mammal. This can be therapeutic to the mammal if under or over-expression of SIP1 or Gemin3 in the mammal mediates a disease or condition associated with altered expression of the protein compared with normal expression of SIP1 and/or Gemin3 in a healthy mammal. Additionally, the nucleic and amino acids of the invention can be used to produce recombinant cells which are useful tools for the study of SMA, the identification of novel SMA therapeutics, and for elucidating the cellular role(s) of SIP1 and Gemin3 in mRNA biosynthesis and other cell processes, among other things. Further, the nucleic and amino acids of the invention can be used diagnostically, either by assessing the level of gene expression or protein expression and the biological activity of the protein, to assess severity and prognosis of SMA.

In other related aspects, the invention includes a nucleic acid encoding a eukaryotic SIP1 operably linked to a nucleic acid comprising a promoter/regulatory sequence such that the nucleic acid is preferably capable of directing expression of the protein encoded by the nucleic acid.

Expression of SIP1 either alone or fused to a detectable tag polypeptide in cells which either do not normally express SIP1 or which do not express SIP1 comprising a tag polypeptide, can be accomplished by operably linking the nucleic acid encoding SIP1 to a promoter/regulatory sequence which serves to drive expression of the protein, with or without a tag polypeptide, in cells in which the exogenous nucleic acid (i.e. transgene) is introduced.

Many promoter/regulatory sequences useful for driving constitutive expression of a gene are available in the art and include, but are not limited to, for example, the cytomegalovirus immediate early promoter enhancer sequence, the SV40 early promoter, both of which were used in the experiments disclosed herein, as well as the Rous sarcoma virus promoter, and the like. Moreover, inducible and tissue specific expression of the nucleic acid encoding SIP1 may be accomplished by placing the nucleic acid encoding SIP1, with or without a tag, under the control of an inducible or tissue specific promoter/regulatory sequence. Examples of tissue specific or inducible promoter/regulatory sequences which are useful for his purpose include, but are not limited to the MMTV LTR inducible promoter, and the SV40 late enhancer/promoter. In addition, promoters which are well known in the art which are induced in response to inducing agents such as metals, glucocorticoids, and the like, are also contemplated in the invention. Thus, it will be appreciated that the invention includes the use of any promoter/regulatory sequence, which is either known or unknown, and which is capable of driving expression of the desired protein encoded by a nucleic acid operably linked to the promoter/regulatory sequence.

Similarly, the invention includes a nucleic acid encoding a mammalian Gemin3 operably linked to a nucleic acid comprising a promoter/regulatory sequence such that the nucleic acid is preferably capable of directing expression of the protein encoded by the nucleic acid. Further, the present invention encompasses a nucleic acid encoding a chicken SMN operably linked to a nucleic acid comprising a promoter/regulatory sequence.

Expressing SIP1, Gemin3, or chicken SMN using a promoter/regulatory sequence allows the isolation of large amounts of recombinantly produced protein. Further, where the lack or decreased level of SIP1, Gemin3, or SMN expression causes a disease or condition associated with such expression, the expression of the protein driven by a promoter/regulatory sequence can provide useful therapeutics including, but not limited to, gene therapy whereby the protein is provided.

Vectors and Recombinant Cells

The invention also includes a vector comprising a nucleic acid encoding a eukaryotic SIP1, a mammalian Gemin3, or a chicken SMN. The incorporation of a desired nucleic acid into a vector and the choice of vectors is well-known in the art as described in, for example, Sambrook et al., supra, and Ausubel et al., supra. Further, the invention encompasses expression vectors and methods for the introduction of exogenous nucleic acid encoding SMN, SIP1, and Gemin3 into a cell with concomitant expression of the exogenous nucleic acid in the cell using such methods as those described in, for example, Sambrook et al. (1989, supra), and Ausubel et al. (1997, supra), and as disclosed elsewhere herein.

Expression of chicken SMN from a plasmid under the control of an inducible promoter/regulatory sequence allows the selective expression of SMN in a cell lacking endogenous SMN expression. As more fully set forth below, this cell provides a stable genetic system for the study of the role(s) of SMN in SMA and for the identification of SMA therapeutics to treat the effects of the lack of SMN in the cell.

Selection of any particular plasmid vector or other DNA vector is not a limiting factor in this invention and a wide plethora vectors is well-known in the art. Further, it is well within the skill of the artisan to choose particular promoter/regulatory sequences and operably link those promoter/regulatory sequences to a DNA sequence encoding a desired polypeptide. Such technology is well known in the art and is described, for example, in Sambrook, supra, and Ausubel, supra.

The invention includes also cells, viruses, proviruses, and the like, containing such vectors. Methods for producing cells comprising vectors and/or exogenous nucleic acids are well-known in the art. See, e.g., Sambrook et al., supra; Ausubel et al., supra.

The nucleic acids encoding SIP1, Gemin3, or chicken SMN can be cloned into various plasmid vectors. However, the present invention should not be construed to be limited to plasmids or to any particular vector. Instead, the present invention should be construed to encompass a wide plethora of vectors which are readily available and/or well-known in the art.

The invention also includes the expression of human SIP1 in non-human cells where it is not normally expressed or expression of SIP1-tagged fusion protein in cells where this fusion protein is not normally expressed. In a preferred embodiment, human SIP1, human SMN, and Gemin3 nucleic acid tagged with a nucleic acid expressing a tag polypeptide was used to transiently transfect a mammalian cell. Plasmid constructs containing SMN, SIP1, or Gemin3, or mutants, variants, derivatives and fragments thereof, were cloned into several vectors comprising a nucleic acid encoding a tag polypeptide (see, e.g., Nakielny and Dreyfuss, 1996, J. Cell. Biol. 134:1365–1373). The plasmids were introduced into the cell using standard methods (e.g., calcium phosphate, electroporation, and the like).

In another embodiment, human SIP1, or SMN were expressed in *Xenopus laevis* oocytes where the exogenous nucleic acid encoding the mammalian proteins were introduced into the oocytes by standard microinjection techniques. The present invention also encompasses expression of these exogenous nucleic acids in amphibian and other non-mammalian cells (e.g. yeast, insect, and avian cells) using methods well-known in the art such as those disclosed elsewhere herein. Thus, it is clear that the invention is not limited to any particular vector or to any particular method of introducing the exogenous nucleic acid encoding at least one of SMN, SIP1, and Gemin3 into a cell.

Expression of proteins of interest (e.g., SMN, SIP1, and Gemin3) in a cell, especially when the protein comprises a tag polypeptide, allows localization of the nucleic acid and/or the protein expressed therefrom within the cell under selected conditions such that the function(s) of the protein in the cell can be studied and identified.

One skilled in the art would appreciate, based upon the disclosure provided herein, that the invention also includes expression of SIP1, SMN, Gemin3, and the like, in prokaryotic cells (e.g., bacterial cells such as, for example, *E. coli*). Accordingly, the invention includes expression of the proteins of the invention in such cells as well.

In another preferred embodiment, SMN and SIP1 nucleic acids which expressed a tag polypeptide were also expressed in an in vitro transcription-translation system as well as in various E. coli strains to produce SMN or SIP1 protein variants or fragments fused to a tag polypeptide. Thus, the invention encompasses the expression of SMN, SIP1, and Gemin in a cell free system in addition to the expression of such proteins in a cell.

However, the invention should not be construed as being limited to these plasmid vectors, bacterial strains, or to these tag polypeptides. Further, the invention is not limited to calcium phosphate transfection or to HeLa cells as exemplified herein. Instead, the invention encompasses other expression vectors and methods for the introduction of exogenous DNA into cells with concomitant expression of the exogenous DNA in the cells such as those described, for example, in Sambrook et al. (1989, supra), and Ausubel et al. (1997, supra).

The invention also includes a cell comprising an isolated nucleic acid encoding at least one of an SIP1, and a Gemin3, or a vector comprising the same. The invention relates to a cell line as an in vitro model of SMA for the study of defects in SMN and its associated proteins in mRNA biogenesis and for the screening of compounds which affect SMN activity. The cell line of the invention is one which exhibits reduced expression of SMN when compared with normal levels of expression of SMN in cells or, alternatively, exhibits increased or altered expression of SMN when compared to the level of SMN expression in an otherwise identical cell which does not comprise the exogenous nucleic acid encoding SMN.

Cell lines can be created which exhibit enhanced expression of SMN; however, the preferred cell line of the invention is one in which the expression of SMN is reduced when compared with normal expression of SMN. The cell line of the invention should not be construed to be limited by the manner in which the expression of SMN is reduced when compared with normal expression of SMN, in that there are any number of ways to reduce expression of SMN in a cell.

In one embodiment, the cell line is mammalian cell comprising an expression vector comprising the human SMN cDNA constitutively expressed under the control of a high-level expression promoter/regulatory sequence. The cells may be transfected with constructs which comprise SMN cDNA in either a sense (i.e., sense cells) or an antisense orientation (i.e., antisense cells).

In another embodiment exemplified herein, the SMN modulating sequence was a plasmid wherein a sequence encoding a fusion protein comprising an HA tag polypeptide fused to the amino-terminus of chicken SMN (HA-cSMN) was expressed under a tetracycline repressible promoter. As the data disclosed herein demonstrate, removal of tetracycline allowed derepression of the promoter such that the HA-cSMN fusion was expressed in the cell (e.g., a chicken pre-B lymphoid DT40 cell although other cell lines can be used). Without wishing to be bound by theory, expression of the HA-cSMN caused expression of endogenous cSMN to be inhibited such that only expression of HA-SMN was detected in the cell. This apparent autoregulation of SMN expression, in turn, was lethal since the HA-cSMN did not replace endogenous wild type cSMN in the cell. Thus, one skilled in the art would appreciate, based upon the disclosure provided herein, that this cell, wherein a non-functional SMN replaces endogenous SMN, provides an important system analogous to a cell of an SMA patient in that the expression and, therefore, function of SMN are inhibited. Thus, this cell of the invention provides a useful system for the study of the role(s) of SMN in SMA and also for the identification of a compound useful for treatment of SMA which is characterized by the lack of endogenous expression of functional SMN.

One skilled in the art would further appreciate that selected forms of SMN may be introduced to the cell of the invention in order to study the effect of any mutant, derivative, and variant of SMN (e.g., fusion proteins comprising at least a portion of SMN and a tag polypeptide) in this system.

Additionally, in another embodiment, the invention relates to a cell line transfected with empty vector only (i.e., vector-only cells also referred to as "control cells").

Additionally, the use of ribozymes to effect a reduction in the expression of SMN in a cell line is contemplated, as is the use of any other means which would effect a reduction in expression of SMN in a cell line such as the use of knock-out and knock-in techniques as described elsewhere herein to affect SMN expression in a cell.

One skilled in the art would appreciate that an antisense cell line, for example, serves as an in vitro model for SMA in that these cells contain reduced amounts of SMN which is analogous to the diseased motor neurons of SMA patients. Further, these cells can also demonstrate altered morphologies and growth characteristics which are also similar to naturally occurring SMA cell pathology. However, the invention is not limited to a cell line expressing lower levels of SMN protein. Indeed, the invention also discloses methods of producing cell lines which exhibit increased levels of SMN, i.e., cells transfected with vector encoding SMN in a sense orientation under the control of a constitutive promoter/regulatory sequences which drives expression of SMN protein at higher levels than that found in cells which are not transfected or which are transfected with an empty vector only.

The invention is not limited to these cell lines or to any particular altered growth characteristics. Rather, other cell lines may be developed using the methods described herein to produce in vitro models of SMA. The identity of the cell line is not critical, except that the cell line must exhibit reduced expression of SMN protein which is analogous to the reduced level of expression exhibited by the cells of SMA patients. Alternatively, the invention encompasses production of a cell that exhibits an increased level of SMN protein expression compared with an otherwise identical cell which is not altered in any way. Examples of cell lines which may produce proteins encoded by a variety of expression vectors are found throughout the scientific literature. Also, the manner of providing the SMN modulating sequence to the cell is not critical except that, whether it is transcribed or translated, the nucleic acid must decrease or increase the levels of SMN available to participate in mRNA biogenesis compared with otherwise identical cells to which the SMN modulating sequence has not been provided.

One skilled in the art will appreciate, based on the disclosure provided herein, that the level of SMN protein in a cell can be decreased by reducing or inhibiting expression of the SMN gene. Thus, the level of SMN protein in a cell can be decreased using a molecule or compound that inhibits or reduces gene expression such as, for example, antisense molecules or ribozymes.

In a preferred embodiment, the SMN modulating sequence is a SMN antisense nucleic acid sequence which is expressed by a plasmid vector and used to transfect a mammalian cell thereby causing reduced endogenous expression of SMN protein in the cells. However, as stated previously herein, the invention should not be construed to be limited to inhibiting expression of SMN by transfection of cells with antisense molecules. Rather, the invention encompasses other methods known in the art for inhibiting expression of SMN protein in cells including, but not limited to, the use of ribozymes, and expression of a non-functional SMN under the control of, for example, an inducible promoter, and the like.

In another preferred embodiment, the transfected cells exhibit altered growth characteristics compared with cells which are either not transfected or which are transfected with an empty plasmid vector or with a vector containing SMN in a sense orientation.

The invention should not be construed as being limited to a cell exhibiting any particular altered growth characteristics or to a cell exhibiting any particular combination of altered characteristics. Rather, the invention includes other altered morphological or growth features and combinations thereof.

Further, the invention includes a recombinant cell comprising an antisense nucleic acid which cell is a useful model for the study of SMA and/or other conditions associated with or mediated by inhibition of mRNA biosynthesis and for elucidating the role(s) of SIP1, SMN, and/or Gemin3 in such processes. That is, the lack of expression of SMN in SMA patients, among other things, indicated that SMN was involved in SMA. Accordingly, a recombinant (i.e., transgenic) cell comprising an antisense nucleic acid complementary to SMN is a useful tool for the study of the mechanism(s) of action of SMN and its role(s) in the cell and for the identification of therapeutics that ameliorate the effect(s) of decreased levels of SMN expression.

One skilled in the art will appreciate that one way to decrease the levels of SMN mRNA and/or protein in a cell is to inhibit expression of the nucleic acid encoding the protein. Expression of SMN may be inhibited using, for example, antisense molecules, nucleic acids encoding non-functional SMN, and also by using ribozymes.

Antisense molecules and their use for inhibiting gene expression are well known in the art (see, e.g., Cohen, 1989, In: Oligodeoxyribonucleotides, Antisense Inhibitors of Gene Expression, CRC Press). Antisense nucleic acids are DNA or RNA molecules that are complementary, as that term is defined elsewhere herein, to at least a portion of a specific mRNA molecule (Weintraub, 1990, Scientific American 262:40). In the cell, antisense nucleic acids hybridize to the corresponding mRNA, forming a double-stranded molecule thereby inhibiting the translation of genes.

The use of antisense methods to inhibit the translation of genes is known in the art, and is described, for example, in Marcus-Sakura (988, Anal. Biochem. 172:289). Such antisense molecules may be provided to the cell via genetic expression using DNA encoding the antisense molecule as taught by Inoue, 1993, U.S. Pat. No. 5,190,931.

Alternatively, antisense molecules of the invention may be made synthetically and then provided to the cell. Antisense oligomers of between about 10 to about 30, and more preferably about 15 nucleotides, are preferred, since they are easily synthesized and introduced into a target cell. Synthetic antisense molecules contemplated by the invention include oligonucleotide derivatives known in the art which have improved biological activity compared to unmodified oligonucleotides (see Cohen, supra; Tullis, 1991, U.S. Pat. No. 5,023,243, incorporated by reference herein in its entirety).

Ribozymes and their use for inhibiting gene expression are also well known in the art (see, e.g., Cech et al., 1992, J. Biol. Chem. 267:17479–17482; Hampel et al., 1989, Biochemistry 28:4929–4933; Eckstein et al., International Publication No. WO 92/07065; Altman et al., U.S. Pat. No. 5,168,053, incorporated by reference herein in its entirety). Ribozymes are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech, 1988, J. Amer. Med. Assn. 260:3030). A major advantage of this approach is that, because they are sequence-specific, only mRNAs with particular sequences are inactivated.

There are two basic types of ribozymes, namely, tetrahymena-type (Hasselhoff, 1988, Nature 334:585) and hammerhead-type. Tetrahymena-type ribozymes recognize sequences which are four bases in length, while hammerhead-type ribozymes recognize base sequences 11–18 bases in length. The longer the sequence, the greater the likelihood that the sequence will occur exclusively in the target mRNA species. Consequently, hammerhead-type ribozymes are preferable to tetrahymena-type ribozymes for inactivating specific mRNA species, and 18-base recognition sequences are preferable to shorter recognition sequences which may occur randomly within various unrelated mRNA molecules.

Ribozymes useful for inhibiting the expression of SMN may be designed by incorporating target sequences into the basic ribozyme structure which are complementary to the mRNA sequence of the SMN encoded by SMN or having at least about 80% homology to chicken SMN (SEQ ID NO:9). Ribozymes targeting SMN may be synthesized using commercially available reagents (Applied Biosystems, Inc., Foster City, Calif.) or they may be genetically expressed from DNA encoding them.

The invention further includes a recombinant cell comprising an isolated nucleic acid encoding SMN, SIP1, or Gemin3. The transgenic cell may be transiently transfected with a plasmid encoding a portion of the nucleic acid encoding the protein of interest, .e.g., SMN. The nucleic acid need not be integrated into the cell genome nor does it need to be expressed in the cell. Moreover, the cell may be a prokaryotic or a eukaryotic cell and the invention should not be construed to be limited to any particular cell line or cell type. Such cells include, but are not limited to, Xenopus oocytes, chicken DT40 pre-B lymphoid cells, mammalian neuronal cells, E. coli, and the like.

When the cell is a eukaryotic cell, the cell may be any eukaryotic cell which, when the isolated nucleic acid of the invention is introduced therein, and the protein encoded by the desired gene is no longer expressed therefrom, a benefit is obtained. Such a benefit may include the fact that there has been provided a system in which lack of expression of the desired gene can be studied in vitro in the laboratory or in a mammal in which the cell resides, a system wherein cells comprising the introduced gene deletion can be used as research, diagnostic and therapeutic tools, and a system wherein animal models are generated which are useful for the development of new diagnostic and therapeutic tools for selected disease states in a mammal including, for example, SMA.

Alternatively, the invention includes a eukaryotic cell which, when the transgene of the invention is introduced therein, and the protein encoded by the desired gene is expressed therefrom where it was not previously present or expressed in the cell or where it is now expressed at a level or under circumstances different than that before the transgene was introduced, a benefit is obtained. Such a benefit may include the fact that there has been provided a system wherein the expression of the desired gene can be studied in vitro in the laboratory or in a mammal in which the cell resides, a system wherein cells comprising the introduced gene can be used as research, diagnostic and therapeutic tools, and a system wherein animal models are generated which are useful for the development of new diagnostic and therapeutic tools for selected disease states in a mammal (e.g., SMA).

The present invention is not limited to a cell line wherein expression of SMN is affected by introduction of an SMN modulating sequence to the cell. That is, one skilled in the art would appreciate, based on the disclosure provided herein, that there are other methods of inhibiting or reducing expression of a nucleic acid encoding a protein of interest (e.g., SMN, SIP1, and Gemin3). Thus, the invention further includes a cell line wherein the endogenous nucleic acid encoding the protein of interest has been removed, either in part or in its entirety, from the cell chromosome. Further, the invention includes a cell line where the endogenous nucleic acid encoding a protein has been removed where the cell further comprises a vector comprising a nucleic acid encoding the protein such that the expression of the protein in such cell can be controlled.

Therefore, the present invention includes a cell line wherein endogenous SMN expression has been ablated or significantly reduced and, instead, inducible SMN expression from a stably transfected plasmid has an been provided to the cell. One skilled in the art would appreciate, based upon the disclosure provided herein, that this stable genetic system provides an important tool for the study of effect of SMN expression in a cell, the role(s) of SMN and proteins associated therewith in cell processes, and for the identification of therapeutics useful for the treatment of SMA.

One of ordinary skill would appreciate, based upon the disclosure provided herein, that a targeting vector useful for inserting (i.e., a "knock-in" targeting vector) or deleting (i.e., a "knock-out" targeting vector) nucleic acid sequences of interest in a cell comprises at least two sequences homologous to two portions of the nucleic acid which is to be deleted or replaced. In the case of the knock-out targeting vector, the two sequences are homologous with sequences that flank the gene; that is, one sequence is homologous with a region at or near the 5' portion of the coding sequence of the nucleic acid encoding, for example, SMN, and the other sequence is further downstream from the first. One skilled in the art would appreciate, based upon the disclosure provided herein, that the present invention is not limited to any specific flanking nucleic acid sequences. Instead, the targeting vector may comprise two sequences which remove some or all (in the case of a "knock-in" vector) or which insert (in the case of a "knock-in" vector) a nucleic encoding SMN, or a fragment thereof, into a mammalian genome. The crucial feature of the targeting vector is that it comprise sufficient portions of two sequences located towards opposite, i.e., 5' and 3', ends of the SMN open reading frame (ORF) such as to allow homologous recombination to occur such that all or a portion of the nucleic acid encoding SMN is deleted from a location on a mammalian chromosome. Alternatively, one of ordinary skill in the art would appreciate that a knock-in targeting vector preferably comprises sequences homologous to and flanking a location on a mammalian chromosome which will be exchanged with the gene to be inserted (e.g., SMN, SIP1, and Gemin3). The design of transgenes and knock-in and knock-out targeting vectors is well-known in the art and is described in standard treatises such as Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York), and the like. The upstream and downstream portions flanking or within the chicken SMN coding region, or sequences flanking a region to be replaced with SMN by a knock-in vector, to be used in the targeting vector may be easily selected based upon known methods and following the teachings disclosed herein based on the disclosure provided herein including the nucleic and amino acid sequences of chicken SMN. Armed with these sequences, one of ordinary skill in the art would be able to construct the transgenes and knock-out vectors of the invention.

The invention further includes a knock-out targeting vector comprising a nucleic acid encoding a selectable marker such as, for example, a nucleic acid encoding the $neo^R$ gene thereby allowing the selection of a transgenic (i.e., recombinant) cell where the nucleic acid encoding SMN, or a portion thereof, has been deleted and replaced with the neomycin resistance gene thereby conferring on the recombinant cell the ability to grow in the presence of G418. However, the present invention should not be construed to be limited to neomycin resistance as a selectable marker. Rather, other selectable markers well-known in the art may be used in the knock-out targeting vector to allow selection of transgenic cells where the SMN gene has been deleted and/or inactivated and replaced by the nucleic acid encoding the selectable marker of choice. Methods of selecting and incorporating a selectable marker into a vector are well-known in the art and are described in, for example, Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

Antibodies

The invention also includes an antibody that specifically binds SIP1, or a fragment thereof. In one aspect, the antibody specifically binds a protein having the amino acid sequence of at least one of SEQ ID NO:2, SEQ ID NO:4, and SEQ ID NO:6, or a protein sharing about 20% homology with a protein having those sequences. In one embodiment disclosed herein, the antibody is a murine monoclonal antibody (e.g., 2S7, 2E17). However, the present invention is not limited to the particular antibodies exemplified herein nor is the invention limited to monoclonal antibodies. Rather, the invention encompasses polyclonal, monoclonal, synthetic antibodies, and the like. One skilled in the art would understand, based upon the disclosure provided herein, that the crucial feature of the antibody of the invention is that the antibody bind specifically with SIP1 in a manner similar to those antibodies disclosed herein. More specifically, the antibody of the invention recognizes SIP1 (e.g., human, Xenopus, and mouse), or a fragment thereof, on Western blots, in immunostaining of cells, and immunoprecipitates SIP1 using standard methods well-known in the art. Moreover, selected antibodies of the invention can inhibit mRNA splicing reaction and or the formation of the SMN-SIP1 complex in vivo and/or in vitro.

In addition, the invention includes an antibody that specifically binds with Gemin3, or a fragment thereof. In one aspect, the antibody specifically binds a protein having the amino acid sequence of SEQ ID NO:10. In another aspect, the antibody specifically binds with a protein sharing about 20% homology with a protein having the sequence SEQ ID NO:10, or a fragment thereof.

In one embodiment disclosed herein, the antibody is a murine monoclonal antibody (e.g., 11G9, 12H12). However, the present invention is not limited to the particular antibodies exemplified herein nor is the invention limited to monoclonal antibodies. Rather, the invention encompasses polyclonal, monoclonal, synthetic antibodies, and the like. One skilled in the art would understand, based upon the disclosure provided herein, that the crucial feature of the antibody of the invention is that it bind specifically with Gemin3 in a manner similar to the antibodies disclosed herein. More specifically, the antibody of the invention recognizes Gemin3, or a fragment thereof, on Western blots, in immunostaining of cells, and immunoprecipitates Gemin3 using standard methods well-known in the art.

In addition, the invention includes an antibody that specifically binds with SMN, or a fragment thereof. In one aspect, the antibody specifically binds a protein having the amino acid sequence of SEQ ID NO:8. In another aspect, the antibody specifically binds with a protein sharing about 20% homology with a protein having the sequence SEQ ID NO:8, or a fragment thereof.

In one embodiment disclosed herein, the antibody is a murine monoclonal antibody (e.g., 2B1) that specifically binds with chicken SMN. However, the present invention is not limited to the particular antibody exemplified herein nor is the invention limited to monoclonal antibodies. Rather, the invention encompasses polyclonal, monoclonal, synthetic antibodies, and the like. One skilled in the art would appreciate, based upon the disclosure provided herein, that the crucial feature of the antibody of the invention is that it bind specifically with SMN in a manner similar to those antibodies disclosed herein. More specifically, the antibody of the invention recognizes human SMN, or a fragment thereof, on Western blots, in immunostaining of cells, and immunoprecipitates SMN using standard methods well-known in the art. Further, preincubation of a splicing extract can also inhibit pre-mRNA splicing as disclosed elsewhere herein.

In addition, the invention includes an antibody to chicken SMN. Such antibody can be a monoclonal antibody, a monoclonal antibody, and the like, as previously described elsewhere herein.

The antibodies of the invention are useful for the diagnosis, assessment and treatment of SMA. These antibodies are also useful for elucidating the mechanism(s) for pre-mRNA splicing and the causal relationship between such processes and SMA. Further, the antibodies can be used to localize the relevant protein in a cell and to study the role(s) of the antigen recognized thereby in cell processes. Moreover, the antibodies can be used to detect and or measure the amount of protein present in a biological sample using well-known methods such as, but not limited to, Western blotting and enzyme-linked immunosorbent assay (ELISA). Moreover, the antibodies can be used to immunoprecipitate and/or immuno-affinity purify their cognate antigen as described elsewhere herein.

The generation of polyclonal antibodies is accomplished by inoculating the desired animal with the antigen and isolating antibodies which specifically bind the antigen therefrom using standard antibody production methods such as those described in, for example, Harlow et al. (1988, In: Antibodies, A Laboratory Manual, Cold Spring Harbor, N.Y.).

Monoclonal antibodies directed against full length or peptide fragments of a protein or peptide can be prepared using any well known monoclonal antibody preparation procedures, such as those described, for example, in Harlow et al., 1988, supra, and in Tuszynski et al. (1988, Blood, 72:109–115), and methods set forth elsewhere herein. Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

Nucleic acid encoding the monoclonal antibody obtained using the procedures described herein may be cloned and sequenced using technology which is available in the art, and is described, for example, in Wright et al. (1992, Critical Rev. Immunol. 12:125–168), and the references cited therein. Further, the antibody of the invention may be "humanized" using the technology described in Wright et al. (supra), and in the references cited therein, and in Gu et al. (1997, Thrombosis and Hematocyst 77:755–759).

To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al., supra.

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art and are described for example, in Wright et al. (supra).

Processes such as those described above, have been developed for the production of human antibodies using M13 bacteriophage display (Burton et al., 1994, Adv. Immunol. 57:191–280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al. (1991, J. Mol. Biol. 222:581–597). Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837–839; de Kruif et al. 1995, J. Mol. Biol. 248:97–105).

Compositions

The invention includes a composition comprising an isolated purified polypeptide comprising a eukaryotic SIP1 (e.g., human SIP1, frog SIP1, and yeast homolog Brr1). Preferably, the composition comprises a pharmaceutically acceptable carrier.

The invention includes a composition comprising an isolated purified SMN and a protein that specifically binds SMN (e.g., another SMN, SIP1, Gemin3, and various Sm proteins). The composition comprises the afore-mentioned proteins in any combination or permutation thereof. In one aspect, the composition further comprises a ribonucleic acid, such as, but not limited to, snRNA. The composition and the various permutations thereof, are an important tool for elucidating the precise structure of the mRNA splicing complex and the mechanism(s) involved in mRNA biosynthesis.

Also included in the invention is a composition comprising an antibody that specifically binds SMN. Preferably, the composition comprises a pharmaceutically-acceptable carrier. Such an antibody can be administered to a SMA patient since the data disclosed herein demonstrate that addition of anti-SMN mAb 2B1 increases aggregation of SMN which is deficient in SMA-afflicted humans since the SMN of SMA patients exhibits a decreased ability to aggregate with itself and with SIP1 indicating that such aggregation/binding is important and that compounds that increase such protein interactions should ameliorate or treat SMA by increasing such important interaction(s).

The invention further includes a composition comprising an isolated and purified SIP1 wherein the composition further comprises a pharmaceutically-acceptable carrier. Such a composition can be used to immunize a mammal in order to generate antibodies that specifically bind SIP1. Further, the composition can be used to administer SIP1 to a mammal whereby a condition mediated by or associated with a decreased amount of SIP1 is ameliorated or treated by the administration of the protein to the mammal.

The invention includes a composition comprising an isolated purified SMN and an isolated purified SIP1. Such a novel composition, which is disclosed elsewhere herein, is a useful tool for the study the interaction between SMN and SIP1 which is deficient in SMA patients thereby indicating that such protein-protein interaction is important in SMA. Further, the data disclosed herein demonstrate that SMN and SIP1 associate in vivo as part of a large molecular weight complex of about 800 kDa which complex is involved in mRNA biosynthesis. Thus, elucidation of the nature of the interactions between these proteins is important in the study of mRNA biosynthesis. In addition, the composition is useful in molecular protein modeling assays (e.g., chrystallography, biosensor analyses, and the like) to determine the precise configuration of the complex and further characterize the association kinetics of the complex and to aid in the elucidation of the precise mechanism(s) involved in mRNA biosynthesis.

The invention also includes a composition comprising an isolated purified SMN and an isolated purified Gemin3. The data disclosed herein demonstrate, for the first time, that SMN and Gemin3 associate in vivo as part of a high molecular weight complex. Thus, the study of the interaction between SMN and Gemin3 is important in elucidating SMA disease processes and in studying the role(s) and interaction (s) of these proteins with respect to mRNA biosynthesis. In addition, the composition is useful in molecular protein characterization assays (e.g., chrystallography, biosensor analyses, and the like) to determine the precise configuration of the proteins within the complex and to further characterize the association kinetics of the proteins and to aid in the elucidation of the precise mechanism(s) involved in mRNA biosynthesis.

For administration to of the above-mentioned compositions to a mammal, a polypeptide, or the nucleic acid encoding it, or both, can be suspended in any pharmaceutically acceptable carrier, for example, HEPES buffered saline at a pH of about 7.8. Other pharmaceutically acceptable carriers which are useful include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides.

Pharmaceutical compositions that are useful in the methods of the invention may be administered, prepared, packaged, and/or sold in formulations suitable for oral, rectal, vaginal, parenteral, topical, pulmonary, intranasal, buccal, ophthalmic, or another route of administration. Other contemplated formulations include projected nanoparticles, liposomal preparations, resealed erythrocytes containing the active ingredient, and immunologically-based formulations.

The compositions of the invention may be administered via numerous routes, including, but not limited to, oral, rectal, vaginal, parenteral, topical, pulmonary, intranasal, buccal, or ophthalmic administration routes. The route(s) of administration will be readily apparent to the skilled artisan and will depend upon any number of factors including the type and severity of the disease being treated, the type and age of the veterinary or human patient being treated, and the like.

Pharmaceutical compositions that are useful in the methods of the invention may be administered systemically in oral solid formulations, ophthalmic, suppository, aerosol, topical or other similar formulations. In addition to the compound such as heparan sulfate, or a biological equivalent thereof, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer SMN, alone or in combination with at least one protein specifically associated with SMN (e.g., another SMN, SIP1, Gemin3, and Sm proteins), and/or a nucleic acid encoding the same. In addition, any compound identified using any of the methods described herein can be formulated and administered to a mammal for treatment of SMA, and/or any disease or condition associated with a defect in mRNA biosynthesis.

The invention encompasses the preparation and use of pharmaceutical compositions comprising a compound useful for treatment of SMA identified using a method of the invention as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs. In addition, the administration of the compositions to birds is also contemplated.

Pharmaceutical compositions that are useful in the methods of the invention may be prepared, packaged, or sold in formulations suitable for oral, rectal, vaginal, parenteral, topical, pulmonary, intranasal, buccal, ophthalmic, intrathecal or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology. A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water. A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxy propyl methyl cellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methyl cellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or gel or cream or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject. Douche preparations may further comprise various additional ingredients including, but not limited to, antioxidants, antibiotics, antifungal agents, and preservatives.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrastemal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about I to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken, i.e., by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1–1.0% (w/w) solution or suspension of the active ingredient in an aqueous or oily liquid carrier. Such drops may further comprise buffering agents, salts, or one or more other of the additional ingredients described herein. Other ophthalmalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

Typically dosages of the compound of the invention which may be administered to an animal, preferably a human, range in amount from 1 microgram to about 100 grams per kilogram of body weight of the animal. While the precise dosage administered will vary depending upon any number of factors, including but not limited to, the type of animal and type of disease state being treated, the age of the animal and the route of administration. Preferably, the dosage of the compound will vary from about 1 milligram to about 10 grams per kilogram of body weight of the animal. More preferably, the dosage will vary from about 10 milligrams to about 1 gram per kilogram of body weight of the animal.

The compound may be administered to an animal as frequently as several times daily, or it may be administered less frequently, such as once a day, once a week, once every two weeks, once a month, or even lees frequently, such as once every several months or even once a year or less. The frequency of the dose will be readily apparent to the skilled artisan and will depend upon any number of factors, such as, but not limited to, the type and severity of the disease being treated, the type and age of the animal, etc.

Methods

The invention includes a method of stimulating snRNP assembly. The method comprises contacting an extract comprising snRNP components (e.g., SMN, SmB, SmD, snRNA, and the like) with SMN. This method takes advantage of the novel discovery that SMN mediates snRNP assembly and is a component of the complex involved in snRNP assembly.

The invention includes a method of identifying a compound which affects the level of SMN expression in a cell. The method comprises contacting a cell with a test compound and comparing the level of SMN expression in the cell with the level of SMN expression in an otherwise identical cell which is not contacted with the compound. A higher or lower level of SMN expression in the cell treated with the compound relative to the level of SMN expresison in an untreated cell indicates that the compound affects SMN expression.

One skilled in the art would appreciate, based upon the disclosure provided herein, that such compound would be useful to treat SMA since lack or decreased expression of SMN in a cell is causally linked to SMA. Thus, a compound that affects SMN expression would be an important potential SMA therapeutic.

The invention also includes a method of identifying compounds which affect the level of SMN in a cell wherein the cell comprises an SMN modulating sequence. The method comprises contacting the cell with a test compound and determining whether contact with the compound affects the expression of SMN in the cell compared with the level of SMN expression in an otherwise identical cell not contacted with the compound. Thus, the method allows identification of a compound that affects SMN expression.

A compound that increases the level of expression of SMN compared to the level of SMN expression in the untreated cell is potentially useful for the treatment of SMA which is characterized by decreased levels of SMN in afflicted individuals. Thus, the invention also includes a method of identifying a compound useful for the treatment of SMA. In one aspect, the method comprises contacting a cell comprising an antisense nucleic acid complementary to a nucleic acid encoding SMN with a test compound. Then, the level of expression of SMN in the cell contacted with the compound is compared, using methods such as Northern blotting and the like, to the level of expression of SMN in an otherwise identical cell not treated with the compound. A higher level of SMN expression in the cell contacted with the compound compared with the level in the cell not contacted with the compound indicates that the compound increased SMN expression in the cell. Since decreased SMN expression is associated with SMA, compounds that increase SMN expression are important potential therapeutics to treat the disease. Thus, a method of identifying a compound that affects the level of SMN expression in a cell is an important tool in the development of SMA therapeutics since the disease is associated and apparently mediated by a defect in the level of SMN expressed and/or the ability of the SMN produced in the cell to participate in mRNA biogenesis.

One skilled in the art would appreciate, based upon the disclosure provided herein, that until the present invention, there was no cell model of SMA available for in vitro testing of compounds or for studying the role of decreased or absent SMN expression in the SMA disease process. This cell line comprising an SMN antisense nucleic acid which exhibits decreased or absent SMN expression, is an important tool for the study of SMA and for the identification of compounds useful for treatment of the disease.

Further, the present invention includes method of identifying a compound useful for treatment of SMA wherein the cell comprised an SMN modulating sequence that decreases the expression of endogenous SMN. The SMN modulating sequence, i.e., a nucleic acid encoding SMN, further comprises a tag polypeptide that renders the exogenous SMN fusion protein non-functional. Because expression of the non-functional SMN inhibits expression of functional endogenous SMN, the cell provides a useful system wherein potential SMA therapeutics can be identified and evaluated. Thus, the invention includes a method wherein a cell comprising an SMN modulating sequence which inhibits expression of endogenous SMN is contacted with a test compound. The level of SMN expression in the cell contacted with the compound is compared to the level of SMN expression in an otherwise identical cell not contacted with the compound. A higher level of expression of SMN in the cell contacted with the compound compared with the level of expression of the otherwise identical but untreated cell is an indication that the compound is useful for treatement of SMA One skilled in the art would also appreciate, based upon the disclosure provided herein, that a cell exhibiting decreased or absent expression of SMN would demonstrate altered growth characteristics due to the deleterious effect(s) of decreased levels of SMN expression. Therefore, another cell line was produced wherein the expression of SMN can be controlled thereby allowing the cells to grow and divide so as to produce sufficient cells to permit testing of potential SMN candidate therapeutics. That is, once the cells reach sufficient numbers, the level of SMN can be selectively decreased or completely inhibited.

Therefore, the invention includes a method of identifying a compound useful for treating SMA comprising contacting a cell that has decreased or absent levels of SMN expression thereby mimicking the disease condition of SMA. The cell comprises a knock-out targeting vector such that at least one or both copies of the $SMN^7$ gene has/have been removed. The cell further comprises a copy of the SMN gene present within the cell on a vector (e.g., a plasmid) under the control of an inducible promoter (e.g., the tetracycline repressible promoter, and the like). The promoter is induced to allow the cells to grow and divide in culture. The promoter is turned off such that SMN is not expressed in the cell. The cell then becomes a test system which emulates the condition in the cells of patients afflicted with SMA. The cell is then used for the method of the invention in that the cell is contacted with a test compound. The ability of the compound to treat SMA can then be assessed by determining the growth characteristics of the cell. That is, a compound that mediates cell growth is a potential SMA therapeutic since the "block" in mRNA biosynthesis due to decreased SMN expression has been overcome as a result of the cell having been contacted with the compound. Further, the ability of the compound to increase SMN expression can also be assessed using methods of detecting SMN mRNA such as Northern blotting and RT-PCR assay, and the like.

In one embodiment, a chicken cell (i.e., DT40 which is a pre-B lymphoid cell) was used. This cell was used because it has a high degree of homologous recombination making it a useful cell line for use of a knock-out targeting vector which replaced the nucleic acid sequence encoding SMN through homologous recombination. However, the cell line need not exhibit high degree of homologous recombination; rather, the cell need only exhibit a degree of homologous recombination which allows successful use of a knock-out targeting vector which requires such recombination to remove all or part of the desired target SMN sequence.

Likewise, although DT40 cell comprises only a single SMN allele, the present invention is not limited to using cells comprising a single SMN allele. Rather, the invention includes using cells with at least one SMN allele for the production of knock-out cell lines.

The invention also includes a method of identifying an RNA splicing-modulating compound. As disclosed herein, splicing of RNA is diminished in the absence of SMN. Thus, the method of identifying an RNA splicing-modulating compound comprises incubating an in vitro pre-mRNA processing extract in the absence of SMN and in the presence or absence of a test compound, and comparing the level of splicing of RNA in the extract in the presence of the test compound with the level of splicing of the RNA in the absence of the test compound, wherein a higher or a lower level of RNA splicing in the extract in the presence of the test compound, compared with the level of RNA splicing in the extract in the absence of the test compound, is an indication that the test compound is an RNA splicing-modulating compound. In one preferred embodiment, the RNA splicing modulation is enhancement of RNA splicing. RNA splicing assays are disclosed herein as are methods of assessing splicing and include Northern blotting to identify the various processing species resulting from the various steps in pre-mRNA processing.

A compound that increases RNA-splicing is useful for increasing or decreasing such reactions in vitro. Such a compound would be useful for treating any disease or condition associated with or mediated by a decrease (e.g., SMA) or increase in RNA-splicing.

In one aspect, the invention includes a method of enhancing splicing of RNA. This method comprises incubating an in vitro pre-mRNA processing extract in the presence of SMN or a mutant or variant or a fragment thereof, thereby enhancing splicing of the RNA. As stated previously herein, a compound that enhances RNA splicing would be useful for methods requiring such RNA splicing. Further, such a compound would be a useful candidate therapeutic for treatment of a disease or condition associated with or mediated by a decrease in RNA splicing.

Further included in the invention is a method of assessing the presence or degree of SMA in a mammal. This method is useful to diagnose SMA and is also useful for assessing the progress of SMA or the efficacy of treatment in an SMA patient. The method comprises obtaining a biopsy comprising motor neurons from the mammal and assessing the number and morphology of gems in the motor neurons, wherein a lower number of gems in the motor neurons, compared with the number of gems in motor neurons obtained from an otherwise identical mammal which does not have SMA, is an indication that the mammal has SMA, and further wherein the absence of or the presence of a minimal number of gems in the mammal having SMA is directly related to the severity of the SMA in the mammal. Such a method would be useful in the diagnosis of SMA and in providing an assay for following up on the efficacy of SMA treatments. That is, the number of gems present in the neurons of SMA patients could be evaluated before, during and after treatment and the efficacy of the treatment could thus be assessed. Further, such a method allows a determination of the presence and/or the severity of the disease in a mammal.

Further, the invention includes a method of assessing the level of binding of SMN obtained from a mammal to determine the presence or degree of SMA in a mammal. The method takes advantage of the disclosure provided herein that the SMN of SMA patients exhibits decreased binding with SMN-associated protein (e.g., SMN, SIP1, and Gemin3). Thus, the method compares the level of binding of SMN obtained from a mammal (such as by obtaining SMN from cultured cells or a biopsy obtained from the mammal to an SMN-associated protein with the level of binding of SMNwt with an identical SMN-associated protein. Such binding assay can be performed in vitro using the methods disclosed herein (e.g., immobilized GST-SIP1 or GST-Gemin3 is contacted with the SMN obtained from the patient). The amount of SMN specifically bound to the immobilized protein is determined using, for example, antibodies that bind specifically to SMN, but other methods of assessing the amount of bound SMN are included in the invention, such as using radiolabeled proteins to detect the amount bound to the surface.

The invention includes a method of identifying a test compound that affects binding of SMN with a protein that specifically binds with SMN (i.e., an SMN-associated protein such as another SMN, SIP1, Gemin3, SmB, SmB', SmD1, SmD2, and SmD3, and the like). One skilled in the art, based upon the disclosure provided herein, would appreciate that the protein binding assays disclosed herein can be used to compare the binding of a labeled SMN-associated protein to immobilized SMN as described in the various embodiments exemplified herein. The method of immobilizing the target protein and the identity of the SMN-associated protein or the label present thereon are not crucial and any number of labels (e.g., tag polypeptide epitope, radiolabels, and the like), surfaces (e.g., glutathione-Sepharose, nickel columns), and SMN-associated proteins (e.g., SMN, or a mutant, variant or derivative thereof, SIP1, and Gemin3) can all be employed in the method.

As discussed previously elsewhere herein, a compound that affects binding of SMN with a protein that specifically binds with SMN is an important candidate SMA therapeutic since the binding of SMN to its associated proteins in SMA patients has been demonstrated, by the data disclosed herein, to be affected. Thus, the instant method provides an important assay in the development of useful compounds for the treatment of SMA.

The invention includes a method of assessing whether a test compound is useful for treatment of SMA. In essence the method identifies a test compound that increases binding of SMN with a protein that specifically binds with SMN (i.e., an SMN-associated protein such as another SMN, SIP1, Gemin3, SmB, SmB', SmD1, SmD2, and SmD3, and the like). One skilled in the art, based upon the disclosure provided herein, would appreciate that the protein binding assays disclosed herein can be used to compare the binding of a labeled SMN-associated protein to immobilized SMN as described in the various embodiments exemplified herein. Thus, the method comprises making a preparation comprising the test compound, a labeled protein that specifically binds with SMN (e.g., another SMN, SIP1, Gemin3, SmB, SmB', SmD1, SmD2, and SmD3, and the like), and a surface comprising at least a portion of SMN bound thereon. Preferably, the portion of SMN bound thereon comprises a portion of SMN that specifically binds the protein that specifically binds SMN used in the method.

One skilled in the art would appreciate, based upon the disclosure provided herein, that the method of immobilizing the target protein and the identity of the SMN-associated protein or the label present thereon are not crucial factors in the assay such that any number of labels (e.g., tag polypeptide epitope, radiolabels, and the like), surfaces (e.g., glutathione-Sepharose, nickel columns, immunoaffinity columns), and SMN-associated proteins (e.g., SMN, or a mutant, variant or derivative thereof, SIP1, and Gemin3) can all be employed in the method.

As discussed previously elsewhere herein, a compound that affects binding of SMN with a protein that specifically binds with SMN is an important candidate SMA therapeutic since the binding of SMN to its associated proteins in SMA patients has been demonstrated, by the data disclosed herein, to be affected. Thus, the instant method provides an important assay in the development of useful compounds for the treatment of SMA.

A method of enhancing splicing of mRNA. The method comprises incubating an in vitro pre-mRNA processing extract in the presence of SMN, or any mutant, derivative, variant, and fragment thereof, thereby enhancing splicing of the mRNA. Such extract is disclosed herein and/or it can be any crude nuclear cell extract capable pre-mRNA processing. Further, the substrate used in the method can be any substrate that when processed yields a distinguishable processing product such that the activity of the extract can be assessed. Such substrates include the pre-mRNA processing substrates disclosed elsewhere herein as well as others well known in the art.

The invention includes a method of identifying a compound that affects pre-mRNA splicing. The method comprises incubating an extract capable of pre-mRNA splicing such as those disclosed elsewhere hererin or other extracts well-known in the art, in the presence or absence of a test compound and comparing the level of pre-mRNA splicing in the in the absence and presence of the compound where a higher or lower level of pre-mRNA splicing in the treated extract is an indication that the test compound affects pre-mRNA splicing.

The invention further includes a method of identifying a test compound that is useful to treat SMA. The method comprises incubating an extract capable of pre-mRNA splicing in the presence or absence of a test compound and comparing the level of pre-mRNA splicing in the extract in the presence of the test compound with the level of splicing of pre-mRNA in the absence of the compound. A higher level of pre-mRNA splicing in the extract in the presence of the test compound compared with the level of pre-mRNA splicing in the extract not comprising the test compound, is an indication that the test compound is useful to treat SMA since decreased pre-mRNA splicing is associated with SMA as disclosed, for the first time, herein. Thus, a compound that increases pre-mRNA splicing, which is reduced in SMA, is a potential SMA therapeutic.

Similarly, a compound that increases snRNP assembly, pre-mRNA splicing, SMN binding with an SMN associated protein (e.g., another SMN, SIP1, Gemin3, and the like), is useful for treatment of SMA in that each of these activities are causally linked to SMA.

Thus, the invention includes a method of identifying a compound that affects snRNP assembly. The method comprises incubating an extract capable of snRNP assembly in the presence or absence of a test compound and comparing the level of snRNP assembly in the extract comprising the test compound to the level of snRNP assembly in the extract which does not contain the compound. A higher or lower level of snRNP assembly in the extract containing the compound to the extract not containing the compound is an indication that the test compound affects snRNP assembly.

The invention further includes a method of identifying a test compound that is useful to treat SMA. The method comprises incubating an extract capable of snRNP assembly in the presence or absence of a test compound and comparing the level of snRNP assembly in the extract containing the test compound with the level of snRNP assembly in the extract without the compound. A higher level of snRNP assembly in the extract containing the test compound compared with the level of snRNP assembly in the extract without it is an indication that the test compound is useful to treat SMA.

The invention includes a method of assessing the presence or degree of SMA in a mammal. The method comprises comparing the level of binding of SMN obtained from the mammal to a protein that specifically binds with SMN with the level of binding of SMN wild type to an identical protein that specifically binds with SMN, wherein a lower level of binding of the SMN from the mammal to the protein that specifically binds with SMN compared with the level of binding of SMN wild type with the identical protein that specifically binds with SMN is an indication of the presence or degree of SMA in a mammal. This is because, as the data disclosed herein demonstrate, the SMN of SMA patients exhibits decreased binding to itself, and to other SMN associated proteins, than wild type SMN.

The invention further includes a method of identifying a compound that affects SMN expression in a cell. The method comprises contacting as cell as described herein with a test compound and comparing the level of SMN expression in the cell with the level of SMN expression in an otherwise identical cell which is not contacted with the test compound. A higher or lower level of SMN expression in the cell contacted with the test compound compared with the level of SMN expression in the otherwise identical cell which is not contacted with the compound is an indication that the test compound affects SMN expression in a cell, thereby identifying a compound that affects SMN expression in a cell.

Also included in the invention is a method of identifying a compound that is useful to treat SMA. This method comprises contacting a cell as described herein with a test compound and comparing the level of SMN expression in the cell with the level of SMN expression in an otherwise identical cell which is not contacted with the test compound. A higher level of SMN expression in the cell contacted with the test compound compared with the level of SMN expression in the therwise identical cell which is not contacted with the test compound is an indication that the test compound increases SMN expression in a cell, thereby identifying a compound that is useful to treat SMA.

In addition, there is included in the invention a method of identifying a compound useful for the treatment of SMA. This method comprises contacting a cells as described herein with a test compound and comparing the level of growth of the cell with the level of growth of an otherwise identical cell which is not contacted with the test compound. A higher level of growth of the cell contacted with the test compound compared with the level of growth of the cell which is not contacted with the compound is an indication that the compound is useful to treat SMA.

Definitions

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

As used herein, the term "adjacent" is used to refer to nucleotide sequences which are directly attached to one another, having no intervening nucleotides. By way of example, the pentanucleotide 5'-AAAAA-3' is adjacent the trinucleotide 5'-TTT-3' when the two are connected thus: 5'-AAAAATTT-3' or 5'-TTTAAAAA-3', but not when the two are connected thus: 5'-AAAAACTTT-3'.

As used herein, amino acids are represented by the full name thereof, by the three letter code corresponding thereto, or by the one-letter code corresponding thereto, as indicated in the following table:

| Full Name | Three-Letter Code | One-Letter Code |
| --- | --- | --- |
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

As used herein, to "alleviate" SMA means reducing the severity of the symptoms of the disease or disorder. This includes, but is not limited to, increasing the level of binding of SMN with SIP1, Gemin3, and/or another SMN in a patient afflicted with SMA compared with the level of binding of SMN to these proteins in the patient prior to or in the absence of the method of treatment.

By the term "altered growth characteristics," as the term is used herein, is meant any variation in growth exhibited by a cell compared with an otherwise identical cell into which the SMN modulating sequence has not been introduced.

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

By "biological activity," as the term is used herein, is meant that the protein has the ability to interact with its associated protein(s) and effectuate its normal function(s) within the cell. In a preferred embodiment, the SMN linked to BSA retains its biological activity in that the protein retained its ability to bind avidly to SIP1, as well as the ability to bind to the Sm proteins, and mediate formation of the Sm core domain and to participate in its role in mRNA biogenesis. Further, biological activity as it refers to any form or fragment of SMN, SIP1, and Gemin3 means that the protein has the ability to bind to SMN, SIP1, and/or Gemin3 and/or to participate in mRNA biogenesis.

By "complementary to a portion or all of the nucleic acid encoding SMN" is meant a sequence of nucleic acid which does not encode SMN protein. Rather, the sequence which is being expressed in the cells is identical to the non-coding strand of the nucleic acid encoding SMN and thus, does not encode SMN protein.

The terms "complementary" and "antisense" as used herein, are not entirely synonymous. "Antisense" refers particularly to the nucleic acid sequence of the non-coding strand of a double stranded DNA molecule encoding a protein, or to a sequence which is substantially homologous to the non-coding strand. "Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of an mRNA molecule also consists of the nucleotide residues of the mRNA molecule which are matched with an anticodon region of a transfer RNA molecule during translation of the mRNA molecule or which encode a stop codon. The coding region may thus include nucleotide residues corresponding to amino acid residues which are not present in the mature protein encoded by the mRNA molecule (e.g., amino acid residues in a protein export signal sequence).

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., retroviruses, adenoviruses, and adeno-associated viruses) that incorporate the recombinant polynucleotide.

A first region of an oligonucleotide "flanks" a second region of the oligonucleotide if the two regions are adjacent one another or if the two regions are separated by no more than about 1000 nucleotide residues, and preferably no more than about 100 nucleotide residues.

As used herein, the term "fragment" as applied to a nucleic acid, may ordinarily be at least about 20 nucleotides in length, typically, at least about 100 nucleotides, more typically, from about 100 to about 500 nucleotides, typically at least about forty contiguous amino acids, preferably at least about 500 to about 1,000 nucleotides, even more preferably at least about 1,000 nucleotides to about 2,000 nucleotides, yet even more preferably at least about 2,000 to about 3,500, and most preferably, the nucleic acid fragment will be greater than about 3,500 nucleotides in length.

As used herein, the term "fragment" as applied to a polypeptide, may ordinarily be at least about seven contiguous amino acids, typically, at least about fifteen contiguous amino acids, more typically, at least about thirty contiguous amino acids, typically at least about forty contiguous amino acids, preferably at least about fifty amino acids, even more preferably at least about sixty amino acids and most preferably, the peptide fragment will be greater than about sixty contiguous amino acids in length.

As applied to a protein, a "fragment" of SIP1 is about 50 amino acids in length. More preferably, the fragment of a SIP1 is about 100 amino acids, even more preferably, at least about 200, yet more preferably, at least about 300, even more preferably, at least about 400, yet more preferably, at least about 500, and more preferably, at least about 600 amino acids in length.

A "genomic DNA" is a DNA strand which has a nucleotide sequence homologous with a gene. By way of example, both a fragment of a chromosome and a cDNA derived by reverse transcription of a mammalian mRNA are genomic DNAs. "Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3' ATTGCC5' and 3' TATGGC share 50% homology.

As used herein, "homology" is used synonymously with "identity." In addition, when the term "homology" is used herein to refer to the nucleic acids and proteins, it should be construed to be applied to homology at both the nucleic acid and the amino acid levels.

Percent identity of one polynucleotide or polypeptide with respect to another polynucleotide or polypeptide may be determined using any available algorithm, such as the BLAST program as described in Altschul et al. (1990, J. Mol. Biol. 215:403–410).

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

"Mutants," "derivatives," and "variants" of the peptides of the invention (or of the DNA encoding the same) are peptides which may be altered in one or more amino acids (or in one or more base pairs) such that the peptide (or DNA) is not identical to the sequences recited herein, but has the same property as the peptides disclosed herein, in that the peptide has the property of binding to SMN, SIP1, Sm proteins and/or functioning in mRNA biogenesis.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region. Preferably, when the nucleic acid encoding the desired protein further comprises a promoter/regulatory sequence, the promoter/regulatory is positioned at the 5' end of the desired protein coding sequence such that it drives expression of the desired protein in a cell. Together, the nucleic acid encoding the desired protein and its promoter/regulatory sequence comprise a "transgene."

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a cell substantially only if the cell is a cell of the tissue type corresponding to the promoter.

The term "expression of a nucleic acid" as used herein means the synthesis of the protein product encoded by the nucleic acid.

The use of the term "DNA encoding" should be construed to include the DNA sequence which encodes the desired protein and any necessary 5' or 3' untranslated regions accompanying the actual coding sequence.

By the term "positioned at the 5' end" as used herein, is meant that the promoter/regulatory sequence is covalently bound to the 5' end of the nucleic acid whose expression it regulates, at a position sufficiently close to the 5' start site of transcription of the nucleic acid so as to drive expression thereof.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

A "portion" of a polynucleotide means at least at least about twenty sequential nucleotide residues of the polynucleotide. It is understood that a portion of a polynucleotide may include every nucleotide residue of the polynucleotide.

A "polyadenylation sequence" is a polynucleotide sequence which directs the addition of a poly A tail onto a transcribed messenger RNA sequence.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides. The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T." Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe" refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

By the term "promoter/regulatory sequence" is meant a DNA sequence which is required for expression of a nucleic acid operably linked to the promoter/regulatory sequence. In some instances, the promoter/regulatory sequence may function in a tissue specific manner, in that, the promoter/regulatory sequence is only capable of driving expression in a cell of a particular tissue type. In some instances, this sequence may be the core promoter sequence and in other instances, this sequence may also include an enhancer sequence and other regulatory elements which are required for expression in a tissue-specific manner.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A "recombinant polypeptide" is one which is produced upon expression of a recombinant polynucleotide.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

As used herein, the term "reporter gene" means a gene, the expression of which can be detected using a known method. By way of example, the *Escherichia coli* lacZ gene may be used as a reporter gene in a medium because expression of the lacZ gene can be detected using known methods by adding the chromogenic substrate o-nitrophenyl-β-galactoside to the medium (Gerhardt et al., eds., 1994, Methods for General and Molecular Bacteriology, American Society for Microbiology, Washington, D.C., p. 574).

A "restriction site" is a portion of a double-stranded nucleic acid which is recognized by a restriction endonuclease.

A portion of a double-stranded nucleic acid is "recognized" by a restriction endonuclease if the endonuclease is capable of cleaving both strands of the nucleic acid at the portion when the nucleic acid and the endonuclease are contacted.

By the term "specifically binds," as used herein, is meant a compound, e.g., a protein, a nucleic acid, an antibody, and the like, which recognizes and binds a specific molecule, but does not substantially recognize or bind other molecules in a sample.

A first oligonucleotide anneals with a second oligonucleotide "with high stringency" if the two oligonucleotides anneal under conditions whereby only oligonucleotides which are at least about 75%, and preferably at least about 90% or at least about 95%, complementary anneal with one another. The stringency of conditions used to anneal two oligonucleotides is a function of, among other factors, temperature, ionic strength of the annealing medium, the incubation period, the length of the oligonucleotides, the G-C content of the oligonucleotides, and the expected degree of non-homology between the two oligonucleotides, if known. Methods of adjusting the stringency of annealing conditions are known (see, e.g., Sambrook et al., 1989, Molecular Cloning: A Laboratory Manual, Cold Spring Harbor Laboratory, New York).

By the term "SMN modulating sequence," as used herein, is meant a nucleic acid sequence which when introduced into a cell affects the level of expression of SMN protein. Such altered level of SMN expression may, but the invention does not require, cause the cell to exhibit altered growth characteristics or altered formation of snRNP complexes compared with an otherwise identical cell into which the nucleic acid sequence has not been introduced. The nucleic acid sequence may be a DNA molecule in either a sense or antisense orientation with respect to the SMN coding sequence or the nucleic acid sequence may be, inter alia, a ribozyme specific for human SMN.

As used herein, the term "substantially pure" describes a compound, e.g., a nucleic acid, protein or polypeptide, which has been separated from components which naturally accompany it. Typically, a compound is substantially pure when at least about 10%, preferably at least about 20%, more preferably at least about 50%, still more preferably at least about 75%, even more preferably at least about 90%, and most preferably at least about 99% of the total material (by volume, by wet or dry weight, or by mole percent or mole fraction) in a sample is the compound of interest.

Purity can be measured by any appropriate method, e.g., by column chromatography, gel electrophoresis or HPLC analysis.

A compound, e.g., a nucleic acid, a protein or polypeptide is also "substantially purified" when it is essentially free of naturally associated components or when it is separated from the native contaminants which accompany it in its natural state. Thus, a "substantially pure" preparation of a nucleic acid, as used herein, refers to a nucleic acid sequence which has been purified from the sequences which flank it in a naturally occurring state, e.g., a DNA fragment which has been removed from the sequences which are normally adjacent to the fragment in a genome in which it naturally occurs.

Similarly, a "substantially pure" preparation of a protein or a polypeptide, as used herein, refers to a protein or polypeptide which has been purified from components with which it is normally associated in its naturally occurring state. A substantially pure peptide can be purified by following known procedures for protein purification, wherein an immunological, enzymatic or other assay is used to monitor purification at each stage in the procedure. Protein purification methods are well known in the art, and are described, for example in Deutscher et al. (1990, In: *Guide to Protein Purification*, Harcourt Brace Jovanovich, San Diego).

As used herein, the term "transgene" means an exogenous nucleic acid sequence which exogenous nucleic acid is encoded by a transgenic cell or mammal.

By the term "exogenous nucleic acid" is meant that the nucleic acid has been introduced into a cell or an animal using technology which has been developed for the purpose of facilitating the introduction of a nucleic acid into a cell or an animal.

A cell that comprises a transgene is referred to as a "recombinant cell." Such a cell may be a eukaryotic cell or a prokaryotic cell. A gene which is expressed in a recombinant cell wherein the gene comprises a recombinant polynucleotide, produces a "recombinant polypeptide."

By the term "SMN-associated protein" as used herein, is meant a protein that specifically binds with SMN. Such proteins include another SMN, an SIP1, a Gemin3, and various Sm proteins (e.g., SmB, SmB', SmD1, SmD2, and SmD3).

By "tag" polypeptide is meant any protein which, when linked by a peptide bond to a protein of interest, may be used to localize the protein, to purify it from a cell extract, to immobilize it for use in binding assays, or to otherwise study its biological properties and/or function. A chimeric (i.e., fusion) protein containing a "tag" epitope can be immobilized on a resin which binds the tag. Such tag epitopes and resins which specifically bind them are well known in the art and include, for example, tag epitopes comprising a plurality of sequential histidine residues (His6), which allows isolation of a chimeric protein comprising such an epitope on nickel-nitrilotriacetic acid-agarose, a hemagglutinin (HA) tag epitope allowing a chimeric protein comprising such an epitope to bind with an anti-HA-monoclonal antibody affinity matrix, a myc tag epitope allowing a chimeric protein comprising such an epitope to bind with an anti-myc-monoclonal antibody affinity matrix, a glutathione-S-transferase tag epitope, and a maltose binding protein (MBP) tag epitope, which can induce binding between a protein comprising such an epitope and a glutathione- or maltose-Sepharose column, respectively. Production of proteins comprising such tag epitopes is well known in the art and is described in standard treatises such as Sambrook et al., 1989, and Ausubel et al., supra. Likewise, antibodies to the tag epitope (e.g., anti-HA, anti-myc antibody 9E10, and the like) allow detection and localization of the fusion protein in, for example, Western blots, ELISA assays, and immunostaining of cells.

As used herein, to "treat" means reducing the frequency with which symptoms of SMA are experienced by a patient.

By the term "vector" as used herein, is meant any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector which is suitable as a delivery vehicle for delivery of the SMN, SIP1, Gemin3, or all of the aforementioned, protein or a nucleic acid encoding SMN, SIP1, Gemin3 to the patient, or the vector may be a non-viral vector which is suitable for the same purpose. Examples of viral and non-viral vectors for delivery of DNA to cells and tissues are well known in the art and are described, for example, in Ma et al. (1997, Proc. Natl. Acad. Sci. U.S.A. 94:12744–12746). Examples of viral vectors include, but are not limited to, a recombinant vaccinia virus, a recombinant adenovirus, a recombinant retrovirus, a recombinant adeno-associated virus, a recombinant avian pox virus, and the like (Cranage et al., 1986, EMBO J. 5:3057–3063; International Patent Application No. WO94/17810, published Aug. 18, 1994; International Patent Application No. WO94/23744, published Oct. 27, 1994). Examples of non-viral vectors include, but are not limited to, liposomes, polyamine derivatives of DNA, and the like.

A "knock-out targeting vector," as the term is used herein, means a vector comprising two nucleic acid sequences each of which is complementary to a nucleic acid regions flanking a target sequence of interest which is to be deleted and/or replaced by another nucleic acid sequence. The two nucleic acid sequences therefore flank the target sequence which is to be removed by the process of homologous recombination.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLE 1

Association of SMN With its Associated Protein SIP1 in a Complex With Spliceosomal snRNA Proteins The experiments presented in this example may be summarized as follows.

Previously, molecular characterization of the protein product of the SMN gene that causes SMA, i.e., SMN, led to the discovery of a novel nuclear structure, called gem, in which SMN is concentrated (Liu and Dreyfuss, 1996, EMBO J. 15:3555–3565). Gems appear by size, number, and proximity to be related to coiled bodies, another subnuclear structure of unknown function. Previous studies suggested that gems, like coiled bodies, are involved in RNA metabolism, and, consistent with this, SMN was found to interact with several RNA binding proteins and possibly also with RNA directly (Liu and Dreyfuss, 1996, supra; Liu et al., 1996, Cold Spring Harbor Symp. Quant. Biol. 61:689–697). However, the specific function of SMN remained obscure. The experiments described herein demonstrate that in a yeast two-hybrid screen using SMN as the bait, a novel protein, SIP1, has been identified. SIP1 forms a stable complex with SMN in vivo and in vitro, and it co-localizes with SMN in gems and in the cytoplasm.

The data disclosed herein indicate that SMN and SIP1 function as a complex in vivo. For instance, the interaction of SMN and SIP1 in vitro is resistant to 1 M NaCl, suggesting that the proteins interact avidly. The 300 kDa complex that contains SMN and SIP1 is stable even in 4 M urea. Also, SMN and SIP1 can be coimmunoprecipitated with specific monoclonal antibodies. Further, a yeast two-hybrid screen using SIP1 as the bait under high stringency conditions (15 mM 3-aminotriazole) isolated from a human library only SMN clones. In addition, SMN and SIP1 co-localize in gems, suggesting that these two proteins function together.

Immunopurification of the 300 kDa complex demonstrated that it contains, besides SMN and SIP1, spliceosomal snRNP core proteins including B/B', D, E, F, and G, the snRNP-specific protein U1 A, and several other unidentified proteins. Furthermore, the data disclosed herein demonstrate that SMN interacts directly with several spliceosomal snRNP core Sm proteins, including B/B', D1–3, and E. These data suggest that the SMN-SIP1 complex plays an important role in spliceosomal snRNP biogenesis and/or function. Although BLAST searches of sequence databases with the SIP1 protein did not identify significant homology to any other proteins, visual inspection suggested a limited but significant homology between SIP1 and the yeast protein Brr1 (Noble and Guthrie, 1996, Genetics 143:67–80; 1996, EMBO J. 15:4368–4379). The sequence alignment of human SIP1 and yeast Brr1 is shown in FIG. 1. Brr1 has been shown to be involved in snRNP biogenesis in *Saccharomyces cerevisiae*; deletion of Brr1 causes destabilization of newly synthesized spliceosomal U2 snRNA, and Brr1 interacts genetically with the yeast Sm D1 protein (Noble and Guthrie, 1996, EMBO J. 15:4368–4379). Searching the yeast genome sequence for possible SMN homologs has not identified any proteins with significant similarity to SMN.

SMN, because it can interact with SIP1 and with the spliceosomal snRNP Sm proteins via different domains, can potentially serve as the key bridging component to bring together the various components of the complex. It is therefore particularly interesting to note that many SMA patients have deletions or point mutations encompassing exons 6 and 7 of SMN, the region shown herein to be involved in binding of SMN to the Sm proteins. Further, several missense mutations in the region of SMN corresponding to the P2 peptide have recently been described (Hahnen et al., 1996, Hum. Mol. Genet. 4:1927–1933), and it will be of interest to determine if such mutations exhibit altered binding to the Sm proteins.

The Materials and Methods used in the experiments presented in this example are now described.

Yeast Two-hybrid Screening

The human HeLa cDNA library, yeast strains, and yeast plasmids pGBT9, pGADGH, pVA3, and pTD1 were obtained from Clontech Laboratories, Inc. (Palo Alto, Calif.). The manipulation of yeast and the library screening were carried out according to the conditions suggested by the manufacturer. In brief, the coding region of SMN was cloned into the pGBT9 vector. The *S. cerevisiae* HF7c reporter strain was first transformed with the pGBT9-derived SMN construct and, subsequently, with the HeLa cDNA library.

Approximately $6 \times 10^6$ transformants were seeded on eight 150 mm plates containing synthetic medium lacking histidine, leucine, and tryptophan. His$^+$ colonies were grown on synthetic medium plates lacking leucine and tryptophan and were then assayed for β-galactosidase activity by filter assay as described by the manufacturer. Of 6 million transformants screened, 146 were His$^+$ LacZ$^+$ colonies. These positive colonies fell into ten groups. One of these groups had ten independent cDNA clones that all encoded identical sequences of SIP1. The library plasmid was recovered from these clones into the *Escherichia coli* HB101 strain. True positive clones were confirmed by their ability to transactivate HIS3 and LacZ reporters when cotransforming HF7c with pGBT9 containing SMN.

Production of Monoclonal Antibodies to SIP1

Anti-SIP1 antibodies 2S7 and 2K9 were prepared by immunizing Balb/C mice with His6-tag SMN chimeric protein purified from nickel chelation chromatography using a Novagen (Madison, Wis.) His-Bind buffer kit. Hybridoma production and screening and ascites fluid production were performed as previously described (Choi and Dreyfuss, 1984, J. Cell. Biol. 99:1997–2004).

Production of Proteins in vitro

The $^{35}$[S]-labeled proteins were produced by an in vitro transcriptiontranslation reaction (Promega Biotech, Madison, Wis.) in the presence of $^{35}$[S]-methionine (Amersham, Arlington Heights, Ill.). His6-SMN fusion protein was expressed from a pET bacterial expression system in the *E. coli* strain BL21(DE3)pLysS and purified using nickel chelation chromatography using the same kit as described above. GST-SMN fusion protein was expressed from a GST expression vector pGEX-5X-3 (Pharmacia Biotech, Piscataway, N.J.) in the *E. coli* strain BL21 and purified using glutathione-Sepharose provided by Pharmacia Biotech according to the manufacturer's protocol.

In vitro Protein-binding Assays

Purified GST or GST fusion protein (2 micrograms) was incubated with $10^6$ cpm of the in vitro translated protein product and 25 μl of glutathione-Sepharose beads in 500 μl of binding buffer (50 mM Tris-HCl [pH 7.5], 2 mM EDTA, 0.1% NP40, 2 micrograms per milliliter leupeptin and pepstatin A, and 0.5% aprotinin) containing different salt (NaCl) concentrations. Following incubation for 30 minutes at 4° C., the resin was pelleted, washed with binding buffer, and the bound fraction was eluted by boiling in SDS-PAGE sample buffer. The proteins were analyzed by SDS-PAGE, and they were visualized by fluorography. For the binding experiments described in FIG. 5, 200 to 300 ng of GST or GST-SMN fusion protein was bound to 30 μl of glutathione-Sepharose beads dissolved in phosphate buffered saline (pH 7.4) and incubated with $^{35}$[S]-labeled in vitro translated protein (approximately $1 \times 10^5$ to $2 \times 10^5$ cpm/assay) for 30 minutes at 4° C. The beads were subsequently washed six times with phosphate buffered saline/350 mM NaCl (pH 7.4), and the bound protein fraction was eluted by boiling in SDS-PAGE sample buffer.

Cell Culture and Treatments

HeLa cells and NIH 3T3 cells were cultured in Dulbecco's modified Eagle's medium (DMEM; GIBCO BRL, Gaithersburg, Md.) supplemented with 10% fetal calf serum (FCS, GIBCO BRL). Low temperature incubations were carried out as follows. HeLa cells were shifted to 32° C. and incubated for 24 hours prior to fixation and permeabilization of the cells for immunostaining. For actinomycin D treatment, HeLa cells were incubated with 5 micrograms per milliliter of actinomycin D for 3 hours before fixation for immunostaining. For in vivo labeling with $^{35}$[S]methionine, 50% confluent HeLa cells growing in 100 mm plates were incubated with 10 microCuries per milliliter of $^{35}$[S] methionine in DMEM without methionine and supplemented with 10% FCS overnight before homogenization for immunoprecipitation.

Immunoprecipitation and Immunoblotting

Immunoprecipitation of in vitro translated SIP1 protein was carried out in the presence of 1% Empigen BB buffer as previously described by Choi and Dreyfuss (1984, J. Cell. Biol. 99:1997–2004). Immunoprecipitation and purification of the SMN complex was carried out using total HeLa cell lysate in the presence of 0.5% TritonX-100 as previously described in Piñol-Roma et al. (1988, Genes Dev. 2:215–227). For immunoblotting, proteins were resolved on a 12.5% SDS-polyacrylamide gel and transferred to nitrocellulose membrane (Schleicher and Schuell, Inc., Keene, N.H.) using a BioTrans Model B Transblot apparatus (Gelman Sciences, Ann Arbor, Mich.) according to the instructions of the manufacturer. Filters were incubated in blotting solution (phosphate buffered saline, 5% nonfat milk) for at least 1 hour at room temperature, rinsed with cold phosphate buffered saline, and then incubated with primary antibody for at least 1 hour at room temperature. The filters were washed three times in phosphate buffered saline containing 0.1% Tween 20, and bound antibodies were detected using the peroxidase-conjugated goat anti-mouse IgG plus IgM (Jackson ImmunoResearch Laboratories, Bar Harbor, Me.). The protein bands were visualized using an ECL Western blotting detection kit (Amersham, Arlington Heights, Ill.) after washing the filters three times in phosphate buffered saline containing 0.1% Tween 20.

Immunofluorescence Microscopy

Immunofluorescence microscopy was carried out essentially as previously described (Choi and Dreyfuss, 1984, J. Cell. Biol. 99:1997–2004) with the following modifications. Primary monoclonal antibodies 2B1 and 1816 were diluted 1:1000 in phosphate buffered saline containing 3% bovine serum albumin (BSA). The incubation with the first and second antibody was at room temperature for 1 hour. In double-label immunofluorescence experiments, a mixture of primary or secondary antibodies was incubated at the same time. Laser confocal fluorescence microscopy was performed with a Leica TCS 4D (Germany) confocal microscope. The antibodies used for these experiments were as follows: antibody against p80-coilin; monoclonal antibody Pd and rabbit polyserum R288; antibody against fibrillarin; human autoimmune antibody 1881. Rabbit polyclonal antibody against SMN was raised against exon 7 for SMN protein by Quality Controlled Biochemicals, Hopkinton, Mass. and the polyclonal antibodies were affinity purified.

HeLa Cell Fractionation and Chromatography

HeLa cells were fractionated according to the methods described by Dignam et al. (1983, Nuc. Acids Res. 11: 1475–1489). Fractionation of the nuclear or cytoplasmic S100 fraction was carried out as follows. The nuclear fraction (200 µl of approximately 20 milligrams per milliliter protein) in buffer D (20 mM Tris-HCl [pH 7.4], 0.1 mM EDTA, 1 mM DTT, 20% glycerol, 500 mM KCl) or S100 fraction (400 microliters of approximately 20 milligrams per milliliter protein) in buffer F (20 mM Tris-HCl [pH 7.4], 0.1 mM EDTA, 1 mM DTT, 10% glycerol, 500 mM KCl) was loaded onto a TSK-GEL G3000-SW glass column (TosoHaas, Montgomeryville, Pa.). The column was then washed with buffer A (20 mM Tris-HCl [pH 7.4], 200 mM NaCl, 2.5% glycerol) with or without 4 M urea at 0.25 m/min flow rate. Fractions (0.5 ml) were collected, and 15 µl of each fraction was analyzed on an SDS-PAGE.

Far Western Analyses Using $^{35}$[S]SMN

In vitro purified snRNP proteins were analyzed by SDS-PAGE, and the proteins were then transferred onto a nitrocellulose membrane as described previously herein. The nitrocellulose membrane was incubated in blotting solution (phosphate buffered saline, 5% nonfat milk) for at least 1 hour at room temperature, rinsed with cold phosphate buffered saline, and then incubated with in vitro translated $^{35}$[S]methionine-labeled SMN (2×10$^6$ cpm) for 2 hours at room temperature. The nitrocellulose membrane was washed three times in phosphate buffered saline containing 0.05% NP40, and bound SMN was detected by exposing the membrane to X-ray film.

Preparation of BSA-peptides Conjugates

BSA-peptide conjugates were prepared as described in Fischer et al. (1995, Cell 82:475–483). In brief, peptides starting with a N-terminal cysteine and consisting of amino acids 13–44 (CRRGAGQSDDSDIWDDTALIKAY-DKAVS) and 240–267 (CEDDEALGSMLISWYMSGY-HTGYYLGLKQ) of human SMN or the HIV-1 Rev NES (CLPPLERLTL) (Fischer et al., 1995, supra) were cross-linked to BSA using sulfo-SMCC (Pierce Chemical Co., Rockford, Ill.) as a cross-linker. The cross-linked BSA conjugates were separated from unreacted peptides and cross-linking reagent by dialysis against phosphate buffered saline (pH 7.4) and the conjugates were concentrated using a Centricon30 concentrator (Amicon, Bedford, Mass.).

The Results of the experiments presented in this example are now described.

SIP1, a Novel SMN-interacting Protein

Using SMN as a bait in a yeast two-hybrid screen of a HeLa cDNA library, ten independent partial cDNA clones with insert sizes ranging from about 1 kb to about 1.3 kb were isolated, all of which contained the same open reading frame. The longest of these clones, designated 7–10, contained an insert of approximately 1.3 kb that was completely sequenced. Using the BLAST search program to search the GenBank database, an EST (clone #Z64761) (Cross et al., 1994, Nature Genet. 6:236–244) that is identical to the 5' end of clone 7-10 and which extends further upstream was identified. Conceptional translation of this cDNA revealed another potential methionine 24 amino acids upstream of the first methionine of clone 7-10. Immediately upstream of this methionine was a stop codon. It is not clear which methionine is the actual initiation methionine for the full-length cDNA SIP1. The 3'-untranslated region is very AU-rich and contains a putative polyadenylation site AAUAAA. Thus, this is likely the full-length cDNA clone for the novel protein of the invention that interacts with SMN and which has been term SIP1. The predicted amino acid sequence of SIP1, along with the sequence of the *Xenopus laevis* homolog that is also disclosed herein, is presented in FIG. 1. The nucleic acid sequence of SIP1 disclosed herein encodes a protein of approximately 279 amino acids (including the potential 24 amino acids predicted by the EST sequence) with a calculated molecular mass of 32 kDa and pI of 5.3.

To examine the interaction of SIP1 with SMN and to characterize SIP1 further, monoclonal antibodies to the SIP1 protein were generated by immunizing mice with purified recombinant 6His-tag SIP1 (starting with the second methionine) chimeric polypeptide. Two of these monoclonals, 2E17 and 2S7, were further characterized in detail and were shown to react with SIP1 specifically by both immunoprecipitation and by Western blotting. Monoclonal antibody 2E17 reacted with a protein of similar size in Xenopus; thus, using this as the primary antibody, a Xenopus oocyte cDNA library was screened and the Xenopus homolog of SIP1 was isolated. The predicted amino acid sequence of Xenopus SIP1 is presented in FIG. 1. Interestingly, all of the eight clones obtained by screening the Xenopus library with 2E17 monoclonal antibody lack the first 24 amino acids that are potentially found in the human EST clone but also missing from the clones obtained by screening the human library with this antibody. Xenopus SIP1 is highly similar to human SIP1, the two proteins being approximately 90% homologous in amino acid sequence (see FIG. 1). BLAST searches did not reveal significant homology to any other protein in the databases. However, a yeast protein, termed Brr1, appears to have significant similarity to SIP1 by visual sequence comparison (FIG. 1).

SIP1 Interacts With SMN in vitro and in vivo

The yeast two-hybrid results were confirmed by assessing the interaction of SIP1 with SMN both in vitro and in vivo in HeLa. For the in vitro binding assay, SMN was expressed as a chimeric fusion protein with a glutathione S-transferase (GST) tag polypeptide. SIP1 was produced and labeled with $^{35}$[S]methionine by in vitro transcription and translation in rabbit reticulocyte lysate. GST or GST-SMN proteins immobilized on glutathione-Sepharose were incubated with $^{35}$[S]-labeled SIP1 protein. Following washing at various salt concentrations (200 mM to 1 M), proteins that were still bound to either GST or GST-SMN immobilized on glutathione-Sepharose were dissociated by boiling in SDS-containing sample buffer, and the eluted material was analyzed by SDS-PAGE. As shown in FIG. 2A, full-length SIP1 bound specifically to immobilized GST-SMN but not to immobilized GST alone. This binding appeared to be very avid because it was not disrupted at 1 M NaCl.

Figure 2B:
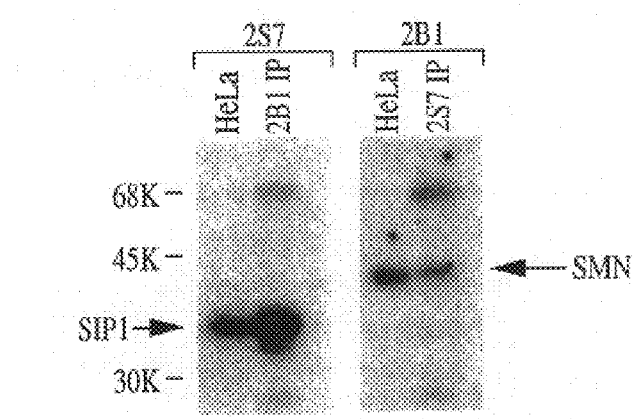
FIG. 2B is an image of a Western blot depicting the fact that SIP1 and SMN are associated with each other in vivo. Immunoprecipitation of total HeLa extract was accomplished using monoclonal antibodies 2B1 directed against SMN and 2S7 directed against SIP1. The immunoprecipitated proteins were analyzed by Western blot using 2S7 and 2B1 (lane 2B1 IP and lane 2S7 IP, respectively).

Immunoprecipitation experiments were performed to examine if SMN and SIP1 interact in vivo. Anti-SMN monoclonal antibody 2B1 (Liu and Dreyfuss, 1996, EMBO J. 15:3555–3565) was used to immunoprecipitate SMN from total HeLa cell extract. The immunoprecipitates were then resolved by SDS-PAGE and immunoblotted with monoclonal antibody 2S7 specific for SIP1. As shown in FIG. 2B (lane designated "2B1 IP"), 2S7 readily detected SIP1 in the 2B1 immunoprecipitates, indicating that SIP1 was coimmunoprecipitated with SMN. In a reciprocal experiment, the SMN protein was also coimmunoprecipitated by the anti-SIP1 monoclonal antibody 2S7 (FIG. 2B, lane designated "2S7 IP"). These results were confirmed using other monoclonal antibodies to SMN and to SIP1. As shown in FIG. 2, there was no crossreactivity between the anti-SMN and anti-SIP1 monoclonal antibodies. These results indicate that SMN and SIP1 are associated in vivo and that they can be coimmunoprecipitated by either anti-SMN or anti-SIP1 monoclonal antibodies.

Figure 2C:
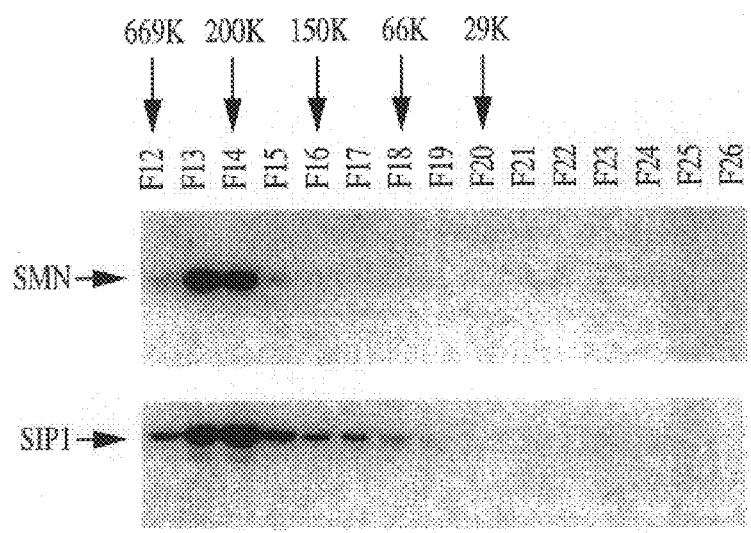
FIG. 2C is an image of a Western blot depicting the formation of a complex by SIP1 and SMN of approximately 300 kDa or more in the cytoplasm. HeLa cytoplasmic S100 extract was fractionated on the basis of protein size on a G3000-SW column. The fractions were analyzed by SDS-PAGE, and the SMN and SIP1 proteins were detected by Western blot.

Gel filtration experiments further confirmed the existence in vivo of a complex containing both SIP1 and SMN. HeLa nuclear and cytoplasmic S100 extracts were fractionated on a high performance gel filtration column, TSK-GEL G3000-SW, and each fraction was subjected to SDS-PAGE. SMN and SIP1 were detected in the column fractions by immunoblotting with specific monoclonal antibodies. FIG. 2C depicts the results of the cytoplasmic fractionation experiments. SMN and SIP1 comigrate, as a peak of approximately 300 kDa, suggesting that they are part of a large macromolecular complex. The observed size suggests that this complex contains either multiple copies of the SMN and SIP1 proteins and/or additional components. This complex is very stable, as it resists dissociation by 4 M urea, and it is observed in both the nuclear and cytoplasmic fractions.

SIP1 and SMN Co-localize in Gems in the Nucleus and in the Cytoplasm

Figure 3A:
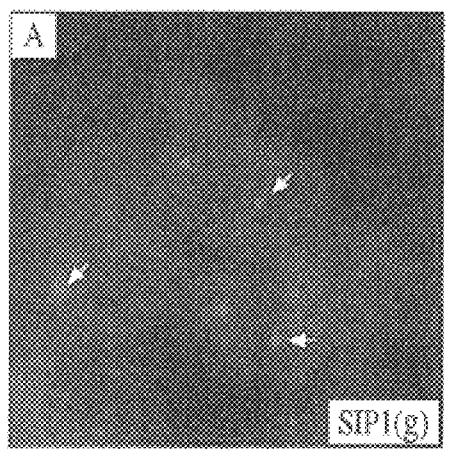
FIG. 3A is an image depicting the co-localization of SIP1 and SMN in gems. The image depicts a light microscopic image of an indirect immunofluorescence experiment on HeLa cells using monoclonal antibody 2S7 against the SIP1 protein. Note the general cytoplasmic staining and discrete nuclear structures.
Figure 3B:
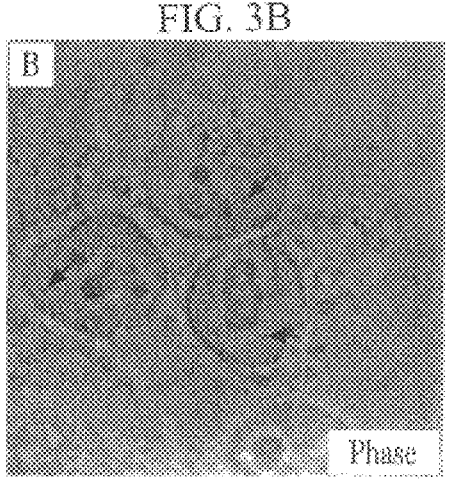
FIG. 3B is an image depicting a contrast image of the same field as depicted in FIG. 3A.

Indirect immunofluorescence microscopy using the anti-SIP1 monoclonal antibodies 2E17 and 2S7 was performed on HeLa cells to determine the cellular localization of SIP1. FIGS. 3A and 3B illustrate that SIP1 is found throughout the cytoplasm and by also displays intense staining of prominent discrete bodies in the nucleus as assessed using standard light microscopy immunofluorescence. This pattern is very similar to that seen for the SMN protein (Liu and Dreyfuss, 1996, EMBO J. 15:3555–3565), except that the nucleoplasmic staining of SIP1 is somewhat stronger than that seen for SMN.

Figure 3C:
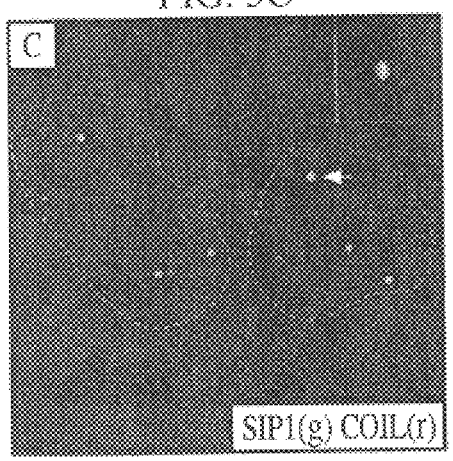
FIG. 3C is an image depicting superimposed laser confocal images of double-label immunofluorescence microscopy experiments using antibodies against SIP1 (green) and antibodies against coiled body marker p80-coilin (red). Co-localization of red and green results in a yellow color.
Figure 3D:
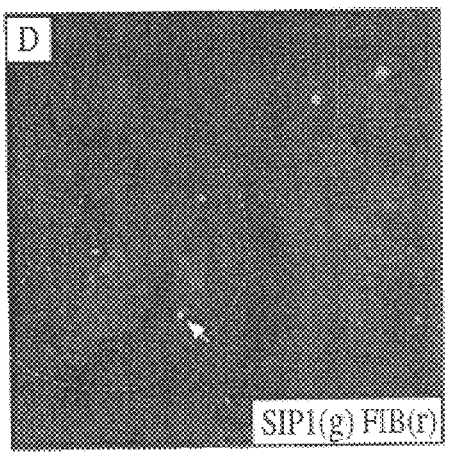
FIG. 3D is an image depicting superimposed laser confocal images of double-label immunofluorescence microscopy experiments using antibodies against SIP1 (green) and antibodies against coiled body marker, fibrillarin (red). Co-localization of red and green results in a yellow color.
Figure 3E:
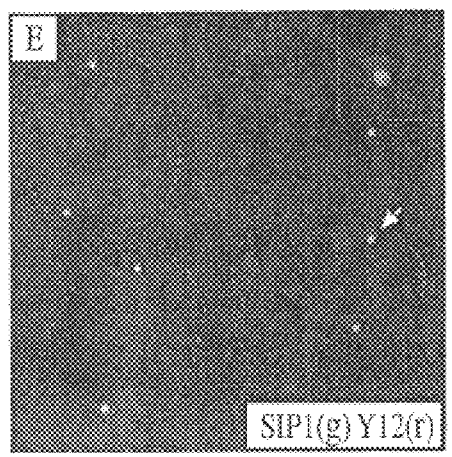
FIG. 3E is an image depicting superimposed laser confocal images of double-label immunofluorescence microscopy experiments using antibodies against SIP1 (green) and anti-Sm antibody Y12 (red). Co-localization of green and red results in a yellow color.
Figure 3F:
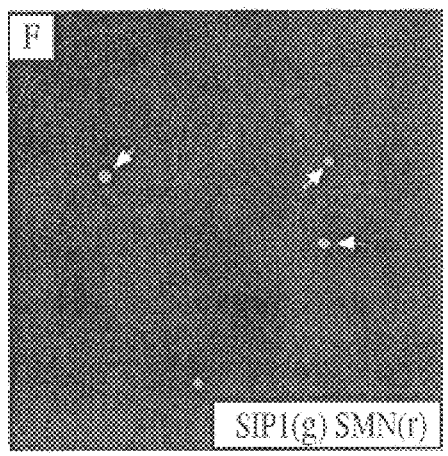
FIG. 3F is an image depicting the superimposed confocal images of double-label immunofluorescence microscopy experiments using monoclonal antibody against SIP1 (green) and a rabbit polyclonal antiserum raised against exon 7 of the human SMN protein (red). Co-localization of green and red results in a yellow color.

In order to determine if the intensely staining nuclear structures are gems or coiled bodies, double-label laser confocal immunofluorescence experiments were performed using antibodies against p80-coilin (FIG. 3C), fibrillarin (FIG. 3D), snRNP proteins (Y12, FIG. 3E) found in coiled bodies, and SMN (FIG. 3F) found in gems. FIGS. 3C, 3D, and 3E depict the results of the double labeling experiments using the anti-coiled body antibodies and the anti-SIP1 2S7. The nuclear structures that contain SIP1 were clearly different from coiled bodies, but the two bodies were, in most cases, closely associated. However, the staining with the anti-SIP1 monoclonal antibody 2S7 and a rabbit serum raised against exon 7 of SMN demonstrate that SMN and SIP1 completely colocalized in gems (FIG. 3F). The weak signal in the cytoplasm makes it impossible to determine whether SMN and SIP1 also completely colocalized in the cytoplasm. However, co-localization of SMN and SIP1 is very likely because of the tight association of SMN with SIP1 described herein. The co-localization of SMN with SIP1 further supports the conclusion that these two proteins exist as a complex in the cell. SIP1 is thus the second constituent of gems described thus far.

The SMN-SIP1 Complex Contains Spliceosomal snRNP Proteins

Figure 4A:
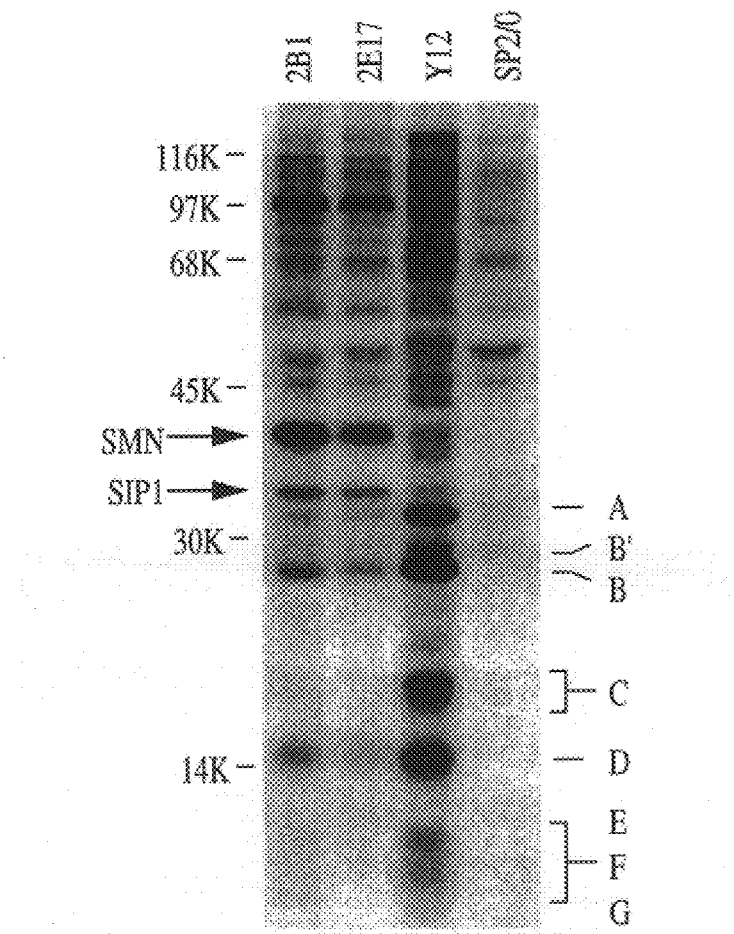
FIG. 4A is an image of an SDS-PAGE gel depicting the coimmunoprecipitation of SMN- and SIP1-containing complexes with monoclonal antibodies against SMN and SIP1. The image demonstrates that the coimmunoprecipitation of SMN and SIP1 obtained from $^{35}$[S]methionine-labeled HeLa total cell extract by monoclonal antibodies 2B1 (lane 2B1) and 2E17 (lane 2E17) resulted in a similar protein pattern. Control anti-Sm monoclonal antibody Y12 immunoprecipitated Sm proteins and some snRNP-specific proteins (lane Y12), while negative control antibody SP2/0 illustrates the background of immunoprecipitation (lane SP2/0).
Figure 4B:
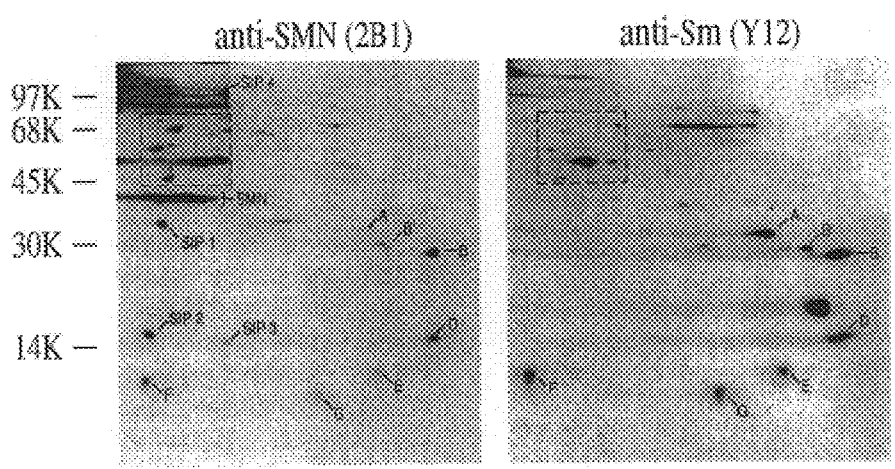
FIG. 4B is an image depicting a two-dimensional non-equilibrium pH gradient gel electrophoresis (NEPHGE) analysis of SMN-immunoprecipitated complex (2B1 panel) and the Sm-immunoprecipitated complexes containing core Sm proteins and some U snRNP-specific proteins from HeLa nuclear fractions immunoprecipitated with monoclonal antibody Y12 (Y12 panel). The dashed boxes indicate background proteins that were also detected in control SP2/0 immunoprecipitations.

The observation that SMN and SIP1 are associated in a large (approximately 300 kDa) complex prompted experiments to identify any possible additional components in this complex. In order to identify additional components of the SMN-SIP1 complex, immunoprecipitations using anti-SMN and anti-SIP1 monoclonal antibodies on $^{35}$[S]-labeled HeLa cell lysates were performed, and the immunoprecipitated proteins were then analyzed by SDS-PAGE. As shown in FIG. 4A, similar patterns were obtained using anti-SMN and anti-SIP1 monoclonal antibodies to immunoprecipitate complex-associated proteins. Several proteins were specifically coimmunopurified by anti-SMN and anti-SIP1 antibodies. Besides SMN and SIP1 proteins, there was a prominent doublet at approximately 97 kDa, the group of proteins of approximately 28 kDa, and the group of proteins of approximately 15 kDa. This protein complex was quite stable, since it was resistant to SDS/Triton X100/deoxycholate-containing buffer and to a high salt wash (500 mM NaCl). As a reference for these immunoprecipitations (and for reasons discussed herein), a lane was included in the gel demonstrating an immunoprecipitation with the monoclonal antibody Y12 (FIG. 4A, lane designated "Y12") which antibody is directed against the Sm proteins common to spliceosomal snRNPs (Lerner and Steitz, 1979, Proc. Natl. Acad. Sci. USA 71:5495–5499; Lerner et al., 1981, Proc. Natl. Acad. Sci. USA 78:2737–2741). To characterize this complex further, the protein samples were subjected to high resolution, two-dimensional nonequilibrium pH gradient gel electrophoresis (NEPHGE). FIG. 4B depicts the major proteins that were specifically found in the anti-SMN (2B1) isolated complex but not in control (SP2/0) immunoprecipitations. The major proteins selectively immunoprecipitated by anti-SMN (2B1) are labeled as SIP1, SIP2, SIP3, and SIP4. Further, the group of basic, low molecular weight proteins in the anti-SMN immunoprecipitate exhibited the same pattern as some of the Sm proteins in immunopurified snRNPs. For direct comparison, anti-Sm (Y12) immunoprecipitate from HeLa nuclear fractions was analyzed in parallel, and U1A, Sm B/B', D1–3, E, F, and G proteins of snRNPs migrated in exactly the same pattern as those proteins in the SMN-SIP1 complex. Immunoblotting experiments using monoclonal antibodies against the U1 snRNP-specific protein U1A and the anti-Sm monoclonal antibody Y12 confirmed that these proteins were indeed the spliceosomal snRNP proteins. Immunoprecipitations using Y12 starting with either total HeLa extract or that derived from nucleoplasm also demonstrated that SMN and SIP1 could be detected in Y12 immunoprecipitates by immunoblotting. The immunoprecipitations shown in FIG. 4 were carried out using nucleoplasm as the starting material. Similar results, although with considerably higher background, were obtained using cytoplasmic or whole cell extracts, and predigestion with RNases did not reduce the signal. This suggests the SMN-SIP1-Sm protein complexes can be found both in the nucleus and in the cytoplasm. It has not been definitively determined whether the immunoprecipitated SMN-SIP1-Sm complexes contain snRNAs since, e.g., the RNase resistance of the complexes may simply be due to the fact that the RNAs were not accessible to RNase. However, experiments described herein demonstrate that SMN and SIP1 immunoprecipitated labeled snRNAs suggesting the complex may contain such ribonucleic acids.

The SMN Protein Interacts With Sm B/B', Sm D, and Sm E Proteins Directly

Most of the snRNAs in snRNP complexes are resistant to RNase digestion and this, therefore, makes it difficult to determine if the SMN-SIP1-snRNP protein complexes result from protein-protein or protein-RNA interactions. To investigate whether SMN interacts with snRNP proteins directly, in vitro translated $^{35}$[S]methionine-labeled SMN was used in a far-Western blot assay to probe SDS-PAGE-resolved proteins of purified snRNPs. The protein composition of purified snRNPs is shown in FIG. 5 (lane designated "snRNPs"). The result of probing these proteins with $^{35}$[S]SMN (FIG. 5, lane designated "$^{35}$[S]SMN") indicates that SMN specifically and directly bound to SmB/B' and also to one or several of the Sm D proteins. When the same experiments were performed with in vitro translated SIP1, no specific binding of SIP1 to snRNP proteins was detected although, in the same assay, SIP1 bound strongly to recombinant SMN protein. These findings suggest that the association of SMN with snRNPs occurs via direct protein-protein interaction between SMN and Sm B/B' and one or more of the D group proteins although the possibility that some component in the rabbit reticulocyte lysate mediates this interaction cannot be excluded.

The binding in solution of SMN to other Sm proteins was examined using in vitro translated and $^{35}$[S]-labeled Sm proteins B, D1, D2, D3, E, F, and G which were tested for their ability to bind to recombinant GST-SMN fusion protein immobilized on glutathione-Sepharose beads pursuant to the methods described by Lehmeier et al. (1994, Proc. Natl. Acad. Sci. USA 91:12317–12321), Herrmann et al. (1995, EMBO J. 14:2076–2088) and Raker et al. (1996, EMBO J. 15:2256–2269). As shown in FIG. 5B, all Sm proteins, except for F and G, bound efficiently to immobilized GST-SMN, whereas there was no detectable binding to immobilized GST alone. Moreover, similar experiments failed to detect any interaction between the Sm proteins and SIP1.

SMN Contains Two Distinct Binding Sites for the Sm Proteins and for SIP1

The data disclosed previously herein demonstrate that SMN interacts with both SIP1 and with several of the Sm proteins; therefore, it was determined whether binding of SMN to Sm proteins and to SIP1 was mutually exclusive or whether SMN could bind both Sm proteins and SIP1 at the same time possibly via two different binding sites on a single SMN protein. Truncated peptides were synthesized corresponding to the two most conserved regions of SMN (determined by comparing the sequence of the human SMN with that of Xenopus SMN) located at the N terminus (at amino acids 13–44) and at the C terminus (at amino acids 240–267), under the assumption that these highly conserved domains may be involved in important protein-protein interactions. These regions are also conserved in several candidate SMN orthologs identified in divergent organisms (Talbot et al., 1997, Hum. Mol. Genet. 3:497–500). These truncated peptides were then coupled to BSA (termed BSA-P1 and BSAP2, respectively) and used as competitors in the binding assays for SMN to SIP1 and for SMN to the Sm proteins. Without competitors, SIP1 and Sm B bound to GST-SMN (FIG. 5C) as noted previously herein. However, BSA-P1 completely abolished binding of SIP1 to SMN, while the binding of Sm B was unaffected (FIG. 5C). In contrast, BSA-P2 strongly inhibited the binding of SMN to Sm B but had no effect on the binding of SMN to SIP1. BSA coupled to HIV-1 Rev NES protein (BSA-Ctrl) (Fischer et al., 1995), was used as a non-specific control and this chimeric protein had no effect on the binding of SMN to either SIP1 or to Sm B protein (FIG. 5C). Additional experiments demonstrated that the corresponding domains of SMN are alone sufficient for binding to SIP1 and Sm B, and similar results were obtained for the other Sm proteins. Thus, the data disclosed herein define two independent binding sites for SIP1 and the Sm proteins on a single SMN protein molecule. SMN may therefore serve as a critical bridge between the Sm proteins and SIP1 and SMN may nucleate the formation of the SMN-SIP1-Sm complex.

EXAMPLE 2

The SMN-SIP1 Complex has an Essential Role in Spliceosomal snRNP Biogenesis

The experiments presented in this example may be summarized as follows.

The data disclosed herein and obtained from micro injection studies in *Xenopus laevis* oocytes provides important insight into the function of the SMA disease gene product, SMN, and its associated protein SIP1. SMN and SIP1 are tightly associated as two subunits of a heteromeric protein complex, and both are found in the oocyte cytoplasm. Further, as previously disclosed herein, SMN and SIP1 are associated in a complex of approximately 300 kDa which also contains the Sm proteins, and several additional spliceosomal snRNP-specific proteins. The present experiments demonstrate that the SMN-SIP1 complex has an essential role in spliceosomal snRNP biogenesis. Several lines of evidence lead to this conclusion. First, SMN and SIP1 are specifically associated in the cytoplasm with U1 and U5 snRNAs but not with nuclear snRNPs and not with other RNAs tested so far. Thus, they are not components of mature nuclear snRNPs but rather are associated with them only during the cytoplasmic phase of their biogenesis. Second, anti-SIP1 antibodies strongly interfere with the assembly of the Sm core domain of spliceosomal U snRNAs and with their nuclear import. Third, anti-SMN antibodies, surprisingly, have the opposite effect and stimulate the assembly of Sm proteins onto the Sm site of spliceosomal U snRNAs. In addition, as previously set forth herein, two distinct domains in SMN, P1 and P2, have been identified that mediate its interaction with SIP1 and with several Sm proteins, respectively, in addition to its capacity to interact with itself (Liu and Dreyfuss, 1996, EMBO J. 15:3555–3565).

The Materials and Methods used in the experiments presented in this example are now described.

Western Blot Analysis

Oocytes were defolliculated and dissected into nuclear and cytoplasmic fractions (see methods set forth herein). The nuclei were precipitated in ethanol. The cytoplasmic fractions were homogenized in 5:1 buffer pursuant to Fischer et al., 1993, EMBO J. 12:573–583) and centrifuged for 15 minutes at 4° C. The supernatant was transferred to a new test tube and precipitated with four volumes of acetone. After centrifugation, the pellets were washed with 70% ethanol, were dried, and the pellets were resuspended in SDS-PAGE sample buffer. For Western blot analysis, proteins were separated on an SDS-polyacrylamide gel (12.5%) and subsequently transferred to a nitrocellulose membrane (Schleicher and Schuell, Inc., Keene, N.H.) using a Bio-Trans Model B Transblot apparatus (Gelman Science) according to the manufacturer's instructions.

After protein transfer, the blotting membrane was incubated in blotting solution (phosphate-buffered saline, phosphate buffered saline, containing 5% nonfat milk) for 1 hour at room temperature, rinsed with phosphate buffered saline, and then incubated in blotting solution with the primary antibody for 1 hour at room temperature. The membrane was then washed three times with phosphate buffered saline containing 0.1% Tween 20, and bound antibodies were detected using peroxidase-conjugated goat antimouse IgG plus IgM (Jackson ImmunoResearch Laboratories, Bar Harbor, Me.). The proteins were visualized using an ECL Western blotting detection kit (Amersham, Arlington Heights, Ill.) after washing the membrane three times in phosphate buffered saline containing 0.1% Tween 20.

Oocyte Injections

Oocyte injections were carried out as described in Fischer et al. (1993, supra). In brief, oocytes were incubated for 3 hours in modified Barth's solution containing 0.2% collagenase type II (Sigma Chemical Co., St. Louis, Mo.). Defolliculated stage V and VI oocytes were collected and usually used on the same day for micro injection.

In a typical injection experiment, 30 nl of $^{32}$[P]-labeled RNA ($1\times10^6$ cpm/$\mu$l; total concentration of 0.7 $\mu$M) was injected either into the nucleus or into the cytoplasm. For the antibody inhibition experiments, oocytes were preinjected with antibody (1 micrograms/$\mu$l or 3 micrograms/$\mu$l in FIG. 9B) and the oocytes were incubated for 1 hour before they received a second injection of $^{32}$[P]-labeled RNA. Nucleocytoplasmic transport of injected RNAs was monitored by dissection of the oocytes into nuclear and cytoplasmic fractions. Both fractions were incubated for 20 minutes in homogenization buffer, and the RNAs were isolated and analyzed by electrophoresis on denaturing RNA gels as described in Hamm et al. (1990, Cell 62:569–577).

Immunoprecipitation of RNA-protein Complexes

Immunoprecipitation of RNA-protein complexes was performed pursuant to Fischer et al., 1993, supra). Briefly, the injected oocytes were homogenized in 300 $\mu$l of ice-cold phosphate buffered saline (pH 7.4). The insoluble fraction was pelleted by centrifugation, and the clear supernatant was transferred into a new 1.5 ml Eppendorf tube containing antibodies bound to protein G-Sepharose beads (Pharmacia). This mixture was incubated with constant shaking for 1 hour at 4° C. and the beads were subsequently washed five times with 1 ml aliquots of ice-cold phosphate buffered saline. Bound RNAs were isolated by phenol extraction for 1 hour, and the RNAs were then precipitated with ethanol, and analyzed by denaturing gel electrophoresis as described previously herein.

Plasmid DNA in vitro Transcription and Translation

Plasmids coding for U1, U2, U4, U5, and U6 snRNAs have been described previously in Hamm et al. (1990, Cell 62:569–577) and Fischer et al. (1993, EMBO J. 12:573–583; 1995, Cell 82:475–483). Plasmids encoding dihydrofolate reductase mRNA (DHFR) and tRNA1 were described in Jarmolowski and Mattaj (1993, EMBO J. 12:223–232), Jarmolowski et al. (1994, J. Cell Biol. 124:627–635), and in Fischer et al. (1995, Cell 82:475–483). A plasmid coding for the human U3 snoRNA. Clones encoding the Sm proteins B, D1, D2, D3, E, F, and G are described in Raker et al. (1996, EMBO J. 15:2256–2269). The clone encoding SIP1 has been described previously herein. In vitro transcription of $^{32}$[P]-labeled RNAs was carried out exactly as described in Fischer et al. (1993, EMBO J. 12:573–583). Labeled RNA was precipitated in ethanol and resuspended in water. For nuclear injection, RNA was dissolved in water containing 10 milligrams per milliliter dextran blue (MW 1,000,000). In vitro translation of $^{35}$[S]-labeled proteins was carried out using a combined transcription and translation kit (TnT) (Promega Biotech, Madison, Wis.) according to the instructions of the manufacturer.

The Results of the experiments presented in this example are now described.

As previously disclosed herein, a novel protein complex containing SMN, SIP1, and spliceosomal snRNP proteins, including several of the Sm proteins, has been discovered in the cytoplasm of human cells. The data presented herein were obtained in the Xenopus oocyte system which is an advantageous, well-characterized system in which to study spliceosomal snRNP biogenesis by use of microinjections (Mattaj and DeRobertis, 1985, Cell 40:111–118; Mattaj, 1986, Cell 46:905–911).

SMN and SIP1 are Associated with Spliceosomal snRNAs in the Cytoplasm

As previously disclosed herein, a novel protein complex containing SMN, SIP1, and spliceosomal snRNP proteins, including several of the Sm proteins is present in the cytoplasm of human cells. Because the Xenopus oocyte provides a particularly advantageous and well-characterized system in which to study spliceosomal snRNP biogenesis by use of microinjections (Mattaj and DeRobertis, 1985; Mattaj, 1986), it was first determined whether SMN and SIP1 are present in these oocytes. If so, the unique features of this system could then be used to investigate the possible functions of these proteins in snRNP biogenesis.

Figure 6A:
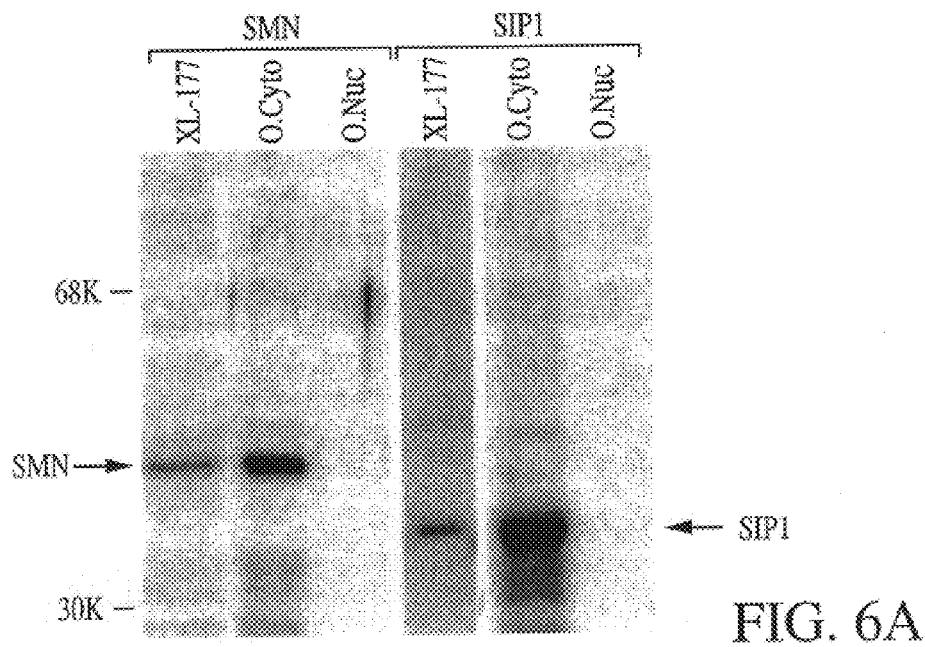
FIG. 6A is an image of a Western blot depicting the presence of SMN and SIP1 in the cytoplasm of Xenopus oocytes and the association of the proteins with spliceosomal snRNAs. Protein obtained from total Xenopus somatic cells (XL-177 cell line) or from oocytes dissected into nucleus and cytoplasm (O. Nuc. and O. Cyto, respectively) were fractionated by SDS-PAGE and analyzed by Western blotting with anti-SMN antibody (2B1) or anti-SIP1 (2E17).

Immunoblotting with monoclonal antibodies to the human SMN and SIP1 proteins (2B1 and 2E17, respectively) on Xenopus tissue culture cells detected proteins of similar size to the corresponding human proteins. cDNA cloning, sequencing, and transfection experiments confirmed that these proteins are the Xenopus homologs of SMN and SIP1. Surprisingly, however, unlike the situation in somatic cells where there is more SMN and SIP1 in the nucleus, both proteins were found almost exclusively in the oocyte cytoplasm (FIG. 6A). The high cytoplasmic concentration of SMN and SIP1 in the Xenopus oocyte is reminiscent of the large amounts of Sm proteins that are stored in the oocyte cytoplasm (Zeller et al., 1983, Cell 32:425–434).

Figure 6B:
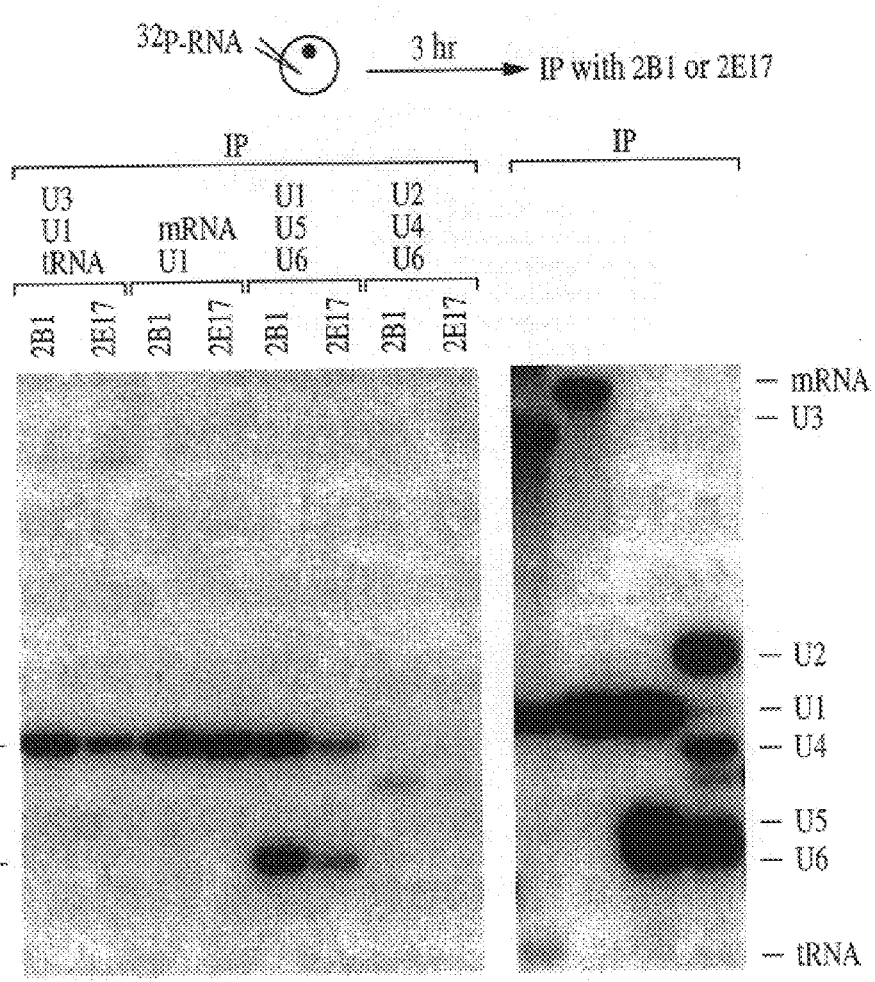
FIG. 6B is an image of a gel depicting the immunoprecipitation of spliceosomal U snRNAs using anti-SIP1 and anti-SMN antibodies. Selected mixtures of the indicated in vitro synthesized $^{32}$[P]-labeled RNAs were injected into the cytoplasm of oocytes. Three hours later, immunoprecipitations were carried out using either anti-SMN antibody 2B1 or anti-SIP1 antibody 2E17. Immunoprecipitated RNA (IP) was analyzed by gel electrophoresis. The supernatants (SUP) of the 2B1 immunoprecipitations are depicted and the supernatants of the 2E17 immunoprecipitations were similar to those of 2B1.

In order to identify potential cellular targets for the SMN-SIP1 complex, the association of the complex with RNA was investigated. Various $^{32}$[P]-labeled RNAs were generated by transcription in vitro, including mRNA, tRNA, U3 snoRNA, 5S RNA, and the spliceosomal snRNAs U1, U2, U4, U5, and U6. Different mixtures of these RNAs were then coinjected into the cytoplasm of oocytes; and immunoprecipitations were carried out with anti-SMN (2B1) and anti-SIP1 (2E17) monoclonal antibodies. As shown in FIG. 6B, only U1 and U5 snRNAs were efficiently immunoprecipitated, indicating that they interact with SMN and SIP1. A weak but reproducible immunoprecipitation of U4 snRNA was also observed. In contrast, other RNAs, including mRNA, tRNA, U3 snoRNA, U6 snRNA, U2 snRNA (FIG. 6B), and 5S rRNA were not immunoprecipitated at significant levels with either the anti-SMN or the anti-SIP1 antibodies.

Figure 7:
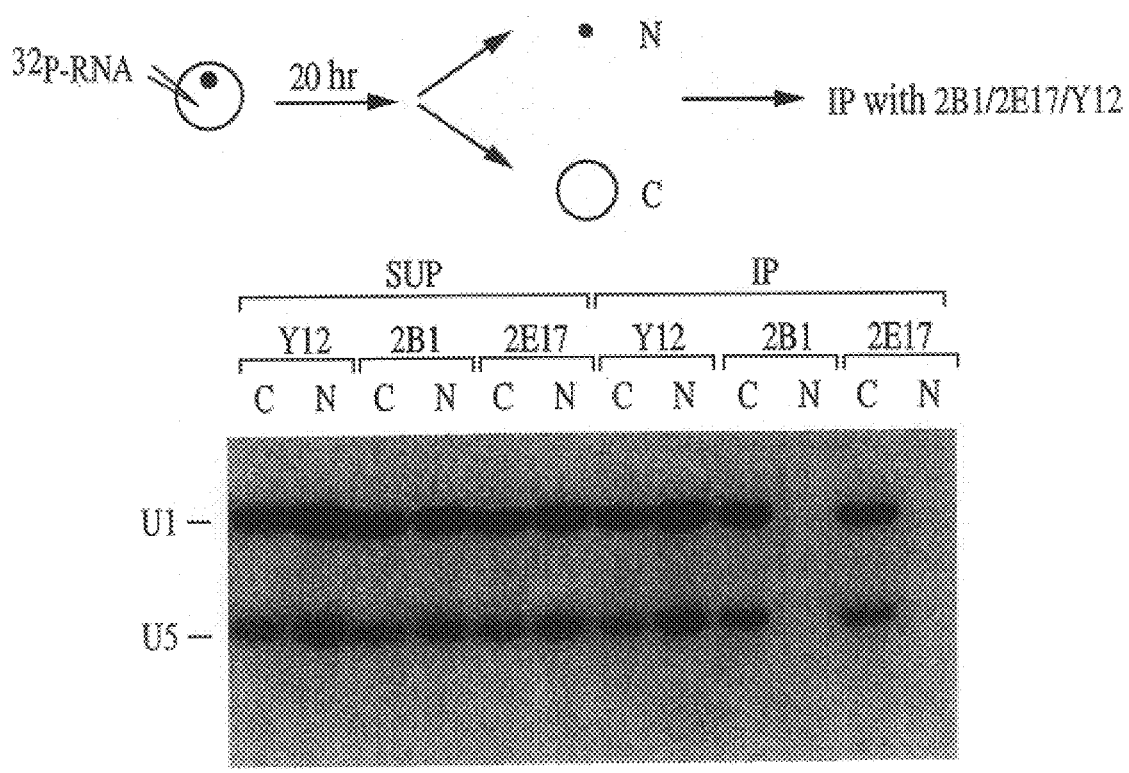
FIG. 7 is an image of a gel depicting the fact that anti-SMN and anti-SIP1 antibodies immunoprecipitated U1 and U5 snRNAs obtained only from the cytoplasm of Xenopus oocytes. A mixture of $^{32}$[P]-labeled U1 and U5 snRNAs was injected into the cytoplasm of oocytes. After incubation for 20 hours, the oocytes were dissected into nuclear (N) and cytoplasmic (C) fractions, as depicted in the illustration at the top of the figure. RNAs from both fractions were immunoprecipitated (IP) using either the anti-Sm antibody Y12, anti-SMN antibody 2B1, or anti-SIP1 antibody 2E17. One-fifth of the total supernatant (SUP) was loaded on the gel.

Since neither SMN nor SIP1 is detectable in the oocyte nucleus (FIG. 6A), it seemed possible that they are not associated with mature U1 and U5 snRNPs but rather only during the cytoplasmic phase of their biogenesis pathway. To ascertain this, U1 and U5 snRNAs were injected into the cytoplasm of oocytes, and the oocytes were incubated for 12 hours (FIG. 7). After this incubation period, approximately 50% of the injected snRNA was transported to the nucleus while the rest was still in the cytoplasm. Immunoprecipitations from the nuclear and cytoplasmic fractions were then carried out using either anti-SMN antibody, anti-SIP1 antibody, or the anti-Sm monoclonal antibody Y12, and the coimmunoprecipitated RNAs were analyzed by denaturing gel electrophoresis followed by fluorography. As previously discussed herein, anti-Sm monoclonal antibody Y12 recognizes a subset of the Sm proteins and was used in this experiment to monitor the assembly of the Sm core domain (Lerner et al., 1981, Proc. Natl. Acad. Sci. USA 78:2737–2741). As previously reported (Mattaj, 1986, Cell 46:905–911; Fischer and Lührmann, 1990, Science 249:786–790), U1 and U5 snRNAs were immunoprecipitated by Y12 in approximately equal amounts from the nucleus and cytoplasm (FIG. 7). This indicated that the Sm proteins associate in the cytoplasm with the snRNA and then move as an assembled and stable snRNP complex to the nucleus. In striking contrast, however, SMN and SIP1 association with U1 and U5 snRNAs was observed only in the cytoplasm (FIG. 7).

Further evidence for the physiological relevance of the interaction of SMN and SIP1 in the cytoplasm with spliceosomal snRNPs was obtained following nuclear injections of U1 snRNA. Only after export to the cytoplasm and during the cytoplasmic phase of their biogenesis could U1 snRNA be immunoprecipitated by anti-SMN or anti-SIP1 antibodies. Thus, the SMN-SIP1 complex interacts with U1 and U5 snRNAs in the cytoplasm but not after these snRNAs have been assembled into snRNPs and have been imported into the nucleus. Therefore, SMN and SIP1 dissociate from the spliceosomal snRNPs either prior to nuclear entry or shortly thereafter.

Anti-SIP1 Antibodies Inhibit Spliceosomal snRNP Assembly and Nuclear Import

Figure 8A:
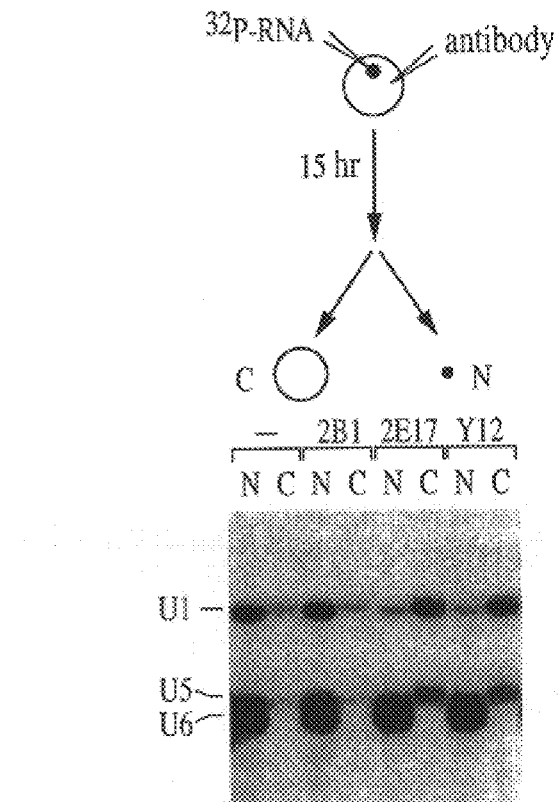
FIG. 8A is an image of a gel depicting the fact that anti-SIP1 antibodies interfere with the biogenesis cycle of spliceosomal U snRNPs. Oocytes received a cytoplasmic injection of either water (−), anti-SMN antibody (2B1), anti-Sm antibody (Y12), or anti-SIP1 antibody (2E17). The same oocytes were injected in the nucleus 1 hour later with a mixture of $^{32}$[P]-labeled U1, U5, and U6 snRNA. Fifteen hours later, the oocytes were dissected into nuclear (N) and cytoplasmic © fractions, and the injected RNAs were analyzed by electrophoresis on an RNA gel.

The association of SMN and SIP1 with U1 and U5 snRNPs in the cytoplasm suggested a role for these proteins in the biogenesis pathway of these snRNPs, i.e., in the assembly of snRNP proteins onto these snRNAs and/or in the nuclear import of these particles. Therefore, whether anti-SMN or anti-SIP1 antibodies have an effect on the nucleo-cytoplasmic transport of spliceosomal snRNPs was examined (FIG. 8). Anti-SMN (2B1), anti-SIP1 (2E17), or anti-Sm (Y12) antibodies were injected into the cytoplasm of oocytes. One hour later, a mixture of U1, U5, and, as a control for nuclear injection, U6 snRNA was injected into the nuclei of the same oocytes, and the incubation was continued for 15 hours. The oocytes were then fractionated, and the RNAs in the nucleus and cytoplasm were analyzed. In control oocytes preinjected with water, nuclear-injected U1 and U5 snRNAs were exported to the cytoplasm and, after cytoplasmic assembly of the Sm core domain, reimported to the nucleus (FIG. 8A) (Hamm et al., 1990, Cell 62:569–577; Neuman de Vegvar and Dahlberg, 1990, Mol. Cell. Biol. 10:3365–3375; Terns et al., 1993, Genes Dev. 7:1898–1906). This was confirmed by immunoprecipitation of U1 and U5 snRNAs with anti-Sm antibodies and by the observation that the nuclear pool of U1 snRNA had undergone 3' end trimming (see FIG. 8A, nuclear fractions). The latter has been previously shown to occur in the cytoplasm prior to nuclear import (Neuman de Vegvar and Dahlberg, 1990, supra; Terns et al., 1993, supra). In oocytes preinjected with anti-Sm antibody Y12, U1 and U5 were also exported to the cytoplasm; however, they were not ramparted to the nucleus, resulting in the accumulation of these RNAs in the cytoplasm (FIG. 8A). This is because upon binding to the Sm proteins, Y12 interferes with the subsequent steps in the biogenesis of snRNPs that are required for their nuclear import as discussed below. Surprisingly, a similar result was obtained in oocytes preinjected with anti-SIP1 antibodies (FIG. 8A). However, no effect on nuclear import of U1 and U5 snRNA was observed in oocytes injected with anti-SMN antibodies (FIG. 8A).

Figure 8B:
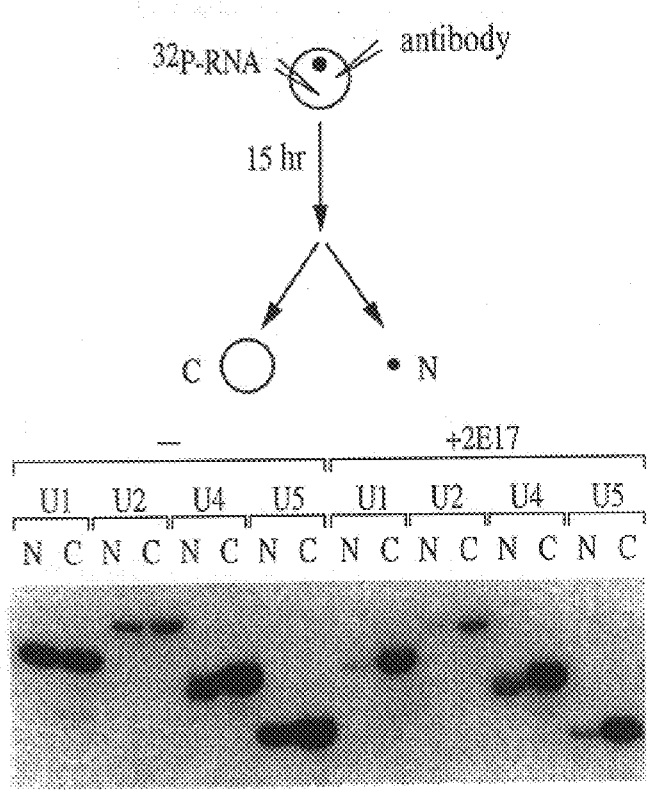
FIG. 8B is an image of a gel depicting inhibition of nuclear import of all spliceosomal snRNAs by anti-SIP1 antibodies. In vitro transcribed, $^{32}$[P]-labeled snRNAs U1, U2, U4, and U5 were injected into the cytoplasm of oocytes either alone (−) or together with anti-SIP1 antibody (2E17). The oocytes were incubated for an additional 15 hours and they were then dissected into nuclear (N) and cytoplasmic (C) fractions. Injected $^{32}$[P]-labeled RNAs were isolated and analyzed by electrophoresis on a denaturing RNA gel.

Next, it was determined whether anti-SIP1 antibodies interfere with the nuclear import of the other spliceosomal snRNPs. In vitro transcribed snRNAs U1, U2, U4, and U5 were injected into the cytoplasm of oocytes, either without or with anti-SIP1 antibody, and nuclear import was then assessed 15 hours later (FIG. 8B). In the absence of anti-SIP1 antibody injection, all snRNAs accumulated in the nucleus to approximately 50%, although the import of U4 was less efficient (FIG. 8B). However, in the presence of anti-SIP1 antibody, the nuclear import of U1, U2, and U5 was almost completely inhibited, and the import of U4 was delayed by at least 50% (FIG. 8B). Thus, anti-SIP1 antibodies interfere with the nuclear import of all spliceosomal U snRNPs tested regardless of whether they can be efficiently immunoprecipitated with the anti-SMN or anti-SIP1 antibodies. This suggests that the interaction of SMN and SIP with some snRNAs is transient and cannot be monitored by immunoprecipitation.

As discussed previously herein, assembly of the Sm core domain and the formation of the $m_3G$ cap are required for the nuclear import of U snRNPs (Mattaj and DeRobertis, 1985, Cell 40:111–118; Fischer and Lührmann, 1990, Science 249:786–790; Hamm et al., 1990, Cell 62:569–577; Fischer et al., 1993, EMBO J. 12:573–583). Therefore, anti-SIP1 antibodies may inhibit U snRNP import by interfering either with the assembly of the Sm core or with the cap hypermethylation or both. Alternatively, and not mutually exclusive, the antibody could directly interfere with the snRNP transport process, e.g., by blocking transport factors.

Figure 9A:
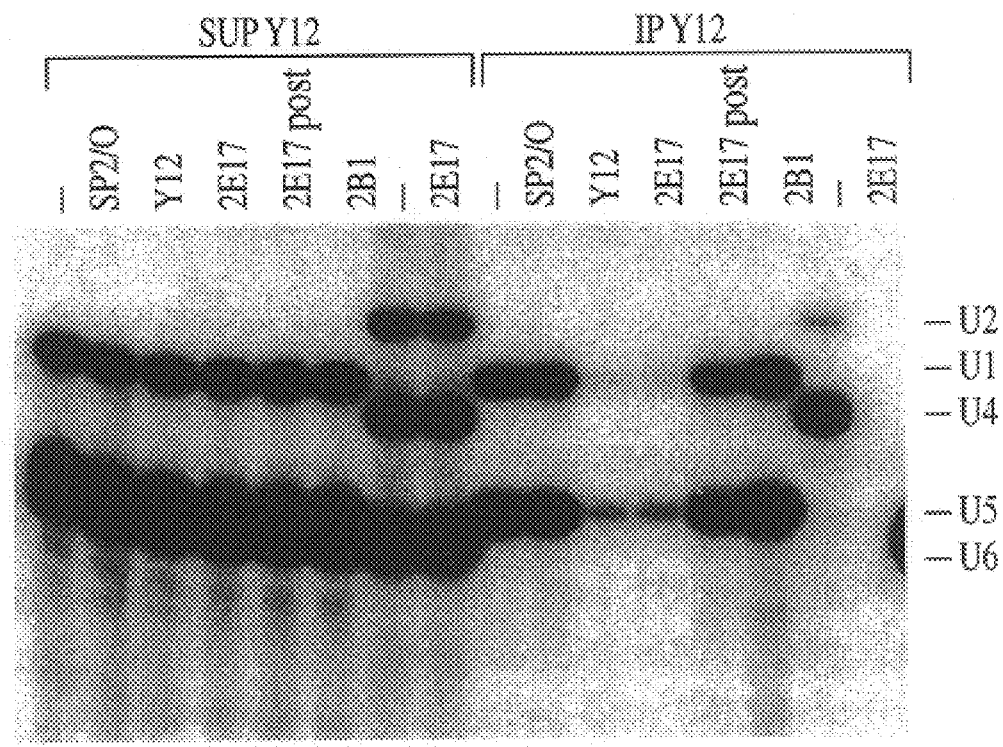
FIG. 9A is an image of a gel depicting the fact that anti-SIP1 and anti-SMN antibodies affected the assembly of the Sm core domain of spliceosomal snRNPs. Anti-SIP1 antibodies inhibited the assembly of the Sm core domain of all spliceosomal U snRNPs. Injections into the oocyte cytoplasm of either water (-), anti-Sm antibody (Y12), anti-SIP1 antibody (2E17), anti-SMN antibody (2B1), or control antibody (SP2/0) were performed. One hour later, the same oocytes were injected a second time in the cytoplasm with a mixture of $^{32}$[P]-labeled U1, U5, and U6 snRNAs. In the experiment shown in the lane designated "SIP1 post", U1, U5, and U6 snRNAs were injected 1 hour prior to the injection of anti-SIP1 antibody. After incubation for an additional 1 hour, the oocytes were homogenized and the RNAs were immunoprecipitated with anti-Sm antibody Y12 (IP Y12). Immunoprecipitated RNAs were analyzed by electrophoresis on an RNA gel with the corresponding supernatants (SUP Y12).

To further examine the inhibitory effect of anti-SIP1 antibodies on U snRNP nuclear import, the effect of anti-SIP1 antibodies on the assembly of the Sm core domain was studied (FIG. 9A). Anti-SIP1, anti-SMN or antiSm (Y12), and, as negative controls, nonimmune antibodies SP2/0 or water, were injected into the cytoplasm of oocytes, followed by incubation for 1 hour before receiving a second cytoplasmic injection of a mixture of $^{32}$[P]-labeled U1, U5, and U6 snRNAs. One hour later, the Sm core assembly on the injected RNAs was analyzed by immunoprecipitation with Y12 (FIG. 9A). In control oocytes preinjected with either water or SP2/0, both U1 and U5 snRNAs were efficiently immunoprecipitated with Y12, indicating that these RNAs assembled with the Sm proteins. As expected, U6 snRNA was not immunoprecipitated because this RNA does not contain an Sm site and thus cannot bind Sm proteins. However, injection with anti-SIP1 antibody completely inhibited the Sm core assembly on U1 and U5 snRNAs (FIG. 9A). Y12 itself strongly reduced the Sm core assembly on both U1 and U5 snRNAs to a similar extent (FIG. 9A). The anti-SMN antibody 2B1, in contrast, did not inhibit but rather slightly stimulated assembly of Sm proteins (FIG. 9A). If the snRNAs are injected 1 hour prior to injection of the anti-SIP1 antibody, no interference with subsequent Y12 immunoprecipitation is observed. The observed inhibition of Sm core assembly by pre-injection of anti-SIP1 is therefore not due to a nonspecific occlusion of the Sm epitope by the anti-SIP1 antibody (FIG. 9A).

The effects of injection of anti-SIP1 antibodies on the assembly of U2 and U4 snRNAs were also determined. As shown in FIG. 9A, pre-injection of anti-SIP1 antibodies strongly interfered with the Sm core assembly on both U2 and U4 snRNAs, while in oocytes preinjected with water, both snRNAs assembled with the Sm proteins. The inhibition of nuclear import of snRNAs U1, U2, U4, and U5 by anti-SIP1 antibodies is, therefore, at least partially due to the interference of the anti-SIP1 antibody with the Sm core domain assembly. Thus, without wishing to be bound by theory, SIP1 is a cytoplasmic assembly factor that mediates the formation of the Sm core domain on spliceosomal U snRNPs.

Figure 9B:
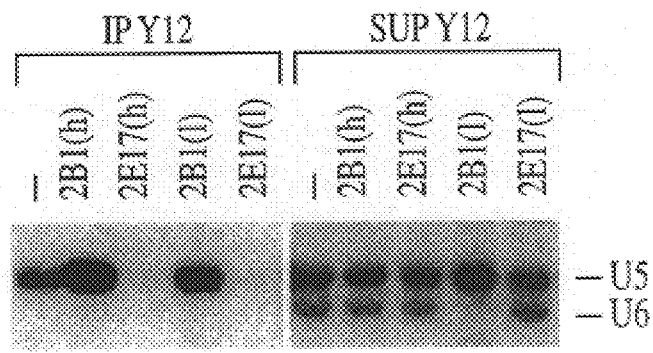
FIG. 9B is an image of a gel depicting stimulation of the formation of the Sm core domain by the anti-SMN monoclonal antibody 2B1. The data disclosed herein demonstrate stimulation of Sm protein binding to U5 snRNA in the presence of high concentrations of the anti-SMN antibody 2B1. A mixture of $^{32}$[P]-labeled U5 and U6 snRNAs was injected into the cytoplasm of oocytes either with water (-) or with anti-SMN and anti-SIP1 antibodies (2B1 and 2E17, respectively) at either high (h, 3 µg/µl) or low (1, 1 µg/µl) concentrations. After a 1 hour incubation, the oocytes were homogenized, and the RNAs were immunoprecipitated with the anti-Sm antibody Y12 (IP Y12). Immunoprecipitated RNAs were analyzed by electrophoresis on an RNA gel alongside one-tenth of the supernatants (SUP Y12).

Anti-SMN Monoclonal Antibody Stimulates Sm Protein Binding Onto the Sm Site of U snRNAs Although SMN is in a tight complex with SIP1 and, therefore, is likely to form a functional unit with SIP1, the anti-SMN antibodies used in the experiments described above, unlike the anti-SIP1 antibodies, did not interfere with U snRNP biogenesis; rather, anti-SMN antibodies stimulated core domain assembly. Therefore, the function of SMN in snRNP assembly was examined further. As shown in FIG. 9B, injection of anti-SMN antibodies (2B1) did not inhibit snRNP assembly. However, upon injection of high concentrations (2 to 3 micrograms/µl) of this anti-SMN antibody, the assembly of snRNPs was often enhanced. In order to analyze this effect in more detail, a mixture of U5 and U6 snRNAs was injected along with either high (3 micrograms/µl) or low (1 micrograms/µl) concentrations of the anti-SMN antibody 2B1 or the anti-SIP1 antibody 2E17 (FIG. 9B). Sm protein binding onto these RNAs was then assessed by immunoprecipitation with the anti-Sm antibody Y12 one hour later. After 1 hour, the assembly of Sm proteins onto U snRNAs was not complete, thus allowing a more quantitative evaluation of the efficiency of Sm protein binding. In the absence of coinjected antibody, U5 but not U6 was precipitated by anti-Sm, indicating Sm core formation on U5 snRNA but not on U6 at that time point. However, while low concentrations of 2B1 had only a slight stimulatory effect on Sm protein binding, coinjection of higher 2B1 concentrations significantly enhanced the assembly approximately 2- to 3-fold (FIG. 9B). Coinjected anti-SIP1 antibody, in contrast, inhibited the assembly of Sm proteins onto U5 snRNA almost entirely at both low and high antibody concentrations (FIG. 9B). Thus, 2B1 stimulates Sm protein binding onto U5 snRNA and hence Sm core formation, indicating that SMN is also involved in spliceosomal U snRNP assembly.

The data disclosed herein further demonstrate that 2B1 stimulates Sm protein binding onto an artificial snRNA, termed SmII RNA, that consists of the Sm site and stem/loop E of U1 snRNA and an artificial stem/loop 5' to the Sm site. The capacity of this RNA to bind Sm protein is severely compromised, and, as a consequence of this, its nuclear import is greatly reduced (Fischer et al., 1993, EMBO J. 12:573–583). Employing the same injection strategy as described above, a strong stimulation of Sm protein binding onto SmII RNA was observed after injection with anti-SMN antibody 2B1, and, as a consequence, SmII was efficiently imported into the nucleus. Taken together, and without wishing to be bound by theory, these data and those presented in the preceding sections strongly suggest that both SIP1 and SMN are directly involved in the assembly of the Sm core domain of spliceosomal U snRNPs.

EXAMPLE 3

Specific Sequences in SMN and SIP1 Which Mediate Their Interactions With Each Other and With Sm Proteins and Which are Associated With Defective Interactions in SMA The experiments presented in this example may be summarized as follows.

Deletion mutants of SMN and SIP1 were prepared and used to identify the domains involved in the interactions between SMN and SIP1 as well as their interactions with their associated proteins such as the Sm proteins. Further, the effects of specific deletions and point mutations on the composition of the SMN complex and on the SMN and SIP1 cellular localization, with particular interest in targeting to gems, were analyzed. The data disclosed herein demonstrate that several SMN interactions are affected by mutations that occur in some SMA patients and that SMN oligomerization greatly enhances its interaction with Sm proteins. These results suggest a model of the SMN complex in which a SMN/SIP1 tetramer (or a higher oligomer) is the functional core required for efficient binding to Sm proteins, and thus snRNP assembly. These findings further strengthen the view that SMA is the result of a defect in snRNP metabolism.

The Materials and Methods used in the experiments presented in this example are now described.

Plasmid Construction

DNA fragments corresponding to the open reading frames (ORFs) of SMN and SIP1 wild-type (wt) and mutant proteins were generated by polymerase chain reaction (PCR) amplification using suitable primers. All of the myc-tagged constructs were generated by cloning the PCR inserts into a modified pcDNA3 vector (InVitrogen, Carlsbad, Calif.) downstream from the myc epitope recognized by the monoclonal antibody 9E10 (Siomi and Dreyfuss, 1995, J. Cell. Biol. 129:551–560). Plasmid constructs containing SMN fusions to the carboxyl-terminal to the myc-pyruvate kinase (PK) were obtained by cloning the SMN coding PCR fragments into a myc-PK vector derived from pcDNA3 as previously described (Nakielny and Dreyfuss, 1996, J. Cell. Biol. 134:1365–1373). Maltose binding protein (MBP)-SMN fusions were obtained by cloning the SMN coding PCR fragments into a modified pcDNA1 vector (InVitrogen, Carlsbad, Calif.) downstream from the MBP sequence. These vectors facilitated the expression driven by the CMV promoter in vivo and by the T7 promoter in vitro. All of the constructs were analyzed using DNA sequencing.

Production of Proteins in vitro

The [$^{35}$S]methionine-labeled proteins were produced by an in vitro coupled transcription-translation reaction (Promega Corp., Madison, Wis.) in the presence of [$^{35}$S] methionine (Amersham, Arlington Heights, Ill.). His$_6$-tagged SMN and SmB fusion proteins were expressed from a pET28 bacterial expression system in the E. coli strain BL21(DE3)pLysS and the fusion protein was purified by Ni+ chelation chromatography with the Novagen (Madison, Wis.) His-bind Buffer Kit following the manufacturer's protocol. All the GST fusion proteins were expressed from the GST expression vector pGEX-5X (Pharmacia) in the E. coli strain BL21(DE3)pLysS and were purified using glutathione-Sepharose according to the manufacturer's protocol (Pharmacia Biotech). SmB cDNA is described in Raker et al. (1996, EMBO J. 15:2256–2269). SMN and SIP1 cDNAs were obtained using a yeast di-hybrid screening assay previously described herein.

In vitro Protein-binding Assay

Purified GST or GST fusion proteins (1–3 micrograms) were incubated with $10^6$ cpm of the in vitro translated protein product and 25 µl of glutathione-Sepharose beads in 1 ml of binding buffer (50 mM Tris-HCl [pH 7.5], 200 mM NaCl, 2 mM EDTA, 0.1% NP-40, 2 micrograms per milliliter leupeptin and pepstatin A, and 0.5% aprotinin). After incubation for 1 hour at 4° C., the resin was pelleted, washed five times with 1 ml of binding buffer, and the bound protein fraction was eluted by boiling the washed beads in SDS-PAGE sample buffer. The eluted proteins were analyzed by SDS-PAGE on a 12% polyacrylamide gel, and the radiolabel signal was enhanced by treatment with Amplify solution (Amersham, Arlington Heights, Ill.).

In the preincubation experiments, the indicated molar excess of purified recombinant His-tagged SMN proteins were incubated with GST or GST-SMN, previously bound to glutathione-Sepharose beads, for 1 hour at 4° C. in 1 ml of binding buffer. Unbound proteins were eliminated using five washes of the beads with binding buffer. After the beads were washed to remove unbound proteins, the in vitro translated proteins were added to the beads and binding was performed as described previously herein.

Gel-filtration Chromatography

Purified recombinant His-tagged SMN, SMNY272C, or SMNΔEx7 (also referred to as SMNΔC16) (50 micrograms), and SmB (25 micrograms) were incubated, individually or mixed as indicated, for 1 hour on ice in 0.25 milliliters of a buffer containing 50 mM Hepes, pH 7.9, 400 mM KCl, 0.5 mM EDTA, 2.5 mM DTT. The samples were then applied to a TSK-GEL G3000-SW glass column (08800; Tosohaas, Montgomeryville, Pa.). The column was equilibrated in the same buffer as mentioned previously herein. One minute fractions were collected at a 0.25 milliliter per minute flow-rate. Selected fractions were pooled as indicated elsewhere herein, and the samples were analyzed using SDS-PAGE and Western blotting using anti-T7 tag monoclonal antibody (Novagen, Madison, Wis.).

Cell Culture and Immunoprecipitation 293T cells were cultured in Dulbecco's modified Eagle's medium (DMEM) (GIBCO BRL, Gaithersburg, Md.) supplemented with 10% fetal bovine serum (FBS) (GIBCO BRL) and transfected by the standard calcium phosphate procedure. Following 36 to 48 hours posttransfection, the cells were collected and processed by immunoprecipitation. Immunoprecipitations were performed using total cell lysates prepared in the presence of 0.5% Triton X-100 as described previously in Piñol-Roma et al. (1988, Genes Dev. 2:215–227).

Immunoblotting was performed as described previously elsewhere herein. The antibodies used for these experiments were as follows: mouse monoclonal anti-SIP1 (2E17, described previously elsewhere herein), mouse monoclonal anti-Sm (Y12; Lerner et al., 1981, Proc. Natl. Acad. Sci. USA 78:2737–2741), mouse monoclonal anti-myc (9E10; ATCC, Manassas, Va.), and mouse monoclonal anti-T7 tag (Novagen, Madison, Wis.).

The Results of the experiments presented in this example are now described.

Figure 10A:
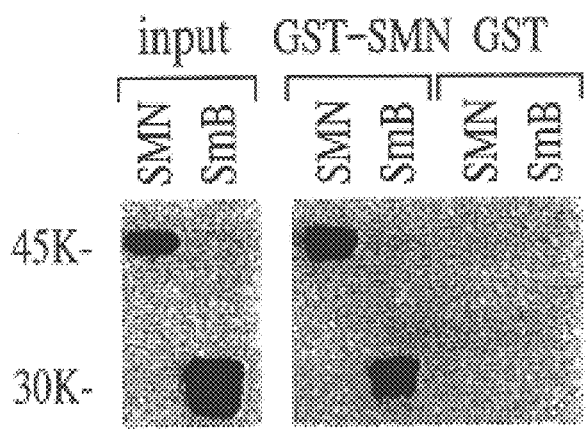
FIG. 10A is an image depicting the fact that SMN interacts directly with itself and with SmB, and that these interactions are affected by mutations found in SMA patients. A binding assay of His-tagged SMN and SmB recombinant proteins (2 mg) with either GST or GST-SMN was performed as described elsewhere herein. Bound SMN and SmB were analyzed by SDS-PAGE and Western blotting with an anti-T7 tag antibody. Ten percent of the input is shown in the first lane.
Figure 10B:
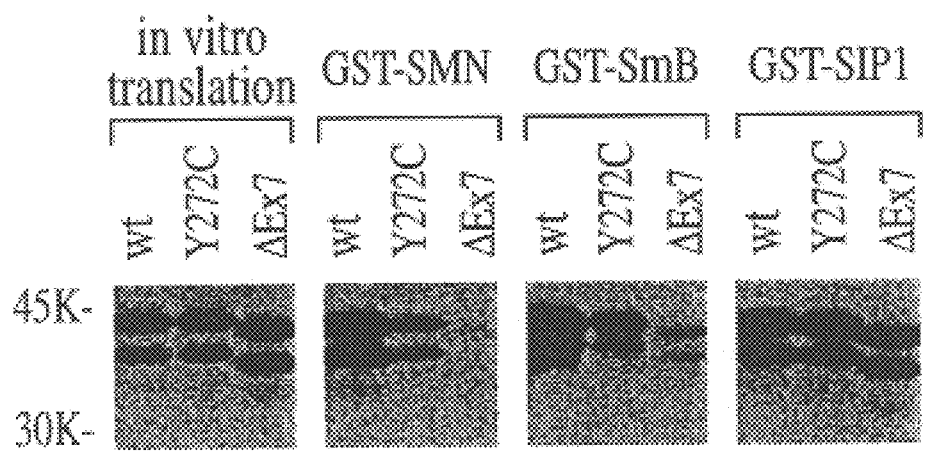
FIG. 10B is an image depicting the fact that SMN interacts directly with itself and with SmB, and that these interactions are affected by mutations found in SMA patients. In vitro translated [$^{35}$S]methionine-labeled, myc-tagged SMN wild-type and mutant proteins were incubated with the indicated purified GST-fusions (SMN, SmB, or SIP1) as described elsewhere herein. Bound proteins were analyzed by SDS-PAGE and fluorography. Twenty percent of the input is depicted in the in vitro translation area. The area corresponding to GST-SmB binding is a 3-fold-longer exposure than the other areas.
Figure 15A:
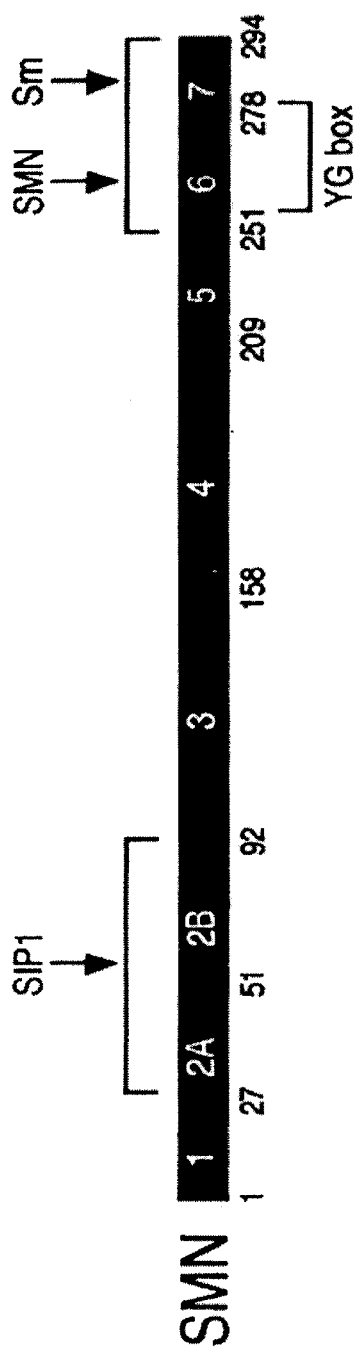
FIG. 15A is a diagram depicting the structure of the SMN protein and its interacting domain. The amino acid numbers and the borders of exons are indicated. SIP1-interacting domain resides at the amino terminus of SMN as determined by competition experiments (see, e.g., Example 1). SMN self-association and SMN/Sm interaction domains overlap with the conserved YG box at the carboxyl-terminus of SMN as determined by deletion, mutation, and competition experiments.

SMN Mutations of SMA Patients Affect the Direct Interaction of SMN With Itself and With SmB In an in vitro binding assay, purified recombinant His-tagged SMN and SmB proteins bound to a GST-SMN fusion protein but not to GST alone (FIG. 10A). This demonstrates that SMN interacts directly with itself and, although with a low affinity, with SmB and rules out a possible bridging effect by other components such as those that may be present in the reticulocyte lysate used in experiments disclosed previously elsewhere herein and in, for example, Lorson et al. (1998, Nature Genet. 19:63–66). Next, the effect on these interactions of two well characterized mutations found in SMA patients, the point mutant SMNY272C and the exon 7 deletion mutant (SMNΔEx7), was examined. FIG. 10B depicts that both mutations severely affected not only SMN self-association (Lorson et al., 1998, Nature Genet. 19:63–66) but also the interaction of SMN with SmB. In contrast, no effect was observed on the interaction of SMN with SIP1, which involves the amino terminus of SMN (as disclosed previously elsewhere herein). GST-SIP1 binds equally efficiently to full-length SMN and to both mutants. GST alone, used as a control, exhibited no detectable binding to SMN. Because SMA is a motor neuron disease, the interaction of the neuronal-specific Sm protein, SmN, with SMN wild type (SMNwt), SMNY272C, and SMNΔEx7 was also analyzed and found them to be identical to those of SmB. These data demonstrate that the SMN self-association and SmB-binding domains share common determinants within the YG box and that both SMN/SMN and SMN/SmB interactions are affected by mutations that cause SMA. A schematic summary of SMN-interacting domains is shown in FIG. 15A.

SMN Self-association Enhances the Interaction with Sm Proteins.

Figure 11A:
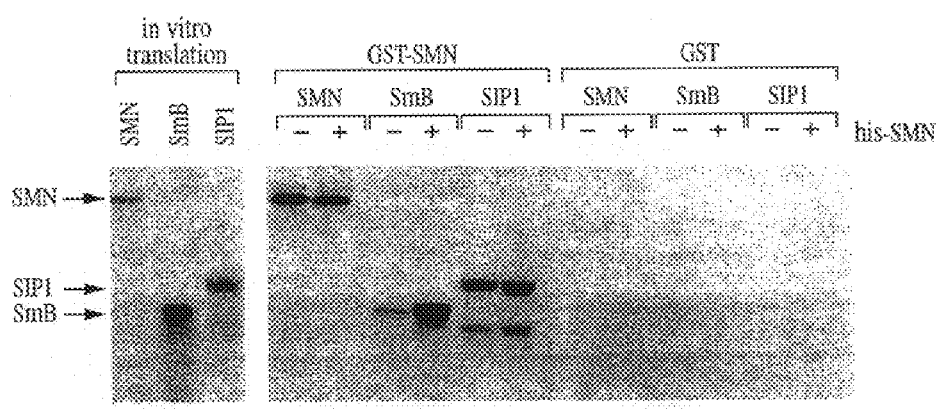
FIG. 11A is an image depicting the fact that SMN self-association specifically increases the binding affinity for Sm proteins. GST or GST-SMN was preincubated with or without a 4-fold molar excess of His-SMN as described elsewhere herein. After washing away unbound His-SMN, in vitro translated [$^{35}$S]methionine-labeled SMN, SmB, or SIP1 was added and the binding assay was performed as described elsewhere herein. Bound proteins were analyzed by SDS-PAGE and fluorography. Ten percent of the input is shown in the in vitro translation area.
Figure 11B:
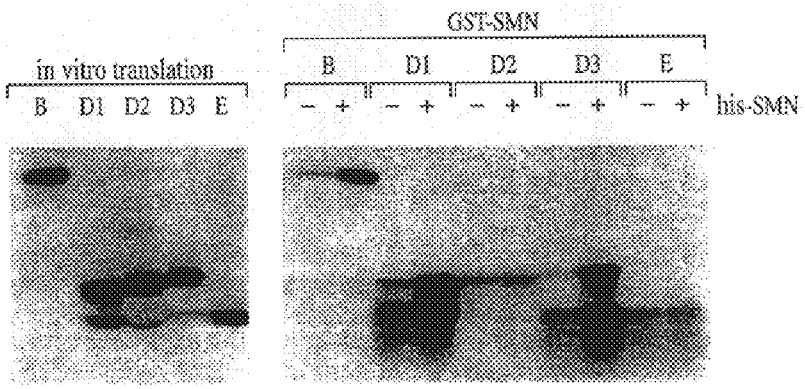
FIG. 11B is an image depicting the fact that SMN self-association specifically increases the binding affinity for Sm proteins. GST-SMN was preincubated with or without a 4-fold molar excess of His-SMN as described above in FIG. 11A. Then, in vitro translated [$^{35}$S]methionine-labeled Sm proteins were added, and the binding assay was performed as described elsewhere herein. Twenty-five percent of the input is shown in the in vitro translation area.

To determine whether or not these SMN/SMN and SMN/SIP1 interactions were mutually exclusive, beads containing GST-SMN, or GST as a control, were preincubated with a molar excess of recombinant His-SMN to form SMN oligomers. Then, after washing away the unbound SMN, in vitro translated, [$^{35}$S]methionine-labeled SMN, SmB, or SIP1 was added to the beads and binding of the labeled proteins was assessed (FIG. 11A). SMN binding was reduced only partially by the preincubation with recombinant His-SMN, suggesting that the oligomerization capacity of SMN on the beads has not been saturated. Surprisingly, SmB binding is dramatically enhanced by SMN self-association. SIP1 binding is slightly increased presumably because additional binding sites become available with the bound His-SMN. The specificity of this effect is demonstrated further by the lack of binding to control GST-bearing beads. Further, it was determined whether this effect was exhibited with other Sm proteins known to bind SMN (e.g., as discussed previously elsewhere herein). FIG. 11B depicts that SMN self-association greatly stimulates its interaction with SmB, SmD1, and SmD3 but not with SmD2 and SmE. SmF and SmG do not bind SMN under any conditions examined. The binding efficiency of Sm proteins to GST- SMN is lower than previously disclosed elsewhere herein (e.g., Example 1) because of the more stringent buffer conditions employed in this study.

Several lines of evidence argue against the possibility that the increased binding of Sm proteins merely reflects the presence of additional interaction sites on the bound His-SMN: (i) even at the highest concentration tested, the amount of bound His-SMN is roughly equivalent to that of GST-SMN; (ii) consistently, SMN contains a binding site for SIP1 independent of that for Sm proteins, and SIP1 binding is only slightly increased by the addition of His-SMN (FIG. 1A); and (iii) the effect of SMN self-association is not observed with SmD2 and SmE, whose basal binding otherwise is similar to the one of SmB, SmD1, and SmD3 (FIG. 11B). These data indicate that SMN self-association and Sm proteins interaction are not mutually exclusive but, on the contrary, that SMN self-association very strongly and specifically increases its affinity for a subset of Sm proteins.

Figures 12A, 12B:
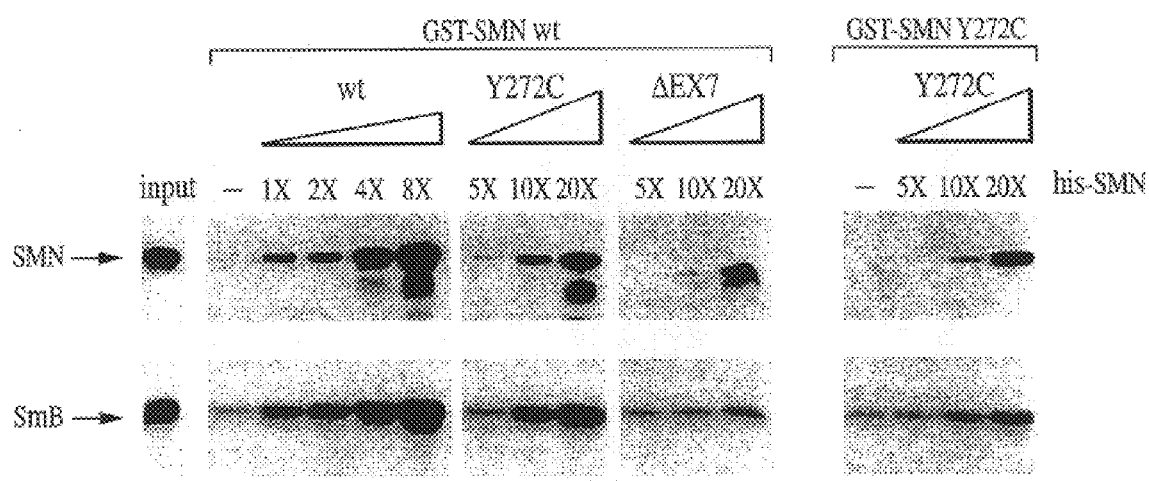
FIG. 12A is an image depicting titration analysis of the effect of SMN self-association on SmB binding. GST-SMN was preincubated with the indicated molar excess of His-tagged SMNwt, SMNY272C, or SMNΔEx7. After washing unbound recombinant proteins, in vitro translated [$^{35}$S] methionine-labeled SmB was added and binding was performed as described elsewhere herein. Each binding assay was analyzed by Western blotting using anti-T7 tag mAb to detect bound His-tagged SMN proteins (SMN) and by autoradiography to detect bound SmB (lower band designated SmB).
FIG. 12B is an image depicting titration analysis of the effect of SMN self-association on SmB binding. GST-SMNY272C was preincubated with the indicated molar excess of His-SMNY272C and processed further as described previously elsewhere herein.

A titration analysis of the stimulating effect of SMN oligomerization on SmB binding is depicted in FIGS. 12A and 12B. The amount of His-SMN bound to GST-SMN immobilized on glutathione-Sepharose beads, after the preincubation step, was determined by Western blotting. The increase in SmB binding correlated with the extent of SMN self-association (FIG. 12A). When the bound amount of wild-type His-SMN was equivalent to the amount of GST-SMN on the beads, SmB binding increased approximately 10-fold (FIG. 12A, lane 4X). SmB binding increased about 30-fold, and more than about 60% of the input was bound when the amount of His-SMN was approximately 2.5-fold greater than GST-SMN (FIG. 12A, lane 8X). Without wishing to be bound by theory, it appears that GST-SMN is predominantly in a monomeric form, probably because the GST fusion or the interaction of the GST with the glutathione-Sepharose interferes with the self-association of GST-SMN on the beads. Proportional to their reduced ability to self-associate, a greater molar excess of recombinant SMNY272C and SMNΔEx7 than wild-type SMN (SMNwt) was required to obtain similar levels of association with GST-SMNwt. Although SMNY272C was still able to stimulate SmB binding, SMNΔEx7 did not (FIG. 12A). In the case of SMNY272C self-association, the extent of stimulation of SmB binding was very low (FIG. 12B). SMNΔEx7 self-association was too inefficient to be analyzed. Thus, SMN self-association most likely creates a high-affinity binding site for Sm proteins and SMN mutations found in SMA patients affect the ability of SMN to form the Sm-binding site. Moreover, the binding site formed with the SMN mutants has a lower affinity for Sm proteins than that formed by wild-type SMN.

SMN Oligomerization is Impaired in Mutants of SMA Patients and is Required for Binding to Sm Proteins.

Although SMN self-associates and is part of a large, macromolecular complex in vivo, it could not be distinguished whether this is due to the presence of multiple copies of SMN and/or of additional proteins (see, e.g., Example 1). Moreover, previous in vitro experiments showing defective self-association of SMN mutants (Lorson et al., 1998, Nature Genet. 19:63–66) were performed under solid-state conditions that did not allow a distinction between dimerization and oligomerization. Dimerization and oligomerization likely are different in terms of the interaction surfaces required for a protein to self-associate because oligomerization would involve at least two independent binding sites. Similarly, the data disclosed herein strongly suggest that SMN oligomerization enhances the interaction of SMN with Sm proteins, but no direct evidence that SMN indeed can oligomerize by itself had been provided so far.

Figure 13A:
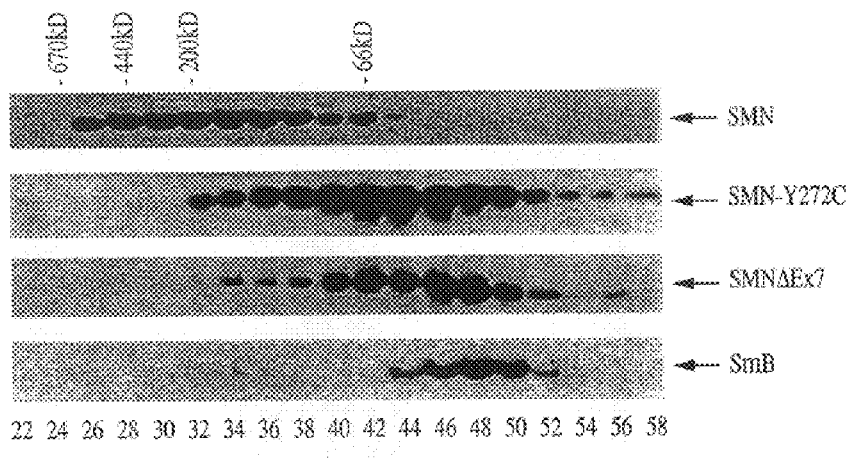
FIG. 13A is an image depicting the fact that SMN mutants found in SMA patients are defective in oligomerization and interaction with Sm proteins. SMN wild type but not SMN mutants of SMA patients form oligomers. Purified recombinant His-tagged SMN, SMNY272C, SMNΔEx7, and SmB proteins were analyzed individually by HPLC gel filtration as described elsewhere herein. The fractions obtained therefrom were analyzed by SDS-PAGE, and the proteins were detected by Western blotting. The indicated positions of the molecular mass markers were determined by independent column chromatographies.
Figure 13B:
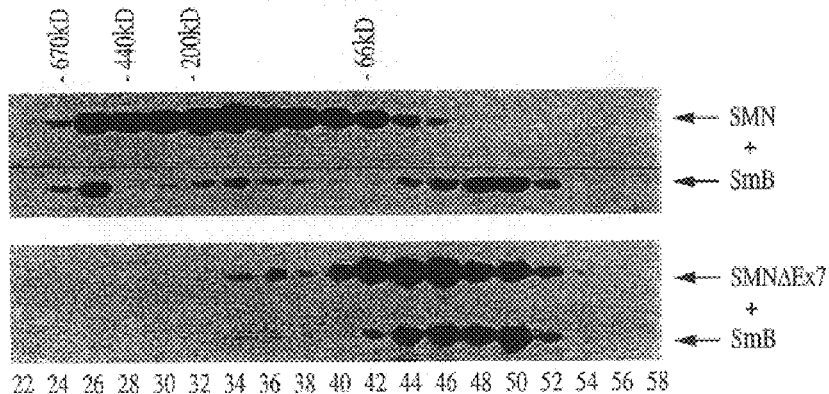
FIG. 13B is an image depicting the fact that SMN oligomers bind to SmB. The indicated mixtures of purified recombinant His-tagged SMN or SMNΔEx7 with His-tagged SmB were analyzed by HPLC gel filtration. The fractions were analyzed by SDS-PAGE, and the proteins were detected by Western blotting. The indicated positions of the molecular mass markers were determined by independent column chromatographies.

The ability of SMN to oligomerize was assessed using gel-filtration chromatography of purified recombinant His-tagged SMN wild-type and mutant proteins. FIG. 13A depicts that SMN alone was able to form large oligomers of up to a molecular mass corresponding to approximately 500 kDa. In contrast, mutants SMNY272C and SMNΔEx7 were severely impaired in their ability to form oligomers. Next, the predicted requirement of SMN oligomerization for Sm protein interaction was examined. As depicted in FIG. 13B, SmB associated with SMN large oligomers in the high-molecular-weight fractions. In contrast, no association between SMNΔEx7 and SmB as larger-size complexes could be detected. These results provide direct evidence that SMN is able to oligomerize and is found almost exclusively self-associated in large oligomeric complexes. Furthermore, SMN mutations found in SMA patients disrupt such oligomerization and the interaction with Sm proteins.

Reduced Association of SMN Mutants With snRNPs in vivo.

Figure 14:
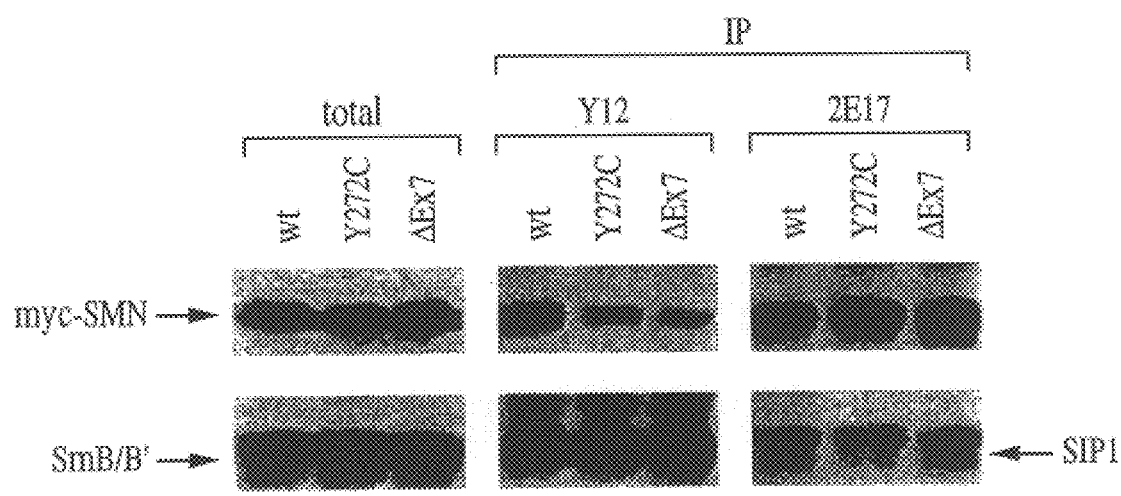
FIG. 14 is an image depicting the reduced association of SMNY272C and SMNΔEx7 with Sm proteins in vivo. 293T cells were transiently transfected with the indicated myc-tagged SMN constructs and cell protein extracts were analyzed by coimmunoprecipitation. Briefly, total cell extracts were immunoprecipitated with either anti-Sm (Y12) or anti-SIP1 (2E17) monoclonal antibodies (mAbs). Total cell extracts (10% of the input) and the anti-Sm immunoprecipitates were analyzed by Western blotting with anti-myc (9E10) and Y12 antibodies; the anti-SIP1 immunoprecipitates were analyzed by Western blotting with 9E10 and 2E17. A relatively low amount of antibody was used in the immunoprecipitations to improve the detection of SmB/B' and SIP1 over the light chains of the immunoglobulins, which migrate very closely. The transfected proteins were overexpressed approximately 5- to 10-fold compared with endogenous SMN. Only SmB is depicted because other Sm proteins were not detected by Western blotting using Y12 antibody. The transfected SMNΔEx7 migrated closer to full-length SMN on a 12.5% polyacrylamide SDS-PAGE.

The data disclosed previously herein suggest that SMN mutants found in vivo such as SMNY272C and SMNΔEx7 would associate with Sm proteins less efficiently than SMN wild type. To test this hypothesis, 293T cells were transfected with either myc-tagged SMN wild type or SMNY272C or SMNΔEx7. All the myc-tagged transfected proteins were expressed at similar levels as determined by Western blotting by using antibodies against the myc tag (FIG. 14). By coimmunoprecipitation with anti-SIP1 antibodies, comparable levels of wild-type and mutant proteins were detected associated with SIP1 as a SMN/SIP1 complex. However, immunoprecipitation using the anti-Sm mAb Y12 demonstrated that the association of SMNY272C and SMNΔEx7 with Sm proteins is reduced markedly compared with the association with SMNwt. A complex comprising the SMN mutants and Sm proteins was still detected because the reduced ability of the mutants to form oligomers with the wild-type SMN is partially overcome by the overexpression and by the possible contribution of other SIPs in vivo (e.g., Example 1).

Figure 15B:
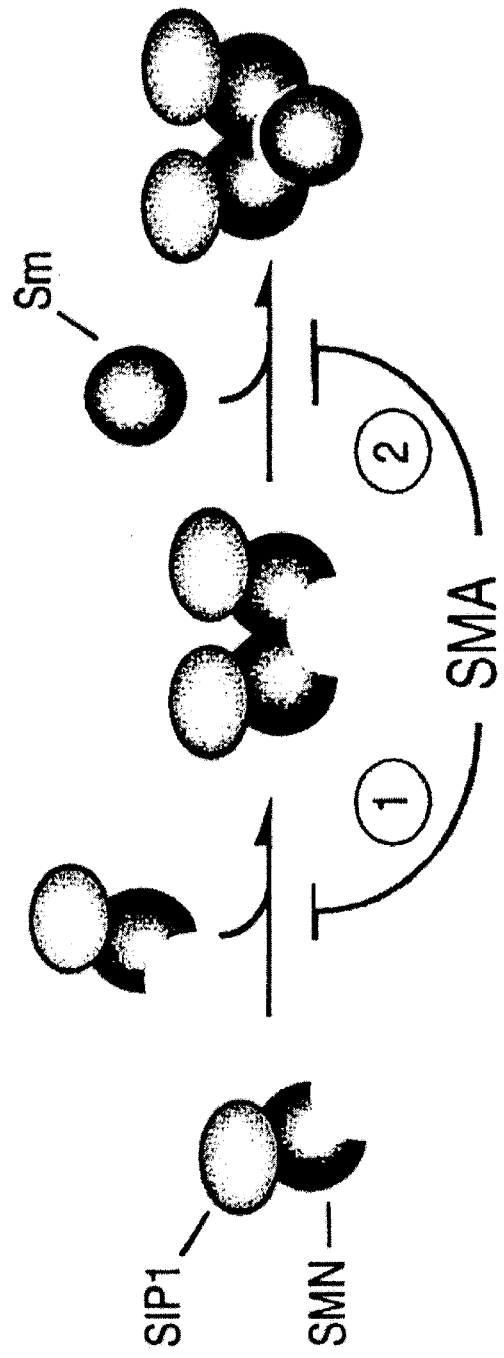
FIG. 15B is a diagram depicting the interactions of SMN/SIP1 with Sm proteins. Monomeric SMN, associated with SIP1, which binds to SMN but not to itself, contains a low-affinity binding site for Sm proteins. SMN self-associates, forming at least a SMN/SIP1 tetrameric complex. In this oligomeric conformation, a binding site is formed with a much higher affinity for the Sm proteins. SMN mutations found in SMA patients result in a reduced ability of SMN to self-associate (Burghes, 1997, Am. J. Hum. Genet. 61:9–15) and also map within the Sm-binding site itself (Brzustowicz et al., 1990, Nature 344:540–541), thus affecting the SMN interaction with Sm proteins.
Figure 18A:
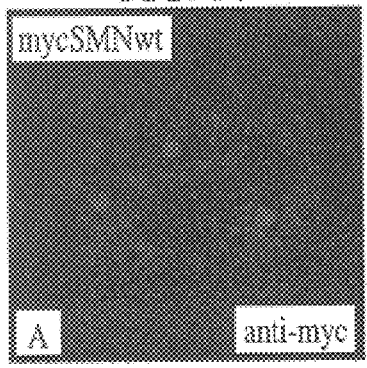
FIG. 18A is an image depicting the distribution SMN wild type in cells transiently transfected myc-SMNwt. HeLa cells transiently transfected with mycSMNwt were immunostained using anti-myc tag monoclonal antibody 9E10 (green signal).
Figure 18B:
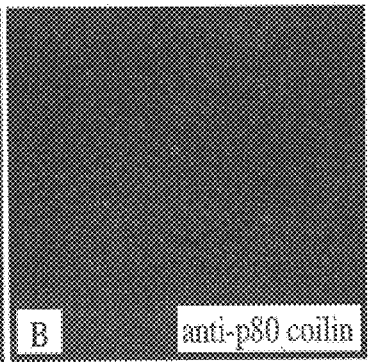
FIG. 18B is an image depicting the localization of p80-coilin in cells expressing mycSMNwt tag recombinant protein. This image depicts a HeLa cell transiently transfected with mycSMN immunostained using anti-p80 coilin rabbit polyserum R288 (red signal).
Figure 18C:
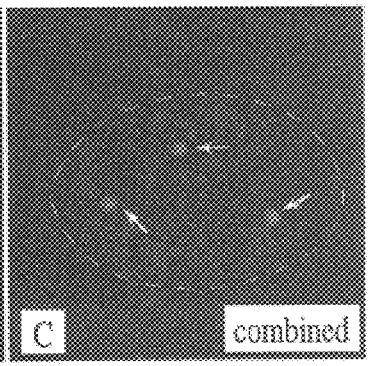
FIG. 18C is an image depicting double-label confocal immunofluorescence demonstrating co-localization of SMNwt and coilin in cells transiently transfected with mycSMN recombinant. HeLa cells transiently transfected with mycSMNwt were immunostained using anti-myc tag (FIG. 18A) and anti-p80 coilin (FIG. 18B) and the two images were combined. Co-localization of red and green signals results in a yellow signal. The nuclear gems are indicated by arrows and the dashed line demarcates the nucleus.
Figure 18D:
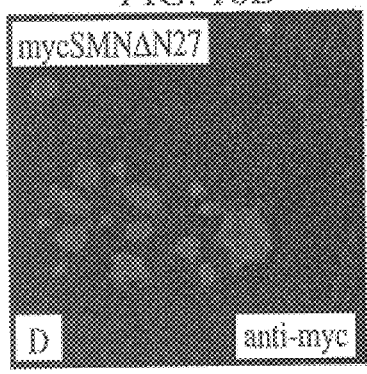
FIG. 18D is an image depicting the distribution SMNΔN27 recombinant in cells transiently transfected with myc-SMNΔN27. HeLa cells transiently transfected with myc SMNΔN27 were immunostained using anti-myc tag monoclonal antibody 9E10 (green signal).
Figure 18E:
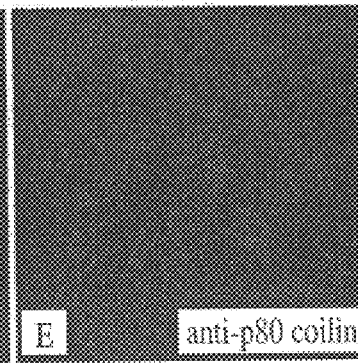
FIG. 18E is an image depicting the localization of p80-coilin in cells expressing myc SMNΔN27 tag recombinant protein. This image depicts a HeLa cell transiently transfected with mycSMNΔN27 immunostained using anti-p80 coilin rabbit polyserum R288 (red signal).
Figure 18F:
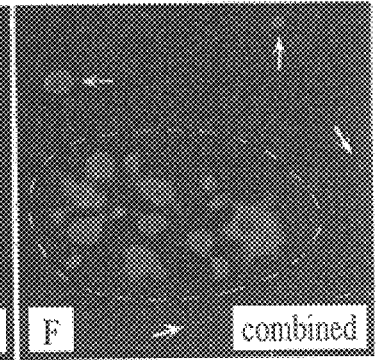
FIG. 18F is an image depicting double-label confocal immunofluorescence demonstrating co-localization of SMNΔN27 and coilin in cells transiently transfected with mycSMN recombinant. HeLa cells transiently transfected with mycSMNΔN27 were immunostained using anti-myc tag (FIG. 18D) and anti-p80 coilin (FIG. 18E) and the two images were combined. Co-localization of red and green signals results in a yellow signal. The cytoplasmic accumulations are indicated by arrows and the dashed line demarcates the nucleus.

FIG. 15B depicts a summary model of several interactions in the SMN complex. SMN appears to be associated with SIP1 most, if not all, of the time (see, e.g., Example 1). Moreover, SIP1 interaction with SMN may have an effect on SMN oligomerization or Sm protein interaction. Monomeric SMN has only a low affinity for Sm proteins because a high-affinity Sm-binding domain forms only upon SMN oligomerization. For simplicity, SMN has been depicted bound to Sm proteins as a dimer; however, the actual stoichiometry of the SMN oligomers is not yet known. Specific protein-protein interactions between the various Sm proteins are required for the ordered assembly of the Sm core (Raker et al., 1996, EMBO J. 15:2256–2269). The data disclosed herein demonstrate that SMN is able to form large oligomers, and, in such a conformation, it binds with high affinity to a subset of Sm proteins. Without wishing to be bound by any particular theory, it may be that the SMN oligomer is the functional core that allows the SMN complex to function in snRNP assembly (e.g., Example 2) and spliceosome regeneration (e.g., Example 4). Importantly, SMN mutations found in SMA patients directly affect SMN oligomerization and Sm protein binding. Thus, the loss-of-function phenotype of mutant proteins such as SMNY272C and SMNΔEx7 in pre-mRNA splicing, as disclosed elsewhere herein, is most likely the direct result of an impaired interaction with the Sm proteins. These findings directly link the molecular mechanism of SMA to a deficiency in the interaction of SMN with spliceosomal snRNP Sm proteins.

A detailed knowledge of the structure of the SMN/SIP1 complex with Sm proteins will lead to further insights into the mechanisms of SMN function and suggest possible therapeutic approaches for SMA.

EXAMPLE 4

Novel Function of SMN in Pre-mRNA Splicing

The experiments presented in this example may be summarized as follows.

As discussed previously elsewhere herein, SMA is a common motor neuron degenerative disease that results from reduced levels of, or mutations in, the Survival of Motor Neurons (SMN) protein. SMN is found in the cytoplasm and the nucleus where it is concentrated in gems. SMN interacts with spliceosomal snRNP proteins and is critical for snRNP assembly in the cytoplasm. The data disclosed herein demonstrate that a dominant-negative mutant SMN (SMNΔN27) causes a dramatic reorganization of snRNPs in the nucleus. Furthermore, SMNΔN27 inhibits pre-mRNA splicing in vitro, while wild-type SMN stimulates splicing. SMN mutants found in SMA patients cannot stimulate splicing. These data demonstrate that SMN plays a crucial role in the generation of the pre-mRNA splicing machinery and thus in mRNA biogenesis, and the data link the function of SMN in this pathway to SMA.

The Materials and Methods used in the experiments presented in this example are now described.

Constructs and Recombinant Proteins Production

DNA fragments corresponding to the open reading frames of SMN wild type (SMN wt), SMNY272C, SMNΔEx7, and SMNΔN27 were generated by PCR amplification using specific primers. In order to effect transient expression of the inserts in HeLa cells, the inserts were cloned downstream of the CMV promoter into a modified pcDNA3 vector (InVitrogen, Carlsbad, Calif.) further containing the myc-tag reporter protein sequence corresponding to the epitope recognized by the monoclonal antibody 9E10 (Siomi and Dreyfuss, 1995, J. Cell Biol. 129:551–560).

For the production of purified recombinant proteins, the same inserts cloned into pcDNA3 were also cloned into the pET28 vector (Novagen Inc., Madison, Wis.). $His_6$-SMN fusion proteins were expressed in the *E. coli* strain BL21 (DE3)pLysS and the proteins were purified by $Ni^{2+}$ chelation chromatography using the Novagen (Madison, Wis.) His-bind Buffer Kit following the manufacturer's protocol. Purified recombinant proteins were dialyzed against buffer D as described by Dignam et al. (1983, Nuc. Acids Res. 11:1475–1489).

The Ad-2 ΔIVS construct, containing L1 exon (41 nucleotides), a deleted form of the first intervening sequence (IVS1, 231 nucleotides) and L2 exon (72 nucleotides) of adenovirus 2 (Ad-2) major late transcription unit, was generated by PCR amplification using pRSP-1-ΔIVS as a template (Konarska et al., 1984, Cell 38:731–736) and the construct was cloned into pcDNA3 (InVitrogen, Carlsbad, Calif.).

Cell Culture and Treatments

HeLa cells were cultured in Dulbecco's modified Eagle's medium (DMEM, GIBCO-BRL, Gaithersburg, Md.) supplemented with 10% fetal calf serum (FCS; GIBCO-BRL).

HeLa cells, plated on glass coverslips, were transfected using the standard calcium phosphate method. Following overnight incubation with DNA, the cells were washed and fresh medium was added. Transfected cells were then fixed and processed for immunofluorescence staining after an additional 24–36 hours of incubation as set forth previously herein.

Immunofluorescence Microscopy

Immunofluorescence staining was carried out essentially as previously described (Choi and Dreyfuss, 1984, J. Cell. Biol. 99:1997–2004). Double-label immunofluorescence experiments were performed by separate sequential incubations of each primary antibody, diluted 1:1000 in PBS containing 3% (w/v) BSA, followed by the specific secondary coupled to fluoresceineisothiocyanate (FITC) or Texas Red (TXRD). All antibody incubations were performed at room temperature for 1 hour. Laser confocal fluorescence microscopy was performed using a Leica TCS 4D (Germany) confocal microscope. Images from each channel were recorded separately and then the data files were merged. Antibodies used in these experiments were as follows: Rabbit polyserum anti-p80 coilin (R288, described in Andrade et al., 1993, Proc. Natl. Acad. Sci. USA 90:1947–1951), mouse IgG1 monoclonal anti-SMN (2B1), mouse IgG1 monoclonal anti-TMG cap (K121; Krainer, 1988, Nucleic Acids Res. 16:9415–9429) (Calbiochem, San Diego, Calif.), mouse IgG3 monoclonal anti-Sm (Y12; Lerner et al., 1981, Proc. Natl. Acad. Sci. USA 78:2737–2741), mouse IgG1 monoclonal anti-myc (9E10), and affinity purified rabbit polyserum anti-myc (A-14, obtained from Santa Cruz Biotech, Santa Cruz, Calif.).

In situ hybridization was performed following the protocol described by Matera and Ward (1993, J. Cell Biol. 121:715–727). Briefly, the oligonucleotide probe was a biotinylated 2'-OMe RNA complementary to U2 snRNA region 30–43 (Wassarman and Steitz, 1991, Mol. Cell. Biol. 11:3432–3445) and the biotinylated probe was detected using streptavidin directly coupled to TXRD (GIBCO-BRL).

In vitro Transcription and Splicing Assay

For use as templates for in vitro transcription, pSP14–15 (Ohno and Shimura, 1996, Genes & Dev. 10:997–1007) and Ad-2 ΔIVS were linearized with SmaI and XbaI, respectively. In vitro transcription was carried out and transcribed RNAs were purified as described by Ohno and Shimura (1996, Genes & Dev. 10:997–1007). In vitro splicing assays in 10 µl were performed essentially as described (Ohno and Shimura, supra) except the amount of HeLa cell nuclear extract used was reduced by a half (13 milligrams per milliliter) in the reaction mixture. In the pre-incubation experiments, the splicing mixture was incubated with the indicated amount of either SMNwt, SMNY272C, SMNΔEx7, or SMNΔN27 recombinant protein for 20 minutes at 30° C. Pre-mRNA was added and the mixture was incubated for an additional 20 or 40 minutes at 30° C. For antibody inhibition experiments, all antibodies were purified using a protein-G Sepharose column (Pharmacia LKB Biotechnology Inc., Piscataway, N.J.) and then dialyzed against buffer D (Dignam et al., 1983, Nucl. Acids Res. 11:1475–1489). Purified antibodies were incubated with HeLa cell nuclear extract and 10×SP buffer (Ohno and Shimura, 1996, Genes & Dev. 10:997–1007) for 20 minutes at 30° C. After addition of labeled pre-mRNA, the mixture was incubated for an additional 20 or 40 minutes at 30° C. RNA products were analyzed by electrophoresis on a 6% acrylamide/8.3 M urea gel for pSP14–15 RNA, and on a 10% acrylamide/8.3 M urea gel for Ad-2 ΔIVS RNA, followed by autoradiography.

Analysis of Splicing Complex Formation by RNP Gel Electrophoresis

For analysis of splicing complexes, splicing reactions were carried out as described previously herein using $\alpha$-$^{32}$P-labeled chicken δ-crystalline pre-mRNA. After a 30 minute incubation at 30° C., 50 micrograms of heparin (Sigma)

were added to each reaction and the reaction was placed on ice for 10 minutes. An RNP native gel electrophoresis on a 3.75% polyacrylamide gel was performed as described in Konarska (1989, Methods Enzymol. 180:442–453).

The Results of the experiments presented in this example are now described.

Dominant-negative SMN Mutant Causes Reorganization of snRNPs, Gems, and Coiled Bodies To define the functional domains of SMN, various deletion mutants were constructed and their interactions with SIP1 and the Sm proteins were examined both in vitro by binding assays, and in vivo by co-immunoprecipitation after transfections into mammalian cells. Moreover, the expression and cellular localization of the myc-tagged mutants was monitored as well as their effect on snRNP localization. A particularly striking effect was observed by transfection of amino terminal deletion mutants, and one of these, a mutant lacking the first 27 amino acids of SMN, SMNΔN27, was investigated in detail.

Double-label immunofluorescence using anti-myc-tag antibodies to detect either the transfected myc-SMN or myc-SMNΔN27, and the anti-Sm antibody Y12, demonstrated accumulation in the cytoplasm of Sm proteins colocalized with the mutant SMNΔN27 in discrete aggregates (FIG. 16A). In the nucleus, a striking rearrangement of snRNPs (and possibly also some Sm proteins) was observed and they also co-localized with SMNΔN27. In contrast, in cells transfected with wild-type myc-tagged SMN (FIGS. 16A and 16C), as in untransfected cells, there was a barely detectable signal of Sm proteins in the cytoplasm, and the nuclear staining of Sm snRNPs demonstrated general nucleoplasmic distribution with higher local concentrations in interchromatin granules (also referred to as "speckles"), and particularly intense staining in coiled bodies (Carmo-Fonseca et al., 1991, EMBO J. 10:195–206; Huang and Spector, 1992, Proc. Natl. Acad. Sci. USA 89:305–308). In these cells, SMN staining of gems was visible adjacent to and in most cases overlapping with that of coiled bodies (FIG. 16C). There was a higher diffuse nucleoplasmic staining of myc-SMN than is normally seen in untransfected cells likely due to the overexpression of the protein, but the size, number and localization of gems was unchanged relative to untransfected cells.

In the SMNΔN27 transfected cells, endogenous SMN and SIP1 were completely co-localized with SMNΔN27 and with snRNPs. The number of the merged SMN- and snRNP-containing bodies in the SMNΔN27 transfected cells was greater than the number of gems (or of coiled bodies) in control cells, and they were much larger than gems and coiled bodies. These merged structures could become as large as the nucleoli.

The localization of a specific spliceosomal snRNA in cells transfected with SMNΔN27 was also studied. To do so, the localization of U2 snRNA was determined by in situ hybridization using a U2-specific antisense probe as described by Matera and Ward (1993, J. Cell Biol. 121:715–727). FIGS. 17A and 17C demonstrate that the cytoplasmic accumulations that stained intensely for both the SMNΔN27 and Sm proteins also contained U2 snRNA, while cells transfected with wild-type SMN exhibited only slight cytoplasmic background staining. This suggests that complexes containing Sm proteins, snRNAs and SMN accumulated in the cytoplasm of SMNΔN27 but not SMN wt cells, likely representing a block in the pathway of cytoplasmic snRNP assembly.

This block in cytoplasmic snRNP assembly was examined further by immunostaining using an anti-trimethyl-G cap (TMG)specific antibody. The TMG cap is formed by hypermethylation of the 5' monomethyl G cap of the snRNAs, and this step has been shown to take place in the cytoplasm after Sm core assembly has occurred (Mattaj, 1986, Cell 46:905–911; Fischer and Luhrmann, 1990, Science 249:786–790). The immunostaining indicated that although the cytoplasmic accumulations caused by SMNΔN27 contained U2 as well as Sm proteins and SMN, the snRNAs within them did not receive the TMG modification (FIGS. 17D and 17F). Although the possibility that lack of TMG immunostaining in the cytoplasm is a result of masking cannot be excluded, the complete absence of signal and the strong staining in the nucleus make this unlikely. Thus, without wishing to be bound by theory, it appears that the snRNP assembly pathway in the cytoplasm is arrested at a step preceding the cap hypermethylation. The snRNAs in the nuclei of the same cells, however, are hypermethylated, since they stain efficiently with the anti-TMG antibody. These effects of SMNΔN27 suggest that the construct has a dominant-negative phenotype over wild type SMN. These data also suggest that SMN and SIP1 (i.e., Gemin2) interact with Sm proteins in the cytoplasm, and, importantly, also with snRNPs in the nucleus. Further, these data demonstrate that mutations in SMN can have profound effects on both the biogenesis and localization of spliceosomal snRNPs in the cell.

Gems, the structures in which SMN and SIP1 are most highly concentrated in the nucleus, are usually found adjacent to and often merged with coiled bodies (Liu and Dreyfuss, 1996, EMBO J. 15:3555–3565; Liu et al., 1997, Cell 90:1013–1021). Therefore, it was determined whether the SMN mutant, SMNΔN27, had any effect on the structure or organization of coiled bodies by staining the cells with antibodies to p80 coilin, a coiled bodies-specific marker (Andrade et al., 1991, J. Exp. Med. 173:1407–1419). The images depicting immunomicrographs demonstrate that coiled bodies and gems became completely merged in the nucleus and that the p80 coilin staining completely coincided with the staining of the enlarged gems (FIGS. 18A–F). These enlarged merged nuclear structures therefore contained snRNPs, coiled bodies, and gem components. The reorganization of coiled bodies that SMNΔN27 brings about suggests a functional relationship between SMN and coiled bodies.

SMNΔN27 Inhibits Pre-mRNA Splicing When Added During Preincubation

The profound effect of SMN on the organization of nuclear snRNPs, particularly the formation of large snRNP-containing aggregates which are similar in appearance to those observed in cells in which snRNPs are inactivated by antisense oligonucleotides (O'Keefe et al., 1994, J. Cell Biol. 124:249–260) or when transcription is inhibited by actinomycin D (Zeng et al., 1997, EMBO J. 16:1401–1412), suggest that SMNΔN27 can cause an inactivation of snRNPs and, possibly, of other pre-mRNA splicing factors. To address this directly, the effect of SMNΔN27 on pre-mRNA splicing was examined in an in vitro system.

Figure 19A:
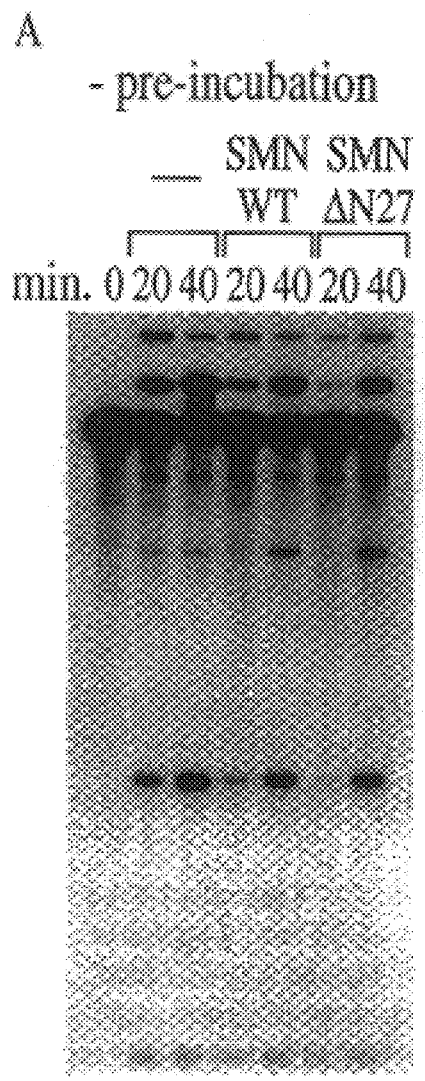
FIG. 19A is an image of a gel depicting the effect of SMN wild type and SMNΔN27 recombinant proteins on pre-mRNA splicing in vitro. This image depicts in vitro splicing assays in the presence of SMN wild type and SMNΔN27 recombinant proteins. [$\alpha$-$^{32}$P]-labeled chicken δ-crystallin pre-mRNA was incubated for 20 or 40 minutes at 30° C. with 50 micrograms of HeLa cell nuclear extracts (13 milligrams per milliliter) in the presence of buffer D (lanes 2 and 3), or 37.5 micrograms per milliliter of recombinant SMN wt (lanes 4 and 5) or 37.5 micrograms per milliliter of SMNΔN27 (lanes 6 and 7). The RNA products were analyzed by gel electrophoresis.

SMN wt and SMNΔN27 were produced in bacteria as recombinant proteins bearing a His-tag, the fusion proteins were purified to homogeneity and then they were added to nuclear splicing extracts. $^{32}$P-labeled chicken δ-crystallin pre-mRNA was used as a splicing probe and the reaction products were analyzed by gel electrophoresis. Addition of SMN wt or the SMNΔN27 mutant fusion protein to the reaction at time zero had almost no effect on the splicing reaction, although both fusion proteins appeared to stabilize the intron (FIG. 19A).

Figure 19B:
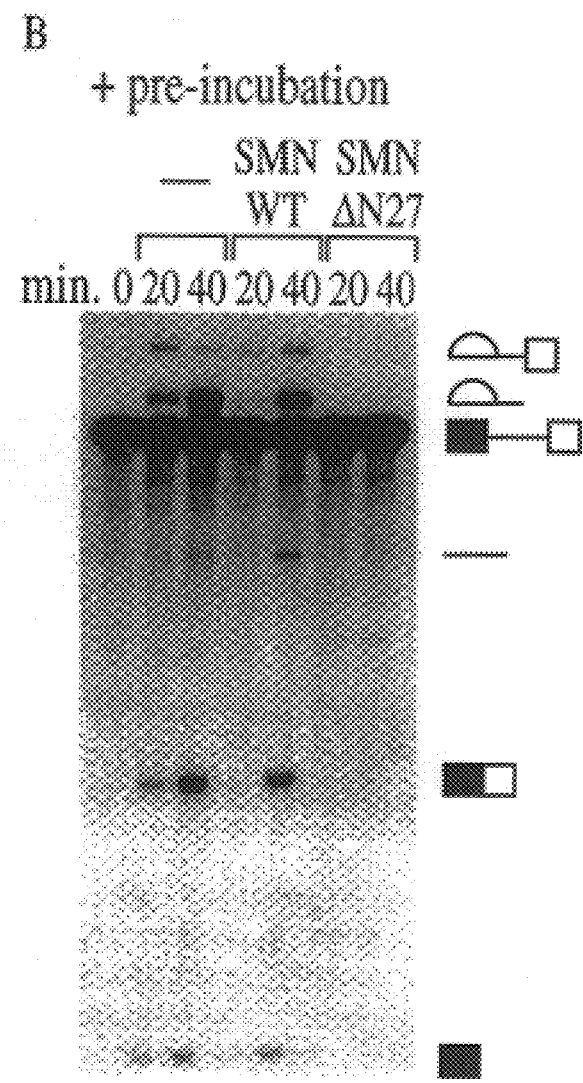
FIG. 19B is an image of an RNA gel depicting in vitro splicing assays after pre-incubation with SMN wild type and SMNΔN27 deletion recombinant proteins. HeLa cell nuclear extracts were first incubated for 20 minutes at 30° C. in the presence of buffer D (lanes 2 and 3), or 37.5 micrograms per milliliter of SMN wt (lanes 4 and 5) or 37.5 micrograms per milliliter of SMNΔN27 (lanes 6 and 7). [α-$^{32}$P] labeled chicken δ-crystallin pre-mRNAs were added and the reactions were incubated further at 30° C. for the indicated additional times. RNA products were analyzed by gel electrophoresis. The structures of the splicing products are shown schematically on the right-hand side of the figure.

It was next determined whether SMN, while not a splicing factor per se, may be important for some function akin to its role in snRNP assembly in the cytoplasm. That is, although nuclear snRNPs are thought to be stable and fully assembled, they may need to be regenerated or reassembled between rounds of splicing, and SMN may be required for this process. To address this possibility, the splicing extract was allowed to run in the presence of SMNΔN27 before the labeled pre-mRNA probe was added. Therefore, the extract was pre-incubated with all the components, including an energy generating system and SMN wt or SMNΔN27, but without the pre-mRNA for 20 minutes, at which time the δ-crystallin pre-mRNA probe was added and the reaction was allowed to proceed for an additional 20 or 40 minutes. A strong inhibition of splicing was observed only in the samples to which the SMNΔN27 was added during the pre-incubation period (FIG. 19B). Identical amounts of SMN wt and of SMNΔN27 were used in the splicing reactions, and the inhibition demonstrated in samples pre-incubated with SMNΔN27 was concentration-dependent. About three- to five-fold mass excess of SMNΔN27 over endogenous SMN was sufficient for complete inhibition of δ-crystallin pre-mRNA splicing.

Figure 20:
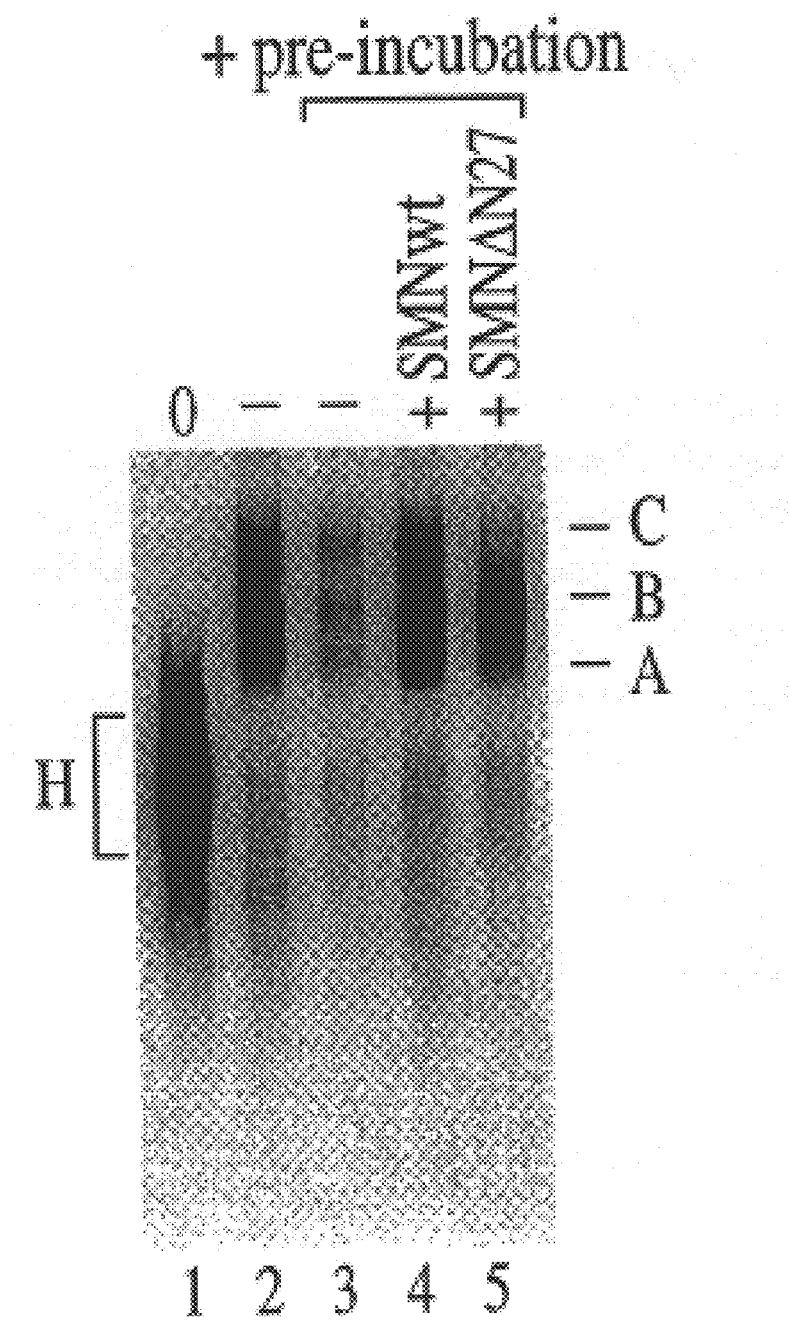
FIG. 20 is an image depicting a gel demonstrating the effect of SMN recombinant proteins on spliceosome formation in vitro. Splicing reactions were carried using [α-$^{32}$P]-labeled chicken δ-crystallin pre-mRNA without (lanes 1 and 2) or with (lanes 3–5) preincubation. Splicing complexes were fractionated using electrophoresis on a native polyacrylamide gel and the complexes were visualized using autoradiography as described elsewhere herein.

SMNΔN27 Blocks the Formation of Spliceosomal Complex C and SMNwt Stimulates Spliceosome Formation When Added During Preincubation The observation that preincubation with SMNΔN27 causes inhibition of splicing, including a block to the first step of the pre-mRNA reaction, cleavage at the 5' splice site, and lariat intron formation, indicated a block to an early step in the spliceosome formation. In order to characterize this block in greater detail and to determine whether the snRNPs could interact with the pre-mRNA at all, the RNP complexes were analyzed by native gel electrophoresis (Konarska, 1989, Methods Enzymol. 180:442–453). Immediately upon addition to a nuclear extract, the pre-mRNA rapidly forms an ATP-independent complex with endogenous RNA-binding hnRNP proteins termed H complex (FIG. 20, lane 1). With further incubation at 30° C. in the presence of ATP, several larger complexes are observed (FIG. 20, lane 2), which are designated A, B, and C complex (FIG. 23; see also Ohno and Shimura, 1996, Genes & Dev. 10:997–1007). Consistent with the notion that allowing the extract to preincubate under splicing conditions leads to a reduction in active components, the capacity of the extract to form splicing complexes was significantly reduced during a 20 minute preincubation (FIG. 20, lane 3). However, SMNwt prevented this reduction so that the extract retained and in fact exhibited increased efficiency of splicing complex formation (FIG. 20, lane 4). In contrast, although extracts to which SMNΔN27 has been added show a higher capacity to form A and B complexes compared with untreated extract, the formation of the C complex, which is the mature spliceosome, is completely inhibited (FIG. 20, lane 5). These results suggest that SMN has an important role in maintaining snRNPs in active form and that the amino-terminal 27 amino acids of the protein are critical for this process.

Antibodies to the Amino Terminus of SMN Inhibit and Antibodies to the Carboxyl Terminus Stimulate Pre-mRNA Splicing When Added During Preincubation Amino terminal deletions in the SMN gene, or other dominant-negative mutations in SMN, have not been found so far in SMA patients, who, in the vast majority of cases, exhibit only dramatic reduction in the level of the wild-type SMN protein. To mimic this situation and to address the role of SMN in pre-mRNA splicing, the available amount of the SMN protein was reduced without the addition of an SMN mutant.

Figure 21:
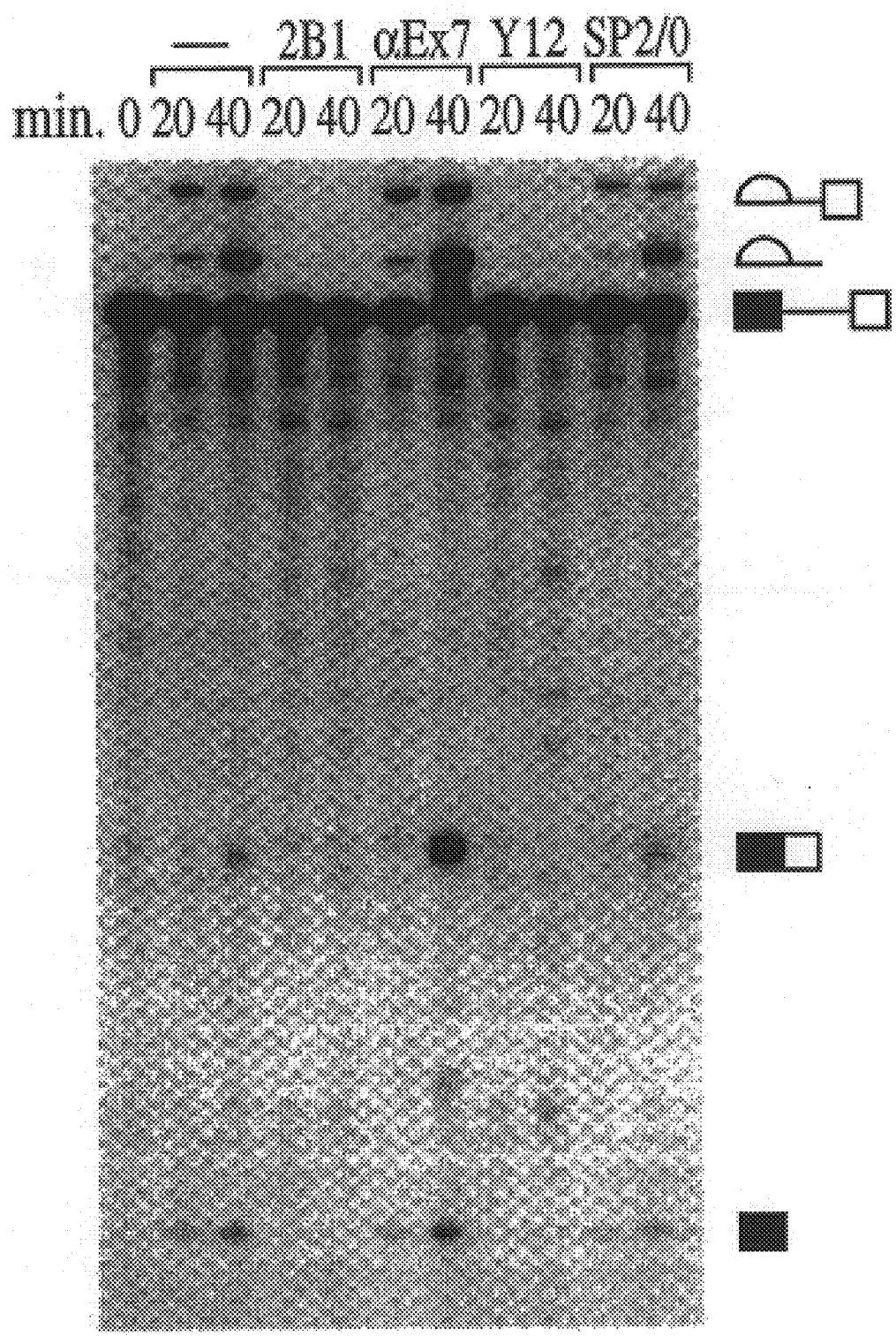
FIG. 21 is an image depicting a gel demonstrating the effect of pre-incubation with of anti-SMN antibodies on pre-mRNA splicing in vitro. Two micrograms of the following purified antibodies were added to the splicing reaction mixture: Y12 (anti-Sm), anti-SMN monoclonal (2B1), anti-SMN exon 7 (αEx7), and control antibody (SP/0). [α-$^{32}$P]-labeled chicken δ-crystallin pre-mRNA was added to the splicing reaction mixture and the mixture was incubated for an additional 20 or 40 minutes at 30° C. The RNA products were analyzed by gel electrophoresis. A schematic representation of the structure of each radiolabeled RNA product is depicted along the right-hand side of the figure.

SMN is tightly associated with SIP1, this interaction being resistant to dissociation with 1 M NaCl, and SMN also associated with other proteins thus precluding the use of immunodepletion as a way of removing exclusively SMN from the extract. Therefore, purified anti-SMN monoclonal antibody (2B1) was added to the extract to determine whether anti-SMN could cause specific immunoinhibition of pre-mRNA splicing. The results, shown in FIG. 21, demonstrate that 2B1 strongly inhibited splicing but, again, only if it was added during the pre-incubation period. The lack of inhibition seen when the antibody was added at the same time as the probe pre-mRNA indicated that 2B1 was not simply toxic to the reaction. Consistent with the dominant-negative effect of SMNΔN27, the first 27 amino acids of SMN are part of the epitope recognized by 2B1. The specificity of the 2B1 effect was illustrated by the lack of inhibition by the control antibody SP2/0, and further by the lack of inhibition by an affinity purified rabbit polyclonal antibody raised against a SMN peptide corresponding to the extreme C-terminus encoded by exon 7. In fact, the anti-exon 7 antibody had a strong stimulatory effect. Further, the data demonstrate that anti-SMN (2B1) was as strong an inhibitor of pre-mRNA splicing as the anti-snRNP antibody Y12 (FIG. 22; Padgett et al., 1983, Cell 35:101–107).

Unlike SMNwt, SMN Mutants Found in SMA Patients do not Stimulate Splicing When Added During Preincubation In addition to the homozygous deletion of both telomeric SMN genes, several point mutations and partial deletions of the carboxyl terminus of SMN have been identified in SMA patients as reviewed in Burghes (1997, Am. J. Hum. Genet. 61:9–15). The effects of two mutations leading to the severe type I SMA phenotype, the Y272C point mutation and the deletion of the amino acid sequence encoded by the exon 7 (Lefebvre et al., 1995, Cell 89:155–165; Burghes, 1997, Am. J. Hum. Genet. 61:9–15), have been investigated. SMN deleted of exon 7 (designated SMNΔEx7) is also thought to be the main form produced by the centromeric SMN gene (Gennarelli et al., 1995, Biochem. Biophys. Res. Commun. 213:342–348). These loss-of-function mutations of SMN are recessive and result in the SMA phenotype in individuals carrying a deletion of the other telomeric SMN allele. As these are recessive mutations, they were not expected to produce the inhibitory effects of SMNΔN27. Nonetheless, it was determined whether these recessive mutations could substitute for SMNwt in providing a stimulatory effect during preincubation. These experiments were performed using the adenovirus 2 major late transcription unit-derived pre-mRNA, Ad-2 ΔIVS (Konarska et al., 1984, Cell 38:731–736), rather than the δ-crystallin pre-mRNA because it was also sought to be determined whether the inhibitory effect of SMNΔN27 was a general phenomenon, as opposed to an effect that is unique to δ-crystallin pre-mRNA.

Figure 22:
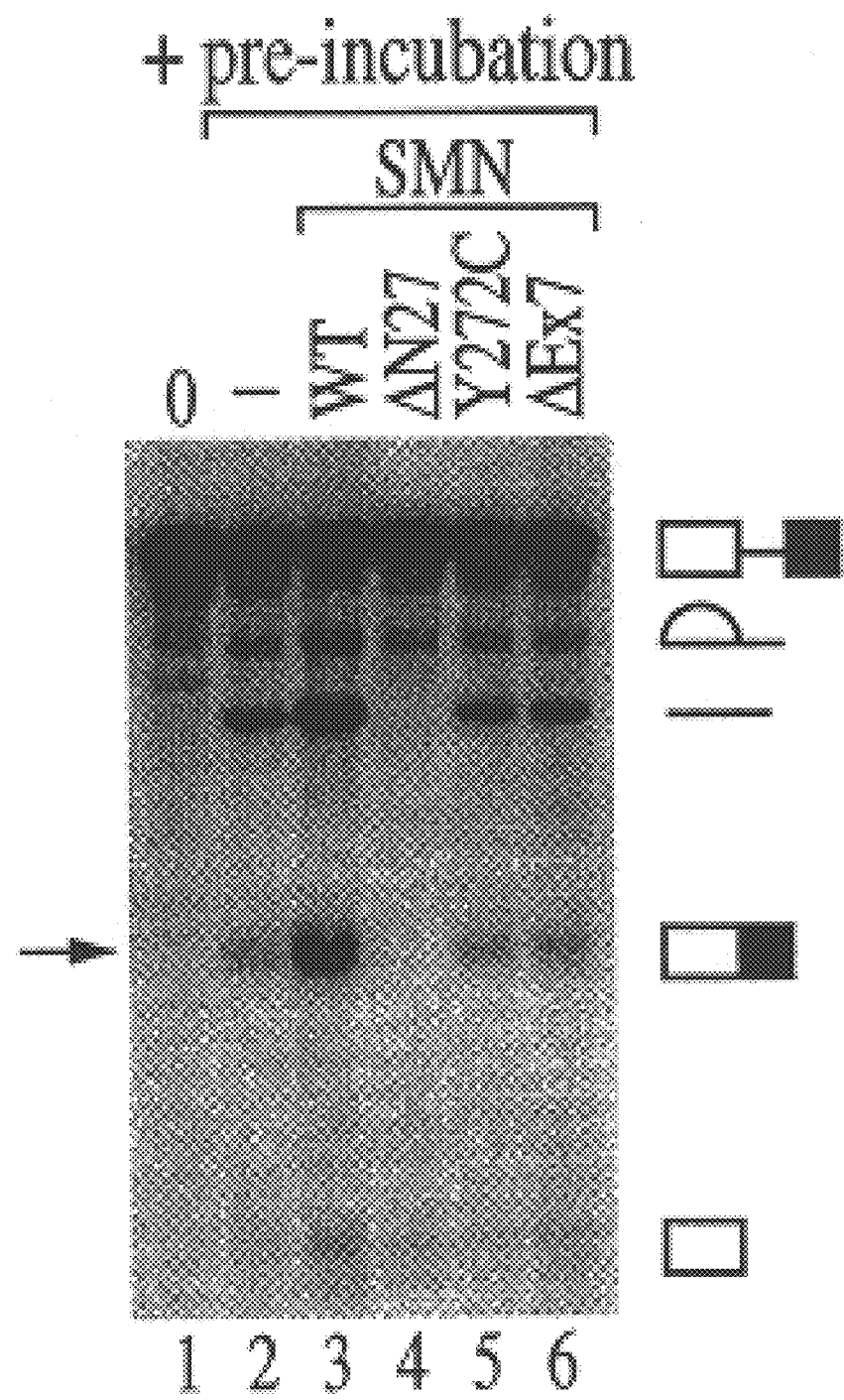
FIG. 22 is an image depicting a gel demonstrating the effect of SMNwt, SMNΔN27, SMNY272C, and SMNΔEx7 recombinant proteins on in vitro splicing of adenovirus 2 major late pre-mRNA (Ad-2 ΔIVS). The splicing reaction mixture was preincubated using either buffer D (lane 2) or 20 micrograms per milliliter of recombinant protein as indicated in lanes 3–6. [α-$^{32}$P]-labeled adenovirus 2 major late pre-mRNA was then added to the mixture and the samples were incubated for 40 minutes at 30° C. The RNA products were analyzed by gel electrophoresis. A schematic representation of the structure of each radiolabeled RNA product is depicted along the right-hand side of the figure. The total inhibition of pre-mRNA cleavage by SMNΔN27 was not as complete as that disclosed previously elsewhere herein (e.g., FIG. 19A) because of the lower amount of recombinant protein used in this experiment.

Similar to its effect on δ-crystallin pre-mRNA splicing, addition of SMNΔN27 during the pre-incubation time inhibited the splicing of Ad-2 ΔIVS pre-mRNA (FIG. 22). In contrast, addition of the wild-type SMN had a strong stimulatory effect on adenovirus pre-mRNA splicing. Neither SMNY272C nor SMNΔEx7 had any detectable effect, demonstrating neither stimulation nor inhibition of pre-mRNA splicing. The recombinant proteins used in these experiments were produced side-by-side using the same procedure, and identical amounts were added to each assay. All these SMN recombinant proteins were able to directly bind a GST-SIP1 fusion protein in vitro, further suggesting that the recombinant proteins were purified in native form. These findings demonstrate that SMN has an important and unexpected general role in pre-mRNA splicing, and these data demonstrate a direct connection between the molecular defect of SMA and the pre-mRNA splicing cycle.

The data disclosed herein demonstrate that SMN has functions both in the cytoplasm and in the nucleus in both snRNP biogenesis and function. Previous experiments in Xenopus oocytes disclosed previously elsewhere herein demonstrated a role for SIP1 in the biogenesis of snRNPs by serving as an assembly factor for the snRNAs and the snRNP Sm core proteins. Those experiments, however, did not reveal as clear and direct a role for SMN as for SIP1, because while microinjections of anti-SIP1 antibodies strongly inhibited snRNP assembly, the anti-SMN antibodies had a stimulatory effect (see Example 2). The experiments in somatic cells reported herein demonstrate that transfection of an SMN mutant blocks snRNP assembly in the cytoplasm, indicating that SMN, like SIP1, is critical for this process. The data disclosed herein further demonstrate that the requirement for SMN in snRNP assembly is a general one and not a phenomenon that is unique to amphibian oocytes.

Although the presence of SMN and SIP1 in the nucleus and their high concentration in gems, adjacent to and often merged with the snRNP-rich coiled bodies, suggested a function for these proteins in the activity of snRNPs in the nucleus, the strong effect of SMNΔN27 on nuclear snRNP organization was unexpected. As this raised the possibility of an involvement of these proteins, particularly of SMN, in the activity of snRNPs in pre-mRNA splicing, this possibility was examined. The data disclosed herein point to a novel function of SMN in the pre-RNA splicing cycle and suggest that some components of the spliceosome, likely snRNPs but possibly also other components, require SMN for their function. The lack of an effect of SMNΔN27 upon its addition to a splicing extract indicates that SMN is neither a general inhibitor of splicing nor a splicing factor per se. Rather, inhibition of splicing by SMNΔN27 and by the anti-SMN antibody 2B1 are seen only if the mutant or the antibody are added to the extract and the reaction is preincubated before the pre-mRNA probe is added. This inhibition, which is not observed with wild-type SMN and which is general rather than pre-mRNA specific, suggest a role for SMN in regeneration of snRNPs (and possibly also of other components). Without wishing to be bound by any particular theory, the data disclosed herein suggest that during the incubation of the nuclear extract under splicing conditions, including an energy-regenerating system, some of its components, likely including snRNPs, become inactivated and their regeneration to functional form requires SMN. Indeed, addition of recombinant SMNwt greatly stimulates both spliceosome formation and splicing. In splicing competent extracts, endogenous SMN is sufficient to provide this activity, but addition of SMNΔN27 causes a block to this regeneration process and acts as a dominant-negative mutant of SMN because it is able to engage in some of the same interactions as SMN but the mutant protein traps complexes in a nonfunctional state. The interactions of SMNΔN27 with Sm proteins, with SIP1, and with SMN are indistinguishable from that of wild-type SMN. SMN mutations found in SMA patients do not show either a stimulation or an inhibition of splicing, confirming that they represent loss-of-function recessive mutants. Since SMNY272C and SMNΔEx7 have a highly reduced oligomerization capacity (Lorson et al., 1998, Nature Genet. 19:63–66), SMN oligomerization may be required for its splicing-regenerating activity. It should be noted that although the general term "regeneration" is used to describe this function of SMN, the actual mechanism involved is not yet known and the present invention is not limited to any particular mechanism of SMN action.

Several recycling factors that are essential for splicing, mostly DEAD/DEAH box RNA helicases, have been described previously. Recycling factors, exemplified by S. cerevisiae Prp22 and Prp43, function in the disassembly of snRNPs, splicing factors, intron lariat, and spliced mRNA from the spliceosome (Staley and Guthrie, 1998, Cell 92:315–326). For example, Prp22 is needed for releasing the mRNA from the spliceosome and therefore yeast cells that are made deficient in functional Prp22 accumulate mRNA on spliceosomes in the nucleus but there is no block in pre-mRNA splicing (Company et al., 1991, Nature 349:487–493). Similarly, deficiency in Prp43, a recycling factor required for disassembly of U snRNPs-intron lariat complex, does not result in inhibition of splicing (Arenas and Abelson, 1997, Proc. Natl. Acad. Sci. USA 94:11798–11802). Splicing extracts preincubated with SMNΔN27 do not show any cleavage of the pre-mRNA indicating that even the first step in the splicing reaction, i.e., the cleavage at the 5' splice site and the concomitant formation of the intron lariat, has not taken place. This is somewhat similar to what is seen upon depletion of Prp24, the recycling factor required for re-annealing of U4 and U6 snRNPs (Raghunathan and Guthrie, 1998, Science 279:857–860). As disclosed herein, the RNP gel analysis suggests that there is a deficiency in functional components that are required for spliceosome complex C formation. Future experiments will characterize the block to C complex formation and attempt to define the specific defect that results from incubation of the extract with SMNΔN27 or from reduced levels of SMN. Further, unlike recycling factors described so far, SMN and SIP1 do not contain DEAD/DEAH motifs. However, as disclosed previously elsewhere herein, additional proteins are found in the SMN/SIP1 complex, and it is possible that one of these proteins has such an activity. Indeed, the data disclosed elsewhere herein demonstrate that a novel SMN-interacting protein, Gemin3, contains a DEAD/DEAH motif (see Example 6).

Figure 23:
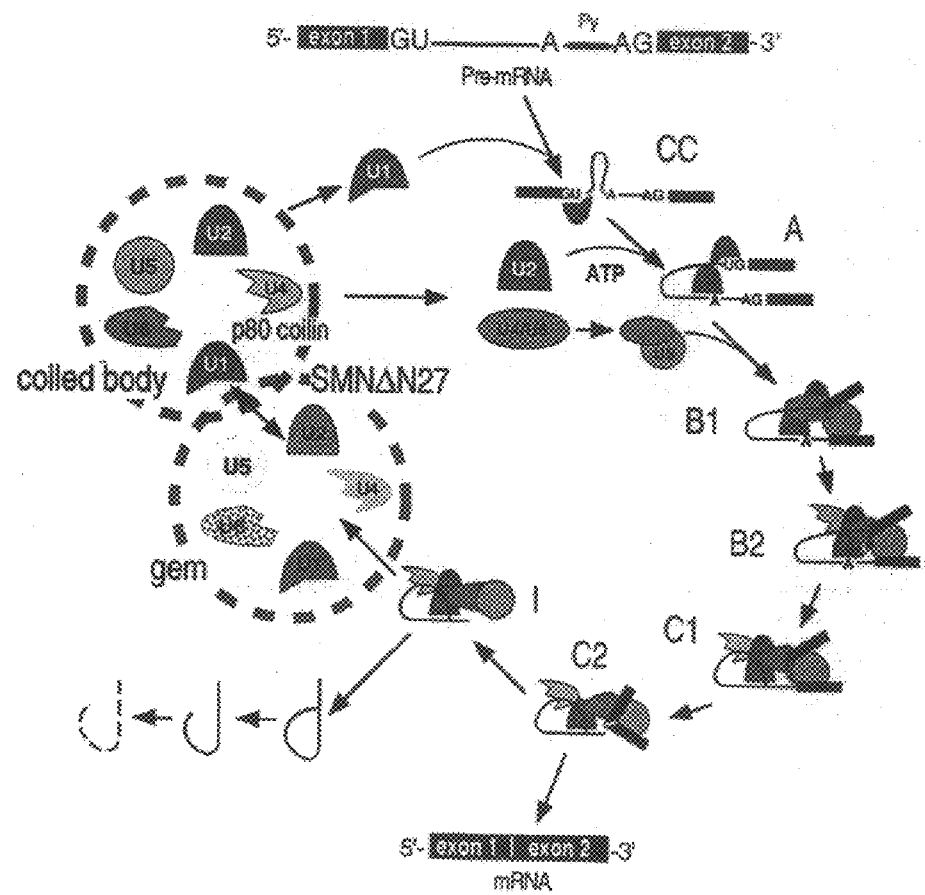
FIG. 23 is a diagram depicting a model of the role of SMN in pre-mRNA splicing. Without wishing to be bound by any particular theory, this diagram depicts the nuclear function (s) of SMN, and of gems and coiled bodies, in recycling snRNPs after pre-mRNA splicing as discussed more fully elsewhere herein.
Figures 24A, 24B:
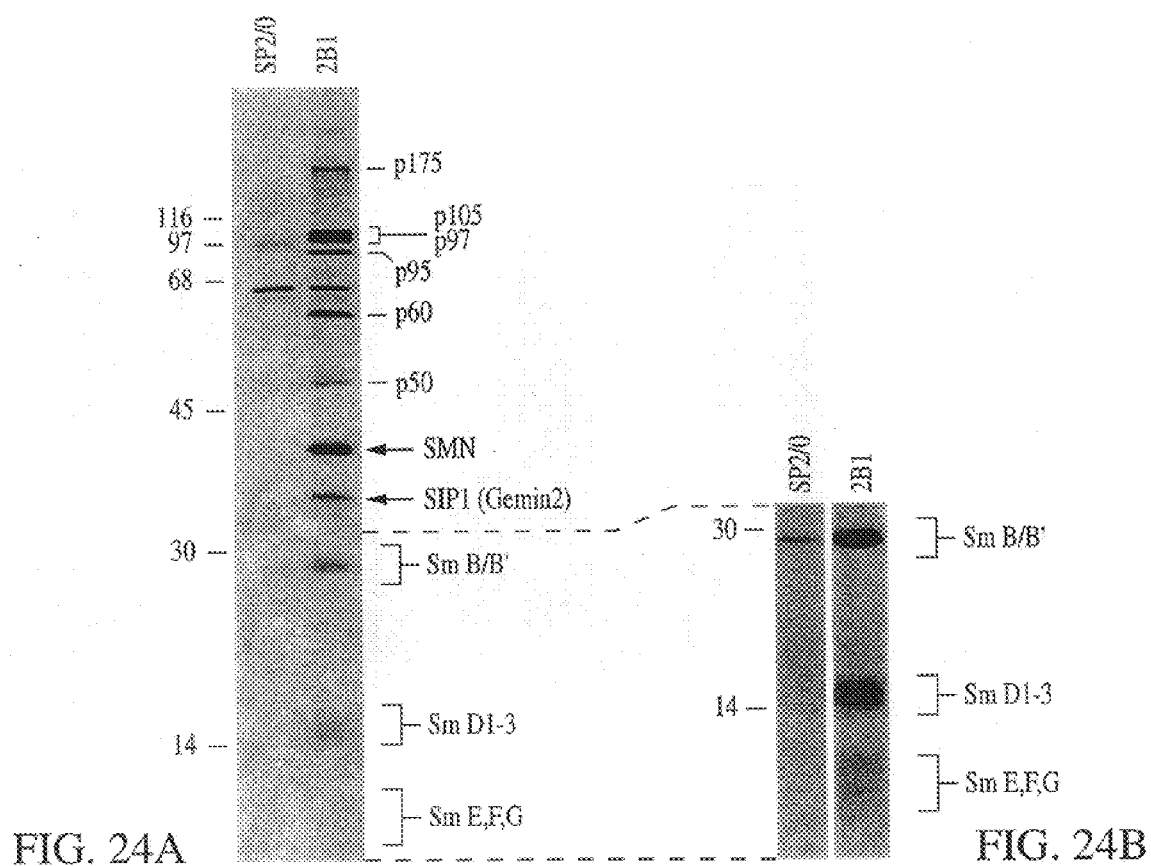
FIG. 24A is an image of a gel depicting immunoprecipitation of the SMN complex using anti-SMN monoclonal antibody 2B1 from [35S]methionine labeled HeLa cell lysate. The immunoprecipitated proteins were analyzed by SDS-PAGE and autoradiography (24 hours exposure). Antibody 2B1 (lane 2B1) immunoprecipitated SMN, Gemin2, Sm proteins B, B', D1–3, E, F and G, and a group of proteins indicated as p175, p105, p97, p95, p60 and p50. The SP2/0 lane demonstrates the background of immunoprecipitation (lane SP2/0).
FIG. 24B is an image depicting a longer exposure (36 hours) of the bottom part of the gel depicted in FIG. 24A. The longer exposure detects Sm proteins more clearly than the shorter 24 hour exposure. The position of the molecular weight markers is indicated on the left of SP2/0 lane in kilodaltons (kDa).

Without wishing to be bound by any particular theory, the data disclosed herein demonstrate that the factors requiring regeneration, presumably snRNPs, must exist in two states, inactive and active, and that the conversion of inactive to active forms requires SMN. The conversion of active to inactive may be a consequence of their function in splicing or it may be an intrinsic switch that they undergo independent of splicing. By analogy to the function of SMN and SIP1 in the cytoplasm, it may be that snRNPs in the nucleus, although thought of as stable, fully assembled, and functional RNPs, in fact undergo some disassembly or rearrangements, and SMN and SIP1 are required for their reassembly to regenerate them into functional form. A scheme depicting this proposed view of the place of SMN in the pre-mRNA splicing cycle is shown in FIG. 23. The nuclear functions of SIP1 are not yet known and are being investigated.

Coiled bodies were first described in 1903 by Ramón y Cajal, who observed them in neuronal cells and named them nucleolar accessory bodies (Ramón y Cajal, 1903, Trab. Lab. Invest. Biol. 2:129–221). Over the past several years, coiled bodies have received much renewed interest as they have been found to contain the highest concentration of snRNPs in the nucleus, and additional data have raised the possibility that they have important, albeit not clearly defined, roles in the formation of both splicing components and the nucleolus (Raska et al., 1990, J. Struct. Biol. 104:120–127; Lamond and Carmo-Fonesca, 1993, Trends Cell Biol. 3:198–204; Bohmann et al., 1995, J. Cell Biol. 131:817–831; Roth, 1995, Curr. Opin. Cell Biol. 7:325–328;

Lamond and Earnshaw, 1998, Science 280:547–553). The effect of SMNΔN27 on coiled bodies provides insight into the function of both gems and coiled bodies. It indicates that there is a functional relationship between these two structures and, in particular, that SMN affects the organization, and likely the function, of coiled bodies. It is possible that gems and coiled bodies represent two stations in a pathway along which snRNPs need to proceed to become functional. At this stage, the order of steps between these stations cannot be assigned. The data disclosed herein directly link the functions of coiled bodies and gems to pre-mRNA splicing components, specifically to a regeneration of snRNPs.

The functions disclosed for the first time herein for SMN and SIP1 define them as critical proteins for the generation of the splicing machinery and thus ultimately for the process of mRNA biogenesis. Consistent with a housekeeping function for SMN, SMN knockout mice display an early embryonic lethal phenotype (Schrank et al., 1997, Proc. Natl. Acad. Sci. USA 94:9920–9925). Most SMA patients, particularly those with the fatal infant form, SMA type I, have a drastic reduction in the amount of SMN in motor neurons (Lefebvre et al., 1997, Nature Genet. 16:265–269). In some cases, SMA patients produce a protein bearing a recessive mutation like the SMNY272C and SMNΔEx7 analyzed here. It is therefore important that, as disclosed herein, these mutants do not have the capacity to provide the activity of wild-type SMN in splicing. Together, these novel findings presented here strongly suggest that motor neurons of SMA patients are impaired in their capacity to produce mRNAs and as a result, become deficient in proteins that are necessary for the growth and functions of these cells.

In conclusion, SMA is a human splicing disease, and better knowledge of the precise molecular details of the mechanism of action of SMN in this process will likely facilitate the search for a therapeutic approach to this devastating disease. Although SMA is considered to be an autosomal recessive disease, the phenotype of SMNΔN27 demonstrates that some mutations in SMN will have a dominant-negative lethal phenotype.

EXAMPLE 5

Gemin3: A Novel DEAD Box Protein That is a Component of Gems and That Interacts With SMN The experiments presented in this example may be summarized as follows.

The data disclosed herein demonstrate the cloning and characterization of a heretofore unknown protein that is a component of the SMN complex, a novel DEAD box putative RNA helicase, designated "Gemin3" (for protein component of Gems number 3). Gemin3 interacts directly with SMN as well as with SmB, SmD2 and SmD3. Immunolocalization studies using monoclonal antibodies to Gemin3 demonstrated that Gemin3 co-localizes with SMN in gems. Gemin3 binds with SMN via its unique C-terminal domain, and SMN mutations found in some SMA patients strongly reduce this interaction. Unlike SMN and SIP1 which do not contain DEAD/DEAH motifs (reviewed in Staley and Guthrie, 1998, Cell 92:315–326), Gemin3 contains a DEAD box motif indicating that the protein is a putative helicase. Thus, the presence of a DEAD motif in Gemin3 suggests that this protein may provide a catalytic activity that plays a critical role in the function of the SMN complex on RNPs.

The data disclosed herein further demonstrate the production of monoclonal antibodies to Gemin3. In addition, immunofluorescence microscopy demonstrated that Gemin3 co-localizes with SMN in gems. Like SMN and SIP1, Gemin3 can be isolated in a complex with several spliceosomal snRNP proteins. Moreover, the data disclosed demonstrate that Gemin3 interacts directly with SMN and with several of the spliceosomal snRNP core Sm proteins including the B and D2–3 proteins. The unique C-terminal domain of Gemin3 mediates interaction with SMN and localization of Gemin3 to gems. The discovery of a DEAD box protein (i.e., a likely RNA helicase) in the SMN complex is of particular interest as the functions revealed so far suggest that this complex has crucial activities in the biogenesis of RNPs. To perform such functions, including assembly of the snRNPs and the regeneration of active components of the spliceosome, the SMN complex may effect structural changes in its RNP targets. Of the known components of the SMN complex, the DEAD box protein Gemin3 is the most likely protein to have the capacity to perform such a function. Importantly, SMN proteins with mutations found in SMA patients exhibited significantly reduced interaction with Gemin3 suggesting that the SMN complexes in these patients are be deficient in this protein.

The Materials and Methods used in the experiments presented in this example are now described.

Identification of p105 Protein by Mass Spectrometry

The p105 protein was co-immonoprecipitated with anti-SMN monoclonal antibody 2B1 and the band was excised from a single one-dimensional Coomassie stained polyacrylamide gel. The protein band was digested with trypsin (unmodified trypsin, sequencing grade, Boehringer Mannheim, Indianapolis, Ind.) in-gel as described in Shevchenko et al. (1996, Anal. Chem. 68:850–858). Tryptic peptides were extracted and recovered from the gel using 5% formic acid and acetonitrile. The combined extracts were pooled together, dried in a speed vacuum, and the dried pellets were redissolved in 5% formic acid. The peptides were analyzed by nanoelectrospray tandem mass spectrometry as described in Wilm and Mann (1996, Anal. chem. 66:1–8). Nano ES MS/MS was performed on a API III triple quadrupole instrument (PE Sciex, Ontario, Canada) equipped with a nanoelectrospray ions source developed in EMBL (Wilm and Mann, 1996, Anal. chem. 66:1–8).

Comprehensive protein and EST databases were searched using PeptideSearch version 3.0 software. No limitations on protein molecular weight and species of origin were imposed.

Production of Proteins in vitro

[$^{35}$S]methionine labeled proteins were produced by an in vitro coupled transcription-translation reaction (Promega Biotech, Madison, Wis.) in the presence of [$^{35}$S]methionine (Amersham, Arlington Heights, Ill.). Gemin3 and SMN fusion proteins, comprising a tag polypeptide comprising a run of histidine amino acid residues (6His) to produce 6His-Gemin3 and 6His-SMN fusion protein, were expressed from a pET bacterial expression system in the E. coli strain BL21 (DE3) and the fusion proteins were purified using nickel chelation chromatography using a kit (His-Bind buffer kit; Novagen, Madison, Wis.) per the manufacturer's instructions.

Gemin3 fusion protein comprising a glutathione-S-transferase (GST) tag polypeptide (i.e., GST-Gemin3) was expressed using a GST expression vector (pGEX-5X-3; Pharmacia LKB Biotechnology Inc., Piscataway, N.J.) in the E. coli strain BL21. The Gemin3-GST fusion protein was purified using glutathione-Sepharose (Pharmacia LKB Biotechnology Inc., Piscataway, N.J.) according to the manufacturer's protocol.

Production of Monoclonal Antibodies That Specifically Bind Gemin3

Anti-Gemin3 antibodies, designated 11G9 and 12H12, were prepared by immunizing BALB/c mice with 6His-tag C-terminal domain of Gemin3 (comprising from about amino acid residue number 368 to about 548) purified from nickel chelation chromatography using a Novagen (Madison, Wis.) His-Bind buffer kit per the manufacturer's instructions. Hybridoma production, screening and ascites fluid production were performed as described previously by Choi and Dreyfuss (1984, J. Cell. Biol. 99:1997–2004).

Immunoprecipitation and Immunoblotting

Immunoprecipitations of in vitro translated proteins were carried out in the presence of 1% Empigen BB buffer as previously described (Choi and Dreyfuss, 1984, J. Cell. Biol. 99:1997–2004). Immunoprecipitations of SMN, the Sm proteins and Gemin3 from cells were carried out using total HeLa cell lysate in the presence of 1% Empigen BB buffer as previously described (Choi and Dreyfuss, 1984, supra). Immunoprecipitations and purifications of the SMN, Gemin2, Sm and Gemin3 complexes were carried out using total HeLa cell lysate in the presence of 0.5% TritonX-100 as previously described in Piñol-Roma et al. (1988, Genes Dev. 2:215–227).

For immunoblotting, the HeLa cell lysate proteins were resolved using 12.5% SDS-polyacrylamide gels and the proteins were then transferred to a nitrocellulose membrane (Schneider and Schuell, Inc., Keene, N.H.) using a BioTrans Model B Transblot apparatus (Gelman Science) according to the manufacturer's instructions. The membranes were then incubated in blocking solution (phosphate-buffered saline, PBS, containing 5% (w/v) nonfat milk) for at least 1 hour at room temperature. The membranes were rinsed with cold PBS, and then were incubated in blocking solution containing a selected primary antibody for at least 1 hour at room temperature. The membranes were subsequently washed three times in PBS containing 0.05% (v/v) NP-40, and any bound antibodies were detected using peroxidase-conjugated goat anti-mouse IgG plus IgM (Jackson Immunoresearch Laboratories, West Grove, Pa.). The antibody-decorated protein bands were visualized using an enhanced chemiluminescence (ECL) Western blotting kit (Amersham, Arlington Heights, Ill.) after washing the membranes an additional three times with PBS containing 0.05% (v/v) NP-40.

Cell Culture and Treatments

HeLa cells were cultured in Dulbecco's modified Eagle's medium (DMEM; GIBCO BRL, Gaithersburg, Md.) supplemented with 10% (v/v) fetal bovine serum (FBS; GIBCO BRL, Gaithersburg, Md.).

Immunofluorescence Microscopy

Immunofluorescence staining was carried out essentially as described previously in Choi and Dreyfuss (1984, J. Cell. Biol. 99:1997–2004). Double-label immunofluorescence experiments were performed using separate, sequential incubations of each primary antibody each diluted in PBS containing 3% (w/v) bovine serum albumin (BSA) followed by incubation using the specific secondary antibody coupled to either fluorescein isothiocyanate (FITC) or Texas Red. All incubations in antibodies were carried out at room temperature for 1 hour. Laser confocal fluorescence microscopy was performed using a Leica Model TCS 4D confocal microscope (Leica, Inc., Exton, Pa.). Images from each channel were recorded separately and stored in separate data files. Subsequently, where indicated, the separate data files were merged.

The antibodies used in these experiments were as follows: mouse IgG1 monoclonal anti-Gemin3 (11G9 and 12H12), mouse IgG1 monoclonal anti-SMN (2B1); rabbit polyserum anti-p80 coilin (R288, Andrade et al., 1993, Proc. Natl. Acad. Sci. USA 90:1947–1951); mouse IgG3 monoclonal anti-Sm (Y12, Lerner et al., 1981, Proc. Natl. Acad. Sci. USA 78:2737–2741) and SP2/0, a non-immunoglobulin chains secreting mouse hybridoma (American Type Tissue Collection [ATTC], Rockville, Md.). The rabbit affinity purified anti-Exon 7 antibody is described elsewhere herein.

In vitro Protein-binding Assay

Purified GST or GST-fusion proteins (2 micrograms) bound to 25 $\mu$l of glutathione-Sepharose beads were incubated with $10^6$ cpm of the in vitro translated protein mixture in 1 ml of binding buffer (50 mM Tris-HCl [pH7.5], 200 mM NaCl, 2 mM EDTA, 0.1% NP40, 2 micrograms per milliliter leupeptin and pepstatin A, and 0.5% aprotinin). Following incubation for 1 hour at 4° C., the resin was washed five times with 1 ml of binding buffer. The bound protein fraction was eluted by boiling the beads in SDS-PAGE sample buffer, and the eluted proteins were run on SDS-PAGE as described previously elsewhere herein. The gels were fixed for 30 minutes and the radiolabeled signal was enhanced by treating the gels with Amplify solution (Amersham, Arlington Heights, Ill.).

For direct in vitro binding, purified GST or GST-Gemin3 proteins (2 micrograms) bound to 25 microliters of glutathione-Sepharose beads were incubated with 5 micrograms of purified 6His-tag-SMN or 6His-tag-SmB in 1 ml of binding buffer (50 mM Tris-HCl [pH7.5], 100 mM NaCl, 2 mM EDTA, 0.05% NP-40, 2 micrograms per milliliter leupeptin and pepstatin A, and 0.5% aprotinin). After incubation for 1 hour at 4° C., the beads were washed five times with 1 ml of binding buffer per wash. The bound protein fraction was eluted by boiling the beads in SDS-PAGE sample buffer, and any 6His-SMN and/or 6His-SmB proteins eluted from the beads were analyzed using SDS-PAGE and Western blot using a rabbit polyclonal anti-His-tag antibody (Santa-Cruz Biotech., Santa Cruz, Calif.).

Cell Fractionation and Chromatography

HeLa cells were fractionated as described in Dignam et al. (1983, Nucl. Acids Res. 11: 1475–1489 1983). S100 fractions (400 microliters comprising about 20 milligrams per milliliter protein) in buffer F (20 mM Tris-HCl [pH 7.4], 0.1 mM EDTA, 1 mM DTT, 10% Glycerol, 500 mM KCl) were loaded on a Superose 6 HR 10/30 column (Pharmacia LKB Biotechnology Inc., Piscataway, N.J.). The column was then washed with buffer A (20 mM Tris-HCl [pH 7.4], 200 mM NaCl, 2.5% Glycerol). Selected protein fractions (0.5 ml) were collected, and 30 $\mu$l of each fraction was resolved on SDS-PAGE followed by Western blotting.

The Results of the experiments presented in this example are now described.

Gemin3, a Novel SMN-interacting Protein With a DEAD Box RNA Helicase Domain

Figure 26:
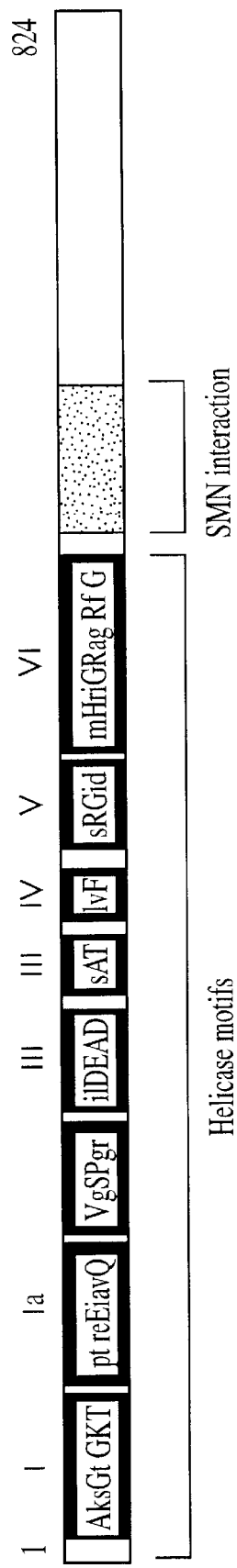
FIG. 26 is a diagram depicting a schematic representation of the modular structure of Gemin3 and the various domains of Gemin3. This diagram illustrates that Gemin3 encodes a DEAD-box containing RNA helicase. Further, the diagram discloses that Gemin3 contains seven helicase motifs (helicase motifs are reviewed in De la Cruz et al., 1999, TIBS 24:192–198) designated I, Ia, II, III, IV, V and VI, which are represented by black boxes with conserved amino acids represented in white letters within the boxes. Amino acid residues designated by upper case letters indicate highly conserved residues, lower cases indicate less conserved residues. The SMN interacting domain (i.e., amino acids 456 to 547) is boxed in grey.

Immunoprecipitations from [$^{35}$S]methionine labeled Hela cell lysates with antiSMN and anti-SIP1 monoclonal antibodies disclosed the presence of several protein components in the SMN-SIP1 complex (Liu et al., 1997, Cell 90:1013–1021). Among the proteins that can be co-immunopurified with anti-SMN and anti-SIP1 antibodies, only some of the major low molecular mass proteins, identified as the Sm proteins, have so far been characterized as disclosed elsewhere herein. In addition to SMN, SIP1, and the Sm proteins, there is a doublet at about 97 kDa and additional bands at 175 kDa, 95 kDa, 60 kDa and 50 kDa that co-immunopurified with the anti-SMN antibody. The two proteins of the 97 kDa doublet were eluted from the gel, digested with trypsin, and the resulting peptides were sequenced using nanoelectrospray mass spectrometry as described previously (Wilm et al., 1996, Anal. Chem. 66:1–8; Shevchenko et al., 1996, Anal. Chemistry 68: 850–858). The data disclosed herein demonstrate the molecular cloning and characterization of the high molecular weight protein of this doublet (i.e., p105). Several peptides from this band identified a human EST sequence (clone #AA303940) using the peptide sequence tag algorithm (FIGS. 2A and 2B. Several additional cDNA clones were obtained by hybridization screening of a human leukemia 5'-STRETCH PLUS cDNA library using this EST clone as a probe. Twelve independent partial cDNA clones with insert sizes ranging from about 1 to 2.5 kb, all of which contained overlapping regions of the same open reading frame (ORF), were isolated. 5' RACE PCR was used to extend this cDNA further upstream. A cDNA clone containing the longest ORF was constructed and conceptual translation of its nucleotide sequence disclosed a potential initiator methionine preceded by an in frame stop codon. This cDNA encodes a putative protein of 824 amino acids with a calculated molecular mass of 92.2 kDa and a pI of 6.5. Next, it was determined that this cDNA encodes the p105 protein co-immunoprecipitates with SMN. Thus, this is a full-length cDNA clone (SEQ ID NO:1) (GenBank accession number AF171063) for a novel component of the SMN complex designated Gemin3 for component of gems number 3 (see below). Because of the existence of several unrelated proteins called SIP1 (Mylin et al., 1994, Genetics 137:689–700; Zhang et al., 1998, Mol. Cell. Biol. 18:676–684; Verschueren et al., 1999, J. Biol. Chem. 274:2089–2098), this protein has been tentatively renamed Gemin2, for component of gems number 2 (SMN is the first component of gems identified, Liu and Dreyfuss, 1996, EMBO J. 15:3555–3565). Gemin3 has high amino acid sequence similarities with the RNA-helicase core region of the human eukaryotic initiation factor 4A-II (eIF4A-II). eIF4A-II is a DEAD-box RNA helicase that belongs to the SFII superfamily of helicases (reviewed in De la Cruz et al., 1999, TIBS 24:192–198). A scheme depicting the modular structure of Gemin3 and the predicted amino acid sequence of Gemin3 aligned with the sequence of eIF4A-II is presented in FIG. 26. This alignment disclosed the presence of seven motifs in the Gemin3 protein, motifs that are characteristic of the RNA helicase core region. Database searches with the C-terminal nonconserved region did not reveal significant homology to any other protein or to any recognizable motifs.

Production of Monoclonal Antibodies to Gemin3

Figure 28A:
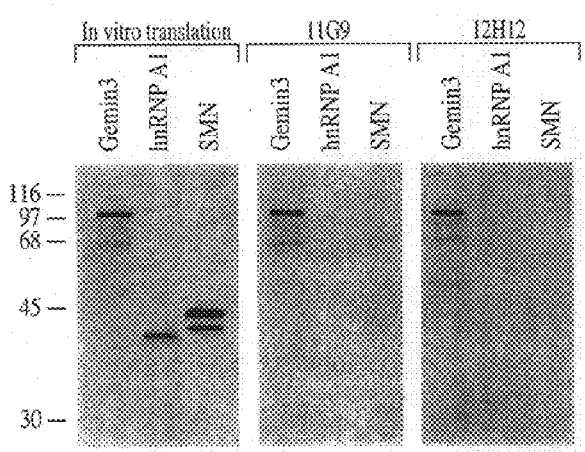
FIG. 28A is an image depicting a gel demonstrating that monoclonal antibodies 11G9 and 12H12 are specific for Gemin3. Myc-tagged Gemin3, hnRNP A1 and SMN proteins were produced using a rabbit reticulocyte lysate in the presence of [$^{35}$S]methionine. The labeled proteins were immunoprecipitated using monoclonal antibody 11G9 and 12H12 and the immunoprecipitated material was analyzed using SDS-PAGE followed by autoradiography. Ten percent (10%) of the total in vitro translated proteins is depicted on the left panel.
Figure 28B:
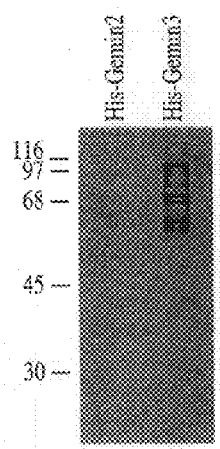
FIG. 28B is an image depicting immunoblotting using monoclonal antibody 11G9 on purified 6His-Gemin2 and 6His-Gemin3. The position of the molecular weight markers is indicated on the left side of the figure (in kDa).
Figure 28C:
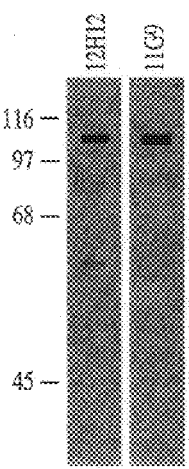
FIG. 28C is an image of a Western blot depicting immunoblotting using monoclonal antibodies 12H12 and 11G9 on total HeLa cell protein extract. In addition to the strong p105 signal, 12H12, but not 11G9, produced a weal signal by binding to a protein of about 55 kDa on Western blots. The position of the molecular weight markers is indicated on the left side of the figure (in kDa).

To investigate the interaction of Gemin3 with SMN and to characterize Gemin3 further, monoclonal antibodies that specifically bind Gemin3 were produced by immunizing mice with a purified, bacterially produced recombinant 6His-tagged Gemin3 fragment (amino-acids 368 to 548). Two hybridomas, 11G9 and 12H12, were selected for additional studies. The data disclosed herein demonstrate that these hybridomas produce monoclonal antibodies that recognize Gemin3 specifically. First, both 11G9 and 12H12 immunoprecipitate Gemin3 produced by in vitro transcription and translation from the Gemin3 cDNA, but do not immunoprecipitate similarly produced hnRNP A1 or SMN proteins (FIG. 28A). Second, the monoclonal antibody 11G9 efficiently recognized purified 6His-Gemin3 on Western blots but did not recognize similarly produced and purified 6His-tagged Gemin2 (Gemin2) (FIG. 28B). Finally, on an immunoblot of total Hela lysate, both 11G9 and 12H12 recognize a single protein of approximately 105 kDa (FIG. 28C). Monoclonal antibodies 11G9 or 12H12 did not recognize a specific protein on a Western blot with total mouse 3T3 cell lysate or Xenopus laevis XL-177 cell lysate. However, 11G9 specifically immunoprecipitated a single protein of about 105 kDa from these cell lysates suggesting that Gemin3, like SMN, is conserved in vertebrates.

Gemin3 and SMN Co-localize in Gems

Figure 29:
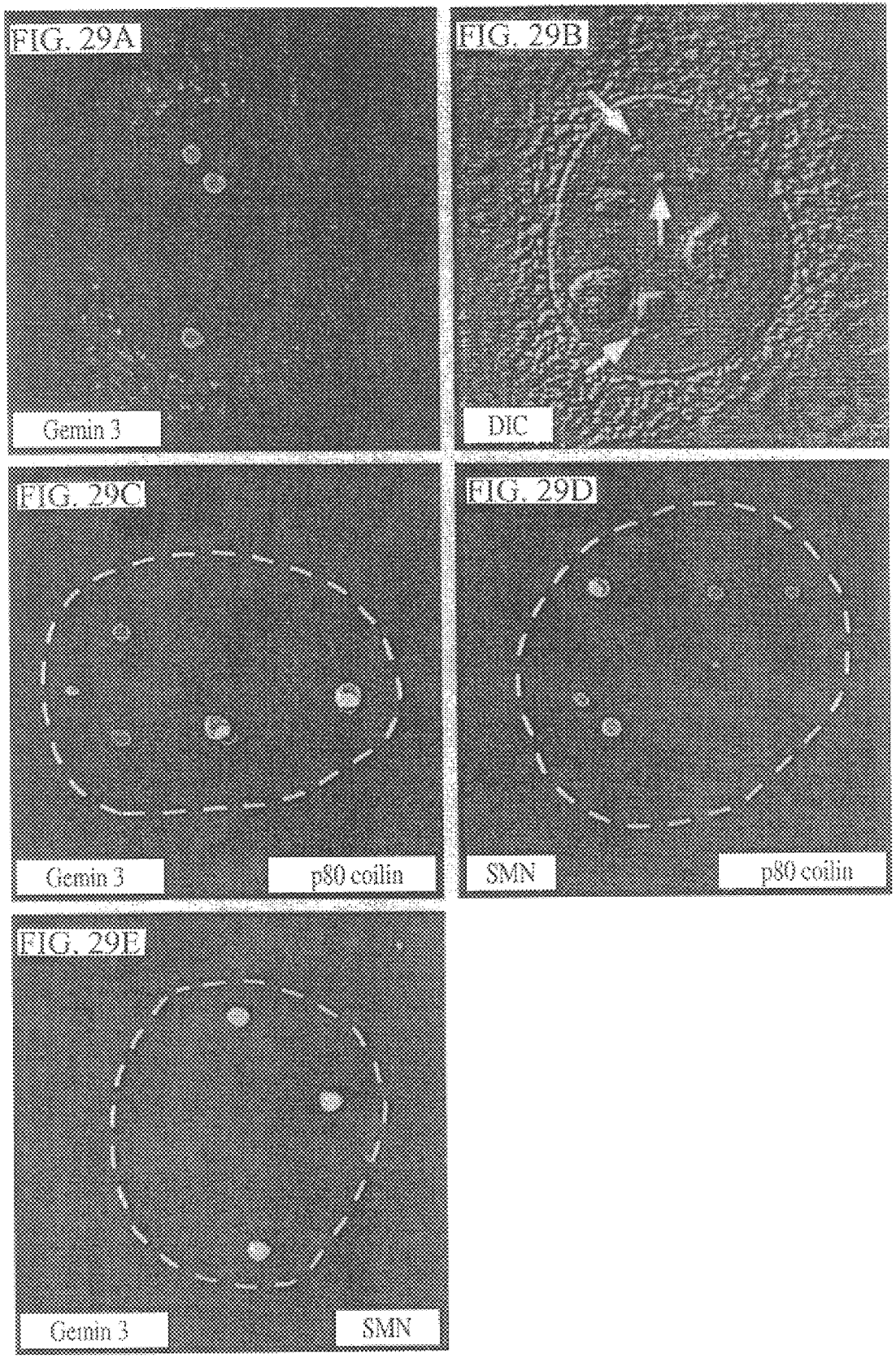
FIG. 29A is an image depicting the localization of Gemin3 in HeLa cells. This image depicts a laser confocal image of indirect immunofluorescence on HeLa cells using monoclonal antibody 12H12 against the Gemin3 protein. The data disclosed herein demonstrate general cytoplasmic staining, as well as nucleoplasmic and discrete nuclear structures.
FIG. 29B is an image depicting a DIC image of the same cell depicted in FIG. 29A. The arrows indicate gems.
FIG. 29C is an image depicting the fact that Gemin3 co-localizes with p80 coilin. This image depicts superimposed laser confocal images of double-label immunofluorescence microscopy experiments using antibodies against coiled bodies marker, p80 coilin (green) and anti-Gemin3 11G9 (red). Co-localization of green and red signals results in a yellow signal. Dashed lines demarcate the nucleus.
FIG. 29D is an image depicting the fact that SMN co-localizes with p80 coilin. This image depicts superimposed laser confocal images of double-label immunofluorescence microscopy experiments using antibodies against coiled bodies marker, p80 coilin (green), and anti-SMN antibody 2B1 (red). Co-localization of green and red signals results in a yellow signal. Dashed lines demarcate the nucleus.
FIG. 29E is an image depicting the fact that SMN co-localizes with Gemin3. This image depicts superimposed laser confocal images of double-label immunofluorescence microscopy experiments using monoclonal anti-Gemin3 11G9 (red) and a rabbit affinity-purified antibody against Exon 7 of human SMN (green). Co-localization of green and red signals results in a yellow signal. Dashed lines demarcate the nucleus.

Indirect laser confocal immunofluorescence microscopy using antibodies 11G9 and 12H12 was performed on Hela cells to determine the subcellular localization of Gemin3. FIG. 29A depicts that Gemin3 is found throughout the cytoplasm and also displays intense staining of prominent discrete nuclear bodies that are also readily discernable by differential interference contrast (DIC) microscopy (FIG. 29B). This pattern is similar to that seen for SMN and Gemin2 (Liu and Dreyfuss, 1996, EMBO J. 15:3555–3565; Example 1, supra), except that the nucleoplasmic staining of Gemin3 was stronger that the patterns detected for SMN and Gemin2 (SIP1).

In order to assess whether the nuclear structures stained by 11G9 were gems or coiled bodies, double-label immunofluorescence experiments were performed using antibodies against Gemin3 and to either p80-coilin as a marker of coiled bodies (Andrade et al., 1991, J. Exp. Med. 173:1407–1419) or to SMN as a marker of gems (Liu and Dreyfuss, 1996, EMBO J. 15:3555–3565; FIG. 29A). In many cell lines gems and coiled bodies entirely overlap by antibody staining, however, in the HeLa PV strain used herein, these two bodies are frequently found separate from each other (Liu and Dreyfuss, 1996, EMBO J. 15:3555–3565; Matera and Frey, 1998, Am. J. Hum. Genet. 63:317–321). Therefore, HeLa PV cells were used to examine whether Gemin3 is located in gems or in coiled bodies. As depicted in FIGS. 29C–29D, the nuclear structures that contain Gemin3 were clearly distinct from coiled bodies but Gemin3 completely co-localized with SMN in gems (FIG. 29E). The co-localization of Gemin3 with SMN strongly supports the conclusion that these two proteins exist as a complex in the cell. Gemin3 is, thus, the third constituent of gems described so far.

Gemin3 is in a Complex With SMN, Gemin2 and the Spliceosomal Sm Proteins

To characterize further the Gemin3 complex, immunoprecipitations using antiGemin3 monoclonal antibodies and [$^{35}$S]methionine labeled HeLa cells were carried out in the presence of either Triton-X 100 or the more stringent detergent Empigen BB (Matunis et al., 1994, Methods Cell Biol. 44:191–205). The immunoprecipitated proteins were then analyzed by SDS-PAGE. As references for these immunoprecipitations, an immunoprecipitation with the anti-Sm monoclonal antibody Y12 (Lerner and Steitz, 1979, proc. Natl. Acad. Sci. USA 76:5495–5499; Lerner et al., 1981, Proc. Natl. Acad. Sci. USA 76:2737–2741) and an immunoprecipitation with the anti-SMN monoclonal antibody 2B1 were also included for purposes of comparison. As shown in FIG. 30A, several proteins can be co-immunoprecipitated with Gemin3 and the pattern of immunoprecipitated proteins is very similar to that obtained with the anti-SMN antibody. In addition to Gemin3, SMN and Gemin2, there are several prominent bands at 175 kDa, 95 kDa and 50 kDa. The two groups of proteins at 28 kDa and 15 kDa have been identified previously as the Sm B/B', DI-3, E, F and G proteins of snRNPs (e.g., Example 1). In addition, there were protein bands which co-immunoprecipitated only with anti-SMN (at 60 kDa) or only anti-Gemin3 (at 115 kDa) monoclonal antibodies. As further evidence for the specificity of the antibodies used, the immunoprecipitations were performed in the presence of Empigen BB. Under these conditions, anti-Gemin3 and anti-SMN antibodies immunoprecipitate Gemin3 and SMN proteins respectively (+Empigen BB, lane 11G9, and lane 2B1, respectively). Even in the presence of Empigen BB, a protein of 95 kDa was still present under these conditions in both of these immunoprecipitations, but not in the control SP2/0 immunoprecipitation suggesting that this unidentified protein interacts tightly with both Gemin3 and SMN.

Figures 30C, 30D:
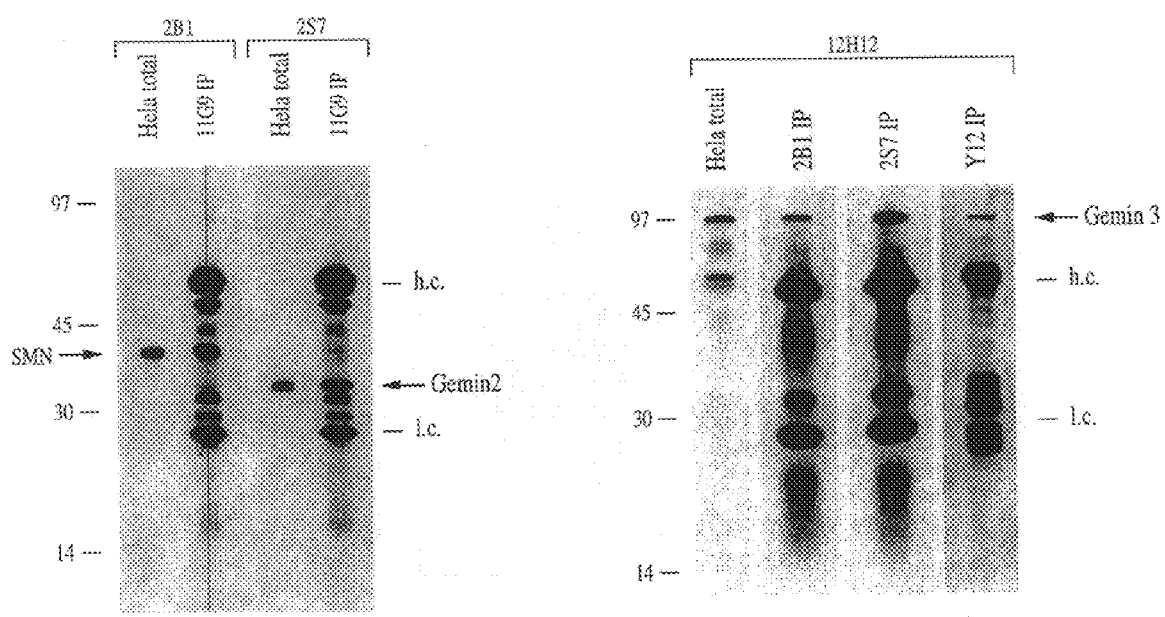
FIG. 30C is an image of a gel depicting the fact that Gemin3, SMN, Gemin2 and the Sm proteins can be co-immunoprecipitated in vivo. This image depicts that monoclonal antibodies against Gemin3 co-immunoprecipitate SMN and Gemin2. Immunoprecipitation using total HeLa protein extract was performed using monoclonal antibody 11G9 and the immunoprecipitated proteins were analyzed by Western blot using 2B1 (anti-SMN) or using 2S7 (anti-Gemin2) antibodies.
FIG. 30D is an image of a gel depicting the fact that monoclonal antibodies against SMN, Gemin2, and the Sm proteins co-immunoprecipitate Gemin3. Immunoprecipitation using total HeLa cell protein extract was performed using monoclonal antibodies against SMN (lane 2B1 IP), Gemin2 (lane 2S7 IP), or the Sm proteins (lane Y12 IP). The immunoprecipitated proteins (IP) were analyzed by Western blot using the anti-Gemin3 monoclonal antibody 12H12. The position of the molecular weight markers is indicated on the left side of the figure (in kDa). The positions of the light chain (l.c.) and heavy chain (h.c.) of the antibodies used for immunoprecipitation are indicated.

To confirm the co-immunopurification results, the interaction of Gemin3 with SMN, Gemin2 and the Sm proteins in HeLa cells was assessed in vivo using immunoprecipitations and Western blot experiments. The anti-Gemin3 monoclonal antibody 11G9 was used for immunoprecipitation from total HeLa cell extracts, and these extracts were then resolved by SDS-PAGE, transferred to nitrocellulose, and an immunoblot was probed with the anti-SMN antibody (Liu and Dreyfuss, 1996, EMBO J. 15:3555–3565). As depicted in FIG. 30C (lane 11G9 IP), 2B1 readily detects SMN in the 11G9 immunoprecipitates indicating that SMN is co-immunoprecipitated with Gemin3. Because SMN is associated with Gemin2 to form a stable complex in vivo and in vitro (see, e.g., Example 1), whether Gemin3 could be co-immunoprecipitated with Gemin2 was determined. As disclosed in FIG. 30C, the anti-Gemin2 monoclonal antibody 2S7 clearly detects Gemin2 in the anti-Gemin3 11G9 immunoprecipitates (lane 11G9 IP). In a reciprocal experiment, the Gemin3 protein could also be co-immunoprecipitated by the anti-SMN monoclonal antibody 2B1 (FIG. 30D, lane 2B1 IP) and the anti-Gemin2 monoclonal antibody 2S7 (FIG. 30D, lane 257 IP). Because SMN and Gemin2 are found in a complex with the Sm proteins, it was determined whether Gemin3 can be co-immunoprecipitated with the spliceosomal snRNP Sm core proteins as well. FIG. 30D demonstrates that Gemin3 is present in the anti-Sm monoclonal antibody Y12 immunoprecipitates (lane IP Y12) like SMN and Gemin2 (Liu et al., 1997, Cell 90:1013–1021). No Gemin3, SMN, Gemin2 or Sm proteins were detected in a SP2/0 immunoprecipitate. These results demonstrate that Gemin3, SMN, Gemin2, and the Sm proteins are associated in vivo in a complex that can be immunoprecipitated by either anti-SMN, anti-Gemin2, anti-Sm or anti-Gemin3 antibodies.

Figure 30E:
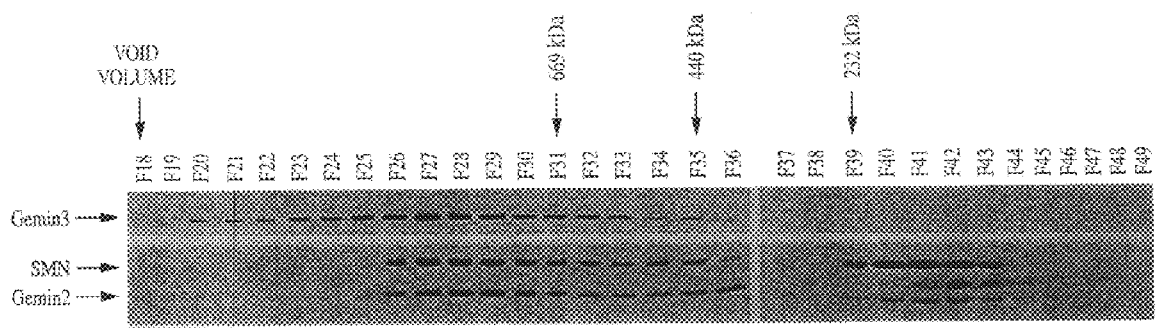
FIG. 30E is an image depicting the fact that Gemin3, SMN, and Gemin2 are found in a complex of about 800 kDa, or more, in the cytoplasm. HeLa cytoplasmic S100 extract was fractionated using a Superose 6 HR 10/30 column. The fractions were analyzed by SDS-PAGE, and the Gemin3, SMN, and Gemin2 proteins were detected by Western blotting. The fraction number and the molecular weight standards were as indicated.

Further support for the existence in vivo of a complex that contains SMN, Gemin2 and Gemin3 was obtained from gel filtration experiments. HeLa cytoplasmic S100 extract was fractionated on a Superose 6 HR 10/30 high performance gel filtration column and each fraction was subjected to SDS-PAGE followed by Western blot with anti-Gemin3, anti-SMN and anti-Gemin2 monoclonal antibodies. Gemin3, SMN and Gemin2 co-migrated and showed a peak at about 800 kDa demonstrating that they are components of a large macromolecular complex (FIG. 30E). A second pool of SMN-Gemin2, lacking Gemin3, was observed in a lower molecular weight complex which peaked at about 150 kDa suggesting that at least two different SMN-Gemin2 sub-complexes exist in vivo. However, without wishing to be bound by any particular theory, the possibility cannot be excluded that the 150 kDa sub-complex corresponded to a fraction of SMN-Gemin2 that dissociated from Gemin3 during cell fractionation and/or chromatography. The data previously disclosed elsewhere herein demonstrate that a SMN-Gemin2 complex migrates at about 300 kDa, or higher, after filtration of a cytoplasmic S100 extract on a TSK-GEL G3000-SW column (Example 1). The Superose 6 HR 10/30 gel filtration column used herein permitted a better resolution of the cytoplasmic SMN complex and permitted a more accurate estimate as to its size which is about 800 kDa.

Gemin3 Interacts Directly With SMN and the Spliceosomal Sm Proteins in vitro.

Figure 31A:
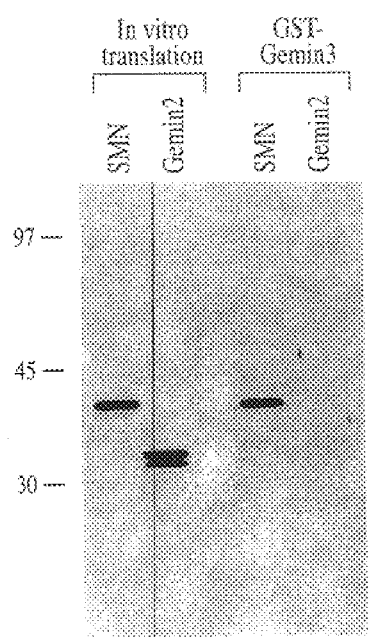
FIG. 31A is an image of a gel depicting the fact that Gemin3 interacts directly with SMN in vitro. In vitro translated [$^{35}$5]methionine labeled mycSMN and myc-Gemin2 proteins were incubated with purified GST-Gemin3 as described elsewhere herein. Bound proteins were analyzed using SDS-PAGE followed by fluorography. The in vitro translation panel depicts 2% of the total input.
Figure 31B:
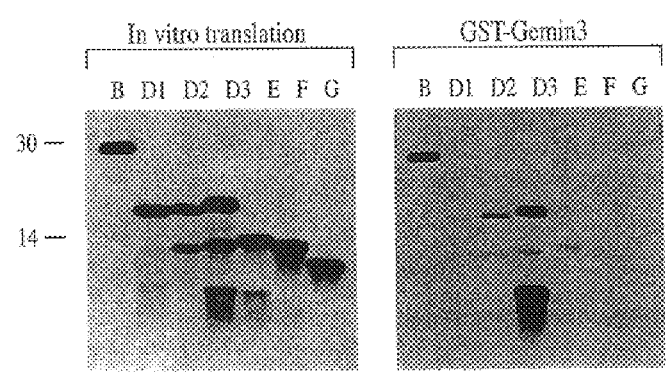
FIG. 31B is an image of a gel depicting that Gemin3 interacts with a subset of the Sm proteins in vitro. In vitro translated [$^{35}$S]methionine labeled mycSm proteins B, D1. D2, D3, E, F, and G were incubated with purified GST-Gemin3 or GST-SMN as described elsewhere herein. Bound proteins were analyzed using SDS-PAGE followed by fluorography. The in vitro translation panel contains 2% of the input.

To further analyze the Gemin3 complex, in vitro protein binding assay between Gemin3 and several components of the SMN complex were performed. For in vitro binding assays, Gemin3 was produced as a fusion protein with glutathione S-transferase (GST), and SMN and Gemin2 were produced and labeled with [$^{35}$S]methionine by in vitro transcription and translation in rabbit reticulocyte lysate. Purified GST or GST-Gemin3 fusion immobilized on glutathione-Sepharose were incubated with labeled SMN or Gemin2 proteins. Following extensive washing, bound proteins were eluted by boiling in SDS-containing sample buffer and the eluted material was analyzed by SDS-PAGE and detected by fluorography. Full length SMN, but not Gemin2, bound specifically to immobilized GST-Gemin3 (FIG. 31A) but not to GST alone. To investigate whether Gemin3 interacts with Sm proteins, purified GST or GST-Gemin3 recombinant proteins were used for binding assays with in vitro [$^{35}$S]methionine labeled Sm proteins B, D1, D2, D3, E, F and G (Lehmeier et al., 1994, Proc. Natl. Acad. Sci. USA 91:12317–12321; Herrmann et al., 1995, EMBO J. 14:2076–2088; Raker et al., 1996, EMBO J. 15:2256–2269). The results, depicted in FIG. 31B demonstrate that the Sm proteins B and D3 bind to GST-Gemin3 whereas there was no detectable binding to GST alone. D2 binds Gemin3 only weakly and the profiles of Sm protein binding to SMN and Gemin3 are not identical (see Example 1). For example, SMN binds to D1 while Gemin3 does not.

Figure 31C:
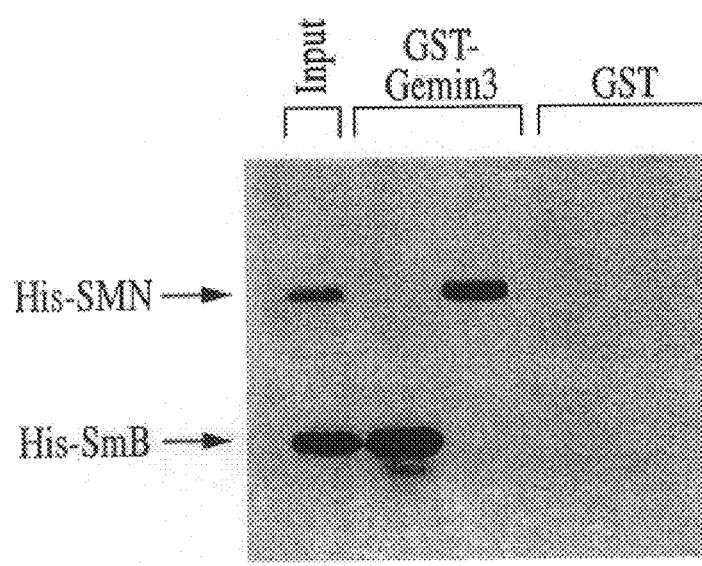
FIG. 31C is an image of a gel depicting the fact that Gemin3 interacts directly with SMN and SmB in vitro. Wild-type recombinant 6His-SMN or 6His-SmB proteins were incubated with purified GST-Gemin3, or with GST alone. The input lane depicts 10% of 6His-SMN and 6His-SmB. Bound proteins were analyzed by SDS-PAGE and Western blotting.

To address the possibility that some component of the rabbit reticulocyte lysate mediates these interactions, wild-type full-length SMN and SmB were produced as recombinant 6His-tagged proteins and were incubated with GST or GST-Gemin3. After several rounds of washing, bound proteins were solubilized by boiling in SDS-sample buffer, resolved by SDS-PAGE, immunoblotted and probed with a rabbit polyclonal antibody specific to the 6His-tag. As depicted in FIG. 31C, SMN and SmB bind specifically to Gemin3 but not to GST alone. Thus, both SMN and SmB interact directly with Gemin3.

Figure 31D:
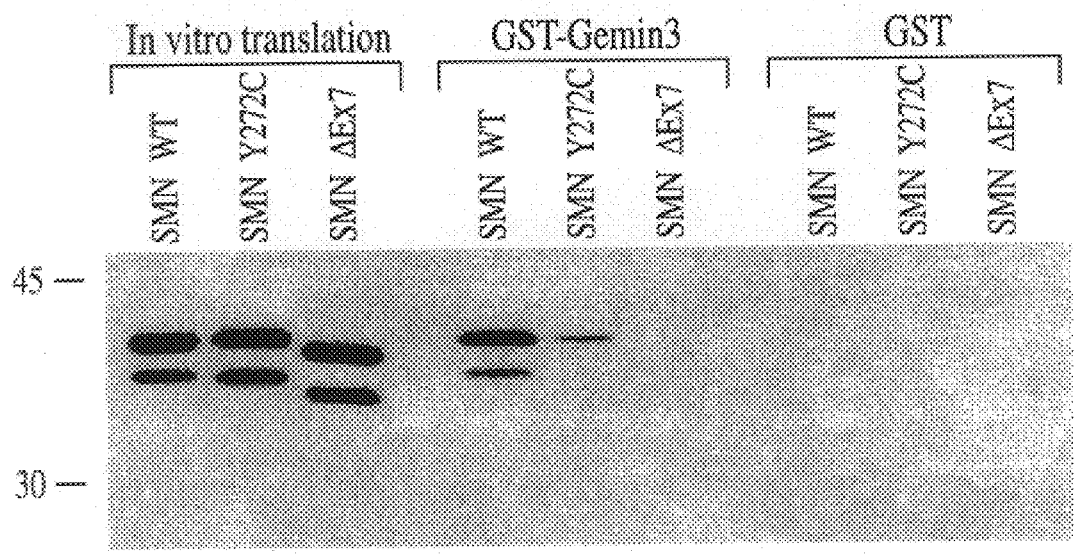
FIG. 31D is an image of a gel depicting the fact that mutations found in SMA severely affect SMN interaction with Gemin3. In vitro translated [$^{35}$S]methionine labeled wild-type myc-SMN and the indicated mutant proteins were incubated with purified GST-Gemin3 as described elsewhere herein. The proteins bound with GST-Gemin3 were analyzed using SDS-PAGE followed by fluorography. The in vitro translation panel shows 2% of the input.

In order to further characterize the interaction between Gemin3 and SMN, it was determined whether SMN carrying two well-characterized mutations found in SMA patients, the Y272C point mutant (SMNY272C) and the exon 7 deletion mutant (SMNΔEx7), the major product of the SMN2 gene (Reviewed in Burghes, 1997, Am. J. Hum. Genet. 61:9–15; Talbot et al., 1997, Hum. Mol. Genet. 6:497–500), was able to interact with Gemin3. SMN wild type and mutants were produced and labeled with [$^{35}$S] methionine using in vitro transcription and translation in rabbit reticulocyte lysate. Full-length wild-type SMN bound specifically to immobilized GST-Gemin3 (FIG. 31D). However, SMNY272C and SMNΔEx7 are severely defective in their ability to bind GST-Gemin3. No detectable binding was observed to GST alone. Similar results were observed using purified recombinant 6His-SMN wild type and mutant proteins instead of in vitro translated products.

Figure 31E:
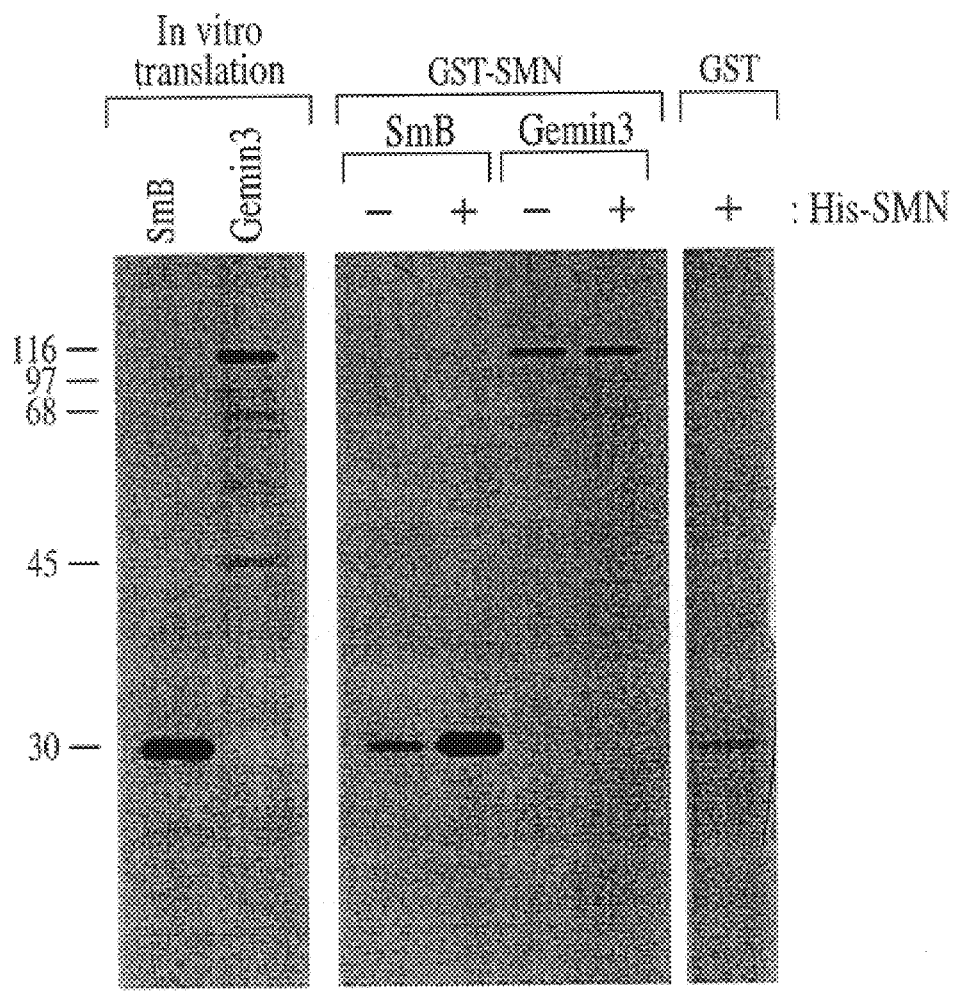
FIG. 31E is an image of a gel depicting the fact that SMN oligomerization does not affect the Gemin3 interaction. In vitro translated [$^{35}$S]methionine labeled myc-Gemin3 or myc-SmB proteins were incubated with purified GST or GST-SMN which had been pre-incubated or not with 6His-SMN wild-type protein as described elsewhere herein. Bound myc-Gemin3 and myc-SmB proteins were analyzed using SDS-PAGE followed by fluorography (top portion of the figure). The in vitro translation panel contains 5% of the input. The position of the molecular weight markers is indicated on the left (in kDa).
Figure 31F:
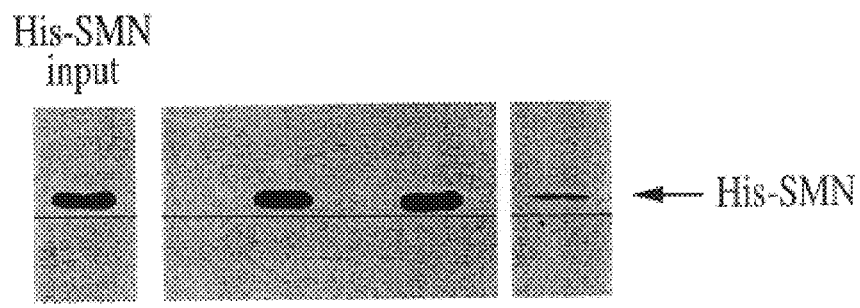
FIG. 31F is an image of a Western blot depicting the amount of 6His-SMN which bound to GST or GST-SMN. The input lane depicts 10% of 6His-SMN. About 5% of the 6His-SMN input is bound to GST-SMN.

SMN oligomerization and Sm binding are not mutually exclusive, and in fact, Sm binding is strongly enhanced by SMN oligomerization (e.g., FIG. 31E). To determine whether SMN self-association enhances Gemin3 interaction, GST-SMN, or GST as a control, was pre-incubated with a molar excess of recombinant 6His-tag SMN to form SMN oligomers. After removing the unbound 6His-tag SMN by washing, in vitro translated [$^{35}$S] methionine-labeled Gemin3 and SmB were added and assayed for binding (FIG. 31E). SmB binding was strongly enhanced by SMN oligomerization, however, Gemin3 binding was not affected.

Gemin3 Interacts With SMN via its Unique C-terminal Domain

Figure 32A:
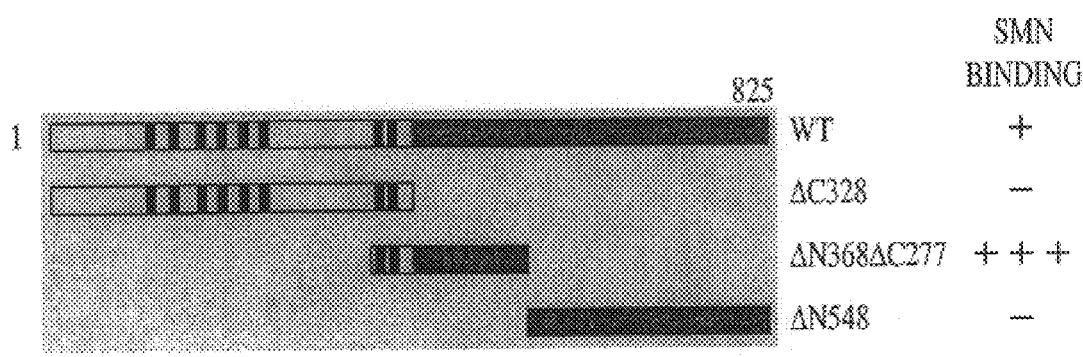
FIG. 32A is a schematic representation of the myc-Gemin3 wild type and deletion mutants used in the binding assays. The black boxes represent the seven helicase domains and the grey box represents the auxiliary domain C-terminal domain.
Figure 32B:
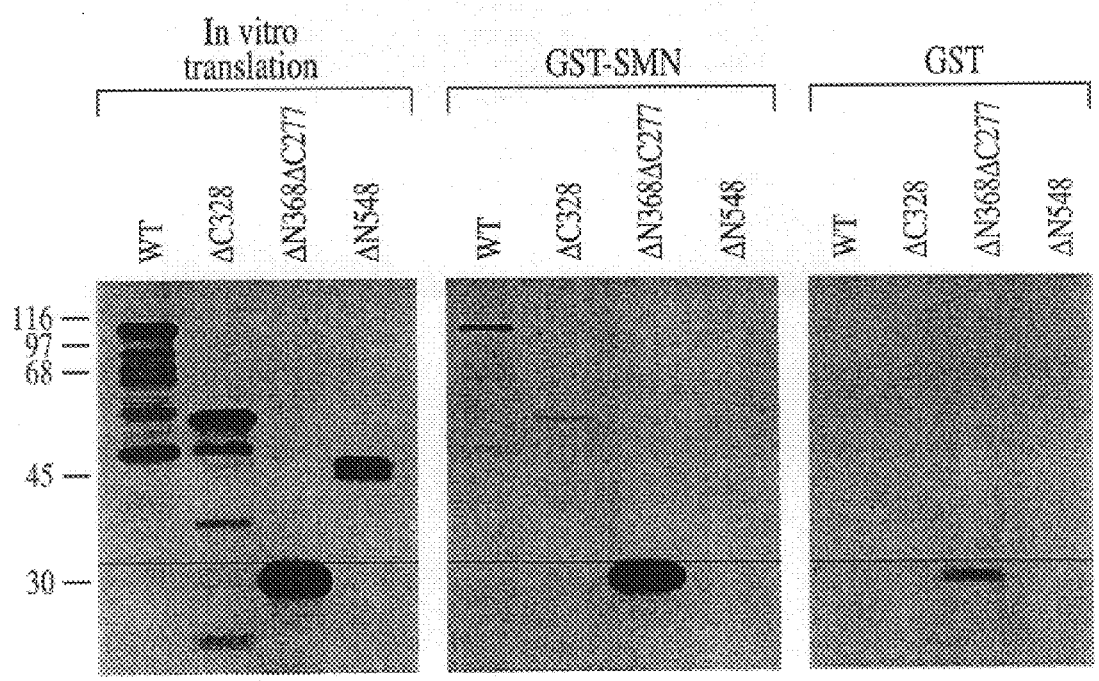
FIG. 32B is an image of a gel depicting that Gemin3 interaction of Gemin3 with SMN is mediated by the non-conserved C-terminal domain of Gemin3. In vitro translated [$^{35}$S]methionine labeled wild-type and mutant myc-Gemin3 proteins were incubated with purified GST-SMN or GST alone. Bound myc-Gemin3 proteins were analyzed using SDS-PAGE followed by fluorography. The in vitro translation panel shows 5% of the input.
Figure 33A:
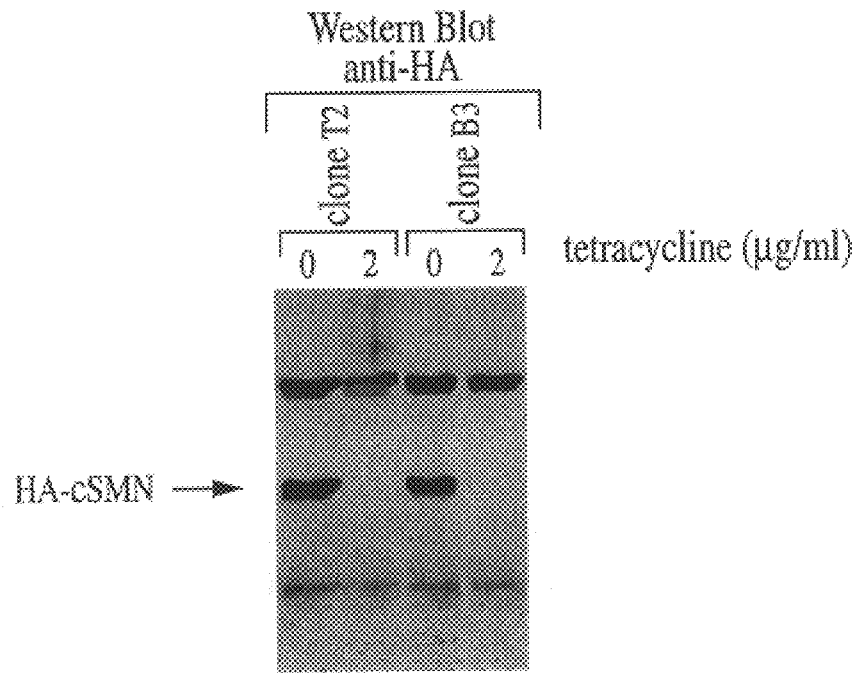
FIG. 33A is an image depicting a Western blot demonstrating that the hemagglutinin-chicken SMN (HA-cSMN) fusion protein was expressed in transfected cells DT40 in the absence of tetracycline from the cell but was not expressed in the presence of 2 micrograms per milliliter of tetracycline.
Figure 33B:
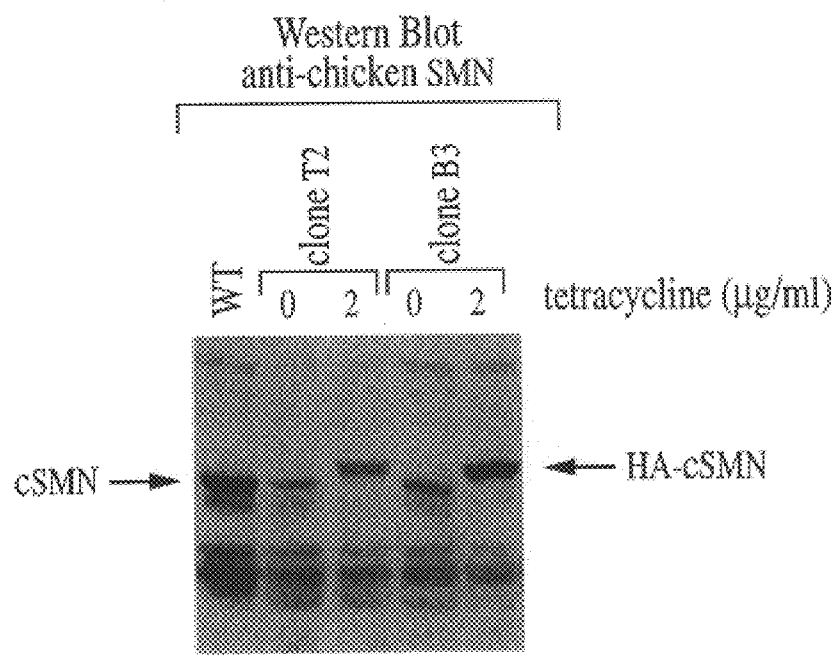
FIG. 33B is an image depicting a Western blot demonstrating the fact that expression of HA-SMN upon removal of tetracycline from the culture medium caused expression of a HA-cSMN fusion protein, which is larger than wild type cSMN because of the additional amino acid residues comprising the HA tag polypeptide, and lack of expression of wild type chicke SMN (cSMN). More specifically, in the presence of 2 micrograms per milliliter tetracycline, only wild type cSMN is detected by Western blot analysis using anti-chicken SMN antibody. In the absence of tetracycline (i.e., in lanes designated "0") only the higher molecular weight HA-cSMN fusion protein was detected and cSMN was not detected.
Figure 34A:
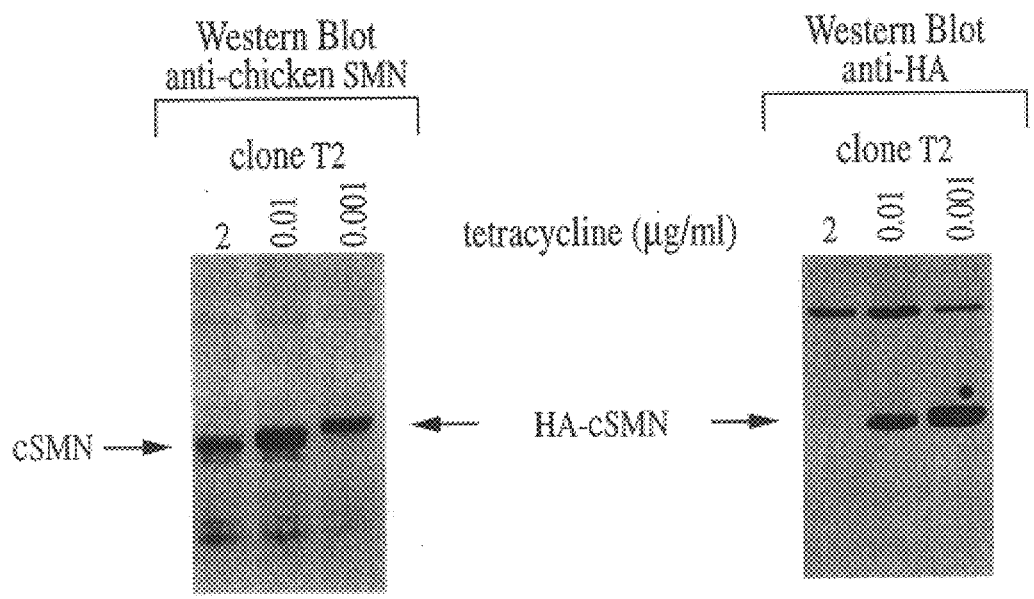
FIG. 34A is an image depicting a Western blot demonstrating that inhibition of cSMN expression and induction of HA-cSMN expression are dose-dependent upon the concentration of tetracycline present in the cell culture medium. That is, decreasing concentration of tetracycline caused increased expression of HA-cSMN and concommitant decreased expression of cSMN.
Figure 34B:
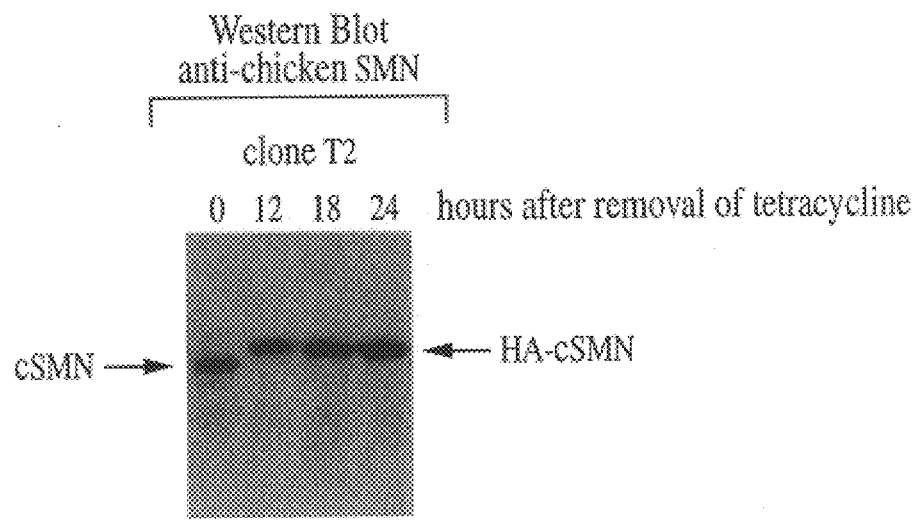
FIG. 34B is an image depicting a Western blot demonstrating the fact that expression of HA-cSMN increases upon removal of tetracycline and that repression of cSMN expression upon removal of tetracycline is permanent. That is, removal of tetrycline results in continued expression of HA-cSMN and permanent lack of expression of cSMN (until cell death occurs since HA-cSMN does not provide necessary SMN function to the cell).

The unwinding activity of DEAD box RNA helicases may not be sequence specific. The target specificity of these proteins is at least in some cases provided by their interaction with specific proteins of the RNP substrate. These interactions appear to be mediated via the unique auxiliary domain that each RNA helicase contains (Staley and Guthrie, 1998, Cell 92:315–326; Hamm and Lamond, 1998, Curr. Biol. 8:532–534). Therefore the role of the unique C-terminal domain of Gemin3 (amino acids 430–825) in the interaction with SMN was determined. To do so, three deletion mutants of Gemin3 were constructed and tested their ability to bind with GST-SMN. Wild-type and mutant myc-Gemin3 constructs were transcribed and translated in rabbit reticulocyte lysate in the presence of [$^{35}$S] methionine, and the resultant translated products were assayed for binding to GST-SMN as described previously elsewhere herein. As FIG. 32B indicates, the wild-type myc-Gemin3 protein and myc-ΔN368C277Gemin3 mutant proteins interact specifically with GST-SMN but not with GST alone. The myc-ΔC328Gemin3 and mycΔN548Gemin3 mutant proteins clearly do not interact with GST-SMN. Thus, the C-terminal domain of Gemin3 (amino acid 456 to 547) mediates the interaction of SMN with Gemin3.

The molecular characterization of the spinal muscular atrophy gene product, SMN, demonstrated that it is concentrated in novel nuclear structures called gems (Liu and Dreyfuss, 1996, EMBO J. 15:3555–3565; Example 1). Coiled bodies and gems represent nuclear structures that appear to be involved in RNA metabolism and in many of the cell lines studied these two bodies are often found in association (Lamond and Carmo-Fonesca., 1993, Trends Cell Biol. 3:198–204; Gall et al., 1995, Dev. Genet. 16:25–35; Liu et al., 1997, Cell 90:1013–1021; Liu and Dreyfuss., 1996, EMBO J. 15:3555–3565; Example 4; Matera and Frey, 1998, Am. J. Hum. Genet. 63:317–321). SMN is also found in the cytoplasm where, together with its tightly associated partner, Gemin2, it functions in the assembly of snRNP particles (Example 2; Example 4). In the nucleus, SMN is required for pre-mRNA splicing, and likely serves to assemble and maintain the splicing machinery in an active form as discussed previously elsewhere herein. To perform these functions, SMN must either have an intrinsic activity or it must recruit to the complex other proteins that can actively affect structural transitions in certain RNP targets. Several factors that have the capacity to serve in such functions, including assembly and disassembly of components of the splicing machinery, have been described. Many of these factors are DEAD/DEAH box RNA helicases that are essential for splicing (reviewed in Staley and Guthrie, 1998,). Prp43, for instance, is required for the disassembly of the snRNP-intron lariat complex (Arenas and Abelson, 1997, Proc. Natl. Acad. Sci. USA 94:11798–11802), Prp22 is needed to release the mature mRNA from the spliceosome (Company et al., 1991, Nature 349:487–493), and Prp24 acts as a recycling factor for U4 and U6 snRNP (Raghunathan et al., 1998, Science 279:857–860).

Using a biochemical approach to characterize new components of the SMN complex, a novel DEAD box RNA helicase termed Gemin3 has been identified. Gemin3 forms a stable complex with SMN in vivo and in vitro and it co-localizes with SMN in nuclear gems. Several lines of evidence suggest that Gemin3 and SMN function as a complex in vivo. SMN and Gemin3 can be co-immunoprecipitated and both are present in a large (approximately 800 kDa) complex that also contains Gemin2. Anti-SMN, anti-Gemin2 or anti-Gemin3 monoclonal antibodies immunoprecipitate the spliceosomal snRNP core Sm proteins, as well as several other unidentified proteins. Gemin3 interacts directly with SMN and with several snRNP Sm core proteins, including B/B', D2 and D3. In addition, Gemin3 is uniformly distributed in the cytoplasm, where snRNP assembly takes place, and it can be specifically co-immonuprecipitated with the cytoplasmic pool of Sm proteins. Together, these findings suggest that Gemin3 plays an important role in spliceosomal snRNP biogenesis.

DEAD box proteins have been found to be involved in many aspects of RNA metabolism, including pre-mRNA splicing, translation, snRNP-snRNP interactions, mRNA degradation, and mRNA transport in eukaryotes and prokaryotes (Arenas and Abelson, 1997, Proc. Natl. Acad. Sci. USA 94:11798–11802; Company et al., 1991, Nature 349:487–493; Ohno and Shimura, 1996, Genes & Dev. 10:997–1007; Staley and Guthrie, 1998, Cell 92:315–326; Hamm and Lamond, 1998, Curr. Biol. 8:532–534; De Ia Cruz et al., 1999, TIBS 24:192–198). One of the major questions about the function of each DEAD/DEAH box RNA helicase is the identification of the specific RNA target for it. Some of the enzymes of this family can unwind generic RNA substrates in vitro. For these enzymes, the specificity towards particular RNAs therefore appears to be determined by factors that interact with their unique auxiliary domains. For example, the DEAH-box RNA helicase Prp16 is recruited to the spliceosome via its unique N-terminal. The specific substrate for Gemin3 has not yet been identified and this remains a central question of interest. Although the RNA helicase or RNA-dependent ATPase activity for recombinant Gemin3 has not been detected, it is possible that such activity will only manifest itself when Gemin3 is associated with other proteins as part of a complex, or that it will be detectable once a specific RNA or RNP target is found. The interaction of Gemin3 with SMN is direct, amino acids 456 to 547 of Gemin3 mediate this interaction and, likely as a consequence of this, also mediate the localization of Gemin3 to the gems. Thus, without wishing to be bound by theory, Gemin3 provides the enzymatic activity of the SMN complex to affect structural transitions in its RNA targets.

The SMN protein is capable of forming an oligomer of more than 400 kDa in vitro and the data disclosed herein demonstrate that SMN co-migrates with an approximately 800 kDa complex that also contains Gemin2 and Gemin3. It is likely that SMN oligomerization is critical for the nucleation of this large complex. In addition to Gemin3 and Gemin2, several Sm proteins interact with SMN, and it may be that SMN forms a docking platform to bring together in the appropriate spatial arrangement the multiple proteins that are involved in the de novo assembly and regeneration of its RNP (e.g., snRNP) substrates. Interestingly, the interaction of SMN with Gemin3 is severely reduced by mutations found in SMA patients, such as the point mutant SMNY272C or the exon 7 deletion. Thus, the formation of the SMN platform seems critical for SMN function because SMA affects both the capacity of SMN to oligomerize as well as to interact with several Sm proteins and Gemin3. Likely as a consequence of these defective interactions, the function of SMN in the regeneration of the splicing machinery is abolished.

Coiled bodies contain the highest local concentration of p80 coilin and are enriched in components of three major RNA processing pathways: pre-mRNA splicing, histone mRNA 3' maturation and pre-mRNA processing. Gems contain the highest local concentration of SMN, Gemin2 and Gemin3 and are often found associated with coiled bodies (see, e.g., Liu and Dreyfuss, 1996, EMBO J. 15:3555–3565; Example 1). Although the definitive function of these two nuclear bodies has not been completely elucidated, the characterization of their protein and RNA contents represents an important step toward the understanding of their functions. Further studies of Gemin3, a novel DEAD box containing protein and component of gems, will shed light on the functions of the SMN complex and gems.

EXAMPLE 6

Production of Cell Line Comprising Reduced Level SMN for Study of SMA

To facilitate the study of the function of SMN in motor neurons and to develop a system that may be useful for testing potential therapeutic approaches, a cell line can be generated that expresses drastically reduced levels of SMN. The cell can be produced by transfecting a neuronal cell line which normally expresses SMN with an SMN-modulating sequence, e.g., antisense nucleic acid complementary to a nucleic acid encoding SMN or an SMN-specific ribozyme. A stable cell line can be obtained having significantly reduced SMN protein levels as demonstrated by decreased SMN mRNA expression.

Generation of Cell Lines

Motor neuron cell lines have been generated (Salazar Grueso et al., Neuroreport. 2:505–508) from embryonic murine spinal cord cells enriched for motor neurons by differential centrifugation, based on the approach originally described by Hammond et al (Science 234:1237–1240). Human SMN cDNA clone BCD541 is available in the art. SMN cDNA constructs, in either sense or antisense orientation, may be subcloned into a mammalian expression vector, for example, pZeoSV2 (InVitrogen, Carlsbad, Calif.), using standard methods (see, e.g., Sambrook et al., supra) and Ausubel et al., supra). After transfection of the motor neuron cell line with sense, antisense, or vector-only constructs, stable integrants may be isolated and the resultant transgenic cell lines can be referred to as "sense", "antisense" or "vector-only" cells, respectively. The cell lines are cultured as described in Salazar Grueso et al., supra.

DNA Isolation and PCR Analysis

The cells are grown in culture and DNA is isolated therefrom using standard methods. PCR assays may be performed using primers and probes specific for human SMN cDNA as described in, for example, Sambrook et al., supra, and Ausubel et al., supra.

RNA Isolation and RT-PCR

Total RNA may be extracted from cells using the Rneasy kit (Qiagen, Chatsworth, Calif.) according to the manufacturer's instructions. Total RNA may be reverse-transcribed using, for example, the SuperScript II reverse transcriptase (GIBCO/BRL) and random hexamers per the manufacturer's instructions. PCR may be performed as described elsewhere herein using human SMN specific primers. The PCR products may be separated on an agarose gel and may then be visualized by staining with ethidium bromide.

Western Blot Analysis

Total cell lysates in the presence of 0.5% TritonX-100 are prepared as previously described by Coovert et al. (1997, Hum. Mol. Gen. 6:1205–1214). Equal amounts of proteins are loaded on each lane of a SDS-PAGE gel and the Western blot is performed as previously described herein. The following monoclonal antibodies can be used: anti-SMN (2B1), anti-SIP1 (2E17), anti-hnRNPA1 (4B10) (Pinol-Roma et al., 1988, Genes & Dev. 2:215–227), and anti-Sm (Y12) (Lerner et al., 1981, Proc. Natl. Acad. Sci. USA 78:2737–2741).

Immunofluorescence Analysis

Immunofluorescence staining is be carried out essentially as previously described (Choi et al., 1984, J. Cell. Biol. 99:1997–2004). Double-label immunofluorescence experiments are performed by separate sequential incubations of each primary antibody, at an appropriate dilution, followed by incubation with the specific secondary coupled to fluoresceineisothiocyanate (FITC) or Texas Red (TXRD). Laser confocal fluorescence microscopy is performed and the images from each channel are recorded separately, and then the data files are merged. The following antibodies may be used: rabbit polyserum anti-p80 coilin (P288) (Andrade et al., 1991, J. Exp. Med. 173:1407–1419), mouse IgG1 monoclonal anti-SMN (2B1), and mouse IgG1 monoclonal anti-SIP1 (2E17).

Cell Growth Study

Cells from each of the three cell lines, sense, antisense and vector-only, may be synchronized by serum-deprivation and the cells may be plated in triplicate for growth analyses.

Transfection of a Neuronal Cell Line With SMN cDNA Constructs

Human SMN cDNA constructs, in either sense or antisense orientation, are subcloned into a mammalian expression vector, pZeoSV2, to allow constitutive expression of the insert driven by the SV40 early enhancer/promoter. A spinal cord neuronal cell line exhibiting the characteristics of primary motor neurons, including high levels of choline acetyltransferase (ChAT), extensive branching neurite formation, and glial-derived neurotrophic factor (GDNF) receptors described by Salazar Grueso et al. (Neuroreport 2:505–508; Trupp et al., Nature 381:785–788), may be used for transfections.

Motor neuron cells are transfected with sense, antisense, or vector-only constructs, and the cells are grown in selective medium (e.g., medium containing zeomycin in the case of pZeoSV2 constructs). Stable transfectants are isolated, and these are referred to as sense, antisense, or vector-only cells, respectively. The introduction of a human cDNA encoding SMN in a cell line permits the confirmation of the presence or absence of the human SMN sequence, as well as facilitating the monitoring of human SMN expression.

Detection of the Presence and Expression of Human SMN in Transfectants

The presence of the human SMN transgene DNA in both the sense and antisense cells, but not in vector-only cells, may be confirmed by PCR of DNA obtained from stable transfectants using human-specific primers. Further, expression of the human SMN sense or antisense cDNA constructs may be demonstrated by RT-PCR of total RNA using human-specific primers. Using these primers, SMN RNA may also be detected in positive control human tissue.

Detection of Altered SMN Protein Level in Transfectants

Immunoblotting using the anti-SMN monoclonal antibody, 2B1, should identify whether the cells exhibit reduced levels of expression of SMN.

EXAMPLE 7

Cell Line Lacking Endogenous SMN Expression

To facilitate the study of the function of SMN in cells and to develop a system for studying the role(s) of SMN in cell processes as well as for testing potential therapeutic approaches for SMA, a cell line was generated that lacked endogenous expression of SMN but was stably transfected with a plasmid vector comprising a nucleic acid encoding SMN under the control of an inducible promoter. More specifically, a chicken pre-B lymphoid cell line, i.e., DT40, which exhibited a high degree (i.e., approximately 1,000-fold higher than normal) of homologous recombination, was used to generate a cell line lacking a nucleic acid encoding chicken SMN. This cell line, wherein the endogenous cSMN expression was repressed by expression of non-functional HA-cSMN expressed under the control of an inducible promoter (i.e., the tetracycline repressible promoter) (see, e.g., FIGS. 33A, 33B, 34A, and 34B), and allows the rapid growth of the recombinant cells as long as tetracycline is present in the culture medium thereby repressing expression of HA-cSMN. However, removal of tetracycline from the medium caused derepression of the promoter, expression of HA-cSMN, and inhibition of endogenous wild type cSMN expression in the cell. Thus, the cell line provides a stable genetic system that can be easily manipulated to emulate the lack of SMN exhibited by the cells of SMA patients thereby providing a useful system for study of the mechanisms associated with SMA and for identifying compounds useful for the treatment of SMA.

Decreased or absent levels of SMN in the cell of the invention impaired cell growth, and eventual cell death, which was presumably mediated by impairment of cellular processes in a manner analogous to the disease process demonstrated by SMA patients. Therefore, the recombinant cell line containing decreased levels of SMN protein is a useful model for SMA which is characterized by reduced, or absent, amounts of SMN. Further, the cell line expressing altered, e.g., decreased or absent levels of SMN, provides an important tool for identifying compounds useful for treatment of SMA. In addition, the cell line can be transfected with mutant, variant, and/or homologous forms of SMN such that the effects of change in SMN can be identified and characterized providing a system for the study of naturally occurring and/or genetically engineered selected forms of SMN.

EXAMPLE 8

SMN Knock-out Cell

To facilitate the study of the function of SMN in cells and to develop a system for studying the role(s) of SMN in cell processes as well as for testing potential therapeutic approaches for SMA, a cell line is generated that lacks an endogenous nucleic acid encoding SMN but which comprises an exogenous nucleic acid encoding SMN under the control of an inducible promoter. More specifically, a chicken pre-B lymphoid cell line, i.e., DT40, which exhibits a high degree (i.e., approximately 1,000-fold higher than normal) of homologous recombination, is used to generate a cell line lacking a nucleic acid encoding chicken SMN. Although other cell lines can be used to generate an SMN "knock-out" cell line, DT40 provides the advantage that SMN is present in the cell as a single allele. Thus, unlike the mammalian genome which comprises centromeric and telomeric alleles of SMN, as discussed previously elsewhere herein, the DT40 cell line comprises a single genetic locus comprising a nucleic acid encoding SMN. Therefore, although other cell lines can be used, DT40 provides an advantageous system for the creation of SMN knock-out cell lines.

This cell line, wherein the endogenous sequence encoding SMN is "knocked-out", is then stably transfected using a plasmid vector comprising an isolated nucleic acid encoding chicken SMN under the control of an inducible promoter. This system allows the rapid growth of the recombinant cells as long as the promoter is induced and SMN is expressed in the cells. However, repression of the promoter inhibits production of SMN and the cells eventually cease growth in culture and or demonstrate altered growth characteristics as discussed elsewhere herein. Thus, the cell line provides a stable genetic system that can be easily manipulated to emulate the lack of SMN exhibited by the cells of SMA patients thereby providing a useful system for study of the mechanisms associated with SMA and for identifying compounds useful for the treatment of SMA.

Decreased or absent levels of SMN in the cell of the invention impairs cell growth which is mediated by impairment of cellular processes in a manner analogous to the disease process demonstrated by SMA patients. Therefore, the recombinant cell line containing decreased levels of SMN protein is a useful model for SMA which is characterized by reduced, or absent, amounts of SMN. Further, the cell line expressing altered, e.g., decreased or absent levels of SMN, provides an important tool for identifying compounds useful for treatment of SMA.

In addition, the cell line can be transfected with mutant, variant, and/or homologous forms of SMN such that the effects of change in SMN can be identified and characterized providing a system for the study of naturally occurring and/or genetically engineered selected forms of SMN.

EXAMPLE 9

Specific Sequences in SMN and SIP1 Which Mediate Their Interactions With Each Other and With SM Proteins and Which are Associated With Defective Interactions in SMA The experiments presented in this example may be summarized as follows.

Deletion mutants of SMN and SIP1 were prepared and used to identify the domains involved in the interactions between SMN and SIP1 as well as their interactions with their associated proteins such as the Sm proteins. Further, the effects of specific deletions and point mutations on the composition of the SMN complex and on the SMN and SIP1 cellular localization, with particular interest in targeting to gems, were analyzed. The data disclosed herein demonstrate that several SMN interactions are affected by mutations that occur in some SMA patients and that SMN oligomerization greatly enhances its interaction with Sm proteins. These results suggest a model of the SMN complex in which a SMN/SIP1 tetramer (or a higher oligomer) is the functional core required for efficient binding to Sm proteins, and thus snRNP assembly. These findings further strengthen the view that SMA is the result of a defect in snRNP metabolism.

The Materials and Methods used in the experiments presented in this example are now described.

Plasmid Construction

DNA fragments corresponding to the open reading frames of SMN and SIP1 wild-type (wt) and mutant proteins were generated by polymerase chain reaction (PCR) amplification using suitable primers. All of the myc-tagged constructs were generated by cloning the PCR inserts into a modified pcDNA3 vector (InVitrogen, Carlsbad, Calif.) downstream from the myc epitope recognized by the monoclonal antibody 9E10 (Siomi and Dreyfuss, 1995, J. Cell. Biol. 129:551–560). Plasmid constructs containing SMN fusions to the carboxyl-terminal to the myc-pyruvate kinase (PK)

were obtained by cloning the SMN coding PCR fragments into a myc-PK vector derived from pcDNA3 as previously described (Nakielny and Dreyfuss, 1996, J. Cell. Biol. 134:1365–1373). Maltose binding protein (MBP)-SMN fusions were obtained by cloning the SMN coding PCR fragments into a modified pcDNA1 vector (Invitrogen, Carlsbad, Calif.) downstream from the MBP sequence. These vectors facilitated the expression driven by the CMV promoter in vivo and by the T7 promoter in vitro.

Production of Proteins in vitro

The [$^{35}$S]methionine-labeled proteins were produced by an (in vitro) coupled transcription-translation reaction (Promega Corp., Madison, Wis.) in the presence of [$^{35}$S] methionine (Amersham, Arlington Heights, Ill.). His6-SMN fusion protein was expressed from a pET28 bacterial expression system in the *E. coli* strain BL21(DE3)pLysS and the fusion protein was purified by Ni+chelation chromatography with the Novagen (Madison, Wis.) His-bind Buffer Kit following the manufacturer's protocol. All the GST fusion proteins were expressed from the GST expression vector pGEX-5X (Pharmacia) in the *E. coli* strain BL21(DE3) pLysS and were purified using glutathione-Sepharose according to the manufacturer's protocol (Pharmacia Biotech). SmB cDNA is described in Raker et al. (1996, EMBO J. 15:2256–2269). SMN and SIP1 cNDAs were obtained using a yeast di-hybrid screening assay previously described herein.

In vitro Protein-binding Assay

Purified GST and GST fusion proteins (2 µg) were incubated with $10^6$ cpm of the in vitro translated protein product and 25 µl of glutathione-Sepharose beads in 500 µl of binding buffer (50 mM Tris-HCl [pH 7.5], 200 mM NaCl, 2 mM EDTA, 0.1% NP40, 2 µg/ml leupeptin and pepstatin A, and 0.5% aprotinin). After incubation for 1 hour at 40° C., the resin was pelleted, washed five times with 1 ml of binding buffer, and the bound fraction was eluted proteins were analyzed by SDS-PAGE, and the radiolabel signal was enhanced by treatment with Ampify solution (Amersham, Arlington Heights, Ill.).

Cell Culture and Treatments

HeLa cells were cultured in Dulbecco's modified Eagle's medium (DMEM) (GIBCO BRL, Gaithersburg, Md.) supplemented with 10% fetal calf serum (FCS) (GIBCO BRL). HeLa cells, plated on glass coverslips, were transfected by the standard calcium phosphate method. Following overnight incubation with DNA, the cells were washed and fresh medium was added to the cells. Transfected cells were fixed and processed for immunofluorescence staining after an additional incubation period of approximately 24–36 hours. 293T cells were plated on 100 mm plastic dishes and transfected as described above for HeLa. At approximately 36–48 hours post-transfection, the cells were collected and processed for immunoprecipitation assay as described herein.

Immunoprecipitation and Western Blotting

Immunoprecipitations were carried out using total cell lysate prepared in the presence of 0.5% Triton-X-100 as described previously (Piñol-Roma et al., 1988, Genes & Dev. 2:215–227). For immunobloting, proteins were resolved on a 12.5% SDS-polyacrylamide gel and transferred to nitrocellulose membrane (Schleicher & Schuell, Inc., Keene, N.H.) using a BioTrans Model B Transblot apparatus (Gelman Science) according to the instructions of the manufacturer. The nitrocellulose filters were incubated in blotting solution (PBS with 5% nonfat milk) for at least 1 hour at room temperature, rinsed with cold PBS, and then incubated with primary antibody for at least 1 hour at room temperature. The filters were washed three times in PBS containing 0.1% Tween 20 and bound antibodies were detected using the peroxidase-conjugated goat anti-mouse IgG+IgM (Jackson ImmunoResearch Laboratories, Bar Harbor, Me.). The protein bands were visualized by a ECL Western blotting detection kit (Amersham, Arlington Heights, Ill.) after washing three times in PBS containing 0.1% Tween 20. The antibodies used for these experiments were as follows: mouse monoclonal anti-SMN (2B1, described previously herein); mouse monoclonal anti-SIP1 (2E17, described previously herein) mouse monoclonal anti-Sm (Y12, described in Lerner et al., 1981, Proc. Natl. Acad. Sci. USA 78:2737–2741), and mouse monoclonal anti-myc (9E10)(ATCC, Manassas, Va.).

Immunofluorescence Microscopy

Immunofluorescence microscopy was carried out essentially as described by Choi and Dreyfuss (1984, J. Cell. Biol. 99:1997–2004). Briefly, primary monoclonal anti-myc antibody (9E10) was diluted 1:1000 in PBS containing 3% BSA. The secondary antibody was a goat anti-mouse IgG1 specific antibody conjugated to FITC. The incubations for both the primary and secondary antibodies were performed at room temperature for 1 hour. Laser confocal fluorescence microscopy was performed with a Leica TCS 4D (Germany) confocal microscope.

The Results of the experiments presented in this example are now described.

In vitro Mapping of SMN Interactions

Figure 39:
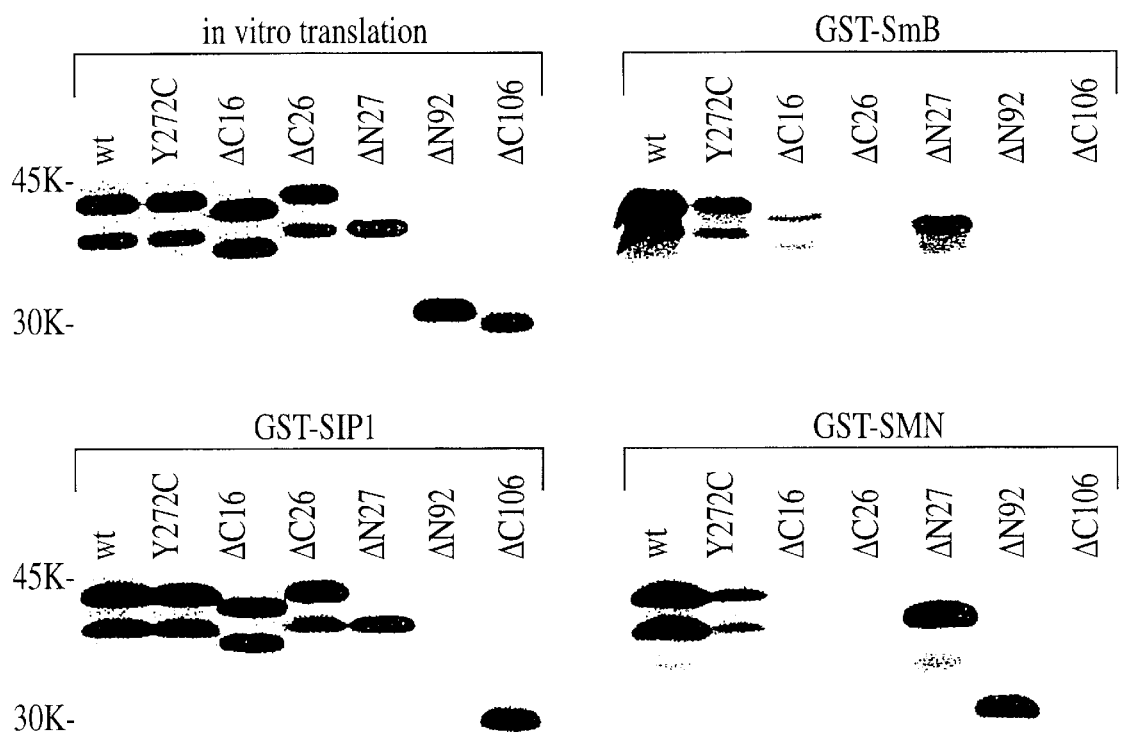
FIG. 39 is an image of an SDS-PAGE gel depicting the in vitro mapping of the SMN interaction domains. In vitro translated [$^{35}$S]methionine labeled myc-tagged-SMN wild-type and mutant proteins were incubated as indicated with purified GST or with GST-fusion proteins (SIP1, SMN or SmB) bound to glutathione-Sepharose beads as described elsewhere herein. Bound proteins were eluted from the beads by boiling the beads in SDS-PAGE sample buffer and the eluted proteins were analyzed by SDS-PAGE and fluorography. The in vitro translation lanes contained 10% of the input used for the binding assay.
Figure 49:
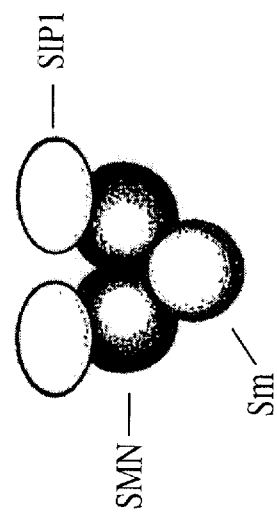
FIG. 49 is a diagram illustrating that, according to the in vivo and in vitro analysis disclosed herein, the SMN/SIP1 complex is at least a tetramer formed by two directly interacting SMN molecules, each of which is also bound to a SIP1 molecule. SIP1 interacts with SMN directly but not with itself. Dimeric SMN has a much higher binding affinity than monomeric SMN for the substrate, namely the Sm proteins.
Figure 48:
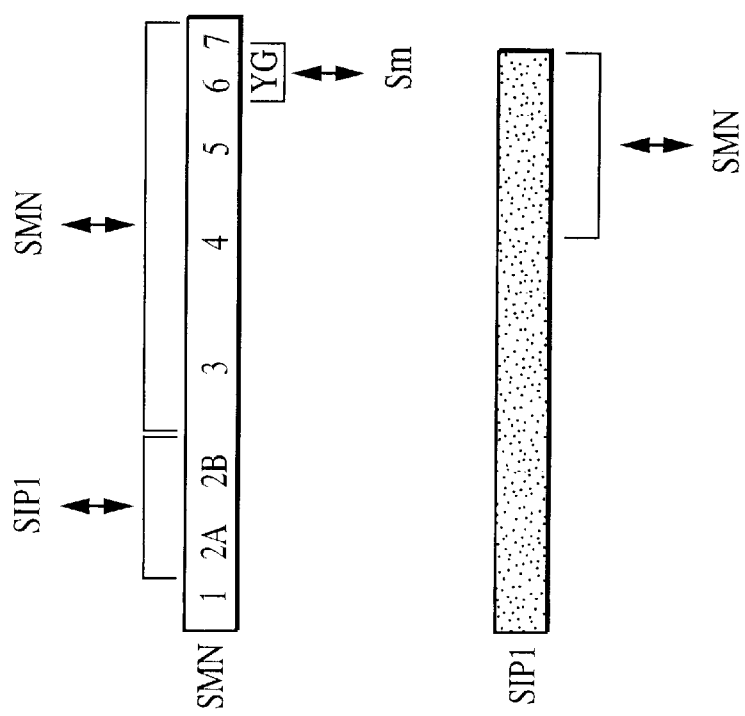
FIG. 48 depicts a schematic representation of SMN and SIP1 interaction domains and depicts a model of the SMN/SIP1 complex. The diagram depicts a summary of the regions of SMN and SIP1 required for their interactions within the complex (SMN exons are indicated). The SMN domain required for SmB binding contains the highly conserved YG box described by Talbot et al., (1997, Hum. Mol. Genet. 6:497–500).

As previously discussed herein, the yeast two-hybrid screen demonstrated that SMN interacts with itself and with SIP1; further, in vitro binding experiments confirmed these to be direct interactions (Liu and Dreyfuss, 1996, EMBO J. 15:3555–3565; Liu et al., 1997, Cell 90:1013–102; Lorson et al., 1998, Nature Genet. 19:63–66). To define the domains of SMN that mediate these interactions, various deletion mutants were constructed and these mutants and their interactions were examined by binding assays with purified recombinant GST chimeric fusion proteins of SMN, SIP1 and SmB. The in vitro translation products of SMN wild-type and mutant constructs, labeled with $^{35}$[S]methionine, are shown in FIG. 39. GST alone, used as a negative control, exhibited no detectable binding. In contrast, GST-SIP1 bound efficiently to full length SMN, to all the SMN carboxyl-terminal deletion mutants tested, and to the amino-terminal deletion mutant of exon 1 (ΔN27), but to a further amino-terminal deletion of exon 2 (ΔN92). These results confirm data previously disclosed herein of binding competition experiments and further identify the highly conserved region within exon 2A as essential for SMN interaction with SIP1 (FIGS. 48–49). Carboxyl-terminal deletions, including the exon 7 deletion (ΔC16) and a point mutation (Y272C) found in severe SMA type I patients, abolished or severely impaired binding to wild type SMN whereas amino-terminal deletions had no effect. Although there was a small amount of SMN and SIP1 in the reticulocyte lysate, bridging by endogenous SMN was unlikely as SMNΔN92, which may interact with SMN, did not bind SIP1 and all of the carboxyl-terminus deletions, which did not interact with SMN, bound SIP1. Therefore the binding assays disclosed above very likely represent direct interactions between the in vitro translated proteins and the GST-chimeric fusion proteins.

As previously disclosed herein, SMN is found in a complex with SIP1 and together they function in the assembly of the Sm proteins onto snRNAs. Thus, the Sm proteins can be thought of as substrates for SMN and SIP1. Therefore, the interaction of SMN with purified recombinant GST-SmB was examined. Both deletion of exon 7 (ΔC16) and the SMA point mutation (Y272C) strongly affect the interaction of SMN with SmB. The binding was completely abolished by a further deletion of the highly conserved "YG box" region (Talbot et al., 1997, Hum. Mol. Genet. 6:497–500; ΔC26 and ΔC106). Deletion of exon 2 near the amino-terminus of the protein also abolishes the interaction with SmB. A summary of these results is presented in FIG. 40 and FIGS. 48–49.

Figure 41:
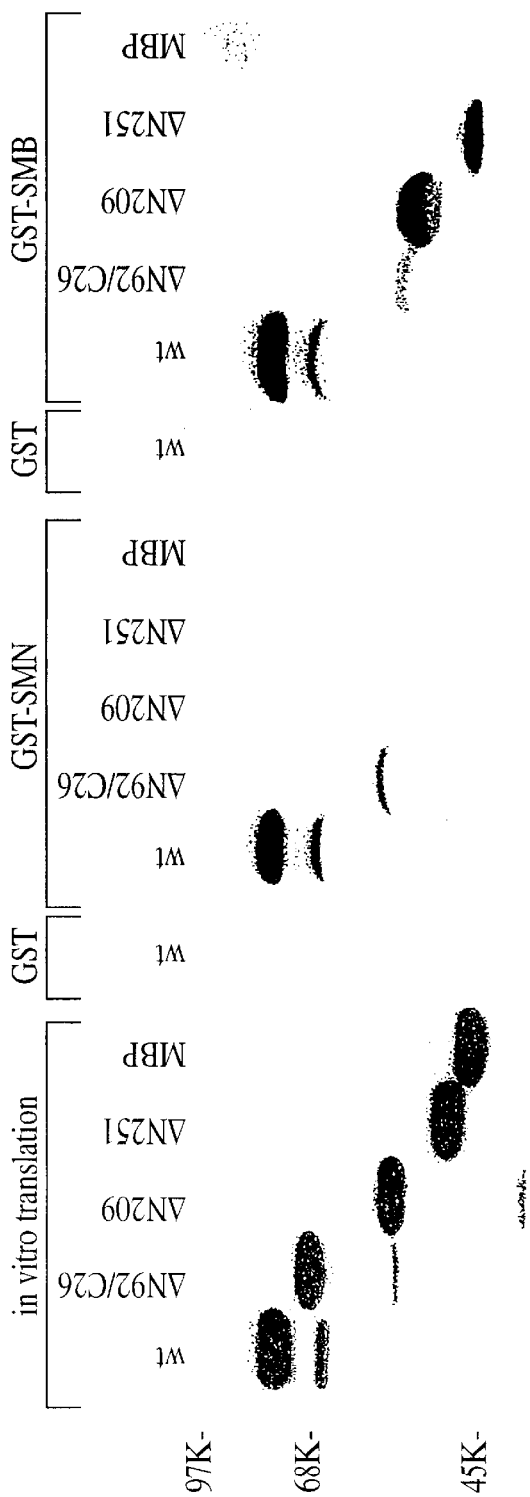
FIG. 41 is an image of a gel depicting the fact that the dimerization and SmB binding domains of SMN are not identical. In vitro translated [$^{35}$S]methionine labeled SMN wild-type and SMN mutant proteins were fused to the maltose binding protein (MBP) and were incubated with purified GST (only the MBP-SMN wild-type fusion), GST-SMN or GST-SmB bound to glutathione-Sepharose beads as described in the Materials and Methods. Bound proteins were eluted from the beads by boiling in SDS-PAGE sample buffer and the eluted proteins were analyzed by SDS-PAGE and fluorography. The in vitro translation lanes contained 10% of the input used for the binding assay.
Figure 42:
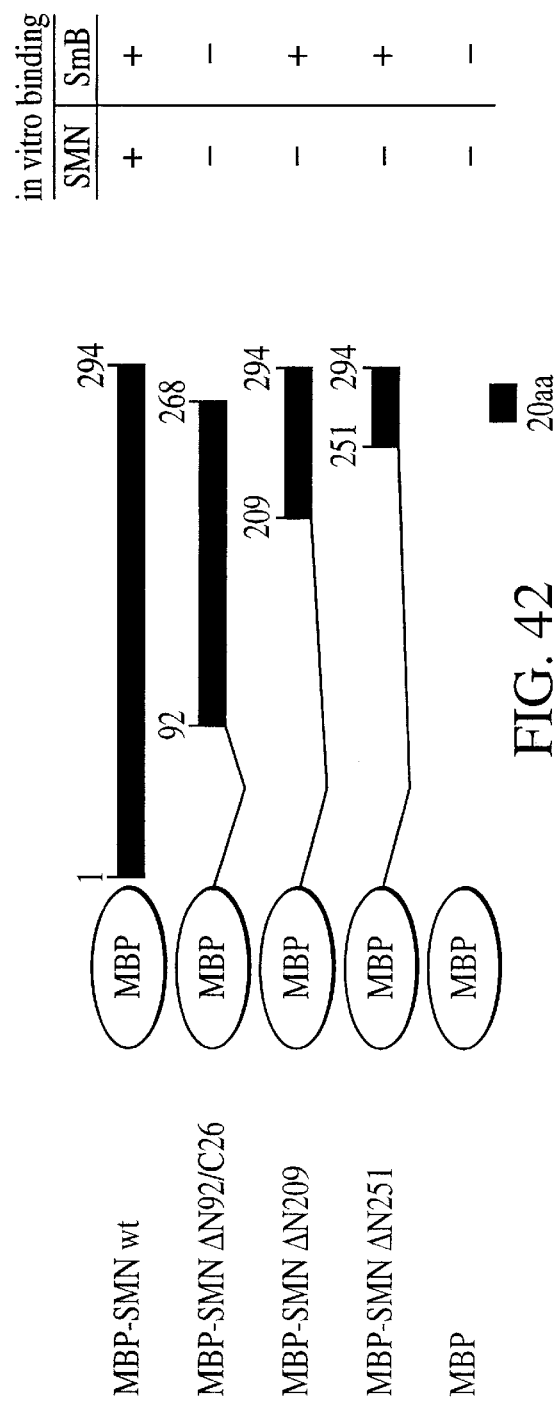
FIG. 42 is a schematic representation of the MBP-SMN fusion proteins and a summary of their in vitro binding properties to GST-SMN and GST-SmB. The first and the last amino acids of SMN proteins are indicated and the abbreviations are as follows: strong binding (+) and no detectable binding (−).

The dimerization and Sm binding domains of SMN are not identical The data disclosed above demonstrate that the SMN dimerization and substrate binding domains include the carboxyl-terminus of the protein and that these domains may be overlapping. The precise relationship of the two domains relative to each other was examined by looking for the minimal SMN region required to bind both SMN itself and SmB. To do so, several constructs were generated containing different portions of SMN fused to the maltose binding protein (MBP) and the binding of the in vitro translated fusions to GST-SMN and to GST-SmB was assayed (FIG. 42). MBP itself did not bind either GST-SMN or GST-SmB, and MBP-SMN did not bind to GST alone but bound efficiently to GST-SMN and to GST-SmB (FIG. 41). MBP fused to SMN lacking both the first 92 amino acids at the amino-terminus and the last 26 at the carboxyl-terminus of SMN (ΔN92/C26) did not bind SMN or SmB, further demonstrating the requirement of these domains for the interactions. Both MBP fusions with the carboxyl-terminus region of SMN which contain the conserved YG box (ΔN209 and ΔN251) bound efficiently to GST-SmB but not to GST-SMN. This suggests that the SMN dimerization and SmB binding domains are not identical. Moreover, these data identify the highly conserved region containing the YG box as necessary and sufficient to mediate SMN interaction with SmB but not sufficient for the SMN oligomerization. This conclusion is in agreement with data previously disclosed herein demonstrating that a peptide corresponding to this highly conserved region can efficiently compete with the interaction between SMN and SmB.

SMN Dimerization Enhances the Interaction With Substrate

Figure 43:
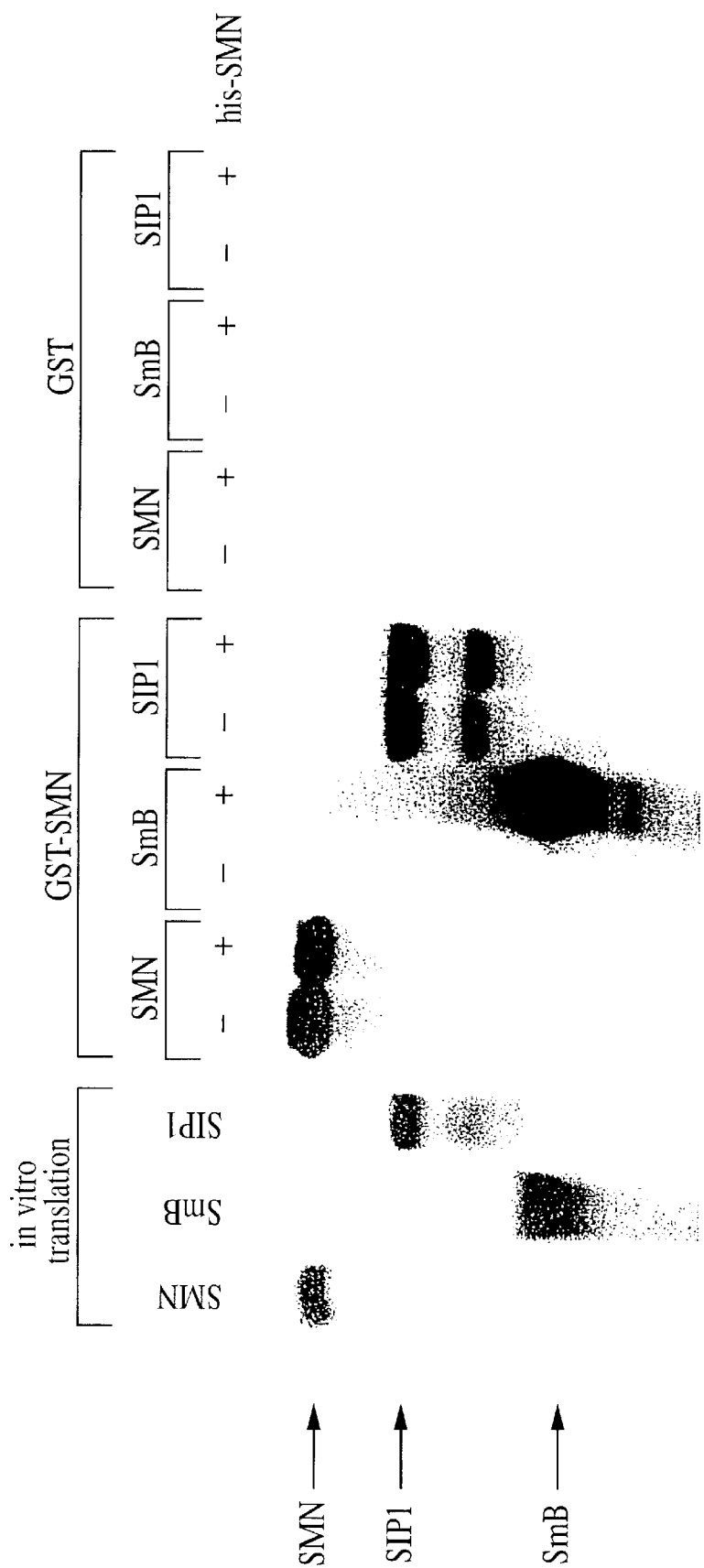
FIG. 43 is an image of an SDS-PAGE gel depicting that SMN dimerization increases the binding affinity of SMN for SmB. GST or GST-SMN bound to glutathione-Sepharose beads were pre-incubated in binding buffer with or without a four-fold molar excess of purified recombinant His6-tagged-SMN for two hours at 4EC in a total volume of 1 ml. Unbound His6-tagged-SMN was eliminated by washing the beads five times with binding buffer. In vitro translated [$^{35}$S]methionine labeled SMN, SmB and SIP1 were then added to the beads. The beads were washed and the bound proteins were eluted by boiling the beads in SDS-PAGE sample buffer. The eluted proteins were analyzed by SDS-PAGE and followed by fluorography. The in vitro translation lanes contained 10% of the input used for the binding assay.

Although the experiments just described demonstrate that there is a difference in the sequence requirements of the interaction of SMN with itself and with SmB, they do not reveal whether or not these interactions are mutually exclusive. The simplest interpretation of the data disclosed previously here (i.e., peptide competition experiments) is that there is direct binding of SmB to SMN. To determine whether the interactions of SMN with SMN and SmB are mutually exclusive, binding experiments were performed and the results are depicted in FIG. 43. GST-SMN, or GST alone as a control, was first pre-incubated with or without a molar excess of purified recombinant His6-tagged SMN under binding conditions for 2 hours. The unbound His6-tagged-SMN was removed by extensive washing after which in vitro translated $^{35}$[S]methionine-labeled SMN, SmB or SIP1 was added to the beads and the binding assay was performed as described previously herein. SMN binding was only slightly decreased by the pre-incubation with His6-SMN, thereby demonstrating that not all the binding sites were saturated and that SMN can oligomerize. However, the pre-incubation with His6-tagged-SMN had a striking effect on SmB binding as almost 100% of the input SmB was now in the bound fraction. The specificity of this binding was further demonstrated by the lack of an effect on SIP1 binding and by the low background obtained using GST alone. These results demonstrate that the binding of SMN and SmB are not mutually exclusive but, on the contrary, that SMN oligomerization greatly enhances the affinity of SMN for SmB.

SIP1 Interaction Domain With SMN

Figure 40:
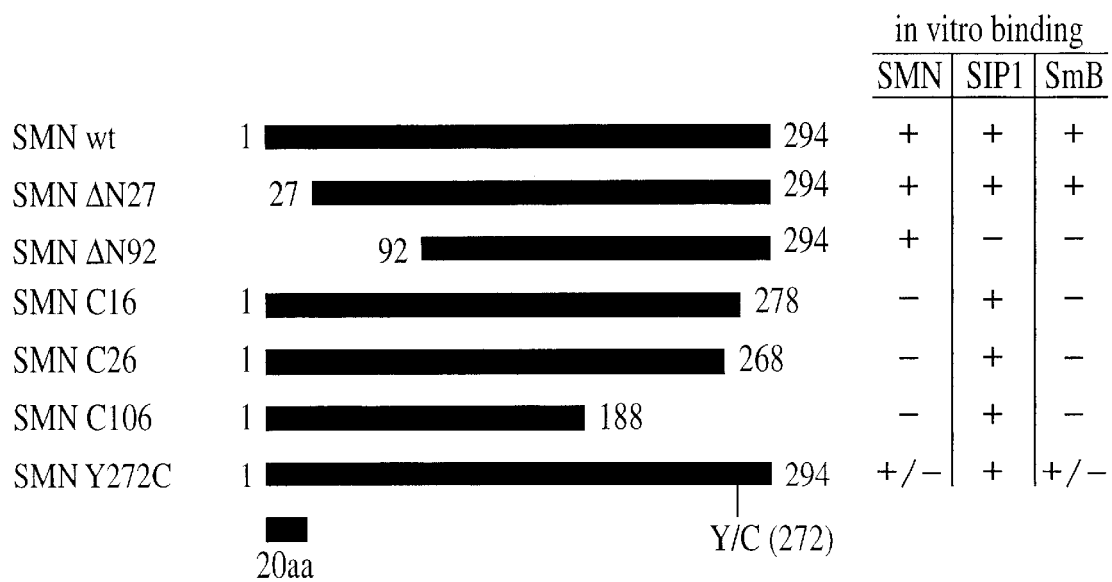
FIG. 40 is a diagram depicting a schematic representation of the SMN mutants and summarizing their in vitro binding properties to the GST-fusion proteins. The first and the last amino acids of the SMN protein fragments are indicated. The abbreviations are as follows: strong binding (+), weak binding (+/−), no detectable binding (−).
Figure 44:
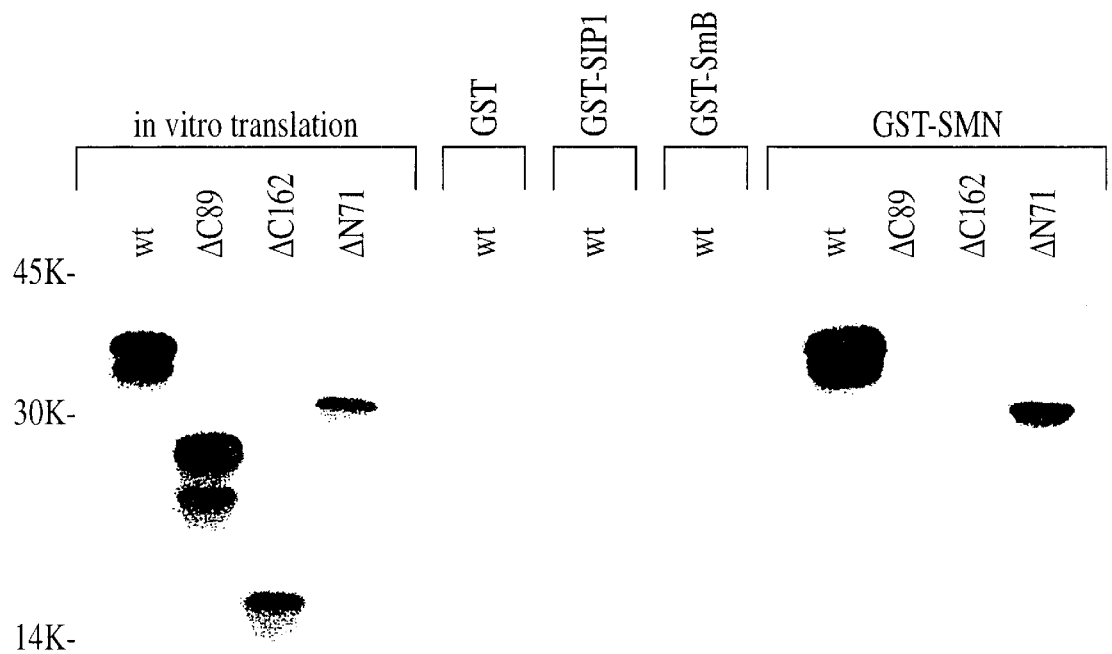
FIG. 44 is an image of a gel depicting the in vitro mapping of the SIP1 interaction domains. In vitro translated [$^{35}$S] methionine labeled myc-tagged-SIP1 wild type and mutant proteins were incubated as indicated with purified GST or GST-fusion proteins (SMN, SIP1 or SmB) bound to glutathione-Sepharose beads. Bound proteins were eluted from the beads by boiling the beads in SDS-PAGE sample buffer and the eluted proteins were analyzed by SDS-PAGE and fluorography. The in vitro translation lanes contained 10% of the input used for the binding assay.
Figure 45:
FIG. 45 is a schematic representation of the SIP1 mutants and a summary of their in vitro binding properties to GST-SMN. The first and the last amino acids of SIP1 proteins are indicated. The abbreviations are as follows: strong binding (+), no detectable binding (−).

The amino-terminal region of SMN is required for interaction with SIP1 (FIGS. 39–40 and data previously disclosed herein). Using deletion mutants of SIP1 (FIG. 45), the regions of SIP1 that are required for its interaction with SMN were mapped. In vitro translated SIP1 bound efficiently to GST-SMN but not to GST alone, or to GST-SmB or GST-SIP1 (FIG. 44). Both carboxy-terminal deletions of SIP1 (ΔC89 and ΔC162), but not the amino-terminal one (ΔN71), completely abolished the binding of SIP1 to SMN. These results demonstrate that SM does not dimerize and also that SIP1 does not bind directly to SmB; instead, SIP1 interacts directly through its carboxyl-terminus with the amino-terminal region of SMN. A schematic summary of these interactions is presented in FIG. 45 and FIGS. 48–49.

SMN Complexes in vivo

As previously disclosed herein, in vivo, SMN is found in a complex that contains SIP1 and Sm proteins as well as several as yet unknown proteins. The SMN-containing complexes were studied in vivo by co-immunoprecipitation experiments after transfections of 293T cells with wild-type or mutant SMN and SIP1. First, whether a SIP1 mutant that does not interact in vitro with SMN can assemble into the SMN complex was assessed. To this end, myc-tagged SIP1 wild type, but not the ΔC89 deletion mutant, was co-immunoprecipitated with the anti-SMN monoclonal antibody 2B1, as expected if other interactions, in addition to the one with SMN, did not bridge the mutant to the complex (FIG. 46A). Both myc-SMN wild-type and myc-SMNΔN92 were co-immunoprecipitated with the anti-SIP1 antibody 2E17 (FIG. 46B). This demonstrates that a SMN deletion mutant (ΔN92) which did not interact with SIP1 and with Sm proteins, was incorporated into the SMN complex that also contained SIP1. This may be due to the fact that the mutant can still interact with endogenous SMN bound to SIP1. Thus, SMN in vivo is in an oligomeric, at least dimeric, complex that also contains SIP1. Next, myc-SMN wild type with a carboxyl-terminal deletion mutant (ΔC26) lacking the YG box that bound SIP1 but did not bind SMN and SmB in vitro (FIGS. 39–40), were compared for their ability to associate with the SMN-SIP1 complex. SMNΔC26 was co-immunoprecipitated with anti-SIP1 antibodies as efficiently as the wild-type SMN suggesting that it was assembled into the SMN/SIP1 complex (FIG. 47). When the immunoprecipitation was performed with the anti-Sm antibody Y12, approximately one third of the SMNΔC26 mutant was co-immuniprecipitated compared with the wild-type SMN (FIG. 47). The SMN Y272C point mutant and SMNΔC16 deletion mutant displayed a similar but reduced effect consistent with the lower effect these mutants demonstrated in the in vitro binding experiments. These results demonstrate that the SMN/SIP1 complex containing the SMN deletion mutant could still assemble with the Sm core proteins albeit less efficiently than wild type SMN.

Subcellular Localization of SMN and SIP1 Mutants

Figure 51A:
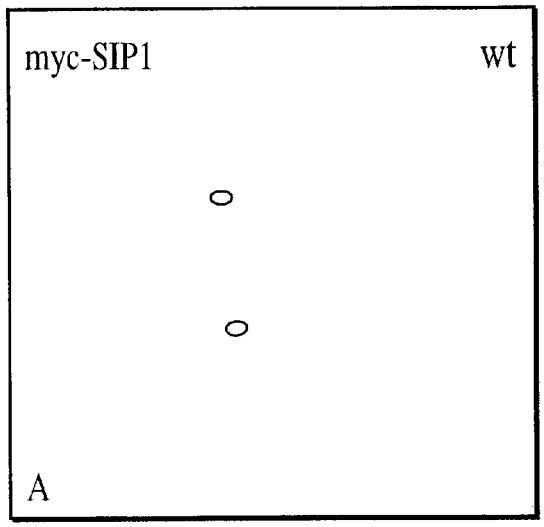
FIGS. 51A–D is an image (comprising four panels) of photomicrographs depicting the subcellular localization of SIP1 deletion mutants using confocal immunofluorescence microscopy. HeLa cells were transiently transfected with SIP1 constructs expressing myc-tagged SIP1 wild-type or with the indicated myc-tagged SIP1 deletion mutants (see FIG. 45). Indirect immunofluorescence was performed using monoclonal antibody 9E10 against the myc-tag protein. Gems staining was detected by anti-myc antibodies which completely co-localize with antibodies to endogenous SMN. The intensity of the cytoplasmic staining is underestimated by approximately two-fold of photomicrographs in the sections shown.
Figure 51B:
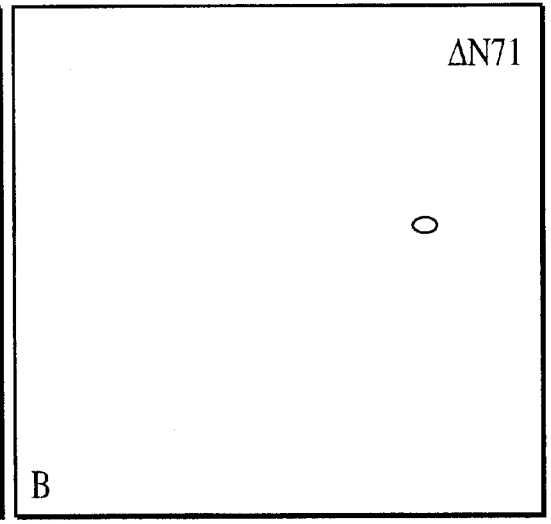
Figure 51C:
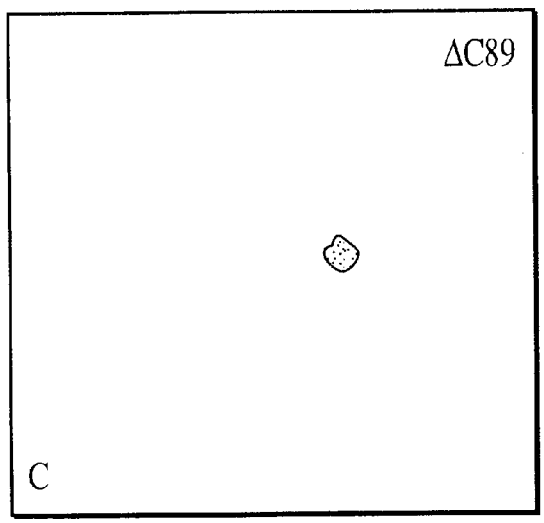
Figure 51D:
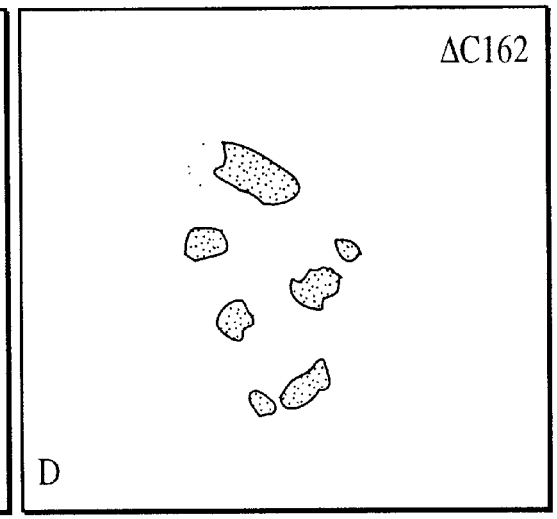

The expression and cellular localization of the myc-tagged SMN and SIP1 mutants was determined by indirect immunofluorescence using anti-myc antibodies. As expected, SMN wild-type localized to gems. All the carboxyl-terminal deletion mutants of SMN and the point mutant Y272C also localized to the gems (FIGS. 50A–E). However, the SMN mutants exhibited stronger nucleoplasmic staining than wild-type SMN, likely reflecting their less efficient assembly into gems which appeared smaller and less bright. Surprisingly, both amino-terminal deletion mutants of SMN (ΔN27 and ΔN92) has a strikingly different localization. In cells transfected with these mutants, SMN-containing accumulations were detected in the cytoplasm, and in the nucleus the gems became much bigger and more numerous (FIGS. 50F and 50G). All these structures which contained SMN mutants co-localized with endogenous SMN and SIP1. The amino-terminal deletions of SMN thus acted as dominant negative mutants, and further detailed analysis of their effects is presented below. The only SMN mutant that did not co-localize with gems is ΔN92/C106 which could not interact with SMN, SIP1 and Sm (FIG. 50H). All the other SMN mutants still retained at least one interaction domain suggesting that the assembly into the SMN/SIP1 complex in vivo is necessary and sufficient to localize the protein into gems. This suggestion is further supported by observations on the subcelluar localization of SIP1 mutants shown in FIG. 51. Myc-tagged wild-type SIP1 transfected into HeLa cells localizes to gems (FIG. 51A). The amino terminal deletion mutant of SIP1 that still bound SMN in vitro (ΔN71 FIGS. 44–45) localized to gems whereas a carboxyl-terminal deletion that did not bind SMN in vitro and did not assemble into SMN/SIP1 complex in vivo (ΔC89, FIGS. 44–45 and 46–47, respectively) did not localize to gems. Interestingly, a further carboxy-terminus deletion of SIP1 (ΔC162) exhibited a nuclear localization in structures resembling speckles (Huang and Spector, 1992, Proc. Natl. Acad. Sci USA 89:305–308). This SIP1 mutant also acted as dominant negative as endogenous SMN and SIP1 became co-localized to these structures, and gems were disassembled.

SMN Regions Necessary and Sufficient for Targeting to Gems

Figure 52A:
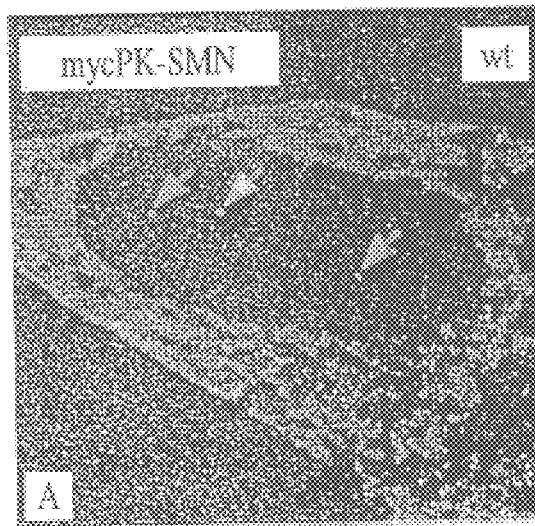
FIGS. 52A–D is an image (comprising four panels) depicting the targeting of pyruvate kinase (PK) to gems. The image depicts the results of confocal immunofluorescence microscopy demonstrating HeLa cells which were transiently transfected with myc-PK constructs expressing myc-tagged pyruvate kinase fused to either SMN wild-type or the indicated SMN deletion mutants (see FIG. 40). Indirect immunofluorescence was performed using monoclonal antibody 9E10 against the myc-tag protein. Gems are indicated by arrows. Gems staining detected by anti-myc antibodies completely co-localize with endogenous SIP1.
Figure 52B:
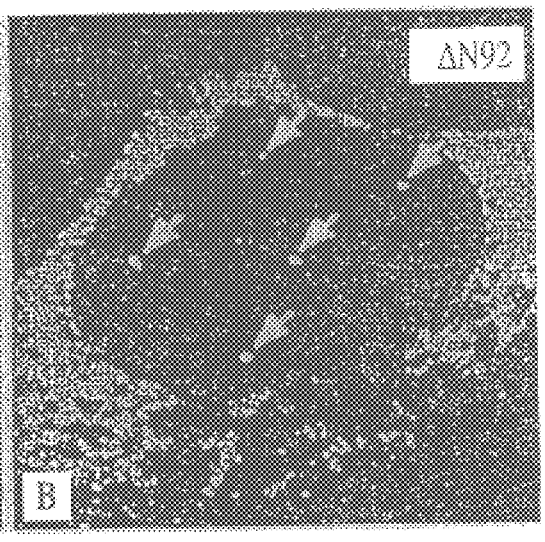
Figure 52C:
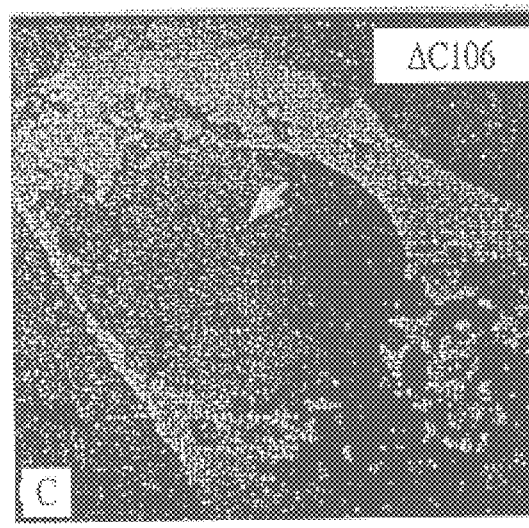
Figure 52D:
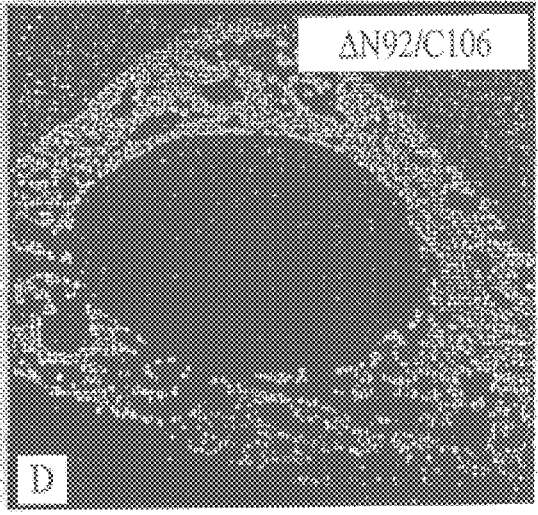

As SMN and SIP1, both wild type and mutants, localized to gems if they interacted with any other components of the complex, the various regions of SMN were tested for their capacity to target a reporter protein to gems. To do so, transient transfections into HeLa cells were performed using constructs expressing SMN regions fused to myc-tagged pyruvate kinase (myc-PK) as the reporter protein. Pyruvate kinase is normally cytoplasmic and is often utilized as a reporter to identify nuclear localization signals (see Siomi and Dreyfuss, 1995, J. Cell Biol. 129:551–560). Indirect immunofluorescence was used with anti-myc antibodies. It was observed that myc-PK fused to full length SMN localized to gems in addition to localizing to the cytoplasm (FIG. 52A). A deletion mutant of SMN lacking the first 92 amino acids, which affected SMN interactions with SIP1 and Sm proteins but not with SMN itself, was sufficient to target PK to gems (FIG. 52B). A deletion mutant lacking the last 106 amino acids, which affected SMN interaction with itself and Sm proteins but not with SIP1, was also sufficient to target PK to gems (FIG. 52C). However, a mutant missing the middle part of SMN, which domain is present in and common to the two previous fusions, and which lacked the ability to interact directly with SMN, SIP1 and Sm proteins, was completely cytoplasmic (FIG. 52D). Although a sequence resembling a classical nuclear localization signal was present in SMN exon 2, no nucleoplasmic staining was detected suggesting the absence of a functional nuclear localization signal in SMN. Thus, SMN (and possibly SIP1) nuclear import apparently occurs when the protein is a component of a complex including snRNPs.

The disclosures of each and every patent, patent application, and publication cited herein are hereby incorporated herein by reference in their entirety.

While the invention has been disclosed with reference to specific embodiments, it is apparent that other embodiments and variations of this invention may be devised others skilled in the art without departing from the true spirit and scope of the invention. The appended claims are intended to be construed to include all such embodiments and equivalent variations.

What is claimed is:

1. An isolated nucleic acid encoding a human Survival of Motor Neuron-Interacting Protein 1, wherein said nucleic acid encodes a protein that differs from the amino acid sequence of SEQ ID NO: 2 by a mutation that inhibits binding of Survival of Motor Neuron-Interacting Protein 1 with Survival of Motor Neuron protein, and further wherein said mutation is selected from the group consisting of a deletion of the carboxyl terminal 89 amino acids relative to the amino acid sequence of SEQ ID NO: 2 and a deletion of the carboxyl terminal 162 amino acids relative to the amino acid sequence of SEQ ID NO: 2.

2. The isolated nucleic acid of claim 1, said nucleic acid further comprising a nucleic acid encoding a promoter/regulatory sequence operably linked thereto.

3. A vector comprising the isolated nucleic acid of claim 1.

4. The vector of claim 3, said vector further comprising a nucleic acid encoding a promoter/regulatory sequence operably linked thereto.

5. A recombinant cell comprising the vector of claim 3.

6. A recombinant cell comprising the isolated nuclei acid of claim 1.

7. An antisense isolated nucleic acid complementary to the nucleic acid of claim 1.

8. A recombinant cell comprising the antisense nucleic acid of claim 7.

* * * * *